United States Patent
Wang et al.

(10) Patent No.: US 7,144,913 B2
(45) Date of Patent: Dec. 5, 2006

(54) DIHYDROPYRROLO[1,2-A]INDOLE AND TETRAHYDROPYRIDO[1,2-A]-INDOLE DERIVATIVES AS PROSTAGLANDIN D2 RECEPTOR ANTAGONISTS

(75) Inventors: Zhaoyin Wang, Kirkland (CA); Christian Beaulieu, Laval (CA); Claude Dufresne, Dollard-des-Ormeaux (CA); Daniel Guay, Notre Dame de l'Ile Perrot (CA); Yves LeBlanc, Kirkland (CA)

(73) Assignee: Merck Frosst Canada & Co., Kirkland (CA)

( * ) Notice: Subject to any disclaimer, the term of this patent is extended or adjusted under 35 U.S.C. 154(b) by 169 days.

(21) Appl. No.: 10/474,929

(22) PCT Filed: May 22, 2002

(86) PCT No.: PCT/CA02/00745

§ 371 (c)(1),
(2), (4) Date: Oct. 15, 2003

(87) PCT Pub. No.: WO02/094830

PCT Pub. Date: Nov. 28, 2002

(65) Prior Publication Data

US 2004/0180934 A1    Sep. 16, 2004

Related U.S. Application Data

(60) Provisional application No. 60/293,077, filed on May 23, 2001.

(51) Int. Cl.
*A61K 31/40* (2006.01)
*C07D 487/00* (2006.01)
(52) U.S. Cl. .......................... 514/411; 548/428; 546/94; 514/294
(58) Field of Classification Search ................ 548/428; 514/411, 214; 546/94
See application file for complete search history.

(56) References Cited

U.S. PATENT DOCUMENTS

2004/0229844 A1 *   11/2004   Cheng et al. .................. 514/64

* cited by examiner

*Primary Examiner*—Joseph K. McKane
*Assistant Examiner*—Robert Shiao
(74) *Attorney, Agent, or Firm*—David L. Rose

(57) ABSTRACT

Dihydropyrroloindoles and tetrahydropyridoindoles are prostaglandin receptor antagonists useful for the treatment of prostaglandin-mediated diseases such as allergic rhinitis, nasal congestion and asthma.

29 Claims, No Drawings

DIHYDROPYRROLO[1,2-A]INDOLE AND TETRAHYDROPYRIDO[1,2-A]-INDOLE DERIVATIVES AS PROSTAGLANDIN D2 RECEPTOR ANTAGONISTS

CROSS REFERENCE TO RELATED APPLICATIONS

This application is the National Stage of International Application No. PCT/CA02/00745, filed May 22, 2002, which claims the benefit under 35 U.S.C. 119(e) of U.S. Provisional Application No. 60/293,077, filed May 23, 2001.

BACKGROUND OF THE INVENTION

The present invention relates to compounds and methods for treating prostaglandin mediated diseases, and certain pharmaceutical compositions thereof. More particularly, the compounds of the invention are structurally different from steroids, antihistamines or adrenergic agonists, and are antagonists of the nasal and pulmonary congestion effects of D-type prostaglandins.

Two review articles describe the characterization and therapeutic relevance of the prostanoid receptors as well as the most commonly used selective agonists and antagonists: *Eicosanoids: From Biotechnology to Therapeutic Applications*, Folco, Samuelsson, Maclouf, and Velo eds, Plenum Press, New York, 1996, chap. 14, 137–154 and Journal of Lipid Mediators and Cell Signalling, 1996, 14, 83–87. An article from T. Tsuri et al. published in 1997 in *Journal of Medicinal Chemistry*, vol 40, pp.3504–3507, states that "PGD2 is considered to be an important mediator invarious allergic diseases such allergic rhinitis, atopic asthma, allergic conjunctivitis and atopic dermatitis." More recently, an article by Matsuoka et al. in *Science* (2000), 287:2013–7, describes PGD2 as being a key mediator in allergic asthma. In addition, patents such as U.S. Pat. No. 4,808,608 refer to prostaglandin antagonists as useful in the treatment of allergic diseases, and explicitly allergic asthma. PGD2 antagonists are described in, for example, European Patent Application 837,052 and PCT Application WO98/25919, as well as WO99/62555.

In Arch. Pharm. (1972), 305(2): 96–103 there is disclosed the compound

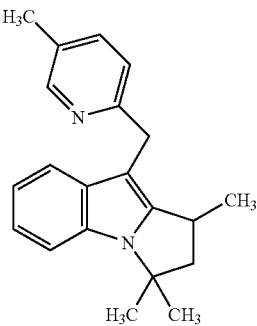

SUMMARY OF THE INVENTION

The present invention provides novel compounds which are prostaglandin receptor antagonists; more particularly, they are prostaglandin D2 receptor (DP receptor) antagonists. Compounds of the present invention are useful for the treatment of various prostaglandin-mediated diseases and disorders; accordingly the present invention provides a method for the treatment of prostaglandin-mediated diseases using the novel compounds described herein, as well as pharmaceutical compositions containing them.

DETAILED DESCRIPTION OF THE INVENTION

The present invention relates to compounds of formula I:

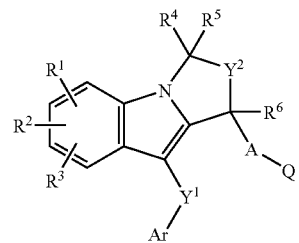

and pharmaceutically acceptable salts and hydrates thereof, wherein:

$R^1$, $R^2$ and $R^3$ are each independently selected from hydrogen and $R^g$;

$R^4$ is selected from H, CN, $C_{1-6}$alkyl optionally substituted with one to six halogen, $OR^a$ and $S(O)_nC_{1-6}$alkyl;

$R^5$ is selected from H and $C_{1-6}$alkyl optionally substituted with one to six halogen; or $R^4$ and $R^5$ together represent an oxo; or $R^4$ and $R^5$ taken together form a 3- or 4-membered ring containing 0 or 1 heteroatom selected from $NR^f$, S, and O optionally substituted with one or two groups selected from F, $CF_3$ and $CH_3$;

$R^6$ is selected from H and $C_{1-6}$alkyl optionally substituted with one to six groups independently selected from $OR^a$ and halogen, Ar is aryl or heteroaryl each optionally substituted with one to four groups independently selected from $R^g$;

A is $C_{1-3}$alkyl optionally substituted with one to four halogen atoms, $O(CH_2)_{1-2}$, $S(CH_2)_{1-2}$;

Q is selected from:
  (1) COOH,
  (2) $CONR^aR^b$,
  (3) $C(O)NHSO_2R^c$,
  (4) $SO_2NHR^a$,
  (5) $SO_3H$,
  (6) $PO_3H_2$, and
  (7) tetrazolyl, $Y^1$ is —$(CR^dR^e)_a$—X—$(CR^dR^e)_b$—, phenylene, $C_{3-6}$cycloalkylidene or $C_{3-6}$cycloalkylene, wherein a and b are integers 0–1 such that the sum of a and b equals 0, 1 or 2;

X is a bond, O, S, $NR^a$, C(O), OC(O), C(O)O, $C(O)NR^a$, $OC(O)NR^a$, $NR^aC(O)$, $CR^d$=$CR^e$ or C≡C;

$Y^2$ is $CR^dR^e$, $CR^dR^e$—$CR^dR^e$, or $CR^d$=$CR^e$, $R^a$ and $R^b$ are independently selected from H, $C_{1-10}$alkyl, $C_{2-10}$alkenyl, $C_{2-10}$alkynyl, Cy and Cy $C_{1-10}$alkyl, wherein alkyl, alkenyl, alkynyl and Cy are optionally substituted with one to six substituents independently selected from halogen, amino, carboxy, $C_{1-4}$alkyl, $C_{1-4}$alkoxy, aryl, heteroaryl, aryl $C_{1-4}$alkyl, hydroxy, $CF_3$, $OC(O)C_{1-4}$alkyl, $OC(O)NR^iR^j$, and aryloxy; or R$^a$ and R$^b$ together with the atom(s) to which they are attached form a heterocyclic ring of 4 to 7 members containing 0–2 additional heteroatoms independently selected from oxygen, sulfur and N—R$^f$;

R$^c$ is selected from C$_{1-6}$alkyl optionally substituted with one to six halogen, aryl and heteroaryl, wherein said aryl and heteroaryl are optionally substituted with halogen, OC$_{1-6}$alkyl, C$_{1-6}$alkyl and wherein said alkyl is optionally substituted with one to six halogen;

R$^d$ and R$^e$ are independently H, halogen, aryl, heteroaryl, C$_{1-6}$alkyl or haloC$_{1-6}$alkyl, or R$^f$ is selected from H, C$_{1-6}$alkyl, haloC$_{1-6}$alkyl, Cy, C(O)C$_{1-6}$alkyl, C(O)haloC$_{1-6}$ alkyl, and C(O)-Cy;

R$^g$ is selected from
(1) halogen,
(2) CN,
(3) C$_{1-6}$alkyl optionally substituted with one to eight groups independently selected from aryl, heteroaryl, halogen, NR$^a$R$^b$, C(O)R$^a$, C(OR$^a$)R$^a$R$^b$, SR$^a$ and OR$^a$, wherein aryl, heteroaryl and alkyl are each optionally substituted with one to six groups independently selected from halogen, CF$_3$, and COOH,
(4) C$_{2-6}$alkenyl optionally substituted with one to six groups independently selected from halogen and OR$^a$,
(5) Cy
(6) C(O)R$^a$,
(7) C(O)OR$^a$,
(8) CONR$^a$R$^b$,
(9) OCONR$^a$R$^b$,
(10) OC$_{1-6}$alkyl, wherein alkyl is optionally substituted with one to six substituents selected from halogen, aryl, heteroaryl, OH and OC(O)R$^a$,
(11) O-aryl
(12) O-heteroaryl
(13) S(O)$_n$C$_{1-6}$alkyl, wherein alkyl is optionally substituted with one to six substituents selected from halogen, aryl, heteroaryl, OH, and OC(O)R$^a$,
(14) S(O)$_n$aryl,
(15) S(O)$_n$heteroaryl,
(16) —NR$^a$S(O)$_n$R$^b$,
(17) —NR$^a$R$^b$,
(18) —NR$^a$C(O)R$^b$,
(19) —NR$^a$C(O)OR$^b$,
(20) —NR$^a$C(O)NR$^a$R$^b$,
(21) S(O)$_n$NR$^a$R$^b$,
(22) NO$_2$,
(23) C$_{5-8}$cycloalkenyl,
wherein Cy is optionally substituted with one to eight groups independently selected from halogen, C(O)R$^a$, OR$^a$, C$_{1-3}$alkyl, aryl, heteroaryl and CF$_3$;

R$^i$ and R$^j$ are independently selected from hydrogen, C$_{1-10}$alkyl, Cy and Cy-C$_{1-10}$alkyl; or R$^i$ and R$^j$ together with the carbon to which they are attached form a ring of 5 to 7 members containing 0–2 heteroatoms independently selected from oxygen, sulfur and nitrogen;

Cy is selected from heterocyclyl, aryl, and heteroaryl;

n is 0, 1 or 2.

The invention also encompasses pharmaceutical compositions containing a compound of formula I, and methods for treatment or prevention of prostaglandin mediated diseases using compounds of formula I.

The invention is described using the following definitions unless otherwise indicated.

The term "halogen" or "halo" includes F, Cl, Br, and I.

The term "alkyl" refers to linear, branched and cyclic and bicyclic structures and combinations thereof, containing the indicated number of atoms. Non-limiting examples of alkyl groups include methyl, ethyl, propyl, isopropyl, butyl, s- and t-butyl, pentyl, hexyl, heptyl, octyl, nonyl, undecyl, dodecyl, tridecyl, tetradecyl, pentadecyl, eicosyl, 3,7-diethyl-2,2-dimethyl-4-propylnonyl, cyclopropyl, cyclobutyl, cyclopentyl, cyclohexyl, cycloheptyl, cyclopropylmethyl, cyclopentylethyl, methyl substituted cyclopropyl, ethyl substituted cyclobutyl, adamantyl cyclododecylmethyl, 2-ethyl-1-bicyclo[4.4.0]decyl and the like. For example, the term C$_{1-6}$alkyl encompasses acyclic alkyl groups having the indicated number of carbon atoms as well as —C$_x$alkyl-C$_z$cycloalkyl wherein x is 0 to 3 and z is 3 to 6 with the proviso that x+z=3 to 6.

"Cycloalkylidene" refers to the following bivalent radical where the points of attachement are on the same carbon atom:

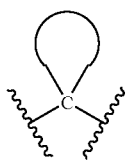

"Cycloalkylene" refers to the following bivalent radical where the points of attachment are on different carbon atoms:

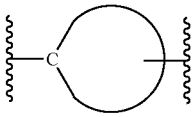

"Phenylene" refers to the following bivalent radical and includes 1,2-phenylene, 1,3-phenylene and 1,4-phenylene:

"Haloalkyl" means an alkyl group as described above wherein one or more hydrogen atoms have been replaced by halogen atoms, with up to complete substitution of all hydrogen atoms with halo groups. C$_{1-6}$haloalkyl, for example, includes —CF$_3$, —CH$_2$CF$_3$, —CF$_2$CF$_3$ and the like.

"Alkoxy" means alkoxy groups of a straight, branched or cyclic configuration having the indicated number of carbon atoms. C$_{1-6}$alkoxy, for example, includes methoxy, ethoxy, propoxy, isopropoxy, and the like.

"Haloalkoxy" means an alkoxy group as described above in which one or more hydrogen atoms have been replaced by halogen atoms, with up to complete substitution of all hydrogen atoms with halo groups. C$_{1-6}$haloalkoxy, for example, includes —OCF$_3$, —OCH$_2$CF$_3$, —OCF$_2$CF$_3$ and the like.

"Alkenyl" means linear or branched structures and combinations thereof, of the indicated number of carbon atoms, having at least one carbon-to-carbon double bond, wherein hydrogen may be replaced by an additional carbon-to-carbon double bond. C$_{2-6}$alkenyl, for example, includes ethenyl, propenyl, 1-methyl-ethenyl, butenyl and the like.

"Heterocyclyl" refers to a non-aromatic ring having 1 to 4 heteroatoms said ring being isolated or fused to a second ring selected from 3- to 7-membered alicyclic ring containing 0 to 4 heteroatoms, aryl and heteroaryl, wherein said heteroatoms are independently selected from O, N and S. Non-limiting examples of heterocyclyl include oxetanyl, 1,3-dithiacyclopentane, dihydrobenzofuran, and the like.

"Aryl" means a 6–14 membered carbocyclic aromatic ring system comprising 1–3 benzene rings. If two or more aromatic rings are present, then the rings are fused together, so that adjacent rings share a common bond. Examples include phenyl and naphthyl.

The term "heteroaryl" (Het) as used herein represents a 5–10 membered aromatic ring system containing one ring or two fused rings, 1–4 heteroatoms, selected from O, S and N. Het includes, but is not limited to, tetrazolyl, benzothienyl, quinolinyl, benzothiazolyl, furanyl, diazinyl, imidazolyl, isooxazolyl, isothiazolyl, oxadiazolyl, oxazolyl, pyrazolyl, pyridyl, pyrrolyl, tetrazinyl, thiazolyl, thiadiazolyl, thienyl, triazinyl, triazolyl, 1H-pyrrole-2,5-dionyl, 2-pyrone, 4-pyrone, pyrrolopyridine, furopyridine and thienopyridine.

"Therapeutically effective amount" means that amount of a drug or pharmaceutical agent that will elicit the biological or medical response of a tissue, a system, animal or human that is being sought by a researcher, veterinarian, medical doctor or other clinician.

The term "treatment" or "treating" includes alleviating, ameliorating, relieving or otherwise reducing the signs and symptoms associated with a disease or disorder.

The term "prophylaxis" means preventing or delaying the onset or the progression of a disease or disorder, or the signs and symptoms associated with such disease or disorder.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, and pharmaceutically acceptable excipients.

For purposes of this specification, the following abbreviations have the indicated meanings:

| | |
|---|---|
| Ac = | acetyl |
| AcO = | acetate |
| BOC = | t-butyloxycarbonyl |
| CBZ = | carbobenzoxy |
| CDI = | carbonyldiimidazole |
| DCC = | 1,3-dicyclohexylcarbodiimide |
| DCE = | 1,2-dichloroethane |
| DIBAL = | diisobutyl aluminum hydride |
| DIEA = | N,N-diisoproylethylamine |
| DMAP = | 4-(dimethylamino)pyridine |
| DMF = | dimethylformamide |
| EDCI = | 1-(3-dimethylaminopropyl)-3-ethylcarbodiimide hydrochloride |
| EDTA = | ethylenediaminetetraacetic acid, tetrasodium salt hydrate |
| FAB = | fast atom bombardment |
| FMOC = | 9-fluorenylmethoxycarbonyl |
| HMPA = | hexamethylphosphoramide |
| HATU = | O-(7-Azabenzotriazol-1-yl)N,N,N',N'-tetramethyluronium hexafluorophosphate |
| HOBt = | 1-hydroxybenzotriazole |

-continued

| | |
|---|---|
| HRMS = | high resolution mass spectrometry |
| ICBF = | isobutyl chloroformate |
| KHMDS = | potassium hexamethyldisilazane |
| LDA = | lithium diisopropylamide |
| MCPBA = | metachloroperbenzoic acid |
| MMPP = | magnesium monoperoxyphthlate hexahydrate |
| Ms = | methanesulfonyl = mesyl |
| MsO = | methanefulfonate = mesylate |
| NBS = | N-bromosuccinimide |
| NMM = | 4-methylmorpholine |
| NMP = | N-methylpyrrolidinone |
| PCC = | pyridinium chlorochromate |
| PDC = | pyridinium dichromate |
| Ph = | phenyl |
| PPTS = | pyridinium p-toluene sulfonate |
| pTSA = | p-toluene sulfonic acid |
| PyH.Br₃ = | pyridine hydrobromide perbromide |
| r.t./RT = | room temperature |
| rac. = | racemic |
| TFA = | trifluoroacetic acid |
| TfO = | trifluoromethanesulfonate = triflate |
| THF = | tetrahydrofuran |
| TLC = | thin layer chromatography |
| TMSCl = | trimethylsilyl chloride |

Alkyl Group Abbreviations

| | |
|---|---|
| Me = | methyl |
| Et = | ethyl |
| n-Pr = | normal propyl |
| i-Pr = | isopropyl |
| c-Pr = | cyclopropyl |
| n-Bu = | normal butyl |
| i-Bu = | isobutyl |
| c-Bu = | cyclobutyl |
| s-Bu = | secondary butyl |
| t-Bu = | tertiary butyl |

Compounds of the present invention have either one of the two following tricyclic core structures, shown below with their numbering system used herein:

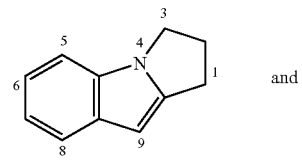 and

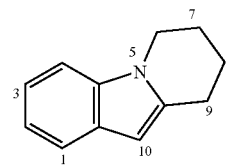

In one embodiment of formula I are compounds wherein $Y^1$ is selected from a bond, O, S, $NR^a$, $CHR^d$, $CHR^dCHR^d$, C(O), C(O)$CHR^d$, phenylene, and $C_{3-6}$cycloalkylidene. In one subset $Y^1$ is phenylene, S, C(O) or $CH_2$; in another subset $Y^1$ is S; in another subset $Y^1$ is C(O); in another subset $Y^1$ is $CH_2$. Examples of $Y^1$ include O, S, C(O), $CH_2$, $CH_2CH_2$, $CH(CH_3)$, $CH(CH_2CH_3)C(O)CH_2$, 1,4-phenylene, 1,3-phenylene, 1,1-cyclopropylidene, 1,4-cyclohexylene, NH, N($CH_3$), N($CH_2CH_3$), OC(O), C(O)O, C(O)NH, NHC(O), CH=CH, C≡C, and the like.

In another embodiment of formula I are compounds where Ar is napthyl or phenyl each optionally substituted with one to three groups independently selected from $R^g$. In one subset, Ar is 1-, or 2-napthyl. In another subset Ar is phenyl optionally substituted with one to three groups independently selected from halogen, aryl, $S(O)_nC_{1-6}$alkyl optionally substituted with one to six halogen, $C_{1-6}$alkyl optionally substituted with one to five halogen atoms, CN, $CONR^aR^b$, and $C(O)R^a$, where $R^a$ and $R^b$ are as defined under formula I. In another subset, Ar is 4-chlorophenyl optionally substituted with a second halogen atom. Examples of Ar in this embodiment include 1-naphthyl, 2-naphthyl, phenyl, 3-(n-butoxy)phenyl, 4-chlorophenyl, 3,4-dichlorophenyl, 2,4-dichlorophenyl, 2,6-dichlorophenyl, 2,4,6-trichlorophenyl, 2,4,5-trichlorophenyl, 2-, 3- or 4-biphenyl, 4-chloro-2-(methylsulfonyl)phenyl, 4-chloro-2-(carboxamido)phenyl, 2-cyano-4-chlorophenyl, 4-chloro-2-iodophenyl, 4-(trifluoromethyl)phenyl, 4-(methylsulfonyl)phenyl, 4-chloro-2-fluorophenyl, 2-chloro-4-fluorophenyl, 2,3,4-trichlorophenyl, 2-chloro-4-cyanophenyl, 4-acetyl-2-chlorophenyl, 3-chloro-4-acetylphenyl, 2-bromo-4-chlorophenyl, 3-bromo-4-chlorophenyl, 4-bromo-2-chlorophenyl, 2-fluoro-4-bromophenyl, 4-cyanophenyl, 2-chloro-4-(trifluoromethyl)phenyl, and the like.

In another embodiment of formula I are compounds wherein Ar is a heteroaryl selected from furyl, pyridyl, benzothiazolyl, quinolinyl and pyrimidinyl, each optionally substituted with one or two halogen atoms.

In another embodiment of formula I are compounds wherein $Y^2$ is selected from $CH_2$ and $CH_2CH_2$. In one subset $Y^2$ is $CH_2$; in another subset $Y^2$ is $CH_2CH_2$. Examples of $Y^2$ include $CH_2$, $CH_2CH_2$, CH=CH, CHCl, $CH_2CHCl$, $CCl_2$, $CCl_2$—$CCl_2$, $CH(CH_3)$, $CH_2CH(Ph)$, $C(Cl)$=$C(Cl)$, and the like.

In another embodiment of formula I are compounds wherein A is $C_{1-3}$alkyl optionally substituted with one to four halogen atoms and Q is COOH or tetrazolyl. In one subset A-Q is selected from $CH_2COOH$, $CF_2COOH$ and $CH(CH_3)COOH$. In another subset A-Q is $CH_2COOH$. Examples of A includes $CH_2$, $CH_2CH_2$, $CH(CH_3)$, $CH(CH_3)_2$, CHF, $CHFCF_2$, CHCl, 1,1-cyclopropylidene, 1,2-cyclopropylene, and the like. Examples of Q include COOH, $CONH_2$, $CONH(CH_3)$, $SO_2NH_2$, tetrazolyl, and the like.

In another embodiment of formula I are compounds wherein $R^1$, $R^2$ and $R^3$ are independently selected from hydrogen, CN, halogen, $S(O)_nC_{1-3}$alkyl, $OC_{1-6}$alkyl (optionally substituted with one to six substituents selected from halogen, aryl, heteroaryl, OH and $OC(O)R^a$), $C_{1-6}$alkyl (optionally substitued with one to eight groups selected from aryl, heteroaryl, halogen, $NR^aR^b$, $C(O)R^a$, $C(OR^a)R^aR^b$, $SR^a$, and $OR^a$, wherein aryl, heteroaryl and alkyl are each optionally substituted with one to six groups independently selected from halogen, $CF_3$, and COOH), aryl, heteroaryl, heterocyclyl, $C_{2-6}$alkenyl (optionally substituted with one to six groups independently selected from halogen and $OR^a$), $C(O)OC_{1-3}$alkyl, $S(O)_nNR^aR^b$, $C(O)R^a$, $C(OH)R^aR^b$, $C_{5-8}$cycloalkenyl, and $C(OC_{1-3}$alkyl$)R^aR^b$, wherein each of aryl, heteroaryl and heterocyclyl is optionally substituted with one to eight groups independently selected from halogen, $C(O)R^a$, $OR^a$, $C_{1-3}$alkyl, aryl, heteroaryl and $CF_3$; n=0, 1 or 2; $R^a$ and $R^b$ are independently selected from hydrogen and $C_{1-6}$alkyl optionally substituted with halogen. Examples of $R^1$, $R^2$ and $R^3$ include hydrogen, fluorine, chlorine, bromine, iodine, methylsulfonyl, ethylsulfonyl, methylsulfinyl, methoxy, isopropyloxy, methylthio, benzyloxy, acetyl, trifluoroacetyl, 1-hydroxy-2,2,2-trifluoroethyl, 1-hydroxy-2-methylpropyl, 1-hydroxyethyl, 1-methoxyethyl, 1-methoxypropyl, 1-methoxy-2,2,2-trifluoroethyl, 1-hydroxypropyl, 1-methoxypropyl, 1-methylthioethyl, ethyl, n-propyl, isopropyl, 3-pentyl, ethenyl, 2-propenyl, 2-penten-3-yl, phenyl, 4-chlorophenyl, 2-methylphenyl, 3-(1-pyrazolyl)phenyl, 2-methoxyphenyl, 3,4-dichlorophenyl, cyano, 1- and 2-methyltetrazole, 1-methyl-2-pyrrolyl, 1-methyl-5-pyrazolyl, 2-thienyl, 3-methyl-2-thienyl, 3-thienyl, 4-methyl-3-thienyl, 2-formyl-3-thienyl, 2-naphthyl, 3-pyridyl, 6- and 8-quinolinyl, 3-benzothienyl, 3,5-dimethyl-4-isoxazolyl, cyclopropyl, cyclopentyl, cyclopentenyl, 2-hydroxy-1,1,1,3,3,3-hexafluoro-2-propyl, 2-methoxy-1,1,1,3,3,3-hexafluoro-2-propyl, and the like. In one subset $R^1$, $R^2$ and $R^3$ are positioned as shown below in formula Ia, and all the variables are as defined under formula I:

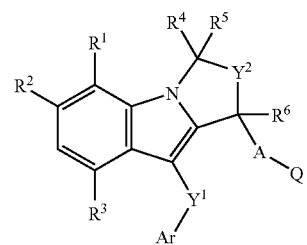

Ia

In one subgroup of formula Ia are compounds wherein $R^1$ is hydrogen. In another subgroup of formula Ia are compounds wherein $R^1$ is hydrogen, A-Q is $CH_2COOH$, and $R^2$ is selected from halogen, $S(O)_nC_{1-3}$alkyl, $OC_{1-6}$alkyl (optionally substituted with aryl), CN, $C_{2-6}$alkenyl, 1- and 2-methyltetrazolyl, 1-methylpyrrolyl and $C_{1-6}$alkyl. In another subgroup of formula Ia are compounds wherein $R^1$ is hydrogen, A-Q is $CH_2COOH$, and $R^3$ is selected from halogen, $S(O)_nC_{1-3}$alkyl, $OC_{1-6}$alkyl, $C(O)R^a$, $C_{1-6}$alkyl (optionally substitued with 3 to 6 halogen atoms, and 0 or 1 group selected from $OR^a$, $SR^a$,), $C_{2-6}$alkenyl, $C_{5-8}$cycloalkenyl, phenyl (optionally substituted with a group selected from $C_{1-3}$alkyl, $OR^a$ and pyrazolyl), naphthyl, and heteroaryl selected from pyrrolyl, thienyl, pyrazolyl, quinolinyl, benzothienyl, isoxalyl, pyridyl, each of which is optionally substituted with $C_{1-3}$alkyl.

In another embodiment of formula I are compounds wherein $R^4$ and $R^5$ are each independently selected from H and $C_{1-4}$alkyl optionally substituted with one to six halogen atoms, preferably fluorine; or $R^4$ is $OR^a$ wherein $R^a$ is as defined under formula I, preferably hydrogen; or $R^4$ and $R^5$ attached to the same carbon atom represent an oxo. In one subset $R^4$ and $R^5$ are each hydrogen.

In a another embodiment of formula I are compounds of formula Ib:

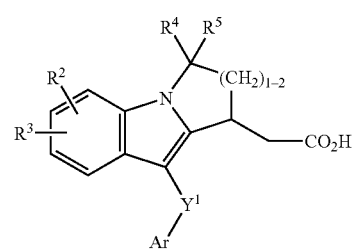

Ib wherein Ar and $R^1$–$R^5$ are as defined under formula I and $Y^1$ is O, S, C(O) or $CH_2$. In one subset, $R^4$ and $R^5$ are each hydrogen, and $R^2$ and $R^3$ represent one or two non-H substituent. In another subset of formula Ib are compounds of formula Ic:

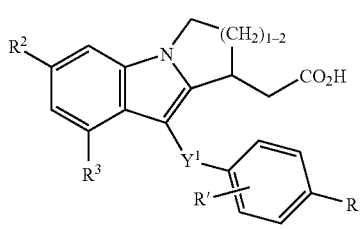

Ic wherein $Y^1$ is C(O), $CH_2$ or S, R and R' are independently hydrogen, halogen, cyano, $C_{1-3}$alkanoyl or $CF_3$, and $R^2$ and $R^3$ are each a non-hydrogen substituent. In one subgroup of formula Ic, $R^2$ is selected from halogen, $S(O)_nC_{1-3}$alkyl, $OC_{1-6}$alkyl (optionally substituted with aryl), CN, $C_{2-6}$alkenyl, 1- or 2-methyltetrazolyl, 1-methylpyroolyl and $C_{1-6}$alkyl. In another subgroup of formula Ic, $R^3$ is selected from halogen, $S(O)_nC_{1-3}$alkyl, $OC_{1-6}$alkyl, $C(O)R^a$, $C_{1-6}$alkyl (optionally substitued with 3 to 6 halogen atoms, and 0 or 1 group selected from $OR^a$, $SR^a$,), $C_{2-6}$alkenyl, $C_{5-8}$cycloalkenyl, phenyl (optionally substituted with a group selected from $C_{1-3}$alkyl, $OR^a$ and pyrazolyl), naphthyl, and heteroaryl selected from pyrrolyl, thienyl, pyrazolyl, quinolinyl, benzothienyl, isoxalyl, pyridyl, each of which is optionally substituted with $C_{1-3}$alkyl. In another subgroup of formula Ic, $R^2$ is F, R is Cl and R' is hydrogen or halogen. In another subgroup of formula Ic are compounds where $R^2$ is F, R is Cl, R' is hydrogen, and $R^3$ is selected from halogen, $S(O)_nC_{1-3}$alkyl, $OC_{1-6}$alkyl, $C(O)R^a$, $C_{1-6}$alkyl (optionally substitued with 3 to 6 halogen atoms, and 0 or 1 group selected from $OR^a$, $SR^a$,), $C_{2-6}$alkenyl, $C_{5-8}$cycloalkenyl, phenyl (optionally substituted with a group selected from $C_{1-3}$alkyl, $OR^a$ and pyrazolyl), naphthyl, and heteroaryl selected from pyrrolyl, thienyl, pyrazolyl, quinolinyl, benzothienyl, isoxalyl, pyridyl, each of which is optionally substituted with $C_{1-3}$alkyl.

Optical Isomers-Diastereomers-Geometric Isomers-Tautomers

Compounds of formula I contain one or more asymmetric centers and can thus occur as racemates and racemic mixtures, single enantiomers, diastereomeric mixtures and individual diastereomers. The present invention is meant to comprehend all such isomeric forms of the compounds of formula I.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers, as well as mixtures thereof, are encompassed with compounds of formula I.

Compounds of the formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of a compound of the general formula I or Ia may be obtained by stereospecific synthesis using optically pure starting materials or reagents of known configuration.

Salts

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium; manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, unless otherwise specified, references to the compound of formula I are meant to also include the pharmaceutically acceptable salts.

Utilities

The ability of compounds of formula I to interact with prostaglandin receptors makes them useful for preventing or reversing undesirable symptoms caused by prostaglandins in a mammalian, especially human subject. This mimicking or antagonism of the actions of prostaglandins indicates that the compounds and pharmaceutical compositions thereof are useful to treat, prevent, or ameliorate in mammals and especially in humans: respiratory conditions, allergic conditions, pain, inflammatory conditions, mucus secretion disorders, bone disorders, sleep disorders, fertility disorders, blood coagulation disorders, trouble of the vision as well as immune and autoimmune diseases. In addition, such a compound may inhibit cellular neoplastic transformations and metastic tumor growth and hence can be used in the treatment of cancer. Compounds of formula I may also be of use in the treatment and/or prevention prostaglandin-mediated proliferation disorders such as may occur in diabetic retinopathy and tumor angiogenesis. Compounds of formula I may also inhibit prostanoid-induced smooth muscle contraction by antagonizing contractile prostanoids or mimicking relaxing prostanoids and hence may be used in the treatment of dysmenorrhea, premature labor and eosinophil related disorders. More particularly compounds of formula I are antagonists of prostaglandin D2.

Accordingly, another aspect of the invention provides a method of treating or preventing a prostaglandin mediated disease comprising administering to a mammalian patient in need of such treatment a compound of formula I in an amount which is effective for treating or preventing said prostaglandin mediated disease. Prostaglandin mediated diseases include, but are not limited to, allergic rhinitis, nasal congestion, rhinorrhea, perennial rhinitis, nasal inflammation, asthma including allergic asthma, chronic obstructive pulmonary diseases and other forms of lung inflammation; sleep disorders and sleep-wake cycle disorders; prostanoid-induced smooth muscle contraction associated with dysmenorrhea and premature labor; eosinophil related disorders; thrombosis; glaucoma and vision disorders; occlusive vascular diseases; congestive heart failure; diseases or conditions requiring a treatment of anti-coagulation such as post-injury or post surgery treatment; inflammation; gangrene; Raynaud's disease; mucus secretion disorders including cytoprotection; pain and migraine; diseases requiring control of bone formation and resorption such as for example osteoporosis; shock; thermal regulation including fever; and immune disorders or conditions in which immunoregulation is desirable. More particularly the disease is to be treated is one mediated by prostaglandin D2 such as nasal congestion, pulmonary congestion, and asthma including allergic asthma.

In one embodiment of the invention is a method of treating or preventing a prostaglandin mediated disease comprising administering to a mammalian patient in need of such treatment a compound of formula I in an amount which is effective for treating or preventing a prostaglandin mediated disease, wherein the prostaglandin mediated disease is nasal congestion, rhinitis including allergic and perennial rhinitis, and asthma including allergic asthma.

In another embodiment of the present invention is a method of treating or preventing a prostaglandin D2-mediated disease comprising administering to a mammalian patient in need of such treatment a compound of formula I in an amount which is effective for treating or preventing a prostaglandin D2 mediated disease wherein said prostaglandin D2 mediated disease is nasal congestion or asthma.

In another embodiment of the present invention is a method for the treatment of nasal congestion in a patient in need of such treatment which comprises administering to said patient a therapeutically effective amount of a compound of formula I.

In yet another embodiment of the present invention is a method for the treatment of asthma, particularly allergic asthma, in a patient in need of such treatment which comprises administering to said patient a therapeutically effective amount of a compound of formula I.

In yet another embodiment of the present invention is a method for the treatment of allergic rhinitis, including seasonal allergic rhinitis and perennial allergic rhinitis, in a patient in need of such treatment which comprises administering to said patient a therapeutically effective amount of a compound of formula I.

Dose Ranges

The magnitude of prophylactic or therapeutic dose of a compound of formula I will, of course, vary with the nature and the severity of the condition to be treated and with the particular compound of formula I and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for the oral administration of humans may contain from 0.05 mg to 5 g of active agent compounded with an appropriate and convenient amount of carrier material which may vary from about 5 to about 99.95 percent of the total composition. Dosage unit forms will generally contain between from about 0.1 mg to about 0.4 g of an active ingredient, typically 0.5 mg, 1 mg, 2 mg, 5 mg, 10 mg, 25 mg, 50 mg, 100 mg, 200 mg, or 400 mg.

Pharmaceutical Compositions

Another aspect of the present invention provides pharmaceutical compositions comprising a compound of formula I with a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

For the treatment of any of the prostanoid mediated diseases compounds of formula I may be administered orally, by inhalation spray, topically, parenterally or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of formula I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing the compound of formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Combinations with Other Drugs

For the treatment and prevention of prostaglandin mediated diseases, compound of formula I may be co-administered with other therapeutic agents. Thus in another aspect the present invention provides pharmaceutical compositions for treating prostaglandin mediated diseases comprising a therapeutically effective amount of a compound of formula I and one or more other therapeutic agents. Suitable therapeutic agents for combination therapy with a compound of formula I include: (1) a prostaglandin D2 antagonist such as S-5751; (2) a corticosteroid such as triamcinolone acetonide; (3) a β-agonist such as salmeterol, formoterol, terbutaline, metaproterenol, albuterol and the like; (4) a leukotriene modifier, including a leukotriene antagonist or a lipooxygenase inhibitor such as montelukast, zafirlukast, pranlukast, or zileuton; (5) an antihistamine such as brompheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (6) a decongestant including phenylephrine, phenylpropanolamine, pseudophedrine, oxymetazoline, ephinephrine, naphazoline, xylometazoline, propylhexedrine, or levo-desoxyephedrine; (7) an antiitussive including codeine, hydrocodone, caramiphen, carbetapentane, or dextramethorphan; (8) another prostaglandin ligand including prostaglandin F agonist such as latanoprost; misoprostol, enprostil, rioprostil, omoprostol or rosaprostol; (9) a diuretic; (10) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (11) cyclooxygenase-2 (COX-2) inhibitors such as celecoxib and rofecoxib; (12) inhibitors of phosphodiesterase type IV (PDE-A) e.g. Ariflo, roflumilast; (13) antagonists of the chemokine receptors, especially CCR-1, CCR-2, and CCR-3; (14) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (15) anti-diabetic agents such as insulin, sulfonylureas, biguanides (metformin), α-glucosidase inhibitors (acarbose) and glitazones (troglitazone, pioglitazone, englitazone, rosiglitazone and the like); (16) preparations of interferon beta (interferon beta-1a, interferon beta-1b); (17) anticholinergic agents such as muscarinic antagonists (ipratropium bromide and tiotropium bromide), as well as selective muscarinic M3 antagonists; (18) steroids such as beclomethasone, methylprednisolone, betamethasone, prednisone, dexamethasone, and hydrocortisone; (19) triptans commonly used for the treatment of migraine such as sumitriptan and rizatriptan; (20) alendronate and other treatments for osteoporosis; (21) other compounds such as 5-aminosalicylic acid and prodrugs thereof, antimetabolites such as azathioprine and 6-mercaptopurine, cytotoxic cancer chemotherapeutic agents, bradykinin (BK2) antagonists such as FK-3657, TP receptor antagonists such as seratrodast, neurokinin antagonists (NK1/NK2), VLA-4 antagonists such as those described in U.S. Pat. No. 5,510,332, WO97/03094, WO97/02289, WO96/40781, WO96/22966, WO96/20216, WO96/01644, WO96/06108, WO95/15973 and WO96/31206. In addition, the invention encompasses a method of treating prostaglandin D2 mediated diseases comprising: administration to a patient in need of such treatment a non-toxic therapeutically effective amount of a compound of formula I, optionally co-administered with one or more of such ingredients as listed immediately above.

Methods of Synthesis

Compounds of Formula I of the present invention can be prepared according to the synthetic routes outlined in Schemes 1 to 21 and by following the methods described herein.

Method 1

Indole 1 can be alkylated with a halide at the 3-position to give 2 under basic conditions. Compound 2 can be halogenated at the 2-position to provide 3, which is alkylated with an approprate halide to yield 4. The acetal group in 4 can be hydrolyzed to give aldehyde 5. Wittig reaction of 5 with a phosphorane provides unsaturated ester 6. Under Heck coupling conditions, compound 6 cyclises to give 7. Hydrogenation of 7, followed by basic hydrolysis yields the final product 9.

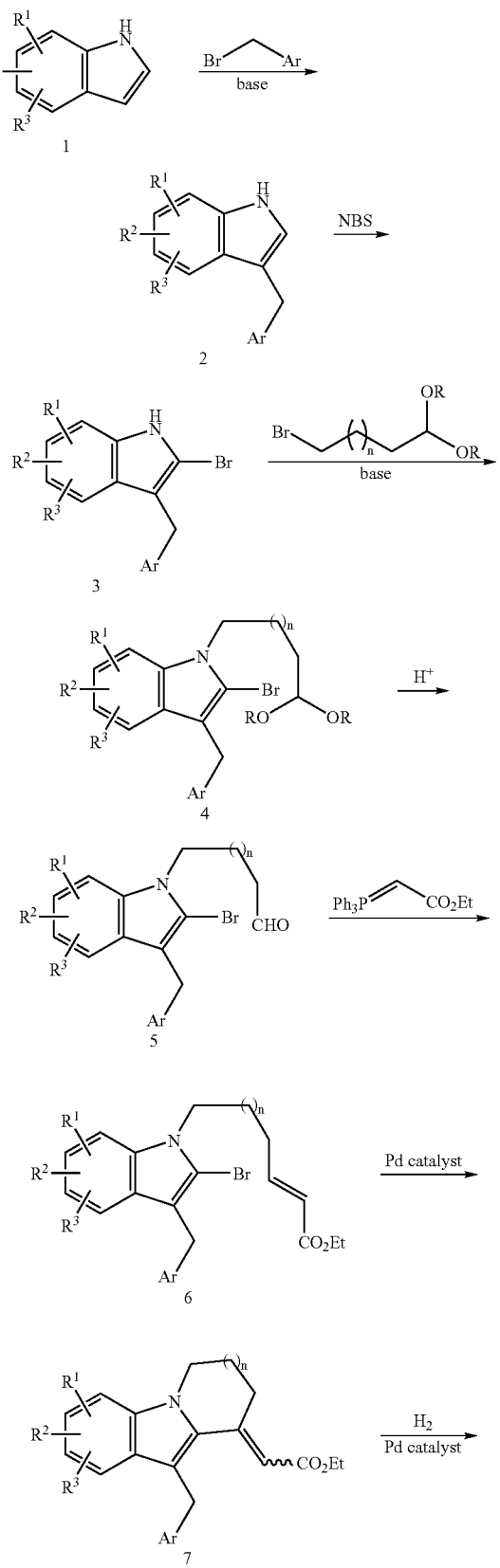

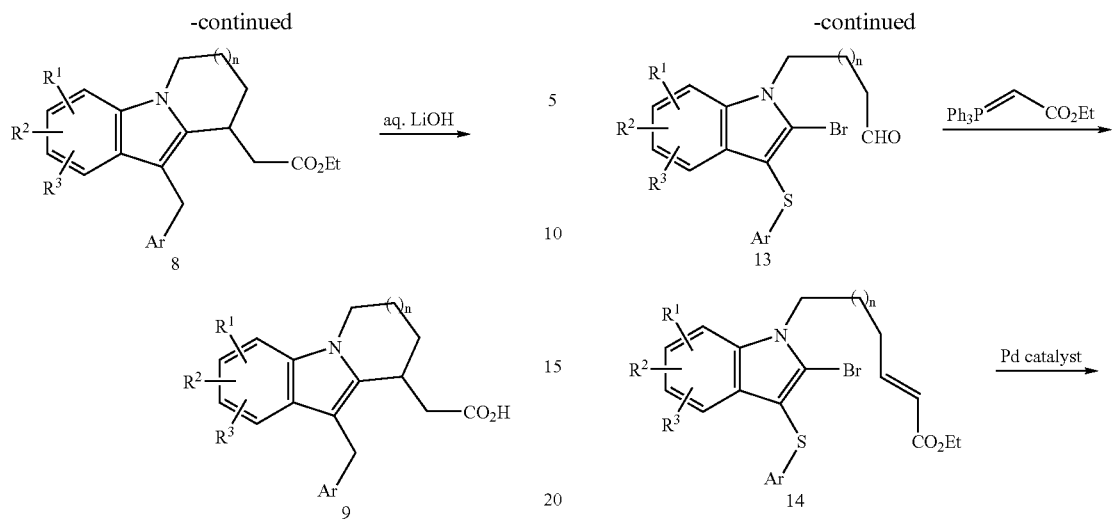
Method 2
Indole 1 can be sulphenylated with a disulfide at the 3-position to give 10 under basic conditions. Compound 10 can be transformed to the final product 17 following the same sequences as described in Method 1.
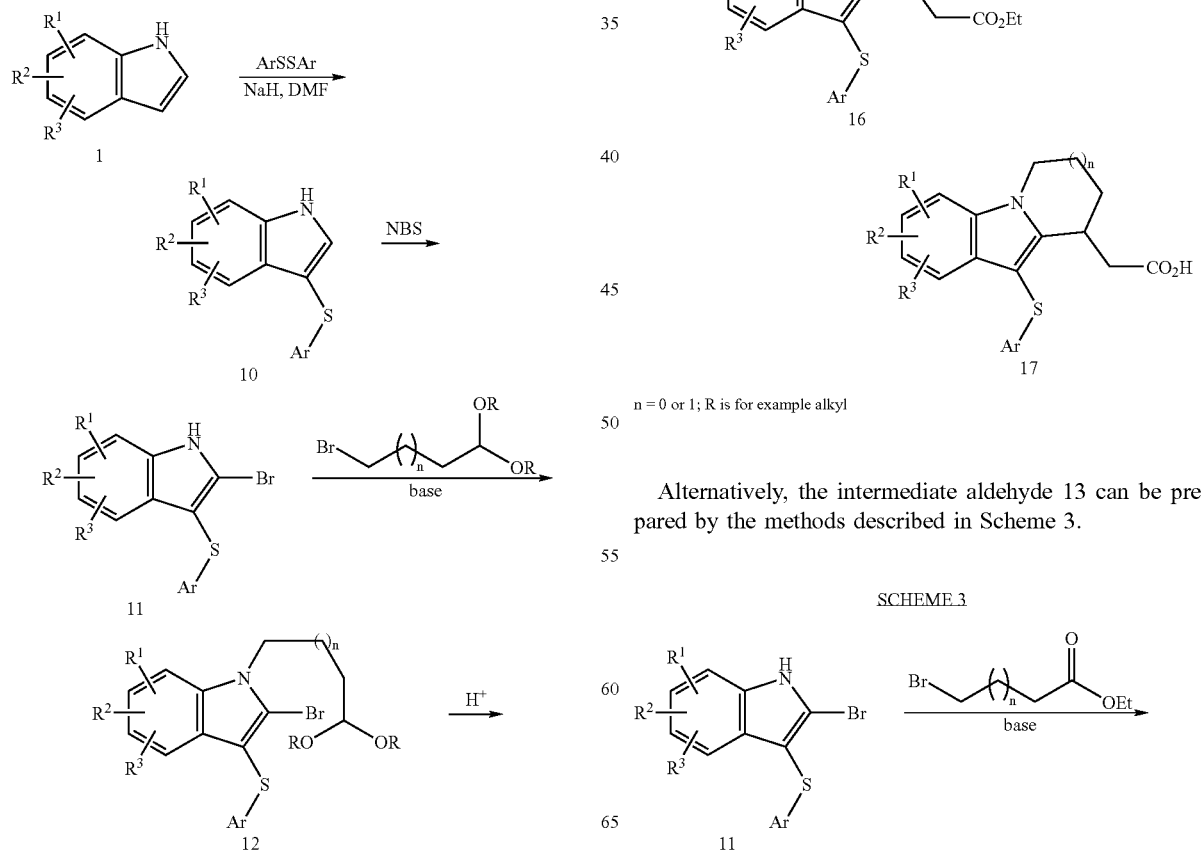
n = 0 or 1; R is for example alkyl
Alternatively, the intermediate aldehyde 13 can be prepared by the methods described in Scheme 3.
SCHEME 3

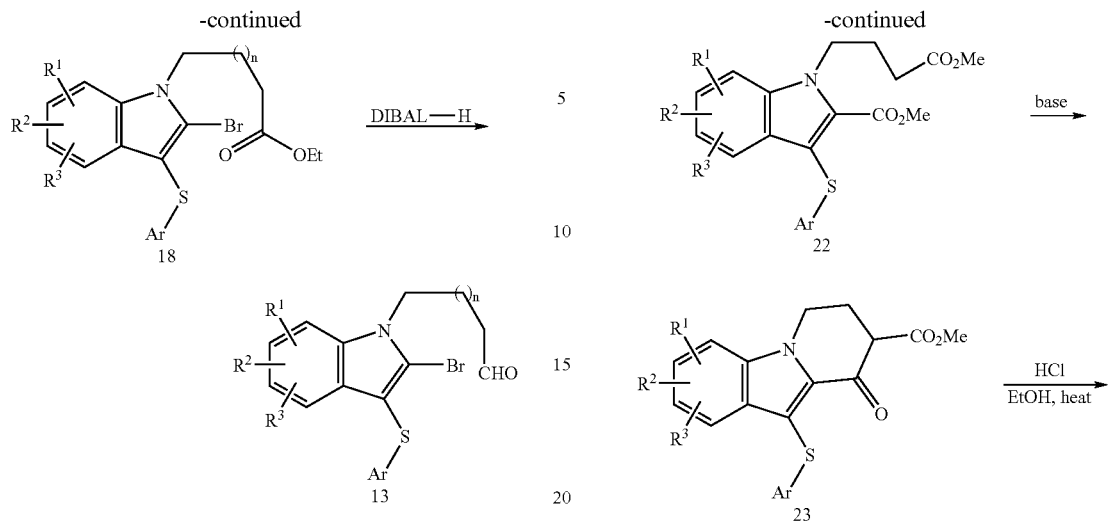

Method 3

Intermediate indole 25 may be prepared by the method presented in Scheme 4. Benzaldehyde 18 is condensed with N₃CH₂CO₂Me under basic conditions to provide ester 19, which may be converted to indole 20 by thermolysis. Sulphenylation of indole 20 with ClSAr gives 21, which is then alkylated with an appropriate bromo-ester to yield diester 22. Base promoted cyclization of 22 affords keto-ester 23, which, upon decarboxylation, provides ketone 24. Wittig reaction of 24, followed by hydrogenation and hydrolysis, affords the final product 27.

SCHEME 4

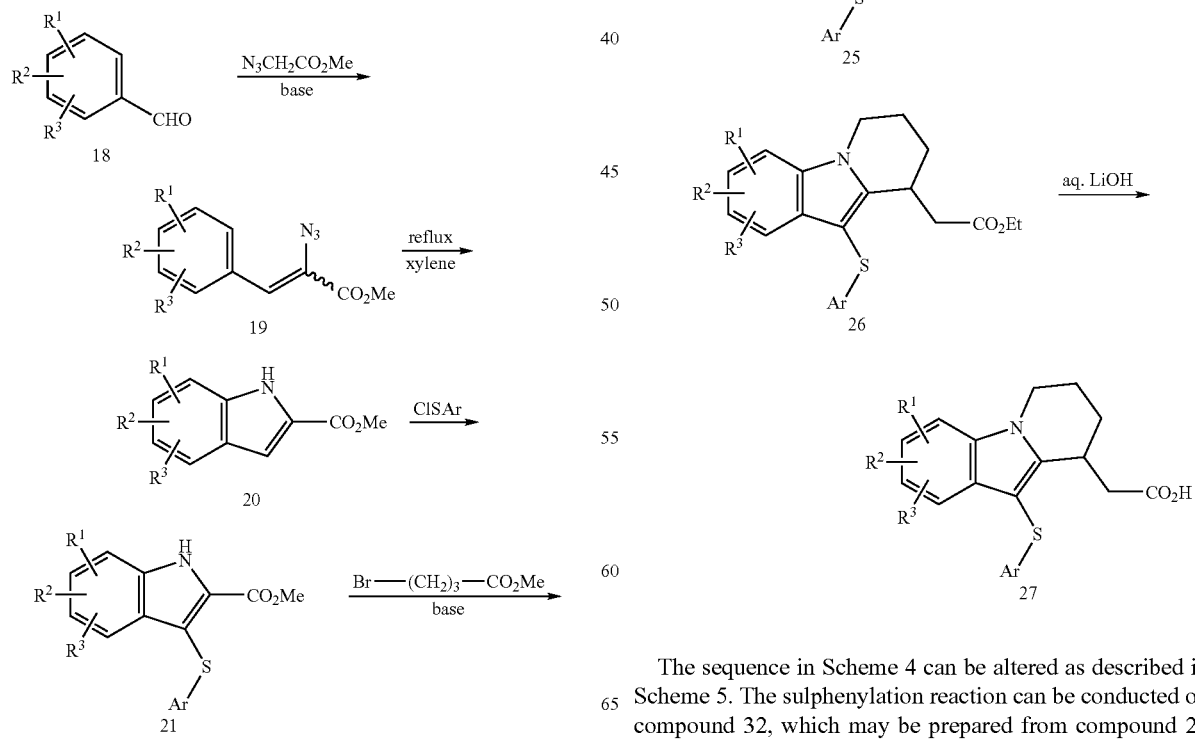

The sequence in Scheme 4 can be altered as described in Scheme 5. The sulphenylation reaction can be conducted on compound 32, which may be prepared from compound 20 under same conditions as described in Scheme 4.

21

SCHEME 5

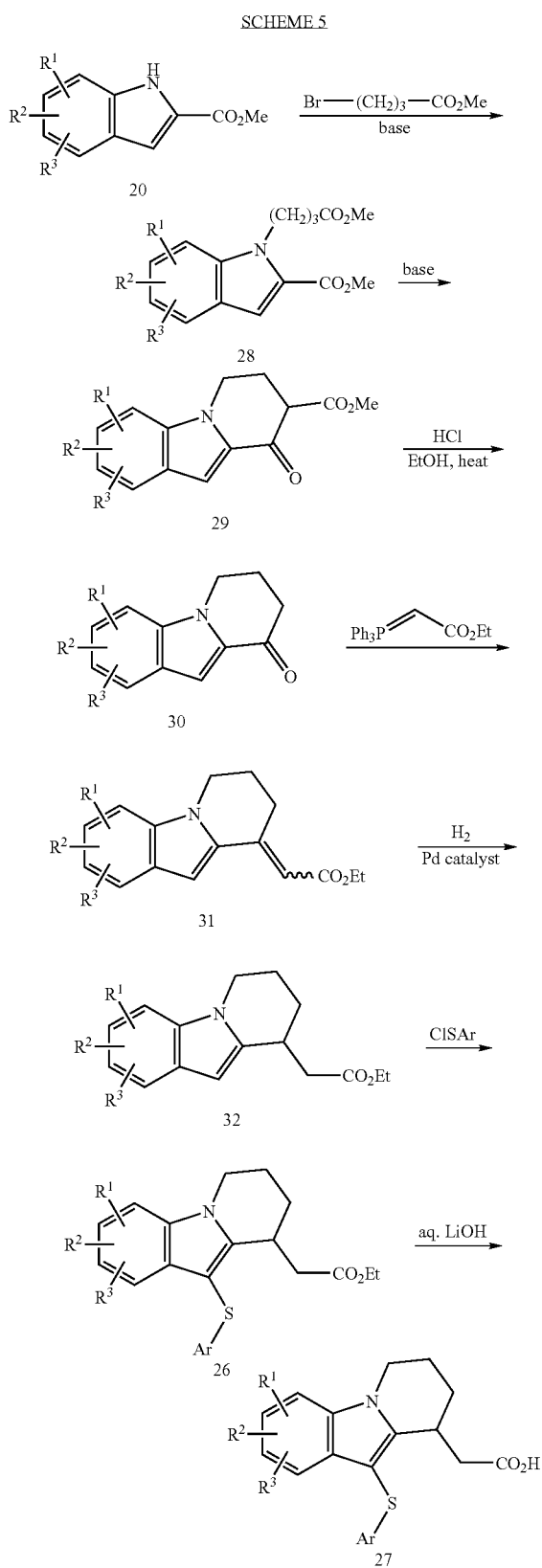

Alternatively, compound with six-membered ring can be prepared by, the sequence described in Scheme 6. Refor-

22 matsky reaction on 30 provides alcohol 35a. Deoxygenation of 35a provides ester 32a, which is then sulphenylated with ClSAr to provide 26. Basic hydrolysis of 26 provides the target compound 27.

SCHEME 6

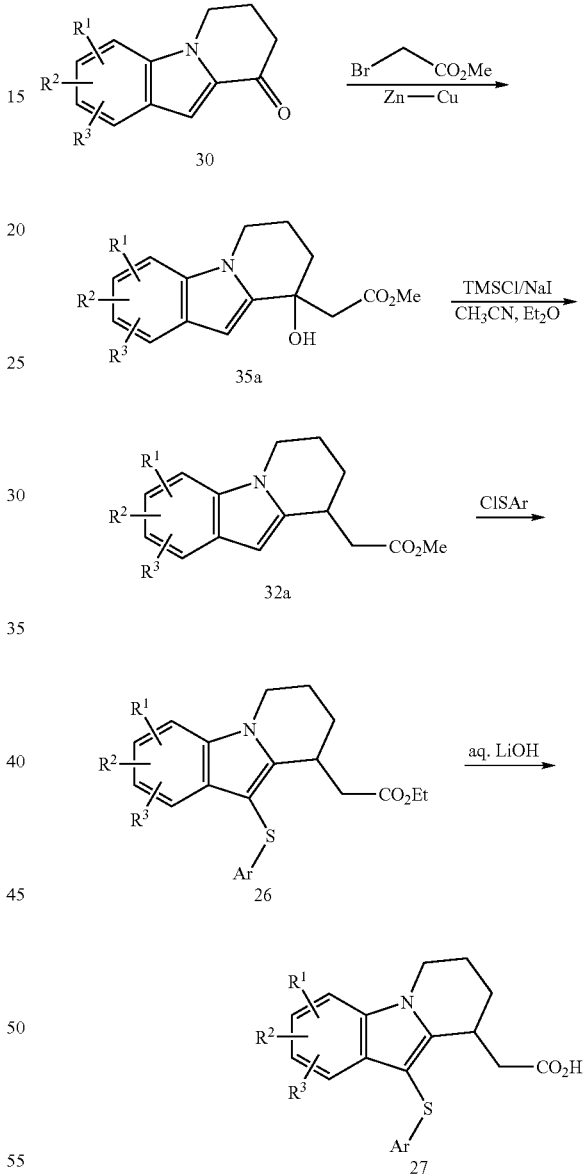

Compounds with five-membered ring may be prepared by the method presented in Scheme 7 from indole 20. Indole 20 is condensed with methyl acrylate under basic conditions to provide keto-ester 33. Decarboxylation of 33, followed by Reformatsky reaction, provides alcohol 35. Deoxygenation of 35 provides ester 36, which is then sulphenylated with ClSAr to provide 37. Basic hydrolysis of 37 provides the target compound 38.

SCHEME 7

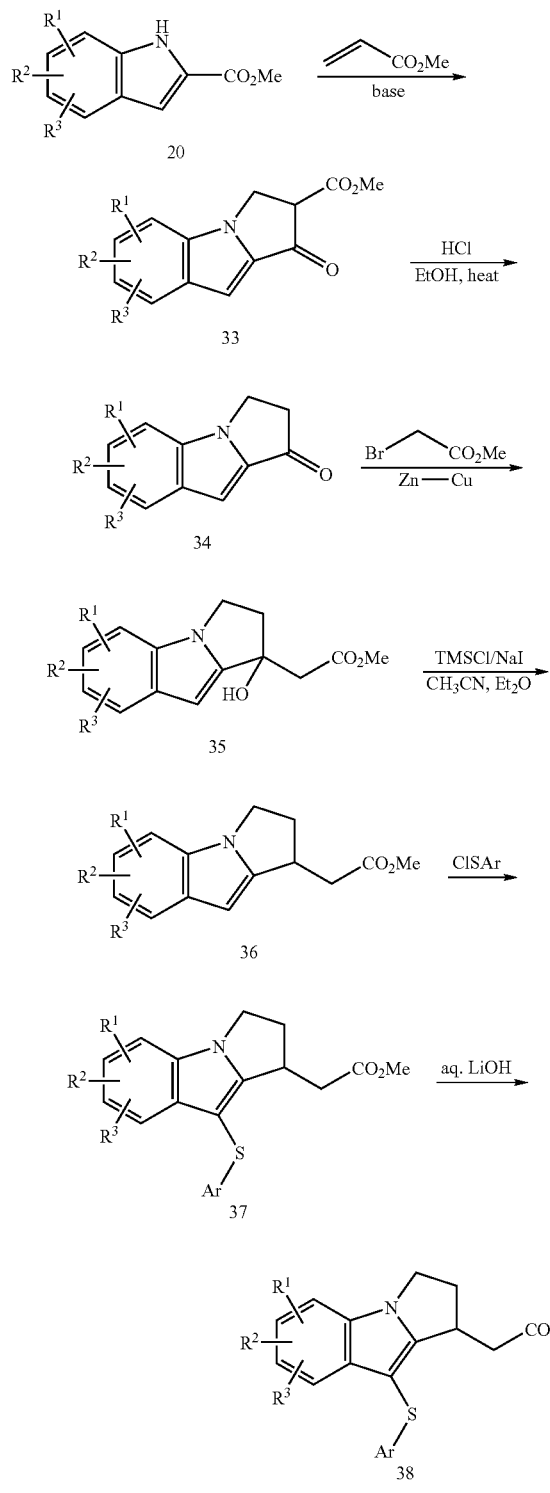

SCHEME 8

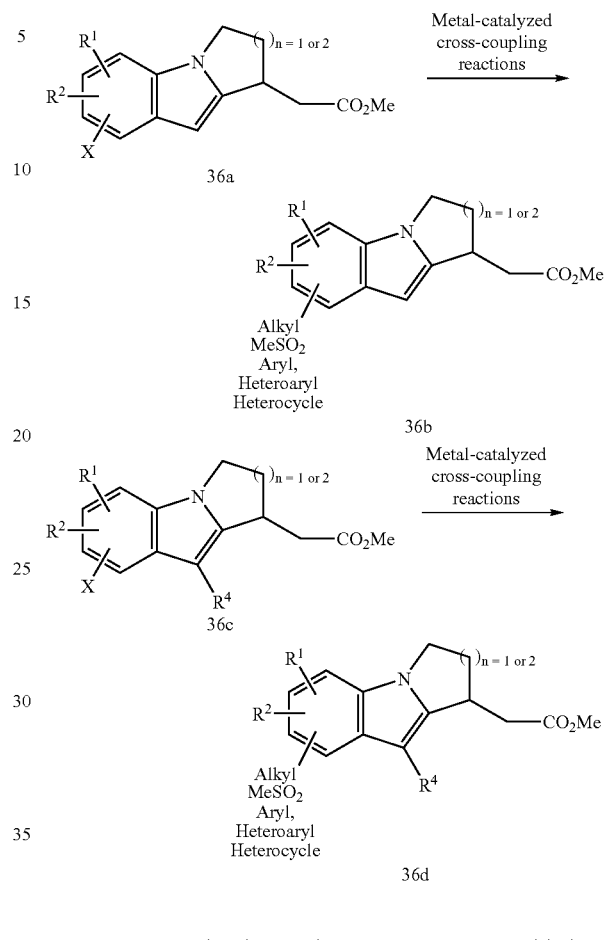

If $R^1$, $R^2$ or $R^3$=X (X could be: Cl, Br, I, OTf), then alkyl methanesulfonyl, cyano, aryl, heteroaryl and heterocycle could be introduced on the indole scaffold by metal-catalyzed cross-coupling reactions on 36a and/or 36c as described in Scheme. 8.

For compounds where X is a Br or I atom, metal halogen exchange on 36e and 36g could be done and the resulting organometallic species could be added to an electrophile such as alkyl disulfides and aldehydes as described in Scheme 9.

SCHEME 9

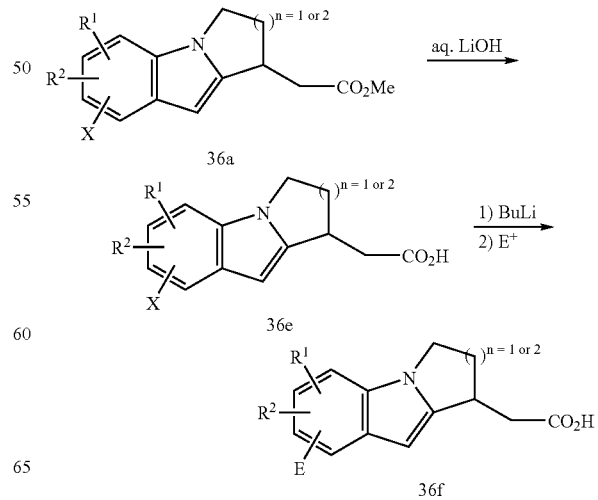

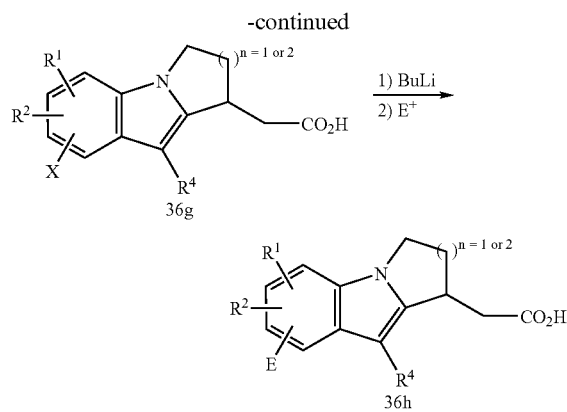

36g

36h

Method 4

Compounds with an aryl group directly attached to the 3-position of indole such as 43 can be synthesized according the sequence described in Scheme 10. The intermediate indole 41 may be prepared from aniline 39 and an α-substituted acetoacetate 40. Decarboxylation of 41 provides indole 42, which can then be converted to the target compound 43 by following the sequences described in Scheme 1–3.

SCHEME 10

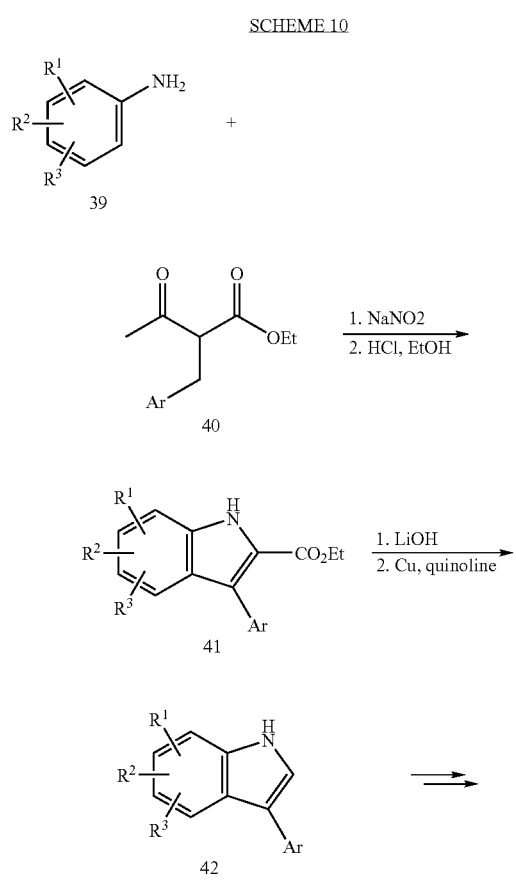

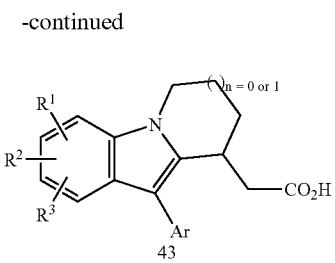

43

Compounds with an aryl group directly attached to the 3-position of indole such as 43 can also be synthesized according the sequence described in Scheme 11. Indole 36i is brominated with NBS to provide the bromo indole 36j which under Suzuki coupling condition can afford the aryl indole 36k. Basic hydrolysis of 36k provided the target compound 36l.

SCHEME 11

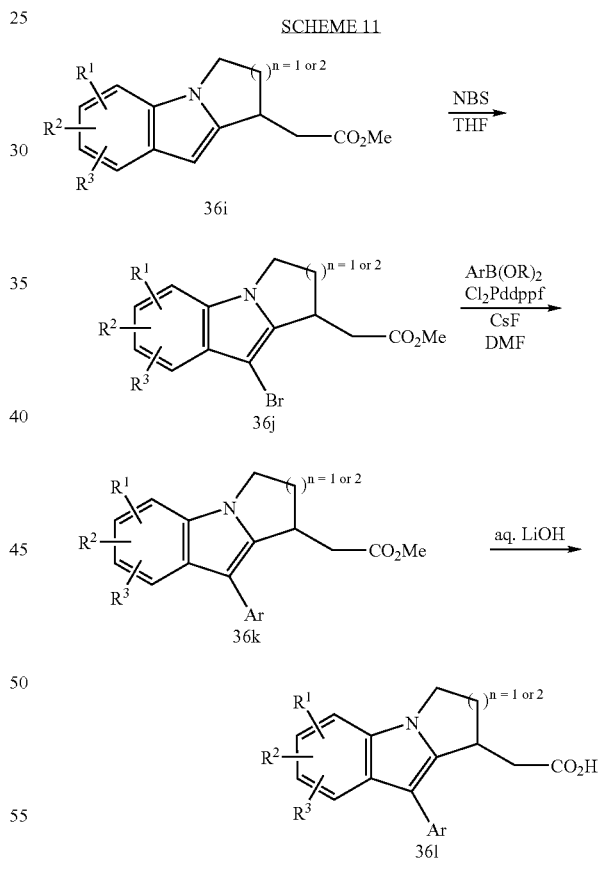

Method 5

3-Substituted indole 2 can also be prepared by the method depicted in Scheme 12. Indole 1 can be silylated with a trialkylsilyl halide under basic conditions to give silylated indole 44. Bromination of 44 provides 45, which may be lithiated with alkyllithium and alkylated with an appropriate halide to afford 3-substituted indole 2.

SCHEME 12

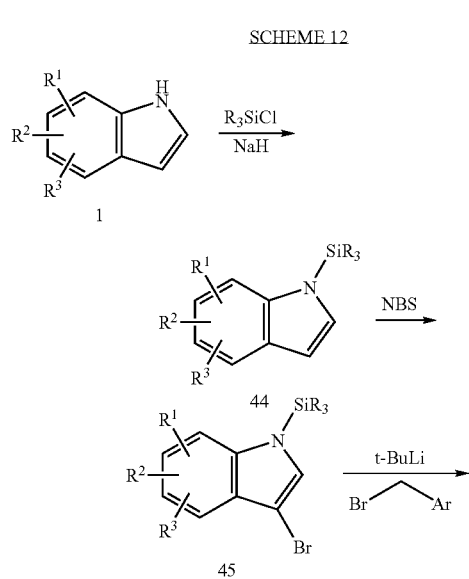

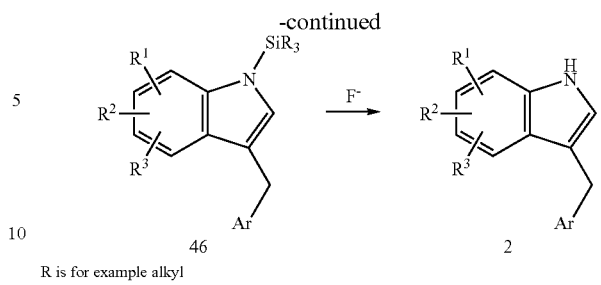

R is for example alkyl

Method 6

The compounds substituted with a variety of alkoxy, aryloxy or heteroaryloxy at the 6-positions of the indole structure can be synthesized according to the reaction sequence depicted in Scheme 13. Intermediate 47 can be prepared by the methods described in Method 3. Methylsulfonylation and demethylation of 47 provide phenol 48, which can react with a variety of alkyl halides, aryl halides or heteroaryl halides and a base to yield 49. Sulphenylation and hydrolysis under the reaction conditions described in Method 3 may afford the final compound 50.

SCHEME 13

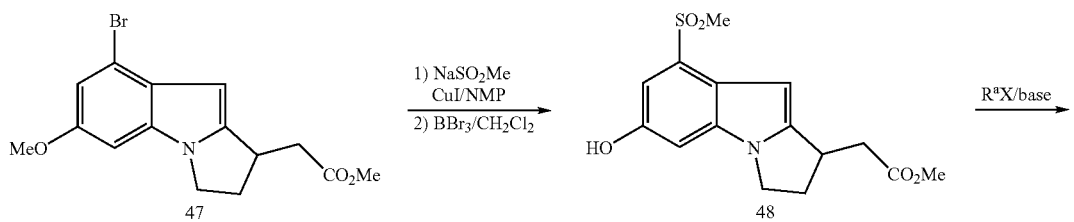

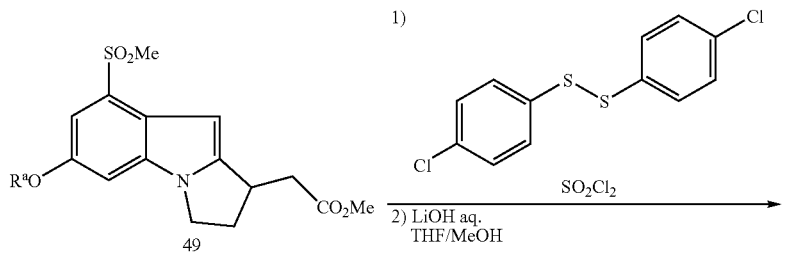

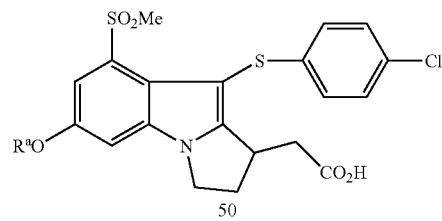

$R^a$ is other than H

Method 7

Intermediate 47 can be transformed to trifluoromethanesulfonate 51. Sulphenylation of 51 provides compound 52 (Scheme 14), which can be subjected to transition metal catalyzed cross coupling reactions to yield the 6-aryl substituted compound 53 after basic hydrolysis.

SCHEME 14

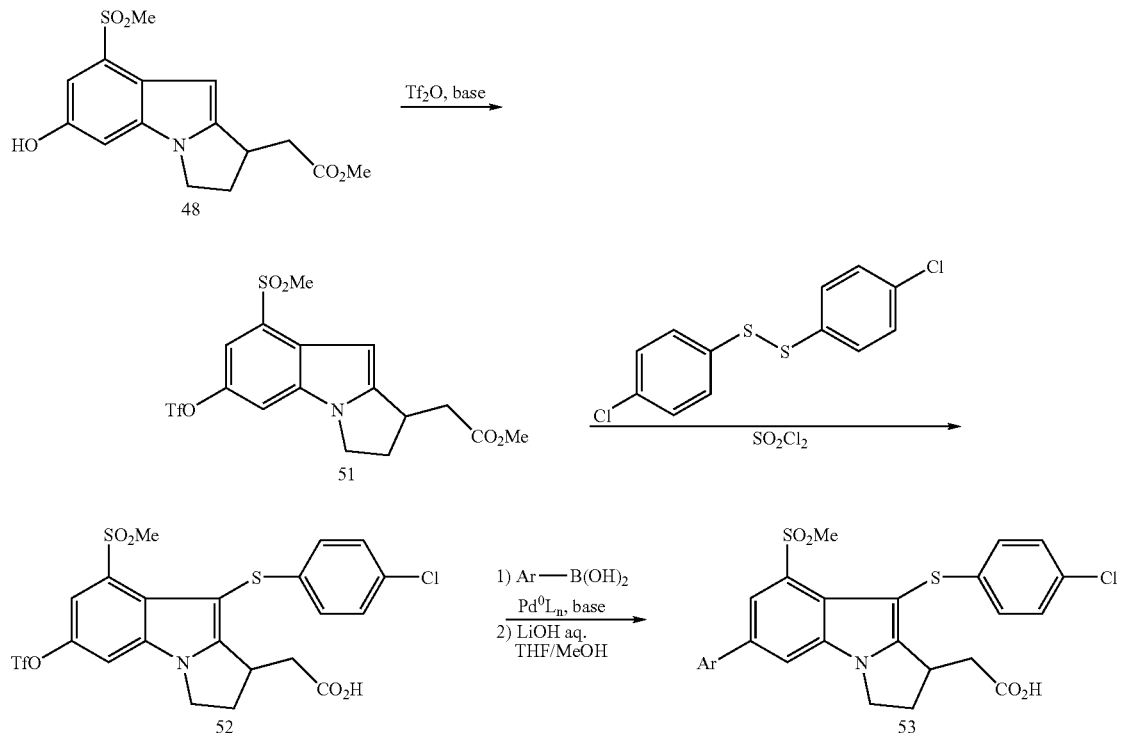

Method 8

The compounds substituted with a variety of alkyl, alkenyl or aryl at the 8-positions of the indole structure can be synthesized according to the reaction sequence depicted in Scheme 15. Intermediate 54 can be prepared by the methods described in Method 3. Transition metal catalyzed cross coupling reaction of 54 with a organometallic reagent RM(R=alkyl, alkenyl, alkynyl or aryl and M=—B(OH)$_2$, —SnBu$_3$, —ZnCl or —ZnBr) affords 55 which can be converted to the final product by following the reaction conditions described in Method 3, 6 and 7.

SCHEME 15

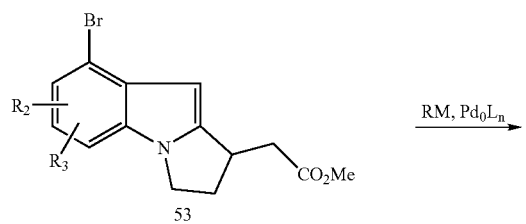

-continued

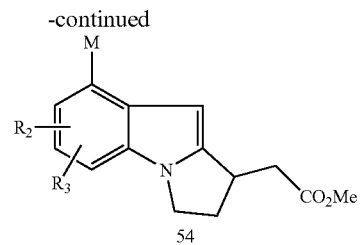

Method 9

3-substituted methylene indole can be prepared by using the sequence described in Scheme 16. Indole 36i is alkylated under acidic condition to give 3-substituted indole 55 which is hydrolyzed under basic condition to afford 56.

SCHEME 16

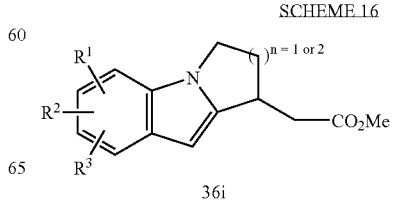

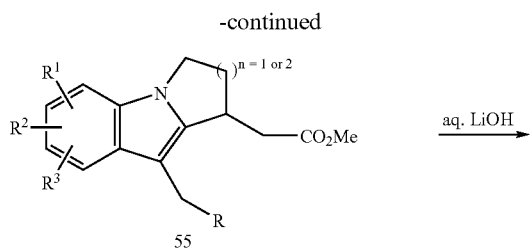

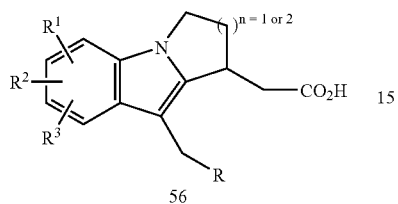

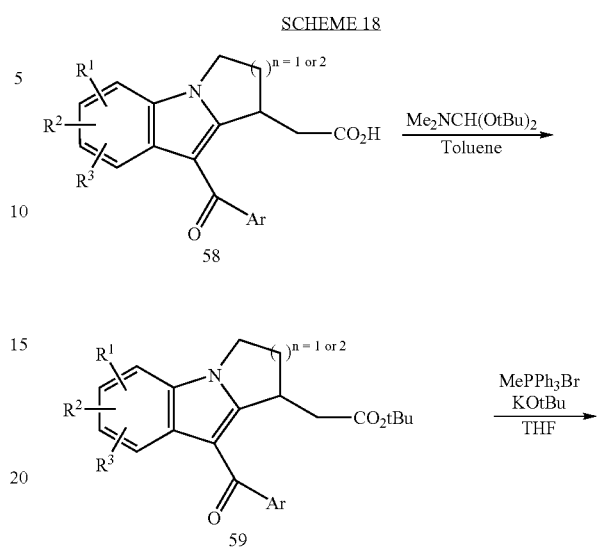

Method 10

3-carbonyl indole can be prepared by using the sequence described in Scheme 17. Indole 36i is acylated under Friedel-Craft condition to give 3-carbonyl indole 57 which is hydrolyzed under basic condition to afford 58.

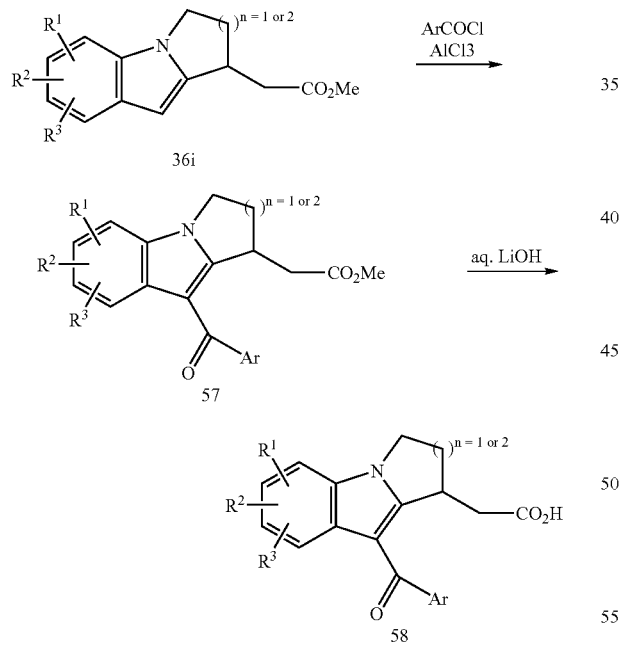

Method 11

3-alpha methyl indole can be prepared by using the sequence described in Scheme 18. Acid 58 is esterified to the t-Butyl ester 59 which after Wittig olefination gives the vinyl indole 60. The vinyl group of indole 60 is reduced by hydrogenation with Pd/C to give 61 which is hydrolyzed under acidic condition with TFA to afford 62.

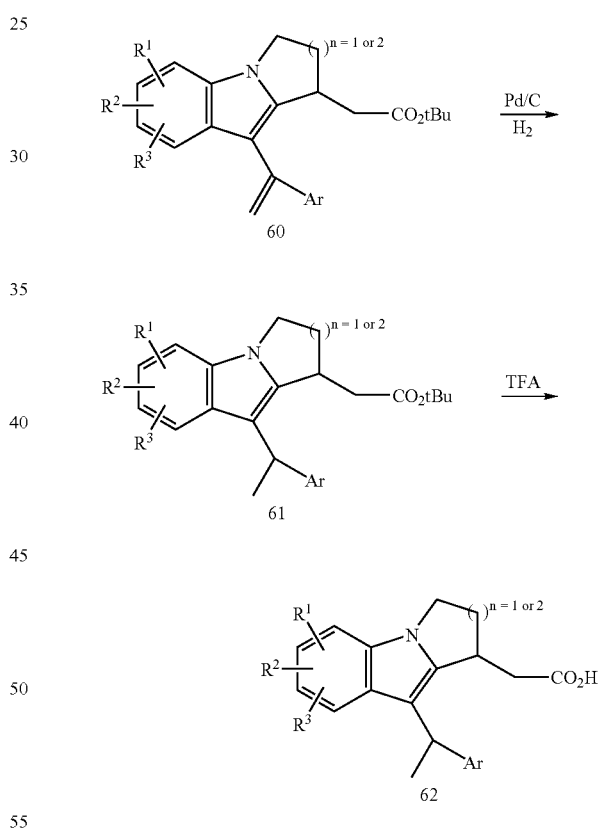

Method 12

Oxo pyrrolo indole can be prepared by using the sequence described in Scheme 19. The indole 20 was reduced to the alcohol 63 with DIBAL. Oxidation of 63 with Dess-Martin periodinane gives the aldehyde 64 which can be converted to unsaturated ester 65 after Wittig reaction with a phosphorane. Addition of the anion of diethyl malonate to unsaturated ester 65 and decarboxylation of the resulting indole 66 gives 67. The indole 67 is sulphenylated with ClSAr to give 68 which is hydrolyzed under acidic condition to give the target compound 69.

If R³=X (X could be: Cl, Br, I, OTf) alkyl group, methane sulfonyl, heteroaryl and heterocycle could be introduced on the indole scaffold by metal-catalyzed cross-coupling reactions on 68a to yield 69a as described in Scheme 20.

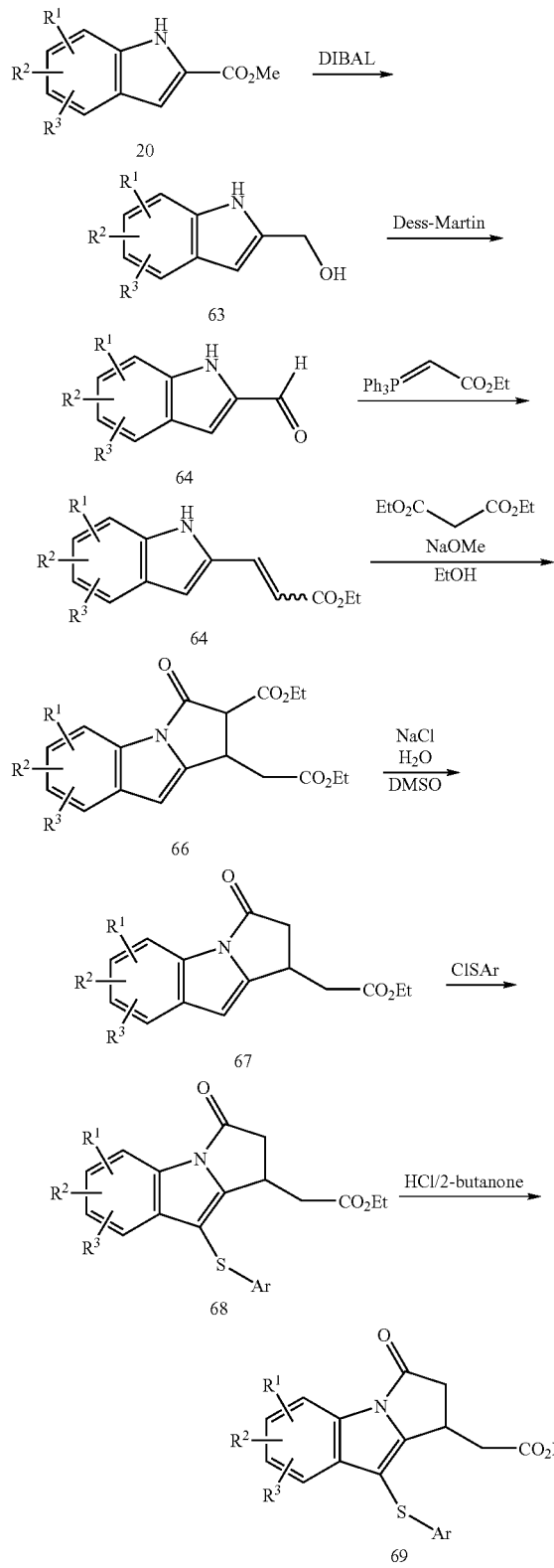

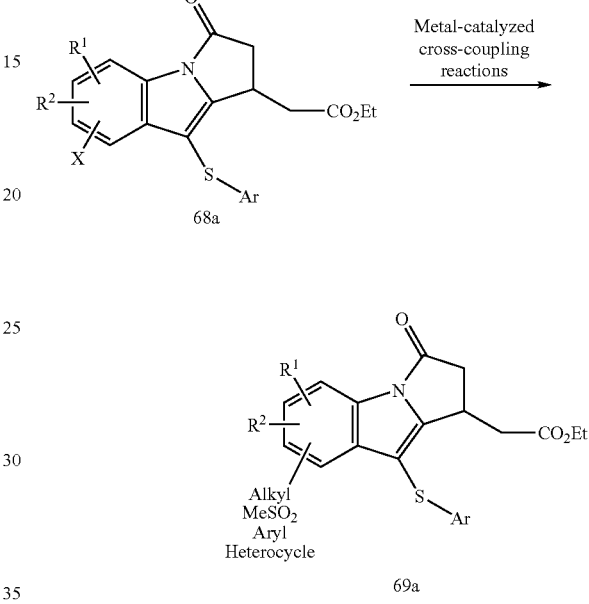

Method 13

6-Hydroxy indole derivative 48 can be converted into triflate 70, which is subjected to a transition metal catalyzed coupling reaction with i-Pr₃SiSK to give 71. Desilylation of 71 followed by alkylation with R^aX can provide 72. Sulphenylation reaction of 72 and aqueous hydrolysis yield the desired product 73.

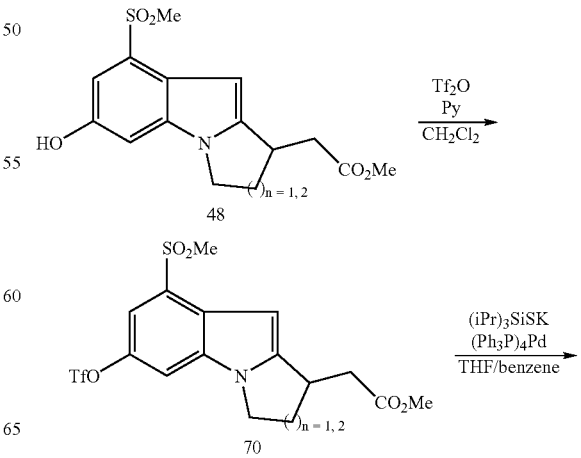

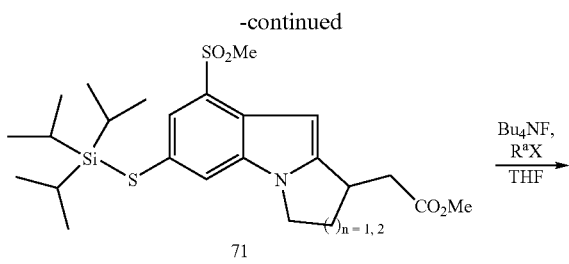

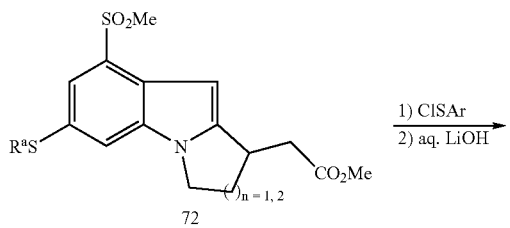

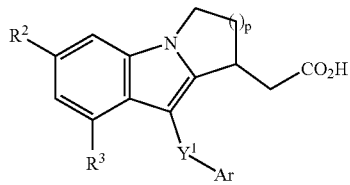

$R^a$ is other than hydrogen

Representative Compounds

Representative compounds of formula I are shown in the following Tables. Each entry is intended to include the racemic or diastereomeric mixture, and the individual enantiomers and/or diastereomers. Methods for the resolution of enantiomers and for the separation of diastereomers are well known to those skilled in the art; selective illustration of such methods are also described in the Examples herein below.

TABLE I

| Ex. | $R^2$ | $R^3$ | $Y^1$ | Ar | p |
|---|---|---|---|---|---|
| 1 | H | H | $CH_2$ | 4-Cl—Ph | 2 |
| 2 | H | H | $CH_2$ | 4-Cl—Ph | 1 |
| 3 | H | H | S | 4-Cl—Ph | 2 |
| 4 | $CH_3S(O)_2$ | H | S | 4-Cl—Ph | 2 |
| 5 | H | $CH_3S(O)$ | — | 4-Cl—Ph | 2 |
| 6 | H | $CH_3S(O)$ | $CH_2$ | 4-Cl—Ph | 2 |
| 7 | F | Br | S | 4-Cl—Ph | 1 |
| 8 | F | Br | S | 4-Cl—Ph | 2 |
| 9 | $CH_3S(O)_2$ | $CH_3O$ | S | 4-Cl—Ph | 2 |
| 10 | F | $CH_3C(O)$ | S | 4-Cl—Ph | 1 |
| 11 | F | $CF_3C(O)$ | S | 4-Cl—Ph | 1 |
| 12 | F | $CF_3CH(OH)$ | S | 4-Cl—Ph | 1 |
| 13 | F | $(CH_3)_2CHCH(OH)$ | S | 4-Cl—Ph | 1 |
| 14 | F | $CH_3CH(OH)$ | S | 4-Cl—Ph | 1 |
| 15 | F | $CH_3CH(OCH_3)$ | S | 4-Cl—Ph | 1 |
| 16 | F | $CH_3C(O)$ | S | Ph | 1 |
| 17 | F | $CH_3C(O)$ | S | 3,4-diCl—Ph | 1 |
| 18 | F | $CF_3CH(OCH_3)$ | S | 4-Cl—Ph | 1 |
| 19 | F | $CH_3CH_2CH(OH)$ | S | 4-Cl—Ph | 1 |
| 20 | F | $CH_3CH_2CH(OCH_3)$ | S | 4-Cl—Ph | 1 |
| 21 | F | $CH_3CH(SCH_3)$ | S | 4-Cl—Ph | 1 |
| 22 | $CH_3O$ | $CH_3S(O)_2$ | S | 4-Cl—Ph | 1 |
| 23 | $PhCH_2O$ | $CH_3S(O)_2$ | S | 4-Cl—Ph | 1 |
| 24 | $CH_3S$ | $CH_3S(O)_2$ | S | 4-Cl—Ph | 1 |
| 25 | $CH_3S(O)_2$ | $(CH_3)_2CH$ | S | 4-Cl—Ph | 1 |
| 26 | $(CH_3)_2CHO$ | $CH_3S(O)_2$ | S | 4-Cl—Ph | 1 |
| 27 | $PhCH_2O$ | $(CH_3)_2CH$ | S | 4-Cl—Ph | 1 |
| 28 | $CH_3O$ | $(CH_3)_2CH$ | S | 4-Cl—Ph | 1 |
| 29 | 4-Cl—Ph | $CH_3S(O)_2$ | S | 4-Cl—Ph | 1 |
| 30 | I | Br | S | 4-Cl—Ph | 1 |
| 31 | CN | Br | S | 4-Cl—Ph | 1 |
| 32 | 2-$CH_3$-5-Tz# | Br | S | 4-Cl—Ph | 1 |
| 33 | 1-$CH_3$-5-Tz | Br | S | 4-Cl—Ph | 1 |
| 34 | 1-$CH_3$-2-pyrrolyl | Br | S | 4-Cl—Ph | 1 |
| 35 | CN | $CH_3C(O)$ | S | 4-Cl—Ph | 1 |
| 36 | 2-$CH_3$-5-Tz | $CH_3C(O)$ | S | 4-Cl—Ph | 1 |
| 37 | F | $CH_3S(O)_2$ | S | 4-Cl—Ph | 1 |
| 38 | F | $CH_3CH_2S(O)_2$ | S | 4-Cl—Ph | 1 |

TABLE I-continued

| Ex. | R² | R³ | Y¹ | Ar | p |
|---|---|---|---|---|---|
| 39 | F | 1-CH₃-2-pyrrolyl | S | 4-Cl—Ph | 1 |
| 40 | F | CH₃CH₂CH₂ | S | 4-Cl—Ph | 1 |
| 41 | F | CH₃CH₂ | S | 4-Cl—Ph | 1 |
| 42 | F | CH₃C(=CH₂) | S | 4-Cl—Ph | 1 |
| 43 | F | 1-CH₃-5-pyrazolyl | S | 4-Cl—Ph | 1 |
| 44 | F | (CH₃)₂CH | S | 4-Cl—Ph | 1 |
| 45 | F | 1-cyclopentenyl | S | 4-Cl—Ph | 1 |
| 46 | F | (CH₃CH=)(CH₃CH₂)C | S | 4-Cl—Ph | 1 |
| 47 | F | (CH₃CH₂)₂CH | S | 4-Cl—Ph | 1 |
| 48 | F | cyclopentyl | S | 4-Cl—Ph | 1 |
| 49 | F | Ph | S | 4-Cl—Ph | 1 |
| 50 | F | 2-thienyl | S | 4-Cl—Ph | 1 |
| 51 | F | 3-CH₃-2-thienyl | S | 4-Cl—Ph | 1 |
| 52 | F | CH₂=CH | S | 4-Cl—Ph | 1 |
| 53 | CH₂=CH | Br | S | 4-Cl—Ph | 1 |
| 54 | F | (CF₃)₂C(OH) | S | 4-Cl—Ph | 1 |
| 55 | F | 3-thienyl | S | 4-Cl—Ph | 1 |
| 56 | cyclopropyl | 1-CH₃-2-pyrrolyl | S | 4-Cl—Ph | 1 |
| 57 | 2-CH₃-5-Tz | 1-CH3-2-pyrrolyl | S | 4-Cl—Ph | 1 |
| 58 | 2-CH₃-5-Tz | Ph | S | 4-Cl—Ph | 1 |
| 59 | F | cyclopropyl | S | 4-Cl—Ph | 1 |
| 60 | F | Br | CH₂ | 4-Cl—Ph | 1 |
| 61 | F | CH₃S(O)₂ | CO | 4-Cl—Ph | 1 |
| 62 | F | CH₃S(O)₂ | CH₂ | 4-Cl—Ph | 1 |
| 63 | F | (CF₃)₂C(OCH₃) | S | 4-Cl—Ph | 1 |
| 64 | F | (CH₃)₂CH | C(O) | 4-Cl—Ph | 1 |
| 65 | F | 1-CH₃-2-pyrrolyl | C(O) | 4-Cl—Ph | 1 |
| 66 | F | (CH₃)₂CH | CH₂ | 4-Cl—Ph | 1 |
| 67 | F | CH₃S(O)₂ | CH₂ | 2,4-diCl—Ph | 1 |
| 68 | F | CH₃S(O)₂ | CH₂ | 2,6-diCl—Ph | 1 |
| 69 | F | Br | C(O) | 4-Cl—Ph | 1 |
| 70 | F | cyclopropyl | C(O) | 4-Cl—Ph | 1 |
| 71 | F | (CH₃O)(CH₃CH₂)CH | C(O) | 4-Cl—Ph | 1 |
| 72 | F | Ph | C(O) | 4-Cl—Ph | 1 |
| 73 | F | 2-thienyl | C(O) | 4-Cl—Ph | 1 |
| 74 | F | CH₃S(O)₂ | CH₂ | 2,4,6-triCl—Ph | 1 |
| 75 | F | CH₃S(O)₂ | S | 2,4,5-triCl—Ph | 1 |
| 76 | F | CH₃S(O)₂ | C(O) | 4-biphenyl | 1 |
| 77 | F | CH₃S(O)₂ | C(O) | 2-naphthyl | 1 |
| 78 | F | Br | C(O) | 2-naphthyl | 1 |
| 79* | F | CH₃S(O)₂ | S | 4-Cl—Ph | 1 |
| 80 | F | CH₃S(O)₂ | C(O) | 2-furyl | 1 |
| 81 | F | CH₃S(O)₂ | C(O) | 2,4-diCl—Ph | 1 |
| 82 | F | CH₃S(O)₂ | C(O) | 4-Cl-2-CH₃S(O)₂—Ph | 1 |
| 83 | F | Br | C(O) | 4-Cl-2-I—Ph | 1 |
| 84 | F | Br | C(O) | 4-Cl-2-CONH₂—Ph | 1 |
| 85 | F | CH₃S(O)₂ | C(O) | 4-Cl-2-CN—Ph | 1 |
| 86 | F | (CH₃)₂CH | C(O) | 4-Cl-2-I—Ph | 1 |
| 87 | F | Br | C(O) | 2-benzothiazolyl | 1 |
| 88 | F | (CH₃)₂CH | C(O) | 4-Cl-2-CH₃S(O)₂—Ph | 1 |
| 89 | F | CH₃S(O)₂ | S | 4-CF₃—Ph | 1 |
| 90 | F | CH₃S(O)₂ | S | 4-CH₃S(O)₂—Ph | 1 |
| 91 | F | Br | C(O) | 2-quinolinyl | 1 |
| 92 | F | CH₃S(O)₂ | C(O) | 2-quinolinyl | 1 |
| 93 | F | Br | S | 2-benzothiazolyl | 1 |
| 94 | F | CH₃S(O)₂ | S | 2-benzothiazolyl | 1 |
| 95 | 2-CH₃-5-Tz | CH₃S(O)₂ | S | 4-Cl—Ph | 1 |
| 96 | F | CH₃S(O)₂ | CH(CH₃) | 4-Cl—Ph | 1 |
| 97** | F | CH₃S(O)₂ | C(O)CH₂ | 4-Cl—Ph | 1 |
| 98 | F | (CH₃)₂CH | S | 1-naphthyl | 1 |
| 99 | F | (CH₃)₂CH | S | 2-naphthyl | 1 |
| 100 | F | Br | S | 2-pyrimidinyl | 1 |
| 101 | F | CH₃S(O)₂ | S | 2-pyrimidinyl | 1 |
| 102 | F | CH₃S(O)₂ | CH₂CH₂ | 4-Cl—Ph | 1 |
| 103 | 2-CH₃-5-Tz | (CH₃O)(CH₃CH₂)CH | S | 4-Cl—Ph | 1 |
| 104 | F | (CH₃)₂CH | C(O) | 2-naphthyl | 1 |
| 105 | F | CH₃S(O)₂ | S | 2-naphthyl | 1 |

TABLE I-continued

| Ex. | R² | R³ | Y¹ | Ar | p |
|---|---|---|---|---|---|
| 106 | F | (CH₃)₂CH | S | 4-Cl-2-F—Ph | 1 |
| 107 | F | CH₃S(O)₂ | S | 4-Cl-2-F—Ph | 1 |
| 108 | F | 2-CH₃—Ph | S | 4-Cl—Ph | 1 |
| 109 | F | 8-quinolinyl | S | 4-Cl—Ph | 1 |
| 110 | F | 3-benzothienyl | S | 4-Cl—Ph | 1 |
| 111 | F | 3,5-diCH₃-4-isoxalyl | S | 4-Cl—Ph | 1 |
| 112 | F | 4-CH₃-3-thienyl | S | 4-Cl—Ph | 1 |
| 113 | F | 3-(1-pyrazolyl)-Ph | S | 4-Cl—Ph | 1 |
| 114 | F | 2-(HC(O))-3-thienyl | S | 4-Cl—Ph | 1 |
| 115 | F | 2-OCH₃—Ph | S | 4-Cl—Ph | 1 |
| 116 | F | 3,4-diCl—Ph | S | 4-Cl—Ph | 1 |
| 117 | F | 6-quinolinyl | S | 4-Cl—Ph | 1 |
| 118 | F | 2-naphthyl | S | 4-Cl—Ph | 1 |
| 119 | F | CN | S | 4-Cl—Ph | 1 |
| 120 | F | (CH₃)₂CH | C(O) | 1-naphthyl | 1 |
| 121 | F | (CH₃)₂CH | C(O) | 3,4-diCl—Ph | 1 |
| 122 | F | (CH₃)₂CH | S | 4-Cl—Ph | 2 |
| 123 | F | (CH₃)₂CH | C(O) | 2-naphthyl | 2 |
| 124 | F | (CH₃)₂CH | C(O) | 4-Cl—Ph | 2 |
| 125 | F | CH₃S(O)₂ | S | 4-Cl—Ph | 2 |
| 126 | F | CH₃S(O)₂ | 1,4-phenylene | Ph | 1 |
| 127 | F | CH₃S(O)₂ | — | 2-naphthyl | 1 |
| 128 | F | CH₃S(O)₂ | 1,3-phenylene | Ph | 1 |
| 129 | CN | (CH₃)₂CH | S | 4-Cl—Ph | 1 |
| 130 | 2-CH₃-5-Tz | (CH₃)₂CH | S | 4-Cl—Ph | 1 |
| 131 | 1-CH₃-5-Tz | (CH₃)₂CH | S | 4-Cl—Ph | 1 |
| 132 | CH₃S(O)₂ | CH₃S(O)₂ | S | 4-Cl—Ph | 1 |
| 133 | H | 1-CH₃-2-pyrrolyl | S | 4-Cl—Ph | 1 |
| 134 | F | 3-pyridyl | S | 4-Cl—Ph | 1 |
| 144 | F | CH₃S(O)₂ | C(O) | 4-Cl—Ph | 2 |
| 145 | F | CH₃S(O)₂ | C(O) | 2-naphthyl | 2 |
| 146 | F | (CH₃)₂CH | C(O) | 3-Br-4-Cl—Ph | 2 |
| 147 | F | (CH₃)₂CH | CH₂ | 4-Cl—Ph | 2 |
| 148 | F | (CH₃)₂CH | S | 3-Br-4-Cl—Ph | 2 |
| 149 | F | (CH₃)(CH₂=)C | C(O) | 4-Cl—Ph | 2 |
| 150 | F | CH₃S(O)₂ | C(O) | 6-Cl-Pyr## | 2 |
| 151 | F | CH₃S(O)₂ | C(O) | 3,4-diCl—Ph | 2 |
| 152 | F | CH₃S(O)₂ | C(O) | 4-nBu—Ph | 2 |
| 153 | F | CH₃S(O)₂ | C(O) | 4-Ph—Ph | 2 |
| 154 | PhCH₂O | CH₃S(O)₂ | S | 4-Cl—Ph | 2 |
| 155 | PhCH₂S | CH₃S(O)₂ | S | 4-Cl—Ph | 1 |
| 156 | F | CH₃S(O)₂ | C(O) | 4-Cl—Ph | 2 |

Tz is tetrazolyl
Pyr is pyridyl
*3-oxo analog of Example 37
**Y¹—Ar = —C(O)—CH₂-(4-Cl—Ph)

TABLE II

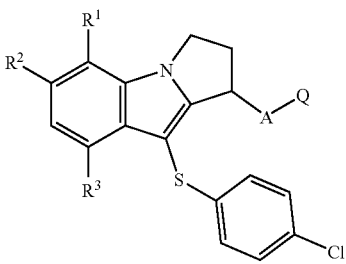

| Ex. | R¹ | R² | R³ | A—Q |
|---|---|---|---|---|
| 135 | F | F | 1-CH₃-2-pyrrolyl | CH₂CO₂H |
| 136 | F | F | CH₃S(O)₂ | CH₂CO₂H |
| 137 | F | F | S-(4-Cl—Ph) | CH₂CO₂H |
| 138 | CH₃S(O)₂ | F | CH₃S(O)₂ | CH₂CO₂H |
| 139 | CH₃S(O)₂ | CH₃O | CH₃S(O)₂ | CH₂CO₂H |

TABLE II-continued

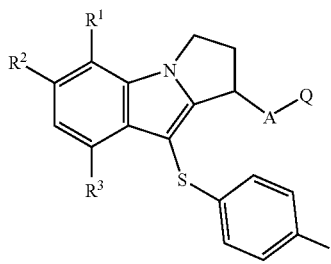

| Ex. | R¹ | R² | R³ | A—Q |
|---|---|---|---|---|
| 140 | F | H | CH₃S(O)₂ | CH₂CO₂H |
| 141 | H | F | Br | CF₂CO₂H |
| 142* | H | F | Br | CF₂CO₂H |
| 143 | H | F | CH₃S(O)₂ | CF₂CO₂H |

*sulfoxide of Example 141

TABLE III

| R¹/R² | R³ | A—Q/R⁶ | Y¹ | Ar |
|---|---|---|---|---|
| H/SO₂Me | C(O)CH₃ | CH₂CO₂H | CH₂ | 4-Cl-phe |
| H/SO₂Me | CH(OH)CH₃ | CH₂CO₂H | CH₂ | 4-Cl-phe |
| H/SO₂Me | Br | CH₂CO₂H | CH₂ | 2,4-Cl₂phe |
| H/SO₂Me | CH=CH₂ | CH₂CO₂H | O | 4-Cl-phe |
| H/SO₂Me | c-pr | CH₂CO₂H | O | 4-Cl-phe |
| H/SO₂Me | thiophen-2-yl | CH₂CO₂H | S | 4-Cl-phe |
| H/SO₂NMe₂ | H | CH₂CO₂H | S | 4-Cl-phe |
| H/F | Br | CH₂CO₂H/CH₃ | S | 4-Cl-phe |
| H/Br | H | CH₂CO₂H | S | 4-Cl-phe |
| H/CN | C(O)CH₃ | CH₂CO₂H | S | 2,4-Cl₂-phe |
| H/CN | H | CH₂CO₂H | S | 3,4-Cl₂-phe |
| H/CN | H | CH₂CO₂H | O | 4-Cl-phe |
| H/5-methyl-1,2,4-oxadiazol-3-yl | H | CH₂CO₂H | CO | 2,4-Cl₂-phe |
| H/3-methyl-1,2,4-oxadiazol-3-yl | H | CH₂CO₂H | CO | 3,4-Cl₂-phe |
| H/2-methyl-2H-tetrazol-5-yl | H | CH₂CO₂H | CO | 4-Cl-phe |
| H/5-(trifluoromethyl)-1,2,4-oxadiazol-3-yl | H | CH₂CO₂H | O | 2,4-Cl₂-phe |
| H/CF₃ | H | CH₂CO₂H | CH₂ | 3,4-Cl₂-phe |
| H/CF₃ | H | CH₂CO₂H | CHCH₃ | 3,4-Cl₂-phe |
| H/CF₃ | H | CH₂CO₂H | CH₂ | 4-Cl-phe |
| H/F | H | CH(CH₃)CO₂H | S | 2,4-Cl₂-phe |
| H/F | H | CH₂CO₂H | CH₂ | 2,4-Cl₂-phe |
| H/3-methyl-1,2,4-thiadiazol-5-yl | H | CH₂CO₂H | S | 3,4-Cl₂-phe |
| H/F | H | CH₂CO₂H | NH | 4-Cl-phe |
| H/F | H | CH₂CO₂H | CH₂ | 2-Cl-4-F—phe |
| H/4-methyl-1,3-thiazol-2-yl | H | CH₂CO₂H | O | 2-F-4-Cl—phe |
| H/F | H | CH₂CO₂H | 1,1-cPr | 4-Cl-phe |
| H/F | H | CH₂CO₂H | CH₂ | 2,4,6-Cl₃-phe |
| H/F | H | CH₂CO₂H | S | 2,3,4-Cl₃-phe |
| H/H | F | CH₂CO₂H | CH₂ | 2-Cl-4-CN-phe |
| H/F | H | CH₂CO₂H | CH₂ | 4-CN-phe |
| H/F | H | CH₂CO₂H | CH₂ | 4-COCH₃-phe |
| H/F | H | CH₂CO₂H | CH₂ | 3-Cl-4-CN-phe |
| H/F | H | CH₂CO₂H | CH₂ | 3-Cl-4-COCH₃-phe |
| H/F | 4-F-Phe | CH₂CO₂H | CH₂ | 4-CF₃-phe |

TABLE III-continued

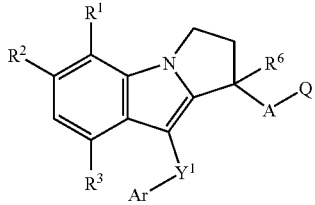

| R¹/R² | R³ | A—Q/R⁶ | Y¹ | Ar |
|---|---|---|---|---|
| H/F | 1-methyl-1H-pyrrol-2-yl | CH₂CO₂H | S | 2-Cl-4-CF₃-phe |
| H/F | H | CH₂CO₂H | S | 3-Cl-4-CF₃-phe |
| H/F | H | CH₂CO₂H | O | 2,6-Cl₂-phe |
| H/F | H | CH₂CO₂H | CH₂ | 2,4,6-F₃-phe |
| H/F | CO₂Me | CH(CH₃)CO₂H | CH₂ | 2,4-Cl₂-phe |
| H/F | CO₂Me | CH₂CO₂H | CH₂ | 2,4-Cl₂-phe |
| H/F | CO₂Me | CH₂CO₂H | S | 3,4-Cl₂-phe |
| H/F | CO₂Me | CH₂CO₂H | CH₂ | 4-Cl-phe |
| H/F | CO₂Me | CH₂CO₂H | CH₂ | 2-Cl-4-F-phe |
| H/F | CO₂Me | CH₂CO₂H | O | 2-F-4-Cl-phe |
| H/F | CO₂Me | CH₂CO₂H | 1,1-c-pr | 4-Cl-phe |
| H/F | CO₂Me | CH₂CO₂H | CH₂ | 2,4,6-Cl₃-phe |
| H/F | CO₂Me | CH₂CO₂H | S | 2,3,4-Cl₃-phe |
| H/F | CO₂Me | CH₂CO₂H | CH₂ | 2-Br-4-Cl-phe |
| H/F | CO₂Me | CH₂CO₂H | CH₂ | 2-Cl-4-Br-phe |
| H/F | CO₂Me | CH₂CO₂H | NH | 2-F-4-Br-phe |
| H/F | CO₂Me | CH₂CO₂H | NMe | 2-Cl-4-CN-phe |
| H/F | CO₂Me | CH₂CO₂H | CH₂ | 2-Cl-4-COCH₃-phe |
| H/F | CO₂Me | CH₂CO₂H | CH₂ | 4-CN-phe |
| H/F | CO₂Me | CH₂CO₂H | NEt | 4-COCH₃-phe |
| H/F | CO₂Me | CH₂CO₂H | CH₂ | 3-Cl-4-CN-phe |
| H/F | CO₂Me | CH₂CO₂H | S | 3-Cl-4-COCH₃-phe |
| H/F | CO₂Me | CH₂CO₂H | CH₂ | 4-CF₃-phe |
| H/F | CO₂Me | CH₂CO₂H | S | 2-Cl-4-CF₃-phe |
| H/F | CO₂Me | CH₂CO₂H | S | 3-Cl-4-CF₃-phe |
| H/F | CO₂Me | CH₂CO₂H | O | 2,6-Cl₂-phe |
| H/F | CO₂Me | CH₂CO₂H | NH | 2,4,6-F₃-phe |
| H/F | SOMe | CH(CH₃)CO₂H | CHMe | 2,4-Cl₂-phe |
| H/F | SOMe | CH₂CO₂H | CH₂ | 2,4-Cl₂-phe |
| H/F | SOMe | CH₂CO₂H | CHEt | 3,4-Cl₂-phe |
| H/F | SOMe | CH₂CO₂H | CH₂ | 4-Cl-phe |
| H/F | SOMe | CH₂CO₂H | O | 2-Cl-4-F-phe |
| H/F | SOMe | CH₂CO₂H | CH₂ | 2-F-4-Cl-phe |
| H/F | SOMe | CH₂CO₂H | 1,1-c-pr | 4-Cl-phe |
| H/F | SOMe | CH₂CO₂H | S | 2,4,6-Cl₃-phe |
| H/F | SOMe | CH₂CO₂H | CH₂ | 2,3,4-Cl₃-phe |
| H/F | SOMe | CH₂CO₂H | CH₂ | 2-Br-4-Cl-phe |
| H/F | SOMe | CH₂CO₂H | CH₂ | 2-Cl-4-Br-phe |
| H/F | SOMe | CH₂CO₂H | S | 2-F-4-Br-phe |
| H/F | SOMe | CH₂CO₂H | CH₂ | 2-Cl-4-CN-phe |
| H/F | SOMe | CH₂CO₂H | CH₂ | 2-Cl-4-COCH₃-phe |
| F/F | SOMe | CH₂CO₂H | CH₂ | 4-CN-phe |
| H/F | SOMe | CH₂CO₂H | CH₂ | 4-COCH₃-phe |
| H/F | SOMe | CH₂CO₂H | S | 3-Cl-4-CN-phe |
| H/F | SOMe | CH₂CO₂H | CH₂ | 3-Cl-4-COCH-phe |
| H/F | SOMe | CH₂CO₂H | O | 4-CF₃-phe |
| H/F | SOMe | CH₂CO₂H | CH₂ | 2-Cl-4-CF₃-phe |
| H/F | SOMe | CH₂CO₂H | CH₂ | 3-Cl-4-CF₃-phe |
| H/F | SOMe | CH₂CO₂H | NH | 2,6-Cl₂-phe |
| H/F | SOMe | CH₂CO₂H | CH₂ | 2,4,6-F₃-phe |
| H/SO₂Me | C(O)CH₃ | CH₂CO₂H | O | 2,4-Cl₂-phe |
| H/SO₂Me | C(O)CH₃ | CH₂CO₂H | CH₂ | 3,4-Cl₂-phe |
| H/SO₂Me | C(O)CH₃ | CH₂CO₂H | CH₂ | 2-Cl-4-F-phe |
| H/SO₂Me | C(O)CH₃ | CH₂CO₂H | CH₂ | 2-F-4-Cl-phe |
| H/SO₂Me | C(O)CH₃ | CH₂CO₂H | 1,1-c-pr | 4-Cl-phe |
| H/SO₂Me | C(O)CH₃ | CH₂CO₂H | CH₂ | 2,4,6-Cl₃-phe |
| H/SO₂Me | C(O)CH₃ | CH₂CO₂H | CH₂ | 2,3,4-Cl₃-phe |
| H/SO₂Me | C(O)CH₃ | CH₂CO₂H | CH₂ | 2-Br-4-Cl-phe |
| H/SO₂Me | C(O)CH₃ | CH₂CO₂H | CH₂ | 2-Cl-4-Br-phe |
| H/SO₂Me | C(O)CH₃ | CH₂CO₂H | CH₂ | 2-F-4-Br-phe |
| H/SO₂Me | C(O)CH₃ | CH₂CO₂H | CH₂ | 2-Cl-4-CN-phe |
| H/SO₂Me | C(O)CH₃ | CH₂CO₂H | CH₂ | 2-Cl-4-COCH₃-phe |
| H/SO₂Me | C(O)CH₃ | CH₂CO₂H | CH₂ | 4-CN-phe |
| H/SO₂Me | C(O)CH₃ | CH₂CO₂H | CH₂ | 4-COCH₃-phe |
| H/SO₂Me | C(O)CH₃ | CH₂CO₂H | CH₂ | 3-Cl-4-CN-phe |
| H/SO₂Me | C(O)CH₃ | CH₂CO₂H | CH₂ | 3-Cl-4-COCH₃-phe |

TABLE III-continued

| R¹/R² | R³ | A—Q/R⁶ | Y¹ | Ar |
|---|---|---|---|---|
| H/SO$_2$Me | C(O)CH$_3$ | CH$_2$CO$_2$H | CH$_2$ | 4-CF$_3$-phe |
| H/SO$_2$Me | C(O)CH$_3$ | CH$_2$CO$_2$H | CH$_2$ | 2-Cl-4-CF$_3$-phe |
| H/SO$_2$Me | C(O)CH$_3$ | CH$_2$CO$_2$H | CH$_2$ | 3-Cl-4-CF$_3$-phe |
| H/SO$_2$Me | C(O)CH$_3$ | CH$_2$CO$_2$H | CH$_2$ | 2,6-Cl$_2$-phe |
| H/SO$_2$Me | C(O)CH$_3$ | CH$_2$CO$_2$H | CH$_2$ | 2,4,6-F$_3$-phe |
| H/SO$_2$Me | CH(OH)CH$_3$ | CH(CH$_3$)CO$_2$H | CH$_2$ | 2,4-Cl$_2$-phe |
| H/SO$_2$Me | CH(OH)CH$_3$ | CH$_2$CO$_2$H | O | 2,4-Cl$_2$-phe |
| H/SO$_2$Me | CH(OH)CH$_3$ | CH$_2$CO$_2$H | CH$_2$ | 3,4-Cl$_2$-phe |
| H/SO$_2$Me | CH(OH)CH$_3$ | CH$_2$CO$_2$H | CH$_2$ | 2-Cl-4-F-phe |
| H/SO$_2$Me | CH(OH)CH$_3$ | CH$_2$CO$_2$H | CH$_2$ | 2-F-4-Cl-phe |
| H/SO$_2$Me | CH(OH)CH$_3$ | CH$_2$CO$_2$H | 1,1-c-pr | 4-Cl-phe |
| H/SO$_2$Me | CH(OH)CH$_3$ | CH$_2$CO$_2$H | CH$_2$ | 2,4,6-Cl$_3$-phe |
| H/SO$_2$Me | CH(OH)CH$_3$ | CH$_2$CO$_2$H | CH$_2$ | 2,3,4-Cl$_3$-phe |
| H/SO$_2$Me | CH(OH)CH$_3$ | CH$_2$CO$_2$H | CH$_2$ | 2-Br-4-Cl-phe |
| H/CH(OH)CH$_3$ | SO$_2$Me | CH$_2$CO$_2$H | CH$_2$ | 2-Cl-4-Br-phe |
| H/CH(OH)CH$_3$ | SO$_2$Me | CH$_2$CO$_2$H | CH$_2$ | 2-F-4-Br-phe |
| H/CH(OH)CH$_3$ | SO$_2$Me | CH$_2$CO$_2$H | CH$_2$ | 2-Cl-4-CN-phe |
| H/CH(OH)CH$_3$ | SO$_2$Me | CH$_2$CO$_2$H | CH$_2$ | 2-Cl-4-COCH$_3$-phe |
| H/CH(OH)CH$_3$ | SO$_2$Me | CH$_2$CO$_2$H | CH$_2$ | 4-CN-phe |
| H/CH(OH)CH$_3$ | SO$_2$Me | CH$_2$CO$_2$H | S | 4-COCH$_3$-phe |
| H/SO$_2$Me | CH(OH)CH$_3$ | CH$_2$CO$_2$H | CH$_2$ | 3-Cl-4-CN-phe |
| H/SO$_2$Me | CH(OH)CH$_3$ | CH$_2$CO$_2$H | CH$_2$ | 3-Cl-4-COCH$_3$-phe |
| H/SO$_2$Me | CH(OH)CH$_3$ | CH$_2$CO$_2$H | CH$_2$ | 4-CF$_3$-phe |
| H/SO$_2$Me | CH(OH)CH$_3$ | CH$_2$CO$_2$H | CH$_2$ | 2-Cl-4-CF$_3$-phe |
| H/SO$_2$Me | CH(OH)CH$_3$ | CH$_2$CO$_2$H | CH$_2$ | 3-Cl-4-CF$_3$-phe |
| H/SO$_2$Me | CH(OH)CH$_3$ | CH$_2$CO$_2$H | CH$_2$ | 2,6-Cl$_2$-phe |
| H/CH(OR)CH$_3$ | SO$_2$Me | CH$_2$CO$_2$H | S | 2,4,6-F$_3$-phe |
| H/CO$_2$CH$_3$ | SO$_2$Me | CH(CH$_3$)CO$_2$H | CH$_2$ | 2,4-Cl$_2$-phe |
| H/CO$_2$CH$_3$ | SO$_2$Me | CH$_2$CO$_2$H | CH$_2$ | 2,4-Cl$_2$-phe |
| H/SO$_2$Me | CO$_2$CH$_3$ | CH$_2$CO$_2$H | O | 3,4-Cl$_2$-phe |
| H/SO$_2$Me | CO$_2$CH$_3$ | CH$_2$CO$_2$H | CH$_2$ | 4-Cl-phe |
| H/SO$_2$Me | CO$_2$CH$_3$ | CH$_2$CO$_2$H | CH$_2$ | 2-Cl-4-F-phe |
| H/CO$_2$CH$_3$ | SO$_2$Me | CH$_2$CO$_2$H | CH$_2$ | 2-F-4-Cl-phe |
| H/CO$_2$CH$_3$ | SO$_2$Me | CH$_2$CO$_2$H | 1,1-c-pr | 4-Cl-phe |
| H/CO$_2$CH$_3$ | SO$_2$Me | CH$_2$CO$_2$H | CH$_2$ | 2,4,6-Cl$_3$-phe |
| H/CO$_2$CH$_3$ | SO$_2$Me | CH$_2$CO$_2$H | CH$_2$ | 2,3,4-Cl$_3$-phe |
| H/CO$_2$CH$_3$ | SO$_2$Me | CH$_2$CO$_2$H | CH$_2$ | 2-Br-4-Cl-phe |
| H/CO$_2$CH$_3$ | SO$_2$Me | CH$_2$CO$_2$H | CH$_2$ | 2-Cl-4-Br-phe |
| H/CO$_2$CH$_3$ | SO$_2$Me | CH$_2$CO$_2$H | CH$_2$ | 2-F-4-Br-phe |
| H/CO$_2$CH$_3$ | SO$_2$Me | CH$_2$CO$_2$H | CH$_2$ | 2-Cl-4-CN-phe |
| H/CO$_2$CH$_3$ | SO$_2$Me | CH$_2$CO$_2$H | CH$_2$ | 2-Cl-4-COCH$_3$-phe |
| H/CO$_2$CH$_3$ | SO$_2$Me | CH$_2$CO$_2$H | CH$_2$ | 4-CN-phe |
| H/CO$_2$CH$_3$ | SO$_2$Me | CH$_2$CO$_2$H | CH$_2$ | 4-COCH$_3$-phe |
| H/CO$_2$CH$_3$ | SO$_2$Me | CH$_2$CO$_2$H | CH$_2$ | 3-Cl-4-CN-phe |
| H/CO$_2$CH$_3$ | SO$_2$Me | CH$_2$CO$_2$H | CH$_2$ | 3-Cl-4-COCH$_3$-phe |
| H/CO$_2$CH$_3$ | SO$_2$Me | CH$_2$CO$_2$H | CH$_2$ | 4-CF$_3$-phe |
| H/CO$_2$CH$_3$ | SO$_2$Me | CH$_2$CO$_2$H | CH$_2$ | 2-Cl-4-CF$_3$-phe |
| H/CO$_2$CH$_3$ | SO$_2$Me | CH$_2$CO$_2$H | CH$_2$ | 3-Cl-4-CF$_3$-phe |
| H/CO$_2$CH$_3$ | SO$_2$Me | CH$_2$CO$_2$H | CH$_2$ | 2,6-Cl$_2$-phe |
| H/CO$_2$CH$_3$ | SO$_2$Me | CH$_2$CO$_2$H | CH$_2$ | 2,4,6-F$_3$-phe |
| H/CO$_2$CH$_3$ | SO$_2$Me | CH$_2$CO$_2$H | S | 2,4-Cl$_2$-phe |
| H/CO$_2$CH$_3$ | SO$_2$Me | CH$_2$CO$_2$H | S | 3,4-Cl$_2$-phe |
| H/CO$_2$CH$_3$ | SO$_2$Me | CH$_2$CO$_2$H | S | 4-Cl-phe |
| H/CO$_2$CH$_3$ | SO$_2$Me | CH$_2$CO$_2$H | CH$_2$ | 2,4-Cl$_2$-phe |
| H/CO$_2$CH$_3$ | SO$_2$Me | CH$_2$CO$_2$H | CH$_2$ | 3,4-Cl$_2$-phe |
| H/CO$_2$CH$_3$ | SO$_2$Me | CH$_2$CO$_2$H | CH$_2$ | 4-Cl-phe |
| H/CO$_2$CH$_3$ | SO$_2$Me | CH$_2$CO$_2$H | CH$_2$ | 2,4-Cl$_2$-phe |
| H/CO$_2$CH$_3$ | SO$_2$Me | CH$_2$CO$_2$H | CH$_2$ | 3,4-Cl$_2$-phe |
| H/CO$_2$CH$_3$ | SO$_2$Me | CH$_2$CO$_2$H | CH$_2$ | 4-Cl-phe |
| H/CO$_2$CH$_3$ | SO$_2$Me | CH$_2$CO$_2$H/CH$_3$ | CH$_2$ | 2,4-Cl$_2$-phe |
| H/CO$_2$CH$_3$ | SO$_2$Me | CH$_2$CO$_2$H/CH$_3$ | CH$_2$ | 3,4-Cl$_2$-phe |
| H/CO$_2$CH$_3$ | SO$_2$Me | CH$_2$CO$_2$H/CH$_3$ | CH$_2$ | 4-Cl-phe |
| H/SO$_2$Me | CO$_2$CH$_2$CH$_3$ | CH$_2$CO$_2$H | CH$_2$ | 3,4-Cl$_2$-phe |
| H/SO$_2$Me | CO$_2$CH$_2$CH$_3$ | CH$_2$CO$_2$H | CH$_2$ | 4-Cl-phe |
| H/C(OH)(CH$_2$)$_2$SO$_2$Me | CH$_2$CO$_2$H | CH$_2$ | 2,4-Cl$_2$-phe | |
| H/C(OH)(CH$_2$)$_2$SO$_2$Me | CH$_2$CO$_2$H | CH$_2$ | 3,4-Cl$_2$-phe | |

TABLE III-continued

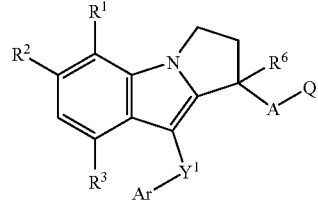

| R¹/R² | R³ | A—Q/R⁶ | Y¹ | Ar |
|---|---|---|---|---|
| H/C(OH)(CH₂)₂SO₂Me | CH₂CO₂H | CH₂ | 4-Cl-phe | |
| H/(thiophen-2-yl) | SO₂Me | CH₂CO₂H | CH₂ | 2,4-Cl₂-phe |
| H/(thiophen-2-yl) | SO₂Me | CH₂CO₂H | CH₂ | 3,4-Cl₂-phe |
| H/(thiophen-2-yl) | F | CH₂CO₂H | CH₂ | 2,4-Cl₂-phe |
| H/(thiophen-2-yl) | F | CH₂CO₂H | CH₂ | 3,4-Cl₂-phe |
| H/(thiophen-2-yl) | F | CH₂CO₂H | CH₂ | 4-Cl-phe |
| H/(2-oxazolyl) | F | CH₂CO₂H | CH₂ | 2,4-Cl₂-phe |
| H/(2-oxazolyl) | F | CH₂CO₂H | CH₂ | 3,4-Cl₂-phe |
| H/(2-oxazolyl) | F | CH₂CO₂H | CH₂ | 4-Cl-phe |
| H/(2-oxazolyl) | SO₂Me | CH₂CO₂H | CH₂ | 2,4-Cl₂-phe |
| H/(2-oxazolyl) | SO₂Me | CH₂CO₂H | CH₂ | 3,4-Cl₂-phe |
| H/(2-oxazolyl) | SO₂Me | CH₂CO₂H | CH₂ | 4-Cl-phe |
| H/i-Pr | SO₂Me | CH₂CO₂H | CH₂ | 2,4-Cl₂-phe |
| H/i-Pr | SO₂Me | CH₂CO₂H | CH₂ | 3,4-Cl₂-phe |
| H/i-Pr | SO₂Me | CH₂CO₂H | CH₂ | 4-Cl-phe |
| H/c-Pr | SO₂Me | CH₂CO₂H | CH₂ | 2,4-Cl₂-phe |
| H/c-Pr | SO₂Me | CH₂CO₂H | CH₂ | 3,4-Cl₂-phe |
| H/c-Pr | SO₂Me | CH₂CO₂H | CH₂ | 4-Cl-phe |
| H/i-Pr | F | CH₂CO₂H | CH₂ | 2,4-Cl₂-phe |
| H/i-Pr | F | CH₂CO₂H | CH₂ | 3,4-Cl₂-phe |
| H/i-Pr | F | CH₂CO₂H | CH₂ | 4-Cl-phe |
| H/c-Pr | F | CH₂CO₂H | CH₂ | 2,4-Cl₂-phe |
| H/c-Pr | F | CH₂CO₂H | CH₂ | 3,4-Cl₂-phe |
| H/c-Pr | F | CH₂CO₂H | CH₂ | 4-Cl-phe |
| H/i-Bu | F | CH₂CO₂H | CH₂ | 2,4-Cl₂-phe |
| H/i-Bu | F | CH₂CO₂H | CH₂ | 3,4-Cl₂-phe |
| H/i-Bu | F | CH₂CO₂H | CH₂ | 4-Cl-phe |
| H/Br | F | CH₂CO₂H | CH₂ | 2,4-Cl₂-phe |
| H/Br | F | CH₂CO₂H | CH₂ | 3,4-Cl₂-phe |
| H/Br | F | CH₂CO₂H | CH₂ | 4-Cl-phe |
| H/I | F | CH₂CO₂H | CH₂ | 2,4-Cl₂-phe |
| H/I | F | CH₂CO₂H | CH₂ | 3,4-Cl₂-phe |
| H/I | F | CH₂CO₂H | CH₂ | 4-Cl-phe |
| H/Cl | F | CH₂CO₂H | CH₂ | 2,4-Cl₂-phe |
| H/Cl | F | CH₂CO₂H | CH₂ | 3,4-Cl₂-phe |
| H/Cl | F | CH₂CO₂H | CH₂ | 4-Cl-phe |
| H/F | c-Bu | CH₂CO₂H | CH₂ | 2,4-Cl₂-phe |
| H/F | c-Bu | CH₂CO₂H | CH₂ | 3,4-Cl₂-phe |
| H/F | c-Bu | CH₂CO₂H | CH₂ | 4-Cl-phe |
| H/F | C(OH)(CH₂)₃ | CH₂CO₂H | CH₂ | 2,4-Cl₂-phe |
| H/F | C(OH)(CH₂)₃ | CH₂CO₂H | CH₂ | 3,4-Cl₂-phe |
| H/F | C(OH)(CH₂)₃ | CH₂CO₂H | CH₂ | 4-Cl-phe |
| H/SO₂Me | C(OH)(CH2)3 | CH₂CO₂H | CH₂ | 2,4-Cl₂-phe |
| H/SO₂Me | C(OH)(CH2)3 | CH₂CO₂H | CH₂ | 3,4-Cl₂-phe |
| H/SO₂Me | C(OH)(CH2)3 | CH₂CO₂H | CH₂ | 4-Cl-phe |
| H/SO₂Me | (2-oxetanyl) | CH₂CO₂H | CH₂ | 2,4-Cl₂-phe |
| H/SO₂Me | (2-oxetanyl) | CH₂CO₂H | CH₂ | 3,4-Cl₂-phe |
| H/SO₂Me | (2-oxetanyl) | CH₂CO₂H | CH₂ | 4-Cl-phe |
| H/F | (2-oxetanyl) | CH₂CO₂H | CH₂ | 2,4-Cl₂-phe |
| H/F | (2-oxetanyl) | CH₂CO₂H | CH₂ | 3,4-Cl₂-phe |
| H/F | (2-oxetanyl) | CH₂CO₂H | CH₂ | 4-Cl-phe |

TABLE IV

| R¹/R² | R³ | A—Q/R⁶ | Y¹ | Ar |
|---|---|---|---|---|
| H/SO₂Me | C(O)CH₃ | CH₂CO₂H | S | 4-Cl-phe |
| H/SO₂Me | CH(OH)CH₃ | CH₂CO₂H | O | 4-Cl-phe |
| H/SO₂Me | Br | CH₂CO₂H | CH₂ | 2,4-Cl₂-phe |
| H/SO₂Me | CHCH₂ | CH₂CO₂H | CH₂ | 4-Cl-phe |
| H/SO₂Me | c-pr | CH₂CO₂H | O | 4-Cl-phe |
| H/SO₂Me | (thiophen-2-yl) | CH₂CO₂H | CH₂ | 4-Cl-phe |
| H/SO₂NMe₂ | H | CH₂CO₂H | S | 4-Cl-phe |
| H/F | Br | CH₂CO₂H/CH₃ | CH₂ | 4-Cl-phe |
| H/Br | C(O)CH₃ | CH₂CO₂H | NH | 4-Cl-phe |
| H/CN | H | CH₂CO₂H | S | 2,4-Cl₂-phe |
| H/CN | H | CH₂CO₂H | S | 3,4-Cl₂-phe |
| H/CN | H | CH₂CO₂H | S | 4-Cl-phe |
| H/F | H | CH₂CO₂H | CO | 2,4-Cl₂-phe |
| H/F | H | CH₂CO₂H | CO | 3,4-Cl₂-phe |
| H/F | H | CH₂CO₂H | CO | 4-Cl-phe |
| H/CF₃ | H | CH₂CO₂H | CH₂ | 2,4-Cl₂-phe |
| H/CF₃ | H | CH₂CO₂H | CH₂ | 3,4-Cl₂-phe |
| H/CF₃ | H | CH₂CO₂H | CHCH₃ | 3,4-Cl₂-phe |
| H/CF₃ | H | CH₂CO₂H | CH₂ | 4-Cl-phe |
| H/F | H | CH(CH₃)CO₂H | CH₂ | 2,4-Cl₂-phe |
| H/F | H | CH₂CO₂H | CH₂ | 2,4-Cl₂-phe |
| H/F | H | CH₂CO₂H | CH₂ | 3,4-Cl₂-phe |
| H/F | H | CH₂CO₂H | CH₂ | 4-Cl-phe |
| H/F | H | CH₂CO₂H | O | 2-Cl-4-F-phe |
| H/F | H | CH₂CO₂H | CH₂ | 2-F-4-Cl-phe |
| H/F | H | CH₂CO₂H | 1,1-cPr | 4-Cl-phe |
| H/F | H | CH₂CO₂H | CH₂ | 2,4,6-Cl₃-phe |
| H/F | H | CH₂CO₂H | CH₂ | 2,3,4-Cl₃-phe |
| H/H | F | CH₂CO₂H | S | 2-Cl-4-CN-phe |
| H/F | H | CH₂CO₂H | CH₂ | 2-Cl-4-COCH₃-phe |
| H/F | H | CH₂CO₂H | CH₂ | 4-CN-phe |
| H/F | H | CH₂CO₂H | CH₂ | 4-COCH₃-phe |
| H/F | H | CH₂CO₂H | CH₂ | 3-Cl-4-CN-phe |
| H/F | H | CH₂CO₂H | CH₂ | 3-Cl-4-COCH₃-phe |
| H/F | H | CH₂CO₂H | CH₂ | 4-CF₃-phe |
| H/F | H | CH₂CO₂H | CH₂ | 2-Cl-4-CF₃-phe |
| H/F | H | CH₂CO₂H | CH₂ | 3-Cl-4-CF₃-phe |
| H/F | H | CH₂CO₂H | CH₂ | 2,6-Cl₂-phe |
| H/F | H | CH₂CO₂H | CH₂ | 2,4,6-F₃-phe |
| H/F | CO₂Me | CH(CH₃)CO₂H | CH₂ | 2,4-Cl₂-phe |
| H/F | CO₂Me | CH₂CO₂H | CH₂ | 2,4-Cl₂-phe |
| H/F | CO₂Me | CH₂CO₂H | NMe | 3,4-Cl₂-phe |
| H/F | CO₂Me | CH₂CO₂H | CH₂ | 4-Cl-phe |
| H/F | CO₂Me | CH₂CO₂H | CH₂ | 2-Cl-4-F-phe |
| H/F | CO₂Me | CH₂CO₂H | CH₂ | 2-F-4-Cl-phe |
| H/F | CO₂Me | CH₂CO₂H | 1,1-c-pr | 4-Cl-phe |
| H/F | CO₂Me | CH₂CO₂H | CH₂ | 2,4,6-Cl₃-phe |
| H/F | CO₂Me | CH₂CO₂H | CH₂ | 2,3,4-Cl₃-phe |
| H/F | CO₂Me | CH₂CO₂H | CH₂ | 2-Br-4-Cl-phe |
| H/F | CO₂Me | CO₂Me | CH₂ | 2-Cl-4-Br-phe |
| H/F | CO₂Me | CO₂Me | CH₂ | 2-F-4-Br-phe |
| H/F | CO₂Me | CO₂Me | CH₂ | 2-Cl-4-CN-phe |
| H/F | CO₂Me | CO₂Me | CH₂ | 2-Cl-4-COCH₃-phe |
| H/F | CO₂Me | CO₂Me | CH₂ | 4-CN-phe |
| H/F | CO₂Me | CO₂Me | CH₂ | 4-COCH₃-phe |
| H/F | CO₂Me | CO₂Me | CH₂ | 3-Cl-4-CN-phe |
| H/F | CO₂Me | CO₂Me | CH₂ | 3-Cl-4-COCH₃-phe |
| H/F | CO₂Me | CO₂Me | CH₂ | 4-CF₃-phe |
| H/F | CO₂Me | CH₂CO₂H | CH₂ | 2-Cl-4-CF₃-phe |
| H/F | CO₂Me | CH₂CO₂H | CH₂ | 3-Cl-4-CF₃-phe |
| H/F | CO₂Me | CH₂CO₂H | CH₂ | 2,6-Cl₂-phe |
| H/F | CO₂Me | CH₂CO₂H | CH₂ | 2,4,6-F₃-phe |
| H/F | SOMe | CH(CH₃)CO₂H | CH₂ | 2,4-Cl₂-phe |
| H/F | SOMe | CH₂CO₂H | CH₂ | 2,4-Cl₂-phe |
| H/F | SOMe | CH₂CO₂H | CH₂ | 3,4-Cl₂-phe |
| H/F | SOMe | CH₂CO₂H | CH₂ | 2 4-Cl-phe |

TABLE IV-continued

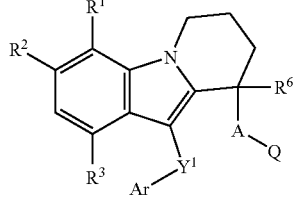

| R¹/R² | R³ | A—Q/R⁶ | Y¹ | Ar |
|---|---|---|---|---|
| H/F | SOMe | CH₂CO₂H | CH₂ | 2-Cl-4-F-phe |
| H/F | SOMe | CH₂CO₂H | CH₂ | 2-F-4-Cl-phe |
| H/F | SOMe | CH₂CO₂H | 1,1-c-pr | 4-Cl-phe |
| H/F | SOMe | CH₂CO₂H | CH₂ | 2,4,6-Cl₃-phe |
| H/F | SOMe | CH₂CO₂H | CH₂ | 2,3,4-Cl₃-phe |
| H/F | SOMe | CH₂CO₂H | CH₂ | 2-Br-4-Cl-phe |
| H/F | SOMe | CH₂CO₂H | CH₂ | 2-Cl-4-Br-phe |
| H/F | SOMe | CH₂CO₂H | CH₂ | 2-F-4-Br-phe |
| H/F | SOMe | CH₂CO₂H | CH₂ | 2-Cl-4-CN-phe |
| H/F | SOMe | CH₂CO₂H | CH₂ | 2-Cl-4-COCH₃-phe |
| F/F | SOMe | CH₂CO₂H | CH₂ | 4-CN-phe |
| H/F | SOMe | CH₂CO₂H | CH₂ | 4-COCH₃-phe |
| H/F | SOMe | CH₂CO₂H | S | 3-Cl-4-CN-phe |
| H/F | SOMe | CH₂CO₂H | CH₂ | 3-Cl-4-COCH₃-phe |
| H/F | SOMe | CH₂CO₂H | CH₂ | 4-CF₃-phe |
| H/F | SOMe | CH₂CO₂H | CH₂ | 2-Cl-4-CF₃-phe |
| H/F | SOMe | CH₂CO₂H | CH₂ | 3-Cl-4-CF₃-phe |
| H/F | SOMe | CH₂CO₂H | CH₂ | 2,6-Cl₂-phe |
| H/F | SOMe | CH₂CO₂H | CH₂ | 2,4,6-F₃-phe |
| H/SO₂Me. | C(O)CH₃ | CH₂CO₂H | CH₂ | 2,4-Cl₂-phe |
| H/SO₂Me | C(O)CH₃ | CH₂CO₂H | CH₂ | 3,4-Cl₂-phe |
| H/SO₂Me | C(O)CH₃ | CH₂CO₂H | CH₂ | 2-Cl-4-F-phe |
| H/SO₂Me | C(O)CH₃ | CH₂CO₂H | CH₂ | 2-F-4-Cl-phe |
| H/SO₂Me | C(O)CH₃ | CH₂CO₂H | 1,1-c-pr | 4-Cl-phe |
| H/SO₂Me | C(O)CH₃ | CH₂CO₂H | CH₂ | 2,4,6-Cl₃-phe |
| H/SO₂Me | C(O)CH₃ | CH₂CO₂H | CH₂ | 2,3,4-Cl₃-phe |
| SO₂Me/H | C(O)CH₃ | CH₂CO₂H | CH₂ | 2-Br-4-Cl-phe |
| H/SO₂Me | C(O)CH₃ | CH₂CO₂H | CH₂ | 2-Cl-4-Br-phe |
| H/SO₂Me | C(O)CH₃ | CH₂CO₂H | CH₂ | 2-F-4-Br-phe |
| H/SO₂Me | C(O)CH₃ | CH₂CO₂H | CH₂ | 2-Cl-4-CN-phe |
| H/SO₂Me | C(O)CH₃ | CH₂CO₂H | CH₂ | 2-Cl-4-COCH₃-phe |
| H/SO₂Me | C(O)CH₃ | CH₂CO₂H | CH₂ | 4-CN-phe |
| H/SO₂Me | C(O)CH₃ | CH₂CO₂H | CH₂ | 4-COCH₃-phe |
| H/SO₂Me | C(O)CH₃ | CH₂CO₂H | CH₂ | 3-Cl-4-CN-phe |
| H/SO₂Me | C(O)CH₃ | CH₂CO₂H | CH₂ | 3-Cl-4-COCH₃-phe |
| H/SO₂Me | C(O)CH₃ | CH₂CO₂H | CH₂ | 4-CF₃-phe |
| H/SO₂Me | C(O)CH₃ | CH₂CO₂H | CH₂ | 2-Cl-4-CF₃-phe |
| H/SO₂Me | C(O)CH₃ | CH₂CO₂H | CH₂ | 3-Cl-4-CF₃-phe |
| H/SO₂Me | C(O)CH₃ | CH₂CO₂H | CH₂ | 2,6-Cl₂-phe |
| H/SO₂Me | C(O)CH₃ | CH₂CO₂H | CH₂ | 2,4,6-F₃-phe |
| H/SO₂Me | CH(OH)CH₃ | CH(CH₃)CO₂H | CH₂ | 2,4-Cl₂-phe |
| H/SO₂Me | CH(OH)CH₃ | CH₂CO₂H | CH₂ | 2,4-Cl₂-phe |
| H/SO₂Me | CH(OH)CH₃ | CH₂CO₂H | CH₂ | 3,4-Cl₂-phe |
| H/SO₂Me | CH(OH)CH₃ | CH₂CO₂H | CH₂ | 2-Cl-4-F-phe |
| H/SO₂Me | CH(OH)CH₃ | CH₂CO₂H | CH₂ | 2-F-4-Cl-phe |
| H/SO₂Me | CH(OH)CH₃ | CH₂CO₂H | 1,1-c-pr | 4-Cl-phe |
| H/SO₂Me | CH(OH)CH₃ | CH₂CO₂H | CH₂ | 2,4,6-Cl₃-phe |
| H/SO₂Me | CH(OH)CH₃ | CH₂CO₂H | CH₂ | 2,3,4-Cl₃-phe |
| H/SO₂Me | CH(OH)CH₃ | CH₂CO₂H | CH₂ | 2-Br-4-Cl-phe |
| H/CH(OH)CH₃ | SO₂Me | CH₂CO₂H | CH₂ | 2-Cl-4-Br-phe |
| H/CH(OH)CH₃ | SO₂Me | CH₂CO₂H | CH₂ | 2-F-4-Br-phe |
| H/CH(OH)CH₃ | SO₂Me | CH₂CO₂H | CH₂ | 2-Cl-4-CN-phe |
| H/CH(OH)CH₃ | SO₂Me | CH₂CO₂H | CH₂ | 2-Cl-4-COCH₃-phe |
| H/CH(OH)CH₃ | SO₂Me | CH₂CO₂H | CH₂ | 4-CN-phe |
| H/CH(OH)CH₃ | SO₂Me | CH₂CO₂H | CH₂ | 4-COCH₃-phe |
| H/SO₂Me | CH(OH)CH₃ | CH₂CO₂H | CH₂ | 3-Cl-4-CN-phe |
| H/SO₂Me | CH(OH)CH₃ | CH₂CO₂H | CH₂ | 3-Cl-4-COCH₃-phe |
| H/SO₂Me | CH(OH)CH₃ | CH₂CO₂H | CH₂ | 4-CF₃-phe |
| H/SO₂Me | CH(OH)CH₃ | CH₂CO₂H | CH₂ | 2-Cl-4-CF₃-phe |
| H/SO₂Me | CH(OH)CH₃ | CH₂CO₂H | CH₂ | 3-Cl-4-CF₃-phe |
| H/SO₂Me | CH(OH)CH₃ | CH₂CO₂H | CH₂ | 2,6-Cl₂-phe |
| H/CH(OH)CH₃ | SO₂Me | CH₂CO₂H | CH₂ | 2,4,6-F₃-phe |
| H/CO₂CH₃ | SO₂Me | CH(CH₃)CO₂R | CH₂ | 2,4-Cl₂2-phe |
| H/CO₂CH₃ | SO₂Me | CH₂CO₂H | CH₂ | 2,4-Cl₂2-Phe |
| H/SO₂Me | CO₂CH₃ | CH₂CO₂H | CH₂ | 3,4-Cl₂-phe |
| H/SO₂Me | CO₂CH₃ | CH₂CO₂H | CH₂ | 4-Cl-phe |

TABLE IV-continued

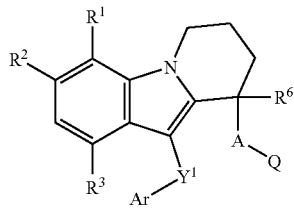

| R¹/R² | R³ | A—Q/R⁶ | Y¹ | Ar |
|---|---|---|---|---|
| H/SO₂Me | CO₂CH₃ | CH₂CO₂H | CH₂ | 2-Cl-4-F-phe |
| H/CO₂CH₃ | SO₂Me | CH₂CO₂H | CH₂ | 2-F-4-Cl-phe |
| H/CO₂CH₃ | SO₂Me | CH₂CO₂H | 1,1-c-pr | 4-Cl-phe |
| H/CO₂CH₃ | SO₂Me | CH₂CO₂H | CH₂ | 2,4,6-Cl₃-phe |
| H/CO₂CH₃ | SO₂Me | CH₂CO₂H | CH₂ | 2,3,4-Cl₃-phe |
| H/CO₂CH₃ | SO₂Me | CH₂CO₂H | CH₂ | 2-Br-4-Cl-phe |
| H/CO₂CH₃ | SO₂Me | CH₂CO₂H | CH₂ | 2-Cl-4-Br-phe |
| H/CO₂CH₃ | SO₂Me | CH₂CO₂H | CH₂ | 2-F-4-Br-phe |
| H/CO₂CH₃ | SO₂Me | CH₂CO₂H | CH₂ | 2-Cl-4-CN-phe |
| H/CO₂CH₃ | SO₂Me | CH₂CO₂H | CH₂ | 2-Cl-4-COCH₃-phe |
| H/CO₂CH₃ | SO₂Me | CH₂CO₂H | CH₂ | 4-CN-phe |
| H/CO₂CH₃ | SO₂Me | CH₂CO₂H | CH₂ | 4-COCH₃-phe |
| H/CO₂CH₃ | SO₂Me | CH₂CO₂H | CH₂ | 3-Cl-4-CN-phe |
| H/CO₂CH₃ | SO₂Me | CH₂CO₂H | CH₂ | 3-Cl-4-COCH₃-phe |
| H/CO₂CH₃ | SO₂Me | CH₂CO₂H | CH₂ | 4-CF₃-phe |
| H/CO₂CH₃ | SO₂Me | CH₂CO₂H | CH₂ | 2-Cl-4-CF₃-phe |
| H/CO₂CH₃ | SO₂Me | CH₂CO₂H | CH₂ | 3-Cl-4-CF₃-phe |
| H/CO₂CH₃ | SO₂Me | CH₂CO₂H | CH₂ | 2,6-Cl₂-phe |
| H/CO₂CH₃ | SO₂Me | CH₂CO₂H | CH₂ | 2,4,6-F₃-phe |
| H/CO₂CH₃ | SO₂Me | CH₂CO₂H | SO₂ | 2,4-Cl₂-phe |
| H/CO₂CH₃ | SO₂Me | CH₂CO₂H | SO₂ | 3,4-Cl₂-phe |
| H/CO₂CH₃ | SO₂Me | CH₂CO₂H | SO₂ | 4-Cl-phe |
| H/CO₂CH₃ | SO₂Me | CH₂CO₂H | CH₂ | 2,4-Cl₂-phe |
| H/CO₂CH₃ | SO₂Me | CH₂CO₂H | CH₂ | 3,4-Cl₂-phe |
| H/CO₂CH₃ | SO₂Me | CH₂CO₂H | CH₂ | 4-Cl-phe |
| H/CO₂CH₃ | SO₂Me | CHCH₃CO₂H | CH₂ | 2,4-Cl₂-phe |
| H/CO₂CH₃ | SO₂Me | CHCH₃CO₂H | CH₂ | 3,4-Cl₂-phe |
| H/CO₂CH₃ | SO₂Me | CHCH₃CO₂H | CH₂ | 4-Cl-phe |
| H/CO₂CH₃ | SO₂Me | CH₂CO₂H/CH₃ | CH₂ | 2,4-Cl₂-phe |
| H/CO₂CH₃ | SO₂Me | CH₂CO₂H/CH₃ | CH₂ | 3,4-Cl₂-phe |
| H/CO₂CH₃ | SO₂Me | CH₂CO₂H/CH₃ | CH₂ | 4-Cl-phe |
| H/SO₂Me | 4-CO₂CH₂CH₃ | CH₂CO₂H | CH₂ | 3,4-Cl₂-phe |
| H/SO₂Me | 4-CO₂CH₂CH₃ | CH₂CO₂H | CH₂ | 4-Cl-phe |
| H/C(OH)(CH₂)₂ | SO₂Me | CH₂CO₂H | CH₂ | 2,4-Cl₂-phe |
| H/C(OH)(CH₂)₂ | SO₂Me | CH₂CO₂H | CH₂ | 3,4-Cl₂-phe |
| H/C(OH)(CH₂)₂ | SO₂Me | CH₂CO₂H | CH₂ | 4-Cl-phe |
| H/(thiophen-2-yl) | SO₂Me | CH₂CO₂H | CH₂ | 2,4-Cl₂-phe |
| H/(thiophen-2-yl) | SO₂Me | CH₂CO₂H | CH₂ | 3,4-Cl₂-phe |
| H/(thiophen-2-yl) | F | CH₂CO₂H | CH₂ | 2,4-Cl₂-phe |
| H/(thiophen-2-yl | F | CH₂CO₂H | CH₂ | 3,4-Cl₂-phe |
| H/(tbiophen-2-yl) | F | CH₂CO₂H | CH₂ | 4-Cl-phe |
| H/(2-oxazolyl) | F | CH₂CO₂H | CH₂ | 2,4-Cl₂-phe |
| H/(2-oxazolyl) | F | CH₂CO₂H | CH₂ | 3,4-Cl₂-phe |
| H/(2-oxazolyl) | F | CH₂CO₂H | CH₂ | 4-Cl-phe |
| H/(2-oxazolyl) | SO₂Me | CH₂CO₂H | CH₂ | 2,4-Cl₂-phe |
| H/(2-oxazolyl) | SO₂Me | CH₂CO₂H | CH₂ | 3,4-Cl₂-phe |
| H/(2-oxazolyl) | SO₂Me | CH₂CO₂H | CH₂ | 4-Cl-phe |
| H/i-Pr | SO₂Me | CH₂CO₂H | CH₂ | 2,4-Cl₂-phe |
| H/i-Pr | SO₂Me | CH₂CO₂H | CH₂ | 3,4-Cl₂-phe |
| H/i-Pr | SO₂Me | CH₂CO₂H | CH₂ | 4-Cl-phe |
| H/c-Pr | SO₂Me | CH₂CO₂H | CH₂ | 2,4-Cl₂-phe |
| H/c-Pr | SO₂Me | CH₂CO₂H | CH₂ | 3,4-Cl₂-phe |
| H/c-Pr | SO₂Me | CH₂CO₂H | CH₂ | 4-Cl-phe |
| H/i-Pr | F | CH₂CO₂H | CH₂ | 2,4-Cl₂-phe |
| H/i-Pr | F | CH₂CO₂H | CH₂ | 3,4-Cl₂-phe |
| H/i-Pr | F | CH₂CO₂H | CH₂ | 4-Cl-phe |
| H/c-Pr | F | CH₂CO₂H | CH₂ | 2,4-Cl₂-phe |
| H/c-Pr | F | CH₂CO₂H | CH₂ | 3,4-Cl₂-phe |
| H/c-Pr | F | CH₂CO₂H | CH₂ | 4-Cl-phe |
| H/i-Bu | F | CH₂CO₂H | CH₂ | 2,4-Cl₂-phe |
| H/i-Bu | F | CH₂CO₂H | CH₂ | 3,4-Cl₂-phe |
| H/i-Bu | F | CH₂CO₂H | CH₂ | 4-Cl-phe |
| H/Br | F | CH₂CO₂H | CH₂ | 2,4-Cl₂-phe |
| H/Br | F | CH₂CO₂H | CH₂ | 3,4-Cl₂-phe |
| H/Br | F | CH₂CO₂H | CH₂ | 4-Cl-phe |
| H/I | F | CH₂CO₂H | CH₂ | 2,4-Cl₂-phe |

TABLE IV-continued

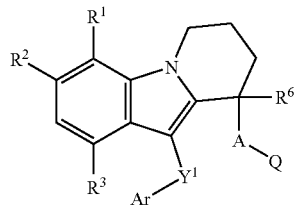

| R¹/R² | R³ | A—Q/R⁶ | Y¹ | Ar |
|---|---|---|---|---|
| H/I | F | $CH_2CO_2H$ | $CH_2$ | 3,4-$Cl_2$-phe |
| H/I | F | $CH_2CO_2H$ | $CH_2$ | 4-Cl-phe |
| H/Cl | F | $CH_2CO_2H$ | $CH_2$ | 2,4-$Cl_2$-phe |
| H/Cl | F | $CH_2CO_2H$ | $CH_2$ | 3,4-$Cl_2$-phe |
| H/Cl | F | $CH_2CO_2H$ | $CH_2$ | 4-Cl-phe |
| H/F | c-Bu | $CH_2CO_2H$ | $CH_2$ | 2,4-$Cl_2$-phe |
| H/F | c-Bu | $CH_2CO_2H$ | $CH_2$ | 3,4-$Cl_2$-phe |
| H/F | c-Bu | $CH_2CO_2H$ | $CH_2$ | 4-Cl-phe |
| H/F | $C(OH)(CH_2)_3$ | $CH_2CO_2H$ | $CH_2$ | 2,4-$Cl_2$-phe |
| H/F | $C(OH)(CH_2)_3$ | $CH_2CO_2H$ | $CH_2$ | 3,4-$Cl_2$-phe |
| H/P | $C(OH)(CH_2)_3$ | $CH_2CO_2H$ | $CH_2$ | 4-Cl-phe |
| H/$SO_2Me$ | $C(OH)(CH_2)_3$ | $CH_2CO_2H$ | $CH_2$ | 2,4-$Cl_2$-phe |
| H/$SO_2Me$ | $C(OH)(CH_2)_3$ | $CH_2CO_2H$ | $CH_2$ | 3,4-$Cl_2$-phe |
| H/$SO_2Me$ | $C(OH)(CH_2)_3$ | $CH_2CO_2H$ | $CH_2$ | 4-Cl-phe |
| H/$SO_2Me$ | (2-oxetanyl) | $CH_2CO_2H$ | $CH_2$ | 2,4-$Cl_2$-phe |
| H/$SO_2Me$ | (2-oxetanyl) | $CH_2CO_2H$ | $CH_2$ | 3,4-$Cl_2$-phe |
| H/$SO_2Me$ | (2-oxetanyl) | $CH_2CO_2H$ | $CH_2$ | 4-Cl-phe |
| H/F | (2-oxetanyl) | $CH_2CO_2H$ | $CH_2$ | 2,4-$Cl_2$-phe |
| H/F | (2-oxetanyl) | $CH_2CO_2H$ | $CH_2$ | 3,4-$Cl_2$-phe |
| H/F | (2-oxetanyl) | $CH_2CO_2H$ | $CH_2$ | 4-Cl-phe |

TABLE V

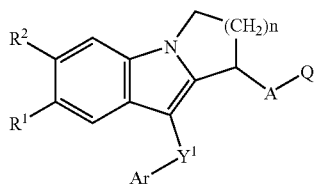

| R¹ | R² | n | A–Q | Y1 | Ar |
|---|---|---|---|---|---|
| F | H | 1 | $CH_2CO_2H$ | O | 2-Br-4-Cl-phe |
| F | H | 1 | $CH_2CO_2H$ | O | 2-Cl-4-Br-phe |
| F | H | 1 | $CH_2CO_2H$ | CH | 2-F-4-Br-phe |
| $C(O)CH_3$ | $SO_2Me$ | 1 | $CH(CH_3)CO_2H$ | $CH_2$ | 2,4-$Cl_2$-phe |
| 5-F | H | 2 | $CH_2CO_2H$ | $CH_2$ | 2-Br-4-Cl-phe |
| 5-F | H | 2 | $CH_2CO_2H$ | O | 2-Cl-4-Br-phe |
| 5-F | H | 2 | $CH_2CO_2H$ | S | 2-F-4-Br-phe |
| $C(O)CH_3$ | $SO_2Me$ | 2 | $CH(CH_3)CO_2H$ | $CH_2$ | 2,4-$Cl_2$-phe |

Assays for Determining Biological Activity

Compounds of formula I can be tested using the following assays to determine their prostanoid antagonist or agonist activity in vitro and in vivo and their selectivity. The prostaglandin receptor activities demonstrated are DP, $EP_1$, $EP_2$, $EP_3$, $EP_4$, FP, IP and TP.

Stable Expression of Prostanoid Receptors in the Human Embryonic Kidney (HEK) 293(EBNA) Cell Line Prostanoid receptor cDNAs corresponding to full length coding sequences are subcloned into the appropriate sites of mammalian expression vectors and transfected into HEK 293(ebna) cells. HEK 293(ebna) cells expressing the individual cDNAs are grown under selection and individual colonies are isolated after 2–3 weeks of growth using the cloning ring method and subsequently expanded into clonal cell lines.

Prostanoid Receptor Binding Assays

HEK 293(ebna) cells are maintained in culture, harvested and membranes are prepared by differential centrifugation, following lysis of the cells in the presence of protease inhibitors, for use in receptor binding assays. Prostanoid receptor binding assays are performed in 10 mM MES/KOH (pH 6.0) (EPs, FP and TP) or 10 mM HEPES/KOH (pH 7.4) (DP and IP), containing 1 mM EDTA, 10 mM divalent cation and the appropriate radioligand. The reaction is initiated by addition of membrane protein. Ligands are added in dimethylsulfoxide which is kept constant at 1% (v/v) in all incubations. Non-specific binding is determined in the presence of 1 μM of the corresponding non-radioactive prostanoid. Incubations are conducted for 60 min at room temperature or 30° C. and terminated by rapid filtration. Specific binding is calculated by subtracting non specific binding from total binding. The residual specific binding at each ligand concentration is calculated and expressed as a function of ligand concentration in order to construct siginoidal concentration-response curves for determination of ligand affinity.

Prostanoid Receptor Agonist and Antagonist Assays

Whole cell second messenger assays measuring stimulation ($EP_2$, $EP_4$, DP and IP in HEK 293(ebna) cells) or inhibition ($EP_3$ in human erythroleukemia (HEL) cells) of intracellular cAMP accumulation or mobilization of intracellular calcium ($EP_1$, FP and TP in HEK 293(ebna) cells stably transfected with apo-aequorin) are performed to determine whether receptor ligands are agonists or antagonists. For cAMP assays, cells are harvested and resuspended in HBSS containing 25 mM HEPES, pH 7.4. Incubations contain 100 µM RO-20174 (phosphodiesterase type IV inhibitor, available from Biomol) and, in the case of the $EP_3$ inhibition assay only, 15 µM forskolin to stimulate cAMP production. Samples are incubated at 37° C. for 10 min, the reaction is terminated and cAMP levels are then measured. For calcium mobilization assays, cells are charged with the co-factors reduced glutathione and coelenterazine, harvested and resuspended in Ham's F12 medium. Calcium mobilization is measured by monitoring luminescence provoked by calcium binding to the intracellular photoprotein aequorin. Ligands are added in dimethylsulfoxide which is kept constant at 1% (v/v) in all incubations. For agonists, second messenger responses are expressed as a function of ligand concentration and both $EC_{50}$ values and the maximum response as compared to a prostanoid standard are calculated. For antagonists, the ability of a ligand to inhibit an agonist response is determined by Schild analysis and both $K_B$ and slope values are calculated.

Prevention of PGD2 or Allergen Induced Nasal Congestion in Allergic Sheep

Animal preparation: Healthy adult sheeps (18–50 kg) are used. These animals are selected on the basis of a natural positive skin reaction to an intradermal injection of Ascaris suum extract.

Measurements of nasal congestion: The experiment is performed on conscious animals. They are restained in a cart in a prone position with their heads immobilized. Nasal airway resistance (NAR) is measured using a modified mask rhinometry technique. A topical anaesthesia (2% lidocaine) is applied to the nasal passage for the insertion of a nasotracheal tube. The maximal end of the tube is connected to a pneumaotachograph and a flow and pressure signal is recorded on an oscilloscope linked to a computer for on-line calculation of NAR. Nasal provocation is performed by the administration of an aerosolized solution (10 puffs/nostril). Changes in the NAR congestion are recorded prior to and for 60–120 minutes post-challenge.

Prevention of PGD2 and Allergen Induced Nasal Obstruction in Cynomolgus Monkey

Animal preparation: Healthy adult male cynomologus monkeys (4–10 kg) are used. These animals are selected on the basis of a natural positive skin reaction to an intradermal injection of *Ascaris suum* extract. Before each experiment, the monkey selected for a study is fasted overnight with water provided at *libitum*. The next morning, the animal is sedated with ketamine (10–15 mg/kg i.m.) before being removed from its home cage. It is placed on a heated table (36° C.) and injected with a bolus dose (5–12 mg/kg i.v.) of propofol. The animal is intubated with a cuffed endotracheal tube (4–6 mm I.D.) and anaesthesia is maintained via a continuous intravenous infusion of propofol (25–30 mg/kg/h). Vital signs (heart rate, blood pressure, respiratory rate, body temperature) are monitored throughout the experiment.

Measurements of nasal congestion: A measurement of the animal respiratory resistance is taken via a pneumotachograph connected to the endotracheal tube to ensure that it is normal. An Ecovision accoustic rhinometer is used to evaluate nasal congestion. This technique gives a non-invasive 2D echogram of the inside of the nose. The nasal volume and the minimal cross-sectional area along the length of the nasal cavity are computed within 10 seconds by a laptop computer equipped with a custom software (Hood Laboratories, Mass, U.S.A.). Nasal challenge is delivered directly to the animal's nasal cavity (50 µL volume). The changes in nasal congestion are recorded prior to and for 60–120 minutes post-challenge. If nasal congestion occurs, it will translate into a reduction in the nasal volume.

Pulmonary Mechanics in Trained Conscious Squirrel Monkeys

The test procedure involves placing trained squirrel monkeys in chairs in aerosol exposure chambers. For control purposes, pulmonary mechanics measurements of respiratory parameters are recorded for a period of about 30 minutes to establish each monkey's normal control values for that day. For oral administration, compounds are dissolved or suspended in a 1% methocel solution (methylcellulose, 65HG, 400 cps) and given in a volume of 1 mL/kg body weight. For aerosol administration of compounds, a DeVilbiss ultrasonic nebulizer is utilized. Pretreatment periods vary from 5 minutes to 4 hours before the monkeys are challenged with aerosol doses of either PGD2 or Ascaris suum antigen; 1:25 dilution.

Following challenge, each minute of data is calculated by computer as a percent change from control values for each respiratory parameter including airway resistance ($R_L$) and dynamic compliance ($C_{dyn}$). The results for each test compound are subsequently obtained for a minimum period of 60 minutes post-challenge which are then compared to previously obtained historical baseline control values for that monkey. In addition, the overall values for 60 minutes post-challenge for each monkey (historical baseline values and test values) are averaged separately and are used to calculate the overall percent inhibition of mediator or Ascaris antigen response by the test compound. For statistical analysis, paired t-test is used. (References: McFarlane, C. S. et al., Prostaglandins, 28, 173–182 (1984) and McFarlane, C. S. et al., Agents Actions, 22, 63–68 (1987).)

Prevention of Induced Bronchoconstriction in Allergic Sheep

Animal Preparation: Adult sheep with a mean weight of 35 kg (range, 18 to 50 kg) are used. All animals used meet two criteria: a) they have a natural cutaneous reaction to 1:1,000 or 1:10,000 dilutions of Ascaris suum extract (Greer Diagnostics, Lenois, N.C.); and b) they have previously responded to inhalation challenge with Ascaris suum with both an acute bronchoconstriction and a late bronchial obstruction (W. M. Abraham et al., Am. Rev. Resp. Dis., 128, 839–44 (1983)).

Measurement of Airway Mechanics: The unsedated sheep are restrained in a cart in the prone position with their heads immobilized. After topical anesthesia of the nasal passages with 2% lidocaine solution, a balloon catheter is advanced through one nostril into the lower esophagus. The animals are then intubated with a cuffed endotracheal tube through the other nostril using a flexible fiberoptic bronchoscope as a guide. Pleural pressure is estimated with the esophageal balloon catheter (filled with one mL of air), which is positioned such that inspiration produces a negative pressure deflection with clearly discernible cardiogenic oscillations. Lateral pressure in the trachea is measured with a sidehole catheter (inner dimension, 2.5 mm) advanced through and positioned distal to the tip of the nasotracheal tube. Transpulmonary pressure, the difference between tracheal pressure and pleural pressure, is measured with a differential pressure transducer (DP45; Validyne Corp., Northridge, Calif.). For the measurement of pulmonary resistance ($R_L$), the maximal end of the nasotrachel tube is connected to a pneumotachograph (Fleisch, Dyna Sciences, Blue Bell, Pa.). The signals of flow and transpulmonary pressure are recorded on an oscilloscope (Model DR-12; Electronics for Medicine, White Plains, N.Y.) which is linked to a PDP-11

Digital computer (Digital Equipment Corp., Maynard, Mass.) for on-line calculation of $R_L$ from transpulmonary pressure, respiratory volume obtained by integration and flow. Analysis of 10–15 breaths is used for the determination of $R_L$. Thoracic gas volume ($V_{tg}$) is measured in a body plethysmograph, to obtain specific pulmonary resistance ($SR_L = R_L \cdot V_{tg}$).

The invention will now be illustrated in the following non-limiting Examples in which, unless otherwise stated:
1. All the end products of the formula I were analyzed by NMR, TLC and elementary analysis or mass spectroscopy.
2. Intermediates were analyzed by NMR and TLC.
3. Most compounds were purified by flash chromatography on silica gel, recrystallization and/or swish (suspension in a solvent followed by filtration of the solid).
4. The course of reactions was followed by thin layer chromatography (TLC) and reaction times are given for illustration only.
5. The enantiomeric excess was measured on normal phase HPLC with a chiral column: ChiralPak AD; 250×4.6 mm.

EXAMPLE 1

(+/−)-[10-(4-Chlorobenzyl)-6,7,8,9-tetrahydropyrido[1,2-a]indol-9-yl]acetic acid

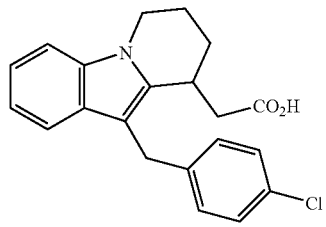

Step 1: 3-(4-Chlorobenzyl)-1H-indole

To a vigorously stirred solution of 30 mL of 3M MeMgBr in ether was added dropwise a solution of 10 g of indole in 100 mL of ether. After addition was finished, the mixture was heated to reflux for 30 minutes and treated with 22 g of p-chlorobenzyl bromide. The reaction mixture was refluxed for 3 hours, quenched with 50 mL of saturated aqueous solution of NH$_4$Cl, and extracted with 200 mL of ether. The ether layer was dried over Na$_2$SO$_4$ and concentrated. The residue was purified by silica gel flash chromatography eluted with toluene to give 6 g of the title compound as a beige solid.

$^1$H NMR (acetone-d$_6$) δ 7.42 (1H, d), 7.38 (1H, d), 7.26 (4H, dd), 7.15 (1H, s), 7.07 (1H, t), 6.95 (1H, t), 4.10 (2H, s).

Step 2: 2-Bromo-3-(4-chlorobenzyl)-1H-indole

To a solution of 2 g of 3-(4-chlorobenzyl)-1H-indole in 50 mL of CCl$_4$ was added 1.8 g of NBS. The reaction mixture was stirred for 1 hour at room temperature and diluted with 50 mL of 5:1 hexane/EtOAc. The mixture was then filtered through a pad of silica gel and the filtrate was concentrated under reduced pressure to give the crude title compound, which was used for the next step without further purification.

$^1$H NMR (acetone-d$_6$) δ 7.40 (1H, d), 7.35 (1H, d), 7.25 (4H, dd), 7.10 (1H, t), 6.09 (1H, t), 4.08 (2H, s)

Step 3: Ethyl 4-[2-bromo-3-(4-chlorobenzyl)-1H-1-indolyl]butanoate

To a vigorously stirred solution of 0.32 g of the product from Step 2 in 5 mL of DMF was added sequentially 0.045 g NaH (60% in mineral oil), 0.2 mL of ethyl 4-bromobutyrate and 0.02 g of n-Bu$_4$NI. The mixture was stirred for 45 minutes at room temperature, quenched with 5 mL of saturated aqueous solution of NH$_4$Cl and 5 mL of water, and extracted with 40 mL of 1:1 hexane/EtOAc. The extract was dried over Na$_2$SO$_4$ and concentrated. The residue was purified by silica gel flash chromatography eluted with 9:1 hexane/EtOAc to give 0.3 g of the title compound as an oil.

$^1$H NMR (acetone-d$_6$) δ 7.49 (1H, d), 7.42 (1H, d), 7.27 (4H, dd), 7.16 (1H, t), 7.02 (1H, t), 4.35 (2H, t), 4.10 (2H, s), 4.05 (2H, q), 2.38 (2H, t), 2.12 (2H, m), 1.18 (3H, t).

Step 4: 4-[2-Bromo-3-(4-chlorobenzyl)-1H-1-indolyl]butanal

To a vigorously stirred solution of 0.3 g of the product from Step 3 in 5 mL of THF cooled at −78° C. was added dropwise a solution of diisobutylaluminum hydride (4 mL, 1 M in hexane). After stirring for 30 minutes at −78° C., the reaction was quenched with 1 mL of acetone followed by 10 mL of 20% aqueous solution of potassium sodium tartrate. The mixture was extracted with 20 mL of 1:1 hexane/EtOAc and the extract was dried over Na$_2$SO$_4$ and concentrated. The residue was purified by silica gel flash chromatography eluted with 8:1 hexane/EtOAc to give 0.19 g of the title compound as an oil.

$^1$H NMR (acetone-d$_6$) δ 9.72 (1H, s), 7.50 (1H, d), 7.42 (1H, d), 7.27 (4H, dd), 7.16 (1H, t), 7.01 (1H, t), 4.32 (2H, t), 4.10 (2H, s), 2.56 (2H, t), 2.06 (2H, m).

Step 5: Ethyl (E)-6-[2-bromo-3-(4-chlorobenzyl)-1H-1-indolyl]-2-hexenoate

To a solution of the product obtained in Step 4 in 8 mL of THF was added 0.3 g (carbethoxymethylene)triphenylphosphorane. The reaction mixture was stirred for 2 hours at 50° C. and diluted with 20 mL of 10:1 hexane/EtOAc. The mixture was then filtered through a pad of silica gel and the filtrate was concentrated under reduced pressure. The residue was purified by silica gel flash chromatography eluted with 9:1 hexane/EtOAc to give 0.2 g of the title compound as an oil.

Step 6: E/Z-Ethyl 2-[10-(4-chlorobenzyl)-6,7,8,9-tetrahydropyrido[1,2-a]indol-9-yliden]acetate

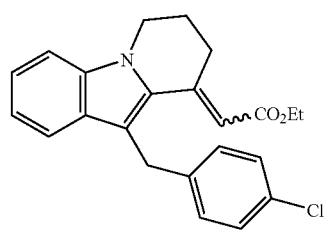

To a vigorously stirred solution of 0.13 g of the product from Step 5 in 4 mL of DMF under N$_2$ atmosphere was added sequentially 0.75 g of n-Bu₄NCl, 0.1 mL of Et₃N and 0.022 g of Pd(AcO)₂. The mixture was stirred for 1 hour at 75° C. and then concentrated under reduced pressure. The residue was purified by silica gel flash chromatography eluted with 6:1 hexane/EtOAc to give 0.07 g of the more mobile isomer followed by 0.06 g of the less mobile isomer.

¹H NMR (acetone-d₆) (more mobile isomer) δ 7.56 (1H, d), 7.43 (1H, d), 7.30 (2H, d), 7.23 (1H, t), 7.18 (2H, d), 7.19 (1H, t), 6.08 (1H, s), 4.35 (2H, s), 4.23 (2H, t), 4.10 (2H, q), 3.28 (2H, m), 2.14 (2H, m), 1.20 (3H, t).

¹H NMR (acetone-d₆) (less mobile isomer) δ 7.38 (1H, d), 7.34 (1H, d), 7.22 (2H, d), 7.10–7.20 (3H, m), 7.45(2H, t), 7.45 (1H, t), 4.27 (2H, s), 4.15 (2H, t), 4.08 (2H, q), 3.47 (2H, s), 2.63 (2H, m), 1.14 (3H, t).

Step 7: (+/−)-Ethyl 2-[10-(4-chlorobenzyl)-6,7,8,9-tetrahydropyrido[1,2-a]indol-9-yl]acetate A mixture of 0.06 g of the less mobile isomer obtained in Step 6 and 0.03 g of Pd/C (5%, w/w) in 25 mL of EtOAc was shaken under 40 psi of H₂ for 3 hours. The mixture was then filtered through a pad of celite and the filtrate was concentrated. The residue was purified by silica gel flash chromatography eluted with 6:1 hexane/EtOAc to give 0.05 g of the title compound as an oil.

¹H NMR (acetone-d₆) δ 7.30 (1H, d), 7.28(1H, d), 7.24 (1H, d), 7.18 (2H, d), 7.09 (1H, t), 6.97 (2H, t), 4.38 (1H, m), 4.02–4.13 (4H, m), 3.78 (1H, td), 3.70 (1H, m), 2.63 (1H, dd), 2.50 (1H, dd), 2.20 (1H, m), 1.85–2.05 (3H, m), 1.18 (3H, t).

Step 8: (+/−)-[10-(4-Chlorobenzyl)-6,7,8,9-tetrahydropyrido[1,2-a]indol-9-yl]acetic acid To a stirred solution of 0.03 g of the product from Step 7 in 2 mL of THF and 1 mL of MeOH was added 1 mL of 1N LiOH solution. The mixture was stirred for 2 hours at room temperature quenched with 1 mL of AcOH and 5 mL of brine. The mixture was extracted with 20 mL of EtOAc and the extract was dried over Na₂SO₄ and concentrated. The residue was swished from 10:1 hexane/EtOAc to give 0.02 g of the title compound as a beige solid.

¹H NMR (acetone-d₆) δ 7.30 (1H, d), 7.22 (4H, dd), 7.08 (1H, t), 6.96 (2H, t), 4.30 (1H, m), 4.12 (2H, q), 3.80 (1H, td), 3.72 (1H, m), 2.65 (1H, dd), 2.52 (1H, dd), 2.22 (1H, m), 1.90–2.05 (3H, m).

MS (−APCI) m/z 352.3 (M−H)⁺.

EXAMPLE 2

(+/−r-[9-(4-chlorobenzyl)-2,3-dihydro-1H-pyrrolo[1,2-a]indol-1-yl]acetic acid

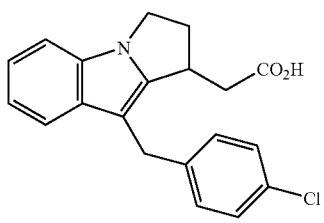

Step 1: 2-Bromo-3-(4-chlorobenzyl)-1-[2-(1,3-dioxolan-2-yl)ethyl]-1H-indole

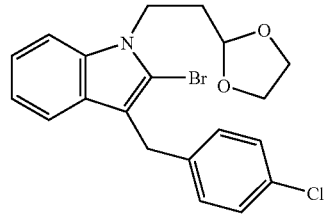

To a vigorously stirred solution of 0.32 g of the product from Step 2 of Example 1 in 5 mL of DMF was added sequentially 0.055 g NaH (60% in mineral oil), 0.27 mL of 2-(2-bromoethyl)-1,3-dioxolane and 0.01 g of n-Bu₄NI. The mixture was stirred for 3 hours at room temperature and then quenched with 5 mL of saturated aqueous solution of NH₄Cl and 5 mL of water, and extracted with 50 mL of 1:1 hexane/EtOAc. The extract was dried over Na₂SO₄ and concentrated. The residue was purified by silica gel flash chromatography eluted with 9:1 hexane/EtOAc to give 0.3 g of the title compound as an oil.

¹HNMR (acetone-d₆) δ 7.43 (2H, d), 7.27 (4H, dd), 7.17 (2H, t), 7.00 (1H, t), 4.90 (1H, t), 4.39 (2H, t), 4.10 (2H, s), 3.96 (2H, m), 3.82 (2H, m), 2.05 2H, m).

Step 2: Ethyl (E)-5-[2-bromo-3-(4-chlorobenzyl)-1H-1-indolyl]-2-pentenoate

A solution of 0.3 g of the product from Step 1 in 8 mL of AcOH and 2 mL of water was stirred for 3 days at 45° C. The mixture was concentrated by co-evaporation with 2×20 mL of toluene and the residue was dissolved in 10 mL of THF and treated with 0.35 g of (carbethoxymethylene)triphenylphosphorane. The reaction mixture was stirred for 2 hours at 50° C., diluted with 50 mL of 5:1 hexane/EtOAc, and then filtered through a pad of silica gel. The filtrate was concentrated under reduced pressure and the residue was purified by silica gel flash chromatography eluted with 9:1 hexane/EtOAc to give 0.3 g of the title compound as an oil.

¹H NMR (acetone-d₆) δ 7.50 (1H, d), 7.42(1H, d), 7.25 (4H, s), 7.18 (2H, t), 7.00 (1H, t), 6.90–7.02 (1H, dt), 5.78 (1H, d), 4.49 (2H, t), 4.00–4.13 (4H, m), 2.70 (2H, m), 1.20 (3H, t).

Step 3: (+/−)-[9-(4-Chlorobenzyl-2,3-dihydro-1H-pyrrolo[1,2-a]indol-1-yl]acetic acid Starting from the product of Step 2 the title compound was prepared as a beige solid by following the procedures described in Steps 6–8 for Example 1.

¹H NMR (acetone-d₆) δ 7.42 (1H, d), 7.20–7.28 (5H, m), 7.03 (1H, t), 6.92 (1H, t), 4.16 (1H, m), 4.12 (2H, s), 4.06 (1H, m), 3.18 (1H, m), 2.75–2,90 (2H, m), 2.55 (1H, dd), 2.40 (1H, m).

MS (−APCI) m/z 338.3 (M−H)⁺.

EXAMPLE 3

(+/−)-[10-[(4-chlorophenyl)sulfanyl]-6,7,8,9-tetrahydropyrido[1,2-a]indol-9-yl]acetic acid

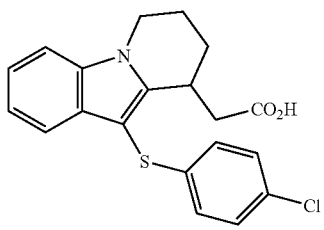

Step 1: 3-[(4-Chlorophenyl)sulfanyl]-1H-indole

To a vigorously stirred solution of 5.2 g of indole in 100 mL of DMF was added 2.9 g of NaH (60% in mineral oil). After stirring for 15 minutes, 14.4 g of bis(4-chlorophenyl) disulfide was added. The resulting mixture was stirred for 14 hours and quenched with 15 mL of AcOH and concentrated under reduced pressure. The residue was dissolved in 200 mL of 1:1 hexane/EtOAc and filtered through a pad of silica gel. The filtrate was concentrated and the crude product was swished from 50 mL of 10:1 hexane/EtOAc to give 8.5 g of the title compound as a white solid.

$^1$H NMR (acetone-$d_6$) δ 7.70 (1H, d), 7.54 (1H, d), 7.47 (1H, d), 7.18–7.25 (3H, m), 7.03–7.13 (3H, m).

Step 2: (+/−)-[9-[(4-Chlorophenyl)sulfanyl]-2,3-dihydro-1H-pyrrolo[1,2-a]indol-1-yl]acetic acid Starting from the product obtained in Step 1, the title compound was synthesized following the procedures described in Step 2–8 of Example 1.

$^1$H NMR (acetone-$d_6$) δ 7.46 (1H, d), 7.40 (11, d), 7.13–7.25 (3H, m), 7.10 (1H, t), 6.99 (2H, d), 4.33 (1H, m), 4.00 (1H, m), 3.78 (1H, m), 2.85 (1H, dd), 2.72 (1H, dd), 2.25 (1H, m), 1.95–2.10 (3H, m).

EXAMPLE 4

(+/−)-[10-[(4-chlorophenyl)sulfanyl]-3-(methylsulfonyl)-6,7,8,9-tetrahydropyrido[1,2-a]indol-9-yl]acetic acid

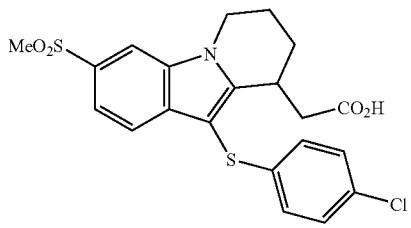

Step 1: Ethyl 6-(methylsulfanyl)-1H-2-indolecarboxylate

Starting from 3-(methylthio)aniline and ethyl 2-methylacetoacetate, th title compound was prepared by following the published procedure for ethyl 6-methoxy-3-methyl-1H-2-indolecarboxylate (T. Gan et al, J. Org. Chem. 1997, 62, 9298–9304).

$^1$H NMR (acetone-$d_6$) δ 7.60 (1H, d), 7.40 (1H, s), 7.13 (1H, d), 7.05 (dd), 4.35 (2H, q), 2.52 (3H, s), 1.35 (3H, t).

Step 2: 1H-6-Indolyl methyl sulfide

Starting from ethyl 6-(methylsulfanyl)-1H-2-indolecarboxylate, the title compound was prepared by following the published decarboxylation procedure (T. Gan et al, J Org. Chem. 1997, 62, 9298–9304).

$^1$H NMR (acetone-$d_6$) δ 7.50 (1H, d), 7.40 (1H, s), 7.28 (1H, m), 7.00 (dd), 6.42 (1H, bs), 2.47 (3H, s).

Step 3: 1H-6-Indolyl methyl sulfone

To a solution of 0.1 g of 1H-6-indolyl methyl sulfide in 5 mL of 2:1 $CH_2Cl_2$/MeOH cooled at 0° C. was added 0.4 g of MMPP. The resulting mixture was stirred at room temperature for 2 hours and then quenched with 5 mL of saturated aqueous solution of $Na_2CO_3$ and 5 mL of brine. The mixture was extracted with 40 mL of 1:2 hexane/EtOAc and the extract was dried over $Na_2SO_4$ and concentrated. The residue was purified by silica gel flash chromatography eluted with 1:1 hexane/EtOAc to give 0.08 g of the title compound as a white solid.

$^1$H NMR (acetone-$d_6$) δ 8.07 (1H, s), 7.78 (1H, d), 7.65 (1H, m), 7.55 (1H, d), 6.63 (1H, bs), 3.08 (3H, s).

Step 4: (+/−)-[10-[(4-chlorophenyl)sulfanyl]-3-(methylsulfonyl-6,7,8,9-tetra-hydropyrido[1,2-a]indol-9-yl]acetic acid Starting from 1H-6-indolyl methyl sulfone, the title compound was synthesized following the procedures described in Step 1 of Example 3 and Steps 2–8 of Example 1.

$^1$H NMR (acetone-$d_6$) δ 8.08 (1H, s), 7.67 (1H, d), 7.60 (1H, d), 7.20 (2H, d), 7.03 (2H, d), 4.50 (1H, m), 4.20 (1H, m), 4.83 (1H, m), 3.10 (3H, s), 2.70–2.90 (2H, m), 2.30 (1H, m), 2.00–2.20 (3H, m).

EXAMPLE 5

(+/−)-[10-(4-chlorophenyl) 1-(methylsulfinyl)-6,7,8,9-tetra-hydro-pyrido[1,2-a]indol-9-yl]acetic acid

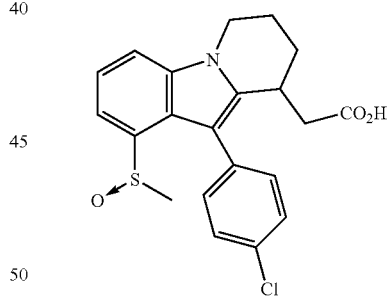

Step 1: (+/−)-Ethyl 2-(4-chlorobenzyl)-3-oxobutanoate

To a suspension of NaH (1.6 g, 40 mmol) in DMF (60 mL) at 0° C. was added ethyl acetoacetate (5.7 g, 44 mmol). The mixture was stirred for 30 minutes and p-chlorobenzyl bromide (8.2 g, 40 mmol) was added. The reaction mixture was stirred at r.t. for 2 hours and then quenched with water and extracted with EtOAc. The combined organic layers were washed with water and brine, dried over $Na_2SO_4$ and concentrated. The residue was purified by silica gel chromatography eluted with 10% EtOAc in Hexanes to provide 6.5 g of the title compound as a colorless oil.

$^1$H NMR (acetone-$d_6$) δ. 7.32–7.20 (4H, m), 4.15–4.03 (2H, m), 3.93 (1H, t), 3.18–3.01 (2H, m), 2.09 (3H, s), 1.15 (3H, t).

Step 2: 2,4-Dibromo-5-(methylsulfanyl)aniline

To a solution of 3-(methylthio)aniline (4 g, 29 mmol) in 150 mL of a 5:1 THF/pyridine mixture at 0° C. was added portionwise PyH.Br$_3$ (18.4 g, 57 mmol). The reaction mixture was stirred for 2 hours at 0° C., warmed and then filtered on a celite pad eluted with EtOAc. The organic layer was washed with saturated aqueous NaHSO$_3$, 1N HCl and brine and concentrated. The residue was purified by silica gel chromatography eluted with 20% EtOAc in Hexanes to provide 7.7 g of the title compound as an orange oil.

$^1$H NMR (acetone-d$_6$) δ 7.47 (1H, s), 6.76 (1H, s), 5.13 (2H, br s), 2.38 (3H, s).

Step 3: Ethyl 5,7-dibromo-3-(4-chlorophenyl)-4-(methylsulfanyl-1H-indole-2-carboxylate To a suspension of the aniline of Step 2 (5.95 g, 20 mmol) in 13 mL of water and 8 mL of concentrated HCl at 0° was added a NaNO$_2$ solution (1.52 g in 3 mL of water). The mixture was stirred for 15 minutes at 0° C. and was adjusted to pH 3 with the addition of NaOAc. In a separate flask, a solution of the ester of Step 1 (5.1 g, 20 mmol) in 27 mL of EtOH was treated with an aqueous solution of KOH (1.12 g in 3 mL of water). The solution was then cooled to −5° C. and the diazonium salt was added to the alkaline solution. The pH was adjusted to 5 with NaOAc and the mixture was stirred at 0° C. for 16 hours. The reaction mixture was extracted with EtOAc and the combined organic layers were dried over MgSO$_4$ and concentrated. The residue was added slowly to a 3N HCl solution in EtOH and was stirred at 70° C. for 2 hours. EtOH was removed by evaporation and water was added. The aqueous layer was extracted with CH$_2$Cl$_2$ and the combined organic layers were dried over Na$_2$SO$_4$ and concentrated. The residue was purified by silica gel chromatography eluted with 25% EtOAc in Hexanes to provide 2.1 g of the title compound as an orange solid.

$^1$H NMR (acetone-d$_6$) δ 7.88 (1H, s), 7.55–7.37 (4H, m), 4.12 (2H, q), 2.01 (3H, s), 1.07 (3H, t). MS (−APCI) m/z 502.0 (M−H)$^-$ Step 4: Ethyl 3-(4-chlorophenyl)-4-(methylsulfanyl)-1H-indole-2-carboxylate To a solution of the indole of step 3 (2.1 g) in 200 mL of EtOAc was added 5% palladium on carbon (1 g). The mixture was shaken under H$_2$ atmosphere (50 psi) for 24 hours, filtered on a silica gel pad eluted with EtOAc and the filtrate concentrated to give the title compound as a white solid (1.5 g) used as such.

Step 5: 3-(4-Chlorophenyl)-4-(methylsulfanyl)-1H-indole-2-carboxylic acid

To a solution of the ester of Step 4 (1.5 g) in EtOH (15 mL) was added 1N KOH solution (13 mL). The reaction mixture was stirred at reflux for 1 hour. The organic solvent was removed by evaporation and the aqueous solution was acidified with 3N HCl and extracted with EtOAc. The combined organic layers were dried over Na$_2$SO$_4$ and concentrated to give the title compound as a white solid (1.4 g).

$^1$H NMR (acetone-d$_6$) δ 7.41–7.35 (5H, m), 7.27 (1H, t), 6.85 (1H, d), 2.29 (3H, s).

Step 6: 3-(4-Chlorophenyl)-1H-indol-4-yl methyl sulfide

To a solution of 1.4 g of the acid of Step 5 in quinoline (10 mL) was added 100 mg of copper powder. The reaction mixture was heated to reflux and stirred for 2 hours. The copper powder was removed by filtration and 6N HCl was added to the filtrate. The aqueous layer was extracted with EtOAc and the combined organic layers were dried over Na$_2$SO$_4$ and concentrated. The residue was purified by silica gel chromatography eluted with 10% EtOAc in Hexanes to provide 750 mg of the title compound as an orange solid foam.

$^1$H NMR (acetone-d$_6$) δ 7.48 (2H, d), 7.37 (2H, d), 7.33–7.29 (2H, m), 7.13 (1H, t), 6.92 (1H, d), 2.31 (3H, s).

Step 7: 2-Bromo-3-(4-chlorophenyl)-1H-indol-4-yl methyl sulfide

To a solution of the indole of Step 6 (650 mg, 2.4 mmol) in CCl$_4$ (15 mL) was added NBS (465 mg, 2.6 mmol). The reaction mixture was heated to 50° C. and stirred for 15 minutes. The resulting suspension was filtered on a SiO$_2$ pad eluted with 50% EtOAc in hexanes and concentrated. The title compound was obtained in a quantitative yield as a brownish solid foam used as such.

Step 8: Ethyl 4-[2-bromo-3-(4-chlorophenyl)-4-(methylsulfanyl-1H-indol-1-yl]butanoate To a solution of the indole of Step 7 (525 mg, 1.5 mmol) in DMF (5 mL) was added NaH (72 mg, 1.8 mmol, 60% in oil) at 0° C. The reaction mixture was stirred at 0° C. for 15 minutes and tetra-n-butylammonium iodide (180 mg) was added, followed by the addition of ethyl 4-bromobutyrate (406 mg, 2.1 mmol). The resulting mixture was stirred for 1 hour 30 minutes at r.t., quenched with saturated aqueous NH$_4$Cl and extracted with EtOAc. The combined organic layers were washed with water and brine, dried over Na$_2$SO$_4$ and concentrated. The residue was purified by silica gel chromatography eluted with 10% EtOAc in Hexanes to provide 330 mg of the title compound as a pale yellow oil.

$^1$H NMR (acetone-d$_6$) δ 7.45–7.38 (5H, m), 7.23 (1H, t), 6.92 (1H, d), 4.41 (2H, t), 4.12 (2H, q), 2.42 (2H, t), 2.29 (3H, s), 2.14–2.04 (2H, m), 1.18 (3H, t).

Step 9: 4-[2-Bromo-3-(4-chlorophenyl)-4-(methylsulfanyl-1H-indol-1-yl]butanal

To a solution of the ester of Step 8 (330 mg, 0.7 mmol) in Et$_2$O (5 mL) at −78° C. was added DIBAL (2 mL, 1M solution in hexanes). The reaction mixture was stirred at −78° C. for 30 minutes and then quenched with 0.5 mL of acetone. 1N HCl was added, the phases were separated and the aqueous layer was extracted with Et$_2$O. The combined organic layers were dried over MgSO$_4$ and concentrated. The residue was purified by silica gel chromatography eluted with 40% EtOAc in Hexanes to provide 270 mg of the title compound as a pale yellow solid.

$^1$H NMR (acetone-d$_6$) δ 9.75 (1H, s), 7.44–7.38 (5H, m), 7.21 (1H, t), 6.90 (1H, d), 4.37 (2H, t), 2.62 (2H, t), 2.29 (3H, s), 2.11–2.02 (2H, m).

Step 10: Ethyl (2 E,Z)-6-[2-bromo-3-(4-chlorophenyl)-4-(methylsulfanyl-1H-indol-1-yl]-2-hexenoate To a solution of the aldehyde of Step 9 (265 mg, 0.6 mmol) in THF (10 mL) at r.t. was added (ethoxycarbonylmethylene)triphenylphosphorane (500 mg, 1.4 mmol). The reaction mixture was stirred at r.t. for 30 minutes, filtered on a SiO$_2$ pad eluted with 30% EtOAc in hexanes and concentrated to give 300 mg of the title compound as a pale yellow oil.

$^1$H NMR (acetone-d$_6$) δ 7.44–7.37 (5H, m), 7.17 (1H, t), 6.95–6.87 (2H, m), 5.84 (1H, d), 4.38 (2H, t), 4.12 (2H, q), 2.36 (2H, q), 2.29 (3H, s), 2.06–1.96 (2H, m), 1.21 (3H, t). MS (+APCI) m/z 413.1, 415.1 (M−Br)$^+$ Step 11: Ethyl (2-E,Z)-(10-(4-chlorophenyl)-1-(methylsulfanyl)-7,8-dihydro-pyrido[1,2-a]indol-9(6H)-ylidene)ethanoate

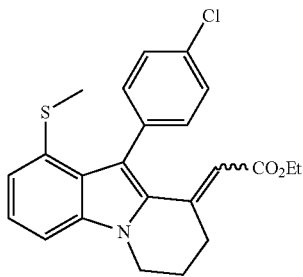

To a solution of the indole of Step 10 (270 mg, 0.6 mmol) in DMF (8 mL) at r.t. was added tetra-n-butylammonium iodide (164 mg, 0.6 mmol), palladium(II) acetate (65 mg) and 200 µL of triethylamine. The reaction mixture was heated to 75° C. and stirred for 2 hours, cooled, filtered on a $SiO_2$ pad eluted with 50% EtOAc in hexanes and the filtrate concentrated to give 300 mg of the desired compound used as such.

Step 12: (+/−)-Ethyl [10-(4-chlorophenyl)-1-(methylsulfanyl)-6,7,8,9-tetrahydro-pyrido[1,2-a]indol-9-yl]acetate To absolution of the indole of Step 11 (300 mg) in EtOAc (15 mL) was added 5% palladium on carbon (100 mg). The mixture was shaken under $H_2$ atmosphere (50 psi) for 12 hours, filtered on a silica gel pad eluted with EtOAc and the filtrate concentrated. The residue was purified by silica gel chromatography eluted with 30% EtOAc in Hexanes to provide 170 mg of the title compound as a pale yellow syrup used as such.

Step 13: (+/−)-Ethyl [10-(4-chlorophenyl)-1-(methylsulfinyl)-6,7,8,9-tetrahydro-pyrido[1,2-a]indol-9-yl]acetate To a solution of the sulfide of Step 12 (110 mg, 0.1 mmol) in 8 ml of $CH_2Cl_2$/MeOH (10:1) at 0° C. was added MMPP (79 mg, 0.1 mmol). The reaction mixture was stirred at 0° C. for 1 hour and then quenched with a saturated aqueous solution of $NaHCO_3$ and extracted with EtOAc. The organic layer was dried over $Na_2SO_4$ and concentrated. The residue was purified by silica gel chromatography eluted with 70% EtOAc in Hexanes to provide 40 mg of the less polar diastereomer and 38 mg of the more polar diastereomer as a white solid.

Less polar diastereomer: $^1$H NMR (acetone-$d_6$) δ 7.70 (1H, dd), 7.58 (1H, dd), 7.56–7.36 (5H, m), 4.37–4.32 (1H, m), 4.15–4.05 (1H, m), 3.95 (2H, q), 3.86–3.78 (1H, m), 2.40 (1H, dd), 2.25–2.03 (4H, m), 2.08 (3H, s), 1.95–1.86 (1H, m), 1.10 (3H, t).

More polar diastereomer: $^1$H NMR (acetone-$d_6$) δ 7.75 (1H, dd), 7.56 (1H, dd), 7.52–7.34 (5H, m), 4.39–4.34 (1H, m), 4.07–3.98 (3H, m), 3.51–3.46 (1H, m), 2.67–2.53 (2H, m), 2.40 (3H, s), 2.31–2.22 (1H, m), 2.11–1.88 (3H, m), 1.12 (3H, t).

Step 14: (+/−)-[10-(4-Chlorophenyl)-1-(methylsulfinyl)-6,7,8,9-tetrahydropyrido[1,2-a]indol-9-yl]acetic acid To a solution of the ester of Step 13 in a THF/MeOH (3:1) mixture at r.t. was added 1N LiOH (aqueous solution). The reaction mixture was stirred at r.t. for 2 hours and AcOH (0.5 mL) and brine (5 mL) were added. The aqueous layer was extracted with EtOAc and the combined organic layers were dried over $Na_2SO_4$ and concentrated. The residue was swished in EtOAc/hexanes to give the desired acid as a white solid. Each isomer from Step 13 was hydrolyzed under these conditions. From the less polar diastereomer of Step 13: $^1$H NMR (methanol-$d_4$) δ 7.65 (1H, d), 7.61 (1H, d), 7.51–7.35 (5H, m), 4.37–4.29 (1H, m), 4.09–4.02 (1H, m), 3.79–3.71 (1H, m), 2.40 (1H, dd), 2.24 (3H, s), 2.23–1.91 (5H, m). MS (−APCI) m/z 400.2 M-H)$^+$.

From the more polar diastereomer of Step 13: $^1$H NMR (methanol-$d_4$) δ 7.67 (1H, d), 7.60 (1H, d), 7.47–7.28 (5H, m), 4.37–4.31 (1H, m), 4.08–3.96 (1H, m), 3.53–3.47 (m, 1H), 2.56 (3H, s), 2.54–1.98 (6H, m). MS (−APCI) m/z 400.2 (M−H)$^-$.

EXAMPLE 6

(+/−)-[10-(4-chlorobenzyl)-1-(methylsulfinyl)-6,7,8,9-tetrahydropyrido[1,2-a]indol-9-yl]acetic acid

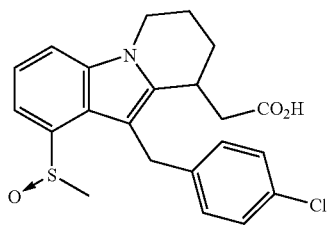

Step 1: 4-Bromo-1H-indole

2-Bromo-6-nitrotoluene (3.2 g, 15 mmol), N,N-dimethylformamide dimethyl acetal (5.4 g, 45 mmol) and pyrrolidine (1.1 g, 15 mmol) were combined in 30 mL of DMF and heated at 110° C. The reaction mixture was stirred at 110° C. for 2.5 hours and then water was added. The aqueous layer was extracted with $Et_2O$ and the combined organic layers were washed with water and brine, dried over $MgSO_4$ and concentrated. The brown syrup was dissolved in 80% aqueous AcOH (80 mL) and heated to 75° C. Zn powder (8.5 g), 130 mmol) was then added portionwise over 1 hour and the temperature was raised to 85° C. for 2 hours. The reaction mixture was filtered and water was added. The aqueous layer was extracted with $Et_2O$ and the combined organic layers were washed with saturated aqueous sodium bicarbonate and water, dried over $Na_2SO_4$ and concentrated. The residue was purified by silica gel chromatography eluted with 20% EtOAc in Hexanes to provide 2 g of the title compound as a greenish oil used as such.

Step 2: 4-Bromo-1-(triisopropylsilyl)-1H-indole

To a solution of the indole of Step 1 (8.9 g, 45 mmol) in DMF (150 mL) at 0° C. was added portionwise NaH (2.2 g, 55 mmol, 60% in oil). The reaction mixture was stirred for 30 minutes at 0° C. and triisopropylsilyl chloride (10.5 g, 55 mmol) was added. The reaction mixture was stirred for 30 minutes and 400 mL of $Et_2O$ was added. The reaction was quenched with saturated aqueous $NH_4Cl$ and extracted with $Et_2O$. The combined organic layers were washed with water and brine, dried over $Na_2SO_4$ and concentrated. The residue was purified by silica gel chromatography eluted with 100% Hexanes to provide 16 g of the title compound as a white solid.

$^1$H NMR (acetone-$d_6$) δ 7.61 (1H, d), 7.47 (1H, d), 7.27 (1H, d), 7.08 (1H, t), 6.65 (1H, d); 1.85–1.75 (3H, m), 1.14 (18H, d).

Step 3: 4-(Methylsulfanyl-1-(triisopropylsilyl)-1H-indole

To a solution of the indole of Step 2 (2.9 g, 8 mmol) in Et$_2$O (50 mL) at −78° C. was added t-BuLi (11 mL, 18 mmol). The reaction mixture was stirred for 10 minutes at −78° C. and dimethyl disulfide (2.3 g, 25 mmol) was added. The reaction mixture was stirred for 30 minutes and the reaction was quenched with water. The phases were separated and the aqueous layer was extracted with Et$_2$O. The combined organic layers were dried over Na$_2$SO$_4$ and concentrated. The residue was purified by silica gel chromatography eluted with 5% EtOAc in Hexanes to provide 2.5 g of the title compound as a colorless oil.

$^1$HNMR (acetone-d$_6$) δ 7.43–7.36 (2H, m), 7.11 (1H, t), 6.97 (1H, d), 6.68 (1H, d), 2.53 (3H, s), 1.82–1.73 (3H, m), 1.14 (18H, d).

Step 4: 3-Bromo-1-(triisopropylsilyl)-1H-indol-4-yl methyl sulfide

To a solution of the indole of Step 3 (500 mg, 1.6 mmol) in THF (10 mL) at −78° C. was added NBS (280 mg, 1.6 mmol). The reaction mixture was stirred for 30 minutes and the solvent was removed by evaporation. The residue was purified by silica gel chromatography eluted with 5% EtOAc in Hexanes to provide 540 mg of the title compound as a pale yellow oil.

$^1$H NMR (acetone-d$_6$) δ 7.45–7.36 (2H, m), 7.13 (1H, t), 6.96 (1H, d), 2.52 (3H, s), 1.82–1.73 (3H, m), 1.14 (18H, d).

Step 5: 3-(4-chlorobenzyl)-1-(triisopropylsilyl)-1H-indol-4-yl methyl sulfide

To a solution of the indole of Step 4 (2.4 g, 6 mmol) in Et$_2$O (50 mL) at −78° C. was added t-BuLi (7 mL, 12 mmol). The reaction mixture was stirred for 10 minutes at −78° C. and p-chlorobenzyl bromide (3.6 g, 18 mmol) was added. The reaction mixture was stirred for 2 hours at r.t. and was quenched with saturated aqueous NH$_4$Cl. The phases were separated and the aqueous layer was extracted with Et$_2$O. The combined organic layers were dried over Na$_2$SO$_4$ and concentrated. The residue was purified by silica gel chromatography eluted with 5% EtOAc in Hexanes to provide 1.9 g of the title compound as a pale yellow oil used as such.

Step 6: 3-(4-Chlorobenzyl)-1H-indol-4-yl methyl sulfide

To a solution of the indole of Step 5 (1.9 g, 4.3 mmol) in THF (20 ml at 0° C. was added 1M TBAF (7 mL, 6 mmol). The reaction mixture was stirred for 1 minutes at 0° C. and water was added. The phases were separated and the aqueous layer was extracted with Et$_2$O. The combined organic layers were dried over MgSO and concentrated The residue was purified by silica gel chromatography eluted with 20% EtOAc in Hexanes to provide 700 mg of the title compound as a pale yellow oil.

$^1$H NMR (acetone-d$_6$) δ 7.28–7.20 (5H, m); 7.08 (1H, t), 6.98 (11, s), 6.87 (1H, d), 4.41 (2H, s), 2.41 (3H, s).

Step 7: 2-Bromo-3-(4-chlorobenzyl)-1H-indol-4-yl methyl sulfide

To a solution of the indole of Step 6 (700 mg, 2.4 mmol) in CCl$_4$ (15 mL) was added NBS (475 mg, 2.7 mmol). The reaction mixture was heated to 50° C. and stirred for 20 minutes. The resulting suspension was filtered on SiO$_2$ pad eluted with 50% EtOAc in hexanes and concentrated. The title compound was obtained in quantitative yield as a brownish solid foam and used as such.

Step 8: Ethyl 4-[2-bromo-3-(4-chlorobenzyl)-4-(methylsulfanyl)-1H-indol-1-yl]butanoate To a solution of the indole of Step 7 (800 mg, 2.4 mmol) in DMF (15 mL) was added NaH (136 mg, 3.4 mmol, 60% in oil) at 0° C. The reaction mixture was stirred at 0° C. for 15 minutes and tetra-n-butylammonium iodide (300 mg) was added, followed by the addition of ethyl 4-bromobutyrate (663 mg, 3.3 mmol). The resulting mixture was stirred for 2 h at r.t., quenched with saturated aqueous NH$_4$Cl and extracted with EtOAc. The combined organic layers were washed with water and brine, dried over Na$_2$SO$_4$ and concentrated. The residue was purified by silica gel chromatography eluted with 20% EtOAc in Hexanes to provide 690 mg of the title compound as a brown oil.

$^1$H NMR (acetone-d$_6$) δ 7.37 (1H, d), 7.25–7.16 (5H, m), 6.93 (1H, d), 4.45 (1H, s), 4.38 (2H, d), 4.07 (2H, q), 2.42–2.37 (5H, m), 2.10–2.01 (2H, m), 1.18 (3H, t).

Step 9: 4-[2-Bromo-3-(4-chlorobenzyl-4-(methylsulfanyl-1H-indol-1-yl]butanal

To a solution of the ester of Step 8 (685 mg, 1.4 mmol) in Et$_2$O (15 mL) at −78° C. was added DIBAL (2.5 mL, 1M solution in hexanes). The reaction mixture was stirred at −78° C. for 30 minutes, quenched with 0.5 mL of acetone and 1N HCl was added. The phases were separated and the aqueous layer was extracted with Et$_2$O. The combined organic layers were dried over MgSO$_4$ and concentrated to give 575 mg of the desired compound as a brownish solid used as such.

Step 10: Ethyl (2 E,Z)-6-[2-bromo-3-(4-chlorobenzyl)-4-(methylsulfanyl)-1H-indol-1-yl]-2-hexenoate To a solution of the aldehyde of Step 9 (575 mg, 1.3 mmol) in THF (15 mL) at r.t. was added (ethoxycarbonylmethylene)triphenylphosphorane (920 mg, 2.6 mmol). The reaction mixture was stirred at r.t. for 2 hours, then filtered on a SiO$_2$ pad eluted with 30% EtOAc in hexanes and concentrated. The residue was purified by silica gel chromatography eluted with 20% EtOAc in Hexanes to provide 520 mg of the title compound as brownish syrup used as such.

Step 11: Ethyl (2 E,Z)-(10-(4-chlorobenzyl)-1-(methylsulfanyl)-7,8-dihydro-pyrido[1,2-a]indol-9(6H)-ylidene)ethanoate

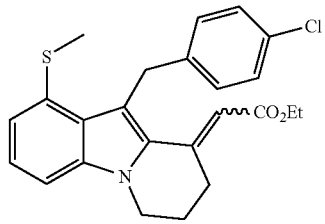

To a solution of the indole of Step 10 (520 mg, 1 mmol) in DMP (12 mL) at r.t. was added tetra-n-butylammonium iodide (300 mg, 1 mmol), palladium(II) acetate (100 mg) and 400 μL of triethylamine. The reaction mixture was heated to 75° C. and stirred for 2 hours. The reaction mixture was cooled, filtered on a SiO$_2$ pad eluting with 50% EtOAc in hexanes and concentrated. The residue was purified by silica gel chromatography eluted with 20% EtOAc in Hexanes to provide 420 mg of the title compound as a pale yellow solid.

Step 12: (+/−)-Ethyl [10-(4-chlorobenzyl)-1-(methylsulfanyl)-6,7,8,9-tetrahydro-pyrido[1,2-a]indol-9-yl]acetate To a solution of the indole of Step 11 (420 mg) in EtOAc (20 mL) was added 5% Palladium on carbon (150 mg). The mixture was shaken under $H_2$ atmosphere (50 psi) for 4 days, filtered on a silica gel pad eluted with EtOAc and concentrated. The residue was purified by silica gel chromatography eluted with 20% EtOAc in Hexanes to provide 275 mg of the title compound as a pale yellow syrup.

$^1$H NMR (acetone-$d_6$) δ 7.28–7.06 (6H, m), 6.91 (1H, d), 4.43 (2H, dd), 4.33–4.28 (1H, m), 4.06 (2H, q), 3.77 (1H td), 3.65–3.61 (1H, m), 2.59 (1H, dd), 2.35 (3H, s), 2.40–2.02 (3H, m), 1.97–1.85 (2H, m), 1.18 (3H, t).

Step 13: (+/−)-Ethyl [10-(4-chlorobenzyl)-1-(methylsulfinyl)-6,7,8,9-tetrahydro-pyrido[1,2-a]indol-9-yl]acetate To a solution of the sulfide of Step 12 (270 mg, 0.6 mmol) in 30 ml of $CH_2Cl_2$/MeOH (10:1) mixture at 0° C. was added MMPP (312 mg, 0.6 mmol). The reaction mixture was stirred at 0° C. for 30 minutes and then quenched with saturated aqueous $NaHCO_3$ and extracted with EtOAc. The combined organic layers were dried over $Na_2SO_4$ and concentrated. The residue was purified by silica gel chromatography eluted with 70% EtOAc in Hexanes to provide 210 mg as a white solid.

(Mixture of diastereomers) $^1$H NMR (acetone-$d_6$) δ 7.71–7.65 (1H, m), 7.57–7.52 (1H, m), 7.38–7.22 (3H, m), 7.12–7.03 (2H, m), 4.47–3.88 (6H, m), 2.75–1.97 (10H, m), 1.21–1.04 (3H, m).

Step 14: (+/−)-[10-(4-Chlorobenzyl)-1-(methylsulfinyl)-6,7,8,9-tetrahydropyrido[1,2-a]indol-9-yl]acetic acid To a solution of the ester of Step 13 (70 mg) in a THF/MeOH (3:1) mixture at r.t. was added 1N LiOH (aqueous solution). The reaction mixture was stirred at r.t. for 2 h and AcOH was added. The aqueous layer was extracted with EtOAc and the combined organic layers were dried over $Na_2SO_4$ and concentrated. The residue was swished in EtOAc/MeOH to give 35 mg of the desired acid as a white solid.

Mixture of diastereomers: $^1$H NMR (acetone-$d_6$) δ 7.58–7.49 (2H, m), 7.29–7.23 (3H, m), 7.08–6.97 (2H, m), 4.39–3.52 (5H, m), 2.28–1.68 (9H, m).

MS (−APCI) m/z 414.1 (M−H)$^−$.

EXAMPLE 7

(+/−)-[8-bromo-9-[(4-chlorophenyl)sulfanyl]-6-fluoro-2,3-dihydro-1H-pyrrolo[1,2-a]indol-1-yl]acetic acid

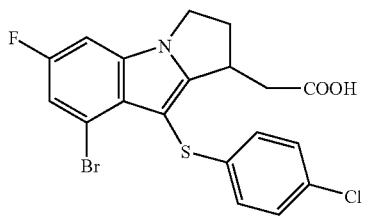

Step 1: 2-Bromo-1-(bromomethyl)-4-fluorobenzene

To a solution of 2-bromo-4-fluorotoluene (50 g, 265 mmol) in $CCl_4$ (1 L) was added NBS (52 g, 291 mmol) and 300 mg of benzoyl peroxide. The mixture was heated to reflux and stirred for 30 minutes under a sun lamp. The reaction mixture was cooled and filtered on a $SiO_2$ pad eluted with hexanes. The filtrate was concentrated to give 70 g of the title compound as a colorless oil and used as such.

Step 2: 2-Bromo-4-fluorobenzaldehyde

To a solution of the benzyl bromide of Step 1 (59 g, 220 mmol) in dioxane (500 mL) at r.t. was added N-methylmorpholine N-oxide monohydrate (89 g, 660 mmol). The reaction mixture was stirred for 1 hour at 70° C. and poured into a mixture of saturated aqueous $NH_4Cl$ and EtOAc. The phases were separated and the aqueous layer was extracted with EtOAc. The combined organic layers were washed with water, dried over $Na_2SO_4$ and concentrated to give 44 g of the title compound as a white solid and used as such.

Step 3: Methyl(2E,Z)-2-azido-3-(2-bromo-4-fluorophenyl)-2-propenoate

To a mixture of NaOMe (36 mL, 25% solution in MeOH) and MeOH (60 mL) at −10° C. was slowly added (over 10 minutes) a mixture of the aldehyde of Step 2 (8 g, 39 mmol) and methyl azidoacetate (18.4 g, 160 mmol) in MeOH (15 mL). The mixture was stirred for 12 hours at 0° C. and then poured into 120 g of ice. The precipitate was filtered and dried by Hi-vacuum (overnight) to give 6.3 g of the title compound as a yellow solid and used as such.

Step 4: Methyl 4-bromo-6-fluoro-1H-indole-2-carboxylate

To 160 mL of boiling xylene was slowly added (over 2 hours time period) a solution of the azidoester of Step 3 (6.3 g) in xylene (100 mL). The reaction mixture was stirred at reflux for 4 hours and cooled. The xylene was removed by evaporation and the yellow solid was swished in toluene to give 3.9 g of the title compound as a white solid.

$^1$H NMR (acetone-$d_6$) δ 11.41 (1H, br s), 7.31 (1H, dd), 7.28 (1H, dd), 7.15 (1H, s), 3.93 (3H, s).

Step 5: (+/−)-Methyl 8-bromo-6-fluoro-1-oxo-2,3-dihydro-1H-pyrrolo[1,2-a]indole-2-carboxylate

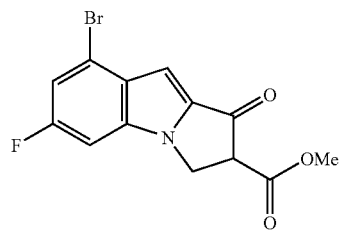

To a suspension of the indole of Step 4 (4 g, 15 mmol) in a mixture of 10:1 toluene/THF (100 mL) at r.t. was added potassium t-butoxide (15 mL of a 1M solution in THF). The reaction mixture was stirred for 2 minutes and methyl acrylate (2.5 g, 30 mmol) was added. The mixture was stirred at reflux for 5 hours and cooled to r.t. Then 1N HCl was added to acidify to pH 3 and the reaction mixture was extracted with EtOAc and the combined organic layers were concentrated. The residue was swished in EtOAc/Hexanes to give 4 g of the desired compound as a pale yellow solid.

$^1$H NMR (acetone-$d_6$) δ 7.54 (1H, dd), 7.36 (1H, dd), 7.04 (1H, s), 4.91–4.83 (2H, m), 4.48–4.43 (1H, m), 3.77 (3H, s).

Step 6: 8-Bromo-6-fluoro-2,3-dihydro-1H-pyrrolo[1,2-a]indol-1-one

To a solution of the ketoester of Step 5 (4 g) in EtOH (150 mL) r.t. was added 40 mL of concentrated HCl. The reaction mixture was stirred at reflux for 1 hour and water was added. The aqueous layer was extracted with $CH_2Cl_2$ and the combined organic layers were concentrated The residue was swished in EtOAc/Hexanes to provide 2.9 g of the title compound as a pale yellow solid.

$^1$H NMR (acetone-d$_6$) δ 7.45 (1H, dd), 7±30 (1H, dd), 6;85 (1H, s), 4.57 (2H, t), 3.23 (2H, t).

Step 7: (+/−)-Methyl (8-bromo-6-fluoro-1-hydroxy-2,3-dihydro-1H-pyrrolo[1,2-a]indol-1-yl)acetate To a suspension of the ketone of Step 6 (800 mg, 3 mmol) in THF (10 mL) was added methyl bromoacetate (2.3 g, 15 mmol) and 1 g of Zn-copper couple. The reaction mixture was put in a sonicator at r.t. until an exotherm was observed. The reaction flask was cooled in an ice bath to keep the internal temperature below 50° C. and the mixture was stirred at r.t. for 1 hour. The reaction mixture was poured into a 2:1 mixture of saturated aqueous NH$_4$Cl/EtOAc (100 mL) and filtered on paper. The filtrate was extracted with EtOAc, the combined organic layers were washed with brine and water, dried over Na$_2$SO$_4$ and concentrated. The residue was purified by silica gel chromatography eluted with 35% EtOAc in Hexanes to provide 780 mg of the title compound as a pale yellow oil.

$^1$H NMR (acetone-d$_6$) δ 7.21 (1H, dd), 7.11 (1H, dd), 6.35 (1H, s), 4.71 (1H, s), 4.29–4.20 (2H, m), 3.70 (3H, s), 3.14 (1H, d), 3.05 (1H, d), 3.02–2.90 (1H, m), 2.81–2.74 (1H, m).

Step 8: (+/−)-Methyl (8-bromo-6-fluoro-2,3-dihydro-1H-pyrrolo[1,2-a]indol-1-yl)acetate To dry CH$_3$CN (2.3 g, 56 mmol) at r.t. was added NaI (8.4 g, 56 mmol) and trimethylsilyl chloride (6.1 g, 56 mmol). Then a solution of the alcohol of Step 7 (1.9 g, 5.6 mmol) in Et$_2$O (60 mL) was slowly added. The reaction mixture was stirred for 5 minutes at r.t. and poured into a 1:1 mixture of saturated aqueous NaHCO$_3$/10% aqueous Na$_2$S$_2$O$_3$ (100 mL) at 0° C. The phases were separated and the aqueous layer was extracted with Et$_2$O. The combined organic layers were washed with brine, dried over Na$_2$SO$_4$ and concentrated. The desired compound was obtained as a brown solid (1.3 g).

$^1$HNMR (acetone-d$_6$) δ 7.12 (1H, d), 7.04 (1H, dd), 6.15 (1H, s), 4.26–4.18 (1H, m), 4.12–4.06 (1H, m), 3.72–3.67 (1H, m), 3.69 (3H, s), 2.93–2.82 (2H, m), 2.71 (1H, dd), 2.37–2.31 (1H, m).

Step 9: (+/−)-Methyl [8-bromo-9-[(4-chlorophenyl)sulfanyl]-6-fluoro-2,3-dihydro-1H-pyrrolo[1,2-a]indol-1-yl]acetate To a solution of bis(4-chlorophenyl) disulfide (1.38 g, 4.8 mmol) in 1,2-dichloroethane (25 mL) at 0° C. was added sulfuryl chloride (536 mg, 4 mmol). The mixture was stirred for 1 hour at r.t. and was added to a solution of the ester of Step 8 (1.3 g, 4 mmol) in DMF (25 mL) at r.t. The reaction mixture was stirred for 10 minutes and saturated aqueous NaHCO$_3$ was added. The aqueous layer was extracted with EtOAc, and the combined organic layers were washed with brine, dried over Na$_2$SO$_4$ and concentrated. The residue was purified by silica gel chromatography eluted with 20% EtOAc in Hexanes to provide 1.2 g of the title compound as pale yellow foam.

$^1$H NMR (acetone-d$_6$) δ 7.30 (1H, dd), 7.24 (2H, d), 7.13 (1H, dd), 7.03 (2H, d), 4.41–4.34 (1H, m), 4.27–4.20 (1H, m), 3.89–3.82 (1H, m), 3.60 (3H, s), 3.18–3.12 (1H, m), 3.05–2.95 (1H, m), 2.78–2.70 (1H, m), 2.51–2.43 (1H, m).

Step 10: (+/−)-[8-Bromo-9-[(4-chlorophenyl)sulfanyl]-6-fluoro-2,3-dihydro-1H-pyrrolo[1,2-a]indol-1-yl]acetic acid To a solution of the ester of Step 9 (80 mg) in a 3:1 mixture of THF/MeOH (3 mL) at r.t. was added 1N LiOH (1 mL, aqueous solution). The reaction mixture was stirred at r.t. for 2 h and AcOH (0.5 mL) and brine (5 mL) were added. The aqueous layer was extracted with EtOAc and the combined organic layers were dried over Na$_2$SO$_4$ and concentrated. The residue was purified by silica gel chromatography eluted with 40% EtOAc/hexane containing 1% AcOH to provide 70 mg of the title compound as a pale yellow solid.

$^1$H NMR (acetone-d$_6$) δ 7.36 (1H, dd), 7.24 (2H, d), 7.13 (1H, dd), 7.05 (2H, d), 4.43–4.35 (1H, m), 4.28–4.21 (1H, m), 3.87–3.81 (1H, m), 3.20 (1H, dd), 3.07–2.98 (1H, m), 2.71 (1H, dd), 2.54–2.45 (1H, m).

MS (−APCI) m/z 453.9 M−H)$^-$.

EXAMPLE 7A (+)-[8-bromo-9-[(4-chloro-phenyl]svulfanyl]-6-fluoro-2,3-dihydro-1H-pyrrolo[1,2-a]indol-1-yl]acetic acid Step 1: (+/−)-(8-bromo-6-fluoro-2,3-dihydro-1H-pyrrolo[1,2-a]indol-1-yl)acetic acid To a solution of (+/−)-methyl (8-bromo-6-fluoro-2,3-dihydro-1H-pyrrolo[1,2-a]indol-1-yl)acetate (11 g) in a THF/MeOH (3:1) mixture at r.t. was added 1N LiOH (50 mL, aqueous solution). The reaction mixture was stirred at r.t. for 12 hours and AcOH (5 mL) and brine (100 mL) were added. The aqueous layer was extracted with EtOAc and the combined organic layers were dried over Na$_2$SO$_4$ and concentrated to provide the title compound as a white solid.

$^1$H NMR (acetone-d$_6$) δ 7.15 (1H, dd), 7.07 (1H, dd), 6.21 (1H, s), 4.28–4.22 (1H, m), 4.14–4.08 (1H, m), 3.79–3.71 (1H, m), 2.98–2.78 (2H, m), 2.73 (1H, dd), 2.42–2.37 (1H, m).

Step 2: (4S)-4-benzyl-3-[(8-bromo-6-fluoro-2,3-dihydro-1H-pyrrolo[1,2-a]indol-1-yl)acetyl]-1,3-oxazolidin-2-one

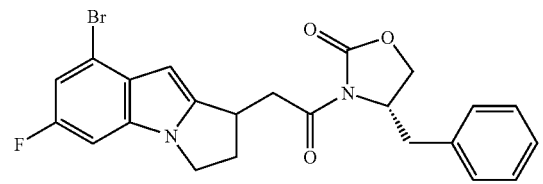

To a solution (S)-(−)-4-benzyl-2-oxazolidinone (7.8 g, 43.8 mmol) in THF (300 mL) at −78° C. was slowly added 1.6M n-butyllithium (27.3 mL, 43.8 mmol). The mixture was stirred for 30 minutes at −78° C. and a mixture of the compound of Step 1 (10.5 g, 33.7 mmol) and 1,1'-carbonyldiimidazole (6 g, 37 mmol) in THF (100 mL) was added. The mixture was stirred for 30 minutes at −78° C. and then warmed to −30° C. and stirred for 2 hours. The reaction was quenched with saturated NH$_4$Cl, the phases were separated and the aqueous layer was extracted with EtOAc. The combined organic layers were washed with brine, dried over Na$_2$SO$_4$ and concentrated. The residue was purified by silica gel chromatography eluted with 10% EtOAc in Toluene, which permitted the separation of the two diastereomers. Both isomers were obtained as an yellow solid with diastereomeric excess >95%.

Isomer A (less polar isomer): $^1$H NMR (DMSO-d$_6$) δ 7.36–7.11 (7H, m), 6.12 (1H, s), 4.77–4.72 (1H, m), 4.37 (1H, t), 4.22–4.15 (2H, m), 4.08–4.02 (1H, m), 3.77–3.71 (1H, m), 3.33–3.18 (2H, m), 3.08–2.93 (2H, m), 2.89–2.80 (1H, m), 2.35–2.25 (1H, m).

Isomer B (more polar isomer): ¹H NMR (DMSO-d$_6$) δ 7.35–7.12 (7H, m), 6.15 (1H, s), 4.78–4.68 (1H, m), 4.35 (1H, t), 4.22–4.12 (2H, m), 4.10–4.02 (1H, m), 3.78–3.72 (1H, m), 3.42–3.28 (1H, m), 3.15 (1H, dd), 3.09–2.98 (2H, m), 2.87–2.80 (1H, m), 2.30–2.21 (1H, m). [α]$_D$=+101°, c=0.1 in acetone.

Step 3: (4S)-4-benzyl-3-[8-bromo-9-[(4-chlorophenyl)sulfanyl]-6-fluoro-2,3-dihydro-1H-pyrrolo[1,2-a]indol-1-yl]acetyl]-1,3-oxazolidin-2-one

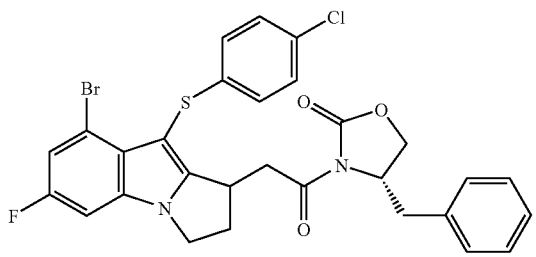

Starting from isomer B (the more polar isomer) obtained in Step 2 (5.0 g, 10.6 mmol) the title compound was synthesized as described in Step 9 of Example 7 as a yellow solid, and used as such.

Step 4: (+)-[8-bromo-9-[(4-chlorophenyl)sulfanyl]-6-fluoro-2,3-dihydro-1H-pyrrolo[1,2-a]indol-1-yl]acetic acid To a solution of the product of Step 3 (6.1 g) in THF (120 mL) at 0° C. were added a solution of LiOH (600 mg in 30 mL of H$_2$O) and H$_2$O$_2$ 30% (6 mL). The reaction mixture was stirred at 0° C. for 1 hour and the reaction was quenched with 1M Na$_2$SO$_3$. The mixture was acidified to pH 4 with 1M NaHSO$_4$. The aqueous layer was extracted with EtOAc and the combined organic layers were dried over Na$_2$SO$_4$ and concentrated. The residue was purified by silica gel chromatography eluted with EtOAc/hexanes/AcOH (30:70:1) to provide the title compound as a pale yellow solid. [α]$_D$=+87°, c=0.1 in MeOH.

EXAMPLE 8

(+/−)-[1-bromo-10-[(4-chlorophenyl)sulfanyl]-3-fluoro-6,7,8,9-tetrahydropyrido[1,2-a]indol-9-yl]acetic acid

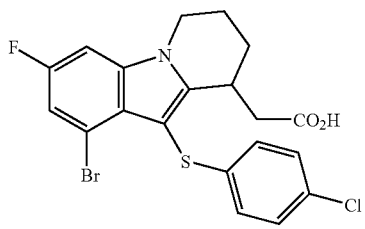

Step 1: Methyl 4-bromo-3-[(4-chlorophenyl)sulfanyl]-6-fluoro-1H-indole-2-carboxylate To a solution of bis(4-chlorophenyl) disulfide (4 g, 14 mmol) in DCE at 0° C. (30 mL) was slowly added sulfuryl chloride (1.8 g, 14 mmol). After 1 hour of stirring the mixture was added to a solution of methyl 4-bromo-6-fluoroindole-2-carboxylate (2.5 g, 9 mmol) in DMF (30 mL) at r.t. The reaction mixture was stirred for 2 hours and saturated aqueous NaHCO$_3$ was added. The phases were separated and the aqueous layer was extracted with EtOAc. The combined organic layers were washed with brine, dried over Na$_2$SO$_4$ and concentrated. The residue was swished in EtOAc to give 1.5 g of desired compound as a white solid.

¹H NMR (acetone-d$_6$) δ 7.38 (1H, dd), 7.31–7.21 (3H, m), 7.07 (2H, d), 3.88 (3H, s).

Step 2: Methyl 4-bromo-3-[(4-chlorophenyl)sulfanyl]-1-(4-ethoxy-4-oxobutyl)-6-fluoro-1H-indole-2-carboxylate To a solution of the indole of Step 1 (500 mg, 1.2 mmol) in DMF (10 mL) at 0° C. was added NaH (63 mg, 1.6 mmol, 60% in oil). The reaction mixture was stirred at 0° C. for 15 minutes and tetra-n-butylammonium iodide (300 mg) was added, followed by the addition of ethyl 4-bromobutyrate (360 mg, 1.8 mmol). The resulting mixture was stirred for 3 hours at r.t., quenched with saturated aqueous NH$_4$Cl and extracted with EtOAc. The combined organic layers were washed with water and brine, dried over Na$_2$SO$_4$ and concentrated. The residue was purified by silica gel chromatography eluted with 30% EtOAc in Hexanes to provide 500 mg of the title compound as a solid.

¹H NMR (acetone-d$_6$) δ 7.64 (1H, dd), 7.28 (1H, dd), 7.23 (2H, d), 7.07 (2H, d), 4.55 (2H, t), 4.08 (2H, q), 3.91 (3H, s), 2.42 (2H, t), 2.18–2.09 (2H, m), 1.10 (3H, t).

Step 3: (+/−)-Ethyl 1-bromo-10-[(4-chlorophenyl)sulfanyl]-3-fluoro-9-oxo-6,7,8,9-tetrahydropyrido[1,2-a]indole-8-carboxylate

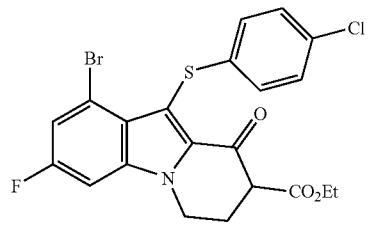

To a solution of the indole of Step 2 (460 mg, 0.9 mmol) in THF (100 mL) at 0° C. was added potassium t-butoxide (1.2 mL of a 1M solution in THF. The reaction mixture was stirred for 2 hours at 0° C. and 1N HCl was added. The phases were separated and the aqueous layer was extracted with EtOAc. The combined organic layers were dried over Na$_2$SO$_4$ and concentrated to give 400 mg of a pale yellow solid used as such.

Step 4: 1-Bromo-10-[(4-chlorophenyl)sulfanyl]-3-fluoro-7,8-dihydropyrido[1,2-a]indol-9(6H)-one To a solution of the ketoester of Step 3 (400 mg) in EtOH (10 mL) at r.t. was added 3 mL of concentrated HCl. The reaction mixture was stirred at reflux for 4 hours, cooled and poured into saturated aqueous NaHCO$_3$. The aqueous layer was extracted with EtOAc and the combined organic layers were dried over Na$_2$SO$_4$ and concentrated. The residue was swished in EtOAc to provide 220 mg of the title compound as a yellow solid.

¹HNMR (acetone-d$_6$) δ 7.51 (1H, dd), 7.30 (1H, dd), 7.18 (2H, d), 7.05 (2H, d), 4.46 (2H, t), 2.75 (2H, t), 2.53–2.43 (2H, m).

MS (+APCI) m/z 425.9 (M+H)$^+$.

Step 5: (+/−)-Methyl [1-bromo-10-[(4-chlorophenyl)sulfanyl]-3-fluoro-9-hydroxy-6,7,8,9-tetrahydropyrido[1,2-a]indol-9-yl]acetate To a boiling suspension of 300 mg of Zn-copper couple in 4 mL of THF was added dropwise methyl bromoacetate (720 mg, 4.7 mmol). The suspension was stirred at reflux for 30 minutes and a solution of the ketone of Step 4 (200 mg, 0.5 mmol) in THF (1 mL) was added. The reaction mixture was stirred at reflux for 5 h and saturated aqueous NH$_4$Cl solution was added and extracted with EtOAc. The combined organic layers were washed with brine and water, dried over Na$_2$SO$_4$ and concentrated. The residue was purified by silica gel chromatography eluted with 20% EtOAc in Hexanes to provide 106 mg of the title compound as a pale brown solid.

$^1$H NMR (acetone-d$_6$) δ 7.38 (1H, dd), 7.21 (2H, d), 7.15 (1H, dd), 6.97 (2H, br d), 4.54 (1H, br s), 4.36–4.28 (1H, m), 4.12–4.01 (1H, m), 3.79–3.71 (1H, m), 3.41 (3H, br s), 3.18–3.07 (1H, m), 2.49–2.05 (4H, m).

Step 6: (+/−)-Methyl [1-bromo-10-[(4-chlorophenyl)sulfanyl]-3-fluoro-6,7,8,9-tetrahydropyrido[1,2-a]indol-9-yl]acetate To a solution of the alcohol of Step 5 (70 mg, 0.1 mmol) in CH$_2$Cl$_2$ (2 mL) at r.t. was added 0.25 mL of trifluoroacetic acid and 0.1 mL of triethylsilane. The reaction mixture was stirred at r.t. for 4 hours Water was added, the phases were separated and the aqueous layer was extracted with CH$_2$Cl$_2$. The combined organic layers were dried over Na$_2$SO$_4$ and concentrated. The residue was swished in EtOAc to provide 22 mg of the title compound as a pale yellow solid.

$^1$H NMR (acetone-d$_6$) δ 7.34 (1H, dd), 7.21 (2H, d), 7.14 (1H, dd), 6.99 (d, 2H), 4.39–4.28 (1H, m), 4.05–3.97 (1H, m), 3.89–3.78 (1H, m), 3.62 (3H, s), 2.85–2.71 (2H, m), 2.33–2.18 (m, 1H), 2.15–1.95 (2H, m).

Step 7: (+/−)-[1-Bromo-10-[(4-chlorophenyl)sulfanyl]-3-fluoro-6,7,8,9-tetrahydropyrido[1,2-a]indol-9-yl]acetic acid To a solution of the ester of Step 6 (45 mg) in a THF/MeOH (3:1) mixture at r.t. was added 1N LiOH (aqueous solution). The reaction mixture was stirred at r.t. for 2 h and AcOH was added. The aqueous layer was extracted with EtOAc and the combined organic layers were dried over Na$_2$SO$_4$ and concentrated. The residue was swished in EtOAc to provide 20 mg of the title compound as a white solid.

$^1$H NMR (acetone-d$_6$) δ 8.56 (1H, br s), 7.24 (1H, dd), 7.15 (2H, d), 7.10 (1H, dd), 6.91 (2H, d), 4.32–4.26 (1H, m), 3.90–3.82 (2H, m), 2.69–2.64 (1H, m), 2.48–2.39 (1H, m), 2.37–2.24 (1H, m), 2.17–2.01 (2H, m), 1.95–1.86 (1H, m).
MS (−APCI) m/z 468.1 (M−H)$^-$.

EXAMPLE 9

(+/−)-[10-[(4-chlorophenyl)sulfanyl]-1-methoxy-3-(methyl-sulfonyl)-6,7,8,9-tetrahydropyrido[1,2-a]indol-9-tl]acetic acid

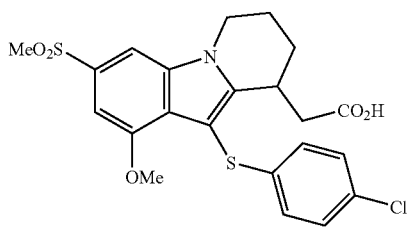

Step 1: 2-Methoxy-4-(methylsulfanyl)benzaldehyde

To a vigorously stirred solution of 11.4 g of methyl 2 methoxy-4-(methylsulfanyl)benzoate in 200 mL of THF cooled at −78° C. was added dropwise a solution of diisobutylaluminum hydride (72 mL, 1.5 M in toluene). After stirring for 1.25 hours at −78° C., the reaction was quenched with 5 mL of acetone followed by 150 mL of 1 N HCl. The mixture was extracted with 2×150 mL of ether and the extracts were dried over Na$_2$SO$_4$, filtered through a pad of silica gel and concentrated.

To a solution of 13.7 g of oxalyl chloride in 250 mL of CH$_2$Cl$_2$ cooled at −78° C. was added slowly 16.9 g of DMSO. After stirring for 5 minutes, a solution of the crude alcohol obtained above in 50 mL of CH$_2$Cl$_2$ was added and the mixture was stirred for 30 minutes at −60° C. and then treated with 54 g of Et$_3$N. The mixture was warmed to room temperature and stirred for 10 minutes, quenched with 100 mL of 1N HCl. The product was extracted with 200 mL of CH$_2$Cl$_2$ and the extract was dried over Na$_2$SO$_4$, concentrated., The residue was purified by silica gel flash chromatography eluted with 1:1 hexane/EtOAc to give 9 g of the title compound as yellow solid.

$^1$H NMR (acetone-d$_6$) δ 10.30 (1H, s), 7.64 (1H, d), 7.00 (1H, s), 6.90 (1H, d), 3.99 (3H, s), 2.58 (3H, s).

Step 2: 1-Methoxy-3-(methylsulfanyl)-6,7,8,9-tetrahydropyrido[1,2-a]indol-9-one

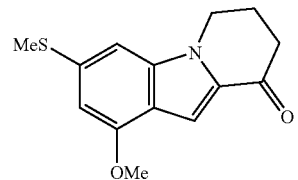

Starting from 2-methoxy-4-(methylsulfanyl)benzaldehyde, the title compound was synthesized following the procedures described in Steps 3–4 of Example 7 and Steps 2–4 of Example 8.

$^1$H NMR (acetone-d$_6$) δ 7.12 (1H, s), 6.95 (1H, s), 6.50 (1H, s), 4.28 (2H, t), 3.95(3H, s), 2.65 (2H, t), 2.57 (3H, s), 2.48 (2H, m).

Step 3: 1-Methoxy-3-(methylsulfonyl)-6,7,8,9-tetrahydropyrido[1,2-a]indol-9-one

A solution of 0.2 g of the product obtained from Step 2, 1 mL of H$_2$O$_2$ and 0.05 g of Na$_2$WO$_4$ (dihydrate) in 5 mL of EtOH was stirred for 1 h at room temperature and 30 minutes at 50° C. The solution was cooled and concentrated. The residue was partitioned between 15 mL of brine and 60 mL of EtOAc. The EtOAc layer was dried over Na$_2$SO$_4$ and concentrated. The crude product was swished from 1:1 hexane/EtOAc to give 0.18 g of the title compound as a white solid.

$^1$H NMR (acetone-d$_6$) δ 7.75 (1H, s), 7.22 (1H, s), 7.05 (1H, s), 4.47 (2H, t), 4.06(3H, s), 3.15 (3H, s), 2.76 (2H, t), 2.48 (2H, m).

Step 4: E/Z-Ethyl 2-[1-methoxy-3-(methylsulfonyl-6,7,8,9-tetrahydropyrido[1,2-a]indol-9-yliden]acetate To a solution of 0.5 mL of triethyl phosphonoacetate in 3.5 mL of DMF was added 0.1 g of NaH (60% in mineral oil). After stirring for 10 minutes, 0.1 g of the product obtained in Step 3 was added and the mixture was stirred for 30 minutes at room temperature and 1 hour at 45° C. The mixture was poured into 20 mL of saturated aqueous NH$_4$Cl and extracted with 2×20 mL of EtOAc. The residue was purified by silica gel flash chromatography eluted with 3:2 hexane/EtOAc to give 0.14 g of the title compound as yellow oil.

$^1$H NMR (acetone-$d_6$) δ 7.58 (1H, s), 7.00 (1H, s), 6.58 (1H, s), 6.10 (1H, bt), 4.27 (2H, t), 4.10 (2H, q), 2.68–2.80 (4H, m).

Step 5: Ethyl 2-[1-methoxy-3-(methylsulfonyl)-6,7,8,9-tetrahydropyrido[1,2-a]indol-9-yl]acetate Starting from the product obtained in Step 4, the title compound was synthesized following the procedures described in Step 7 of Example 1.

$^1$H NMR (acetone-$d_6$) δ 7.57 (1H, s), 7.02 (1H, s), 6.42 (1H, s), 4.32 (1H, m), 4.16 (2H, q), 4.02 (1H, m), 4.00 (3H, s), 3.45 (1H, m), 3.08 (3H, s), 2.95 (1H, dd), 2.61 (1H, dd), 2.25 (1H, m), 2.13 (1H, m), 2.05 (1H, m), 1.63 (1H, m).

Step 6: (+/−)-[10-[(4-Chlorophenyl)sulfanyl]-1-methoxy-3-(methylsulfonyl)-6,7,8,9-tetrahydropyrido[1,2-a]indol-9-yl]acetic acid Starting from the product obtained in Step 5, the title compound was synthesized following the procedures described in Step 9–10 of Example 7.

$^1$H NMR (acetone-$d_6$) δ 7.69 (1H, s), 7.20 (2H, d), 7.08 (1H, s), 7.04 (2H, d), 4.45 (1H, m), 4.08 (1H, m), 3.72 (1H, m), 3.77 (3H, s), 3.10 (3H, s), 2.75–2.82 (2H, m), 2.27 (1H, m), 2.12 (1H, m), 2.05 (2H, m).

EXAMPLE 10

(+/−)-[8-acetyl-9-[(4-chlorophenyl)sulfanyl]-6-fluoro-2,3-dihydro-1H-pyrrolo[1,2-a]indol-1-yl]acetic acid

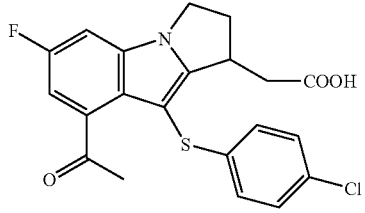

Step 1: (+/−)-Methyl [8-acetyl-9-[(4-chlorophenyl)sulfanl]-6-fluoro-2,3-dihydro-1H-pyrrolo[1,2-a]indol-1-yl]acetate A mixture of palladium (II) acetate (45 mg, 0.2 mmol) and triphenyl arsine (122 mg, 0.4 mmol) in DMF (0.5 mL) was sonicated for 10 minutes and then degassed. A solution of (+/−)-methyl[8-bromo-9-[(4-chlorophenyl)sulfanyl]-6-fluoro-2,3-dihydro-1H-pyrrolo[1,2-a]indol-1-yl]acetate (Example 7, 235 mg, 0.5 mmol) in 2 mL of DMF and 1-ethoxyvinyltri-n-butyltin (451 mg, 1.3 mmol) were added and the mixture was degassed. The reaction mixture was stirred at 90° C. for 12 hours and 1N HCl (4 mL) was added. The mixture was stirred at 90° C. for 2 hours and extracted with EtOAc. The combined organic layers were washed with 1N HCl, brine and water, dried over $Na_2SO_4$ and concentrated. The residue was purified by silica gel chromatography eluted with 20% EtOAc in Hexanes to provide 100 mg (70% pure) of the title compound as a pale yellow oil used as such.

Step 2: (+/−)-[8-Acetyl-9-[(4-chlorophenyl)sulfanyl]-6-fluoro-2,3-dihydro-1H-pyrrolo[1,2-a]indol-1-yl]acetic acid To a solution of the ester of Step 1 (100 mg) in a THF/MeOH (3:1) mixture at r.t. was added 1N LiOH (aqueous solution). The reaction mixture was stirred at r.t. for 2 h and AcOH was added. The aqueous layer was extracted with EtOAc and the combined organic layers were dried over $Na_2SO_4$ and concentrated. The residue was purified by silica gel chromatography eluted with EtOAc/Hexanes/AcOH (20:30:1) to provide 55 mg of the title compound as a pale yellow solid.

$^1$H NMR (acetone-$d_6$) δ 7.35 (1H, dd), 7.21 (2H, d), 7.02–6.96 (311, m), 4.43–4.36 (1H, m), 4.27–4.21 (1H, m), 3.86–3.78 (1H, m), 3.17 (1H, dd), 3.08–2.99 (1H, m), 2.67 (1H, dd), 2.54–2.46 (1H, m), 2.38 (3H, s). MS (−APCI) m/z 416.0 (M−H)$^-$.

EXAMPLE 11

(+/−)-[9-[(4-chlorophenyl)sulfanyl]-6-fluoro-8-(trifluoroacetyl)-2,3-dihydro-1H-pyrrolo[1,2-a]indol-1-yl]acetic acid

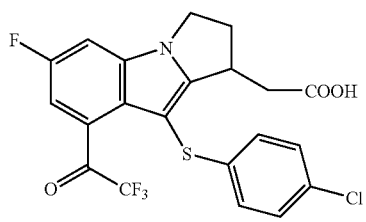

Step 1: (+/−)-[9-[(4-Chlorophenyl)sulfanyl]-6-fluoro-8-(trifluoroacetyl)-2,3-dihydro-1H-pyrrolo[1,2-a]indol-1-yl]acetic acid To a solution of (+/−)-[8-bromo-9-[(4-chlorophenyl)sulfanyl]-6-fluoro-2,3-dihydro-1H-pyrrolo[1,2-a]indol-1-yl] acetic acid (Example 7, 250 mg, 0.6 mmol) in THF (8 mL) at −78° C. was added 3M MeMgBr (0.7 mmol) followed by the addition of sec-BuLi (0.8 mmol, 1.3M solution). The reaction mixture was stirred at −78° C. for 5 minutes and methyl trifluoroacetate (352 mg, 2.8 mmol) was added., The reaction mixture was warmed to r.t., stirred for 4 hours and saturated aqueous $NH_4Cl$ was added. The phases were separated and the aqueous layer was extracted with EtOAc. The combined organic layers were dried over $Na_2SO_4$ and concentrated. The residue was purified by silica gel chromatography eluted with EtOAc/Hexanes/AcOH (20:30:1) to provide 150 mg of the title compound as a white solid.

$^1$H NMR (acetone-$d_6$) δ 7.64 (1H, dd), 7.26–7.20 (3H, m), 6.97 (2H, d), 4.50–4.43 (1H, m), 4.36–4.30 (1H, m), 3.90–3.83 (1H, m), 3.18 (1H, dd), 3.10–3.02 (1H, m), 2.73 (1H, dd), 2.58–2.50 (1H, m). MS (−APCI) m/z 470.1 (M−H)$^-$.

EXAMPLE 12

(+/−)-[9-[(4-chlorophenyl)sulfanyl]-6-fluoro-8-(2,2,2-trifluoro-1-hydroxyethyl)-2,3-dihydro-1H-pyrrolo[1,2-a]indol-1-yl]acetic acid

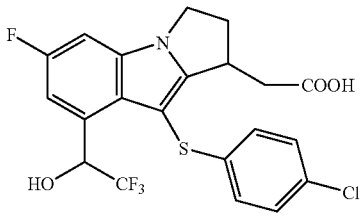

To a solution of (+/−)-[9-[(4-chlorophenyl)sulfanyl]-6-fluoro-8-(trifluoroacetyl)-2,3-dihydro-1H-pyrrolo[1,2-a]indol-1-yl]acetic acid (Example 11, 78 mg) in MeOH (5 mL) at r.t. was added 50 mg of NaBH$_4$. The reaction mixture was stirred at r.t. for 3 hours and 1N HCl was slowly added. The aqueous layer was extracted with EtOAc and the combined organic layers were dried over Na$_2$SO$_4$ and concentrated. The residue was purified by silica gel chromatography eluted with EtOAc/Hexanes/AcOH (20:30:1) to provide 60 mg of the title compound as a white solid.

(Mixture of diastereomers) $^1$H NMR (acetone-d$_6$) δ 7.31–7.23 (8H, m), 7.05–7.03 (4H, m), 6.59–6.54 (1H, m), 6.47–6.43 (1H, m), 5.95–5.75 (2H, br s), 4.42–4.36 (2H, m), 4.28–4.21 (2H, m), 3.88–3.77 (2H, m), 3.29–3.24 (1H, m), 3.10–2.98 (3H, m), 2.74–2.60 (2H, m), 2.54–2.46 (2H, m).

EXAMPLE 13

(+/−)-[9-[(4-chlorophenyl)sulfanyl]-6-fluoro-8-(1-hydroxy-2-methylpropyl)-2,3-dihydro-1H-pyrrolo[1,2-a]indol-1-yl]acetic acid

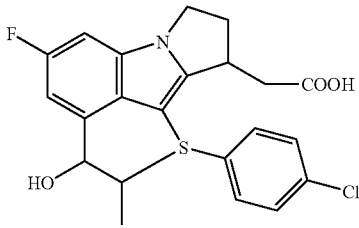

To a solution of (+/−)-[8-bromo-9-[(4-chlorophenyl)sulfanyl]-6-fluoro-2,3-dihydro-1H-pyrrolo[1,2-a]indol-1-yl] acetic acid (Example 7, 100 mg, 0.22 mmol) in THF (4 mL) at −78° C. was added 3M MeMgBr (0.26 mmol) followed by the addition of 1.3M sec-BuLi (0.31 mmol). The reaction mixture was stirred at −78° C. for 20 minutes and an excess of isobutyraldehyde was added. The reaction mixture was slowly warmed to −20° C. over a 30 minute period and quenched with saturated aqueous NH$_4$Cl. The phases were separated and the aqueous layer was extracted with EtOAc. The combined organic layers were dried over Na$_2$SO$_4$ and concentrated. The residue was purified by preparative HPLC using a Zorbax column eluted with 10% iPrOH in Hexanes containing 0.2% of AcOH to provide 40 mg of the title compound as a white solid.

(Mixture of diastereomeres) $^1$H NMR (acetone-d$_6$) δ 7.24 (4H, d), 7.17–7.01 (8H, m), 5.59–5.54 (1H, m), 5.47–5.43 (1H, m), 4.37–4.30 (2H, m), 4.23–4.16 (2H, m), 4.05–3.95 (2H, m), 3.84–3.76 (2H, m), 3.25 (1H, dd), 3.10 (1H, dd), 3.05–2.97 (2H, m), 2.72–2.57 (2H, m), 2.52–2.43 (2H, m), 2.09–1.97 (2H, m), 0.97–0.90 (6H, m), 0.76 (6H, d). MS (−APCI) m/z 446.2 (M−H)$^−$.

EXAMPLE 14

(+/−)-[9-[(4-chlorophenyl)sulfanyl]-6-fluoro-8-(1-hydroxy-ethyl)-2,3-dihydro-1H-pyrrolo[1,2-a]indol-1-yl]acetic acid

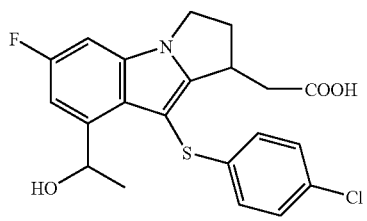

To a solution of (+/−)-[8-bromo-9-[(4-chlorophenyl)sulfanyl]-6-fluoro-2,3-dihydro-1H-pyrrolo[1,2-a]indol-1-yl] acetic acid (Example 7, 100 mg, 0.22 mmol) in THF (4 mL) at −78° C. was added 3M MeMgBr (0.26 mmol) followed by the addition of 1.3M sec-BuLi (0.31 mmol). The reaction mixture was stirred at −78° C. for 5 minutes and an excess of acetaldehyde was added. The reaction was stirred at −78° C. for 30 minutes and quenched with saturated aqueous NH$_4$Cl. The phases were separated and the aqueous layer was extracted with EtOAc. The combined organic layers were dried over Na$_2$SO$_4$ and concentrated. The residue was purified by silica gel chromatography eluted with EtOAc/Hexanes/AcOH (20:30:1) to provide 65 mg of the title compound as a white solid.

(Mixture of diastereomers) $^1$H NMR (acetone-d$_6$) δ 7.26–7.19 (6H, m), 7.08–7.01 (6H, m), 5.91 (1H, q), 5.80 (1H, q), 4.37–4.31 (2H, m), 4.22–4.15 (2H, m), 3.84–3.77 (2H, m), 3.22 (1H, dd), 3.13 (1H, dd), 3.04–2.96 (2H, m), 2.71–2.58 (2H, m), 2.52–2.42 (2H, m), 1.35 (3H, d), 1.30 (3H, d).

MS (−APCI) m/z 418.2 (M−H)$^−$.

EXAMPLE 15

(+/−)-[9-[(4-chlorophenyl)sulfanyl]-6-fluoro-8-(1-methoxy-ethyl-2,3-dihydro-1H-pyrrolo[1,2-a]indol-1-yl]acetic acid

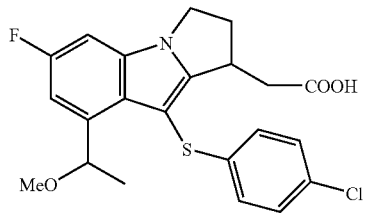

Step 1: (+/−)-Methyl [9-[(4-chlorophenyl)sulfanyl]-6-fluoro-8-(1-hydroxyethyl)-2,3-dihydro-1H-pyrrolo[1,2-a]indol-1-yl]acetate (+/−)-[9-[(4-Chlorophenyl)sulfanyl]-6-fluoro-8-(1-hydroxyethyl)-2,3-dihydro-1H-pyrrolo[1,2-a]indol-1-yl]acetic acid (Example 14, 100 mg) was esterified in Et$_2$O by addition of an excess of CH$_2$N$_2$. After removal of the solvents, the title ester was obtained quantitatively as a pale yellow solid and used as such.

Step 2: (+/−)-Methyl [9-[(4-chlorophenyl)sulfanyl]-6-fluoro-8-(1-methoxyethyl)-2,3-dihydro-1H-pyrrolo[1,2-a]indol-1-yl]acetate To a solution of the alcohol of Step 1 (105 mg, 0.25 mmol) in DMF (5 mL) at 0° C. was added NaH (11 mg, 0.3 mmol). The reaction mixture was stirred at 0° C. for 20 minutes and MeI (51 mg, 0.4 mmol) was added. The reaction was stirred at 0° C. for 30 minutes and quenched with saturated aqueous NH$_4$Cl and extracted with EtOAc. The combined organic layers were washed with brine, dried over Na$_2$SO$_4$ and concentrated. The residue was purified by silica gel chromatography eluted with 30% EtOAc in Hexanes to provide 90 mg of the title compound as a white solid.

(Mixture of diastereomers) $^1$H NMR (acetone-d$_6$) δ 7.29–7.26 (4H, m), 7.13–7.04 (6H, m), 6.98 (2H, dd), 5.48–5.44 (1H, m), 5.30–5.26 (1H, m), 4.38–4.32 (2H, m), 4.24–4.18 (2H, m), 3.87–3.83 (2H, m), 3.63 (3H, s), 3.59 (3H, s), 3.23–2.95 (4H, m), 2.96 (3H, s), 2.90 (3H, s), 2.75–2.68 (2H, m), 2.50–2.43 (2H, m), 1.30 (3H, d), 1.21 (3H, d). MS (+APCI) m/z 416.1 (M-OMe)$^+$.

Step 3: (+/−)-[9-[(4-Chlorophenyl)sulfanyl]-6-fluoro-8-(1-methoxyethyl)-2,3-dihydro-1H-pyrrolo[1,2-a]indol-1-yl]acetic acid The ester of Step 2 (80 mg) was hydrolyzed using the procedure described in Example 10, Step 2 to provide 70 mg of the title acid as a white foam.

Mixture of diastereomer: $^1$H NMR (methanol-d$_4$) δ 7.22–7.19 (4H, m), 7.04–6.91 (8H, m), 5.57–5.52 (1H, m), 5.43–5.39 (1H, m), 4.27–4.23 (2H, m), 4.14–4.08 (2H, m), 3.85–3.80 (2H, m), 3.19–2.88 (4H, m), 2.97 (3H, s), 2.92 (3H, s), 2.46–2.40 (2H, m), 2.34–2.24 (2H, m), 1.30 (3H, d), 1.25 (3H, d).

MS (−APCI) m/z 432.3 (M−H)$^-$.

EXAMPLE 15A

[9-[(4-chlorophenyl)sulfanyl]-6-fluoro-8-(1-methoxy-ethyl)-2,3-dihydro-1H-pyrrolo[1,2-a]indol-1-yl] acetic acid (as a pair of diastereomers)

Step 1: [9-[(4-Chlorophenyl)sulfanyl]-6-fluoro-8-(1-hydroxyethyl-2,3-dihydro-1H-pyrrolo[1,2-a]indol-1-yl]acetic acid The title compound was prepared following the procedures described in Example 14 staring from (+)-[8-bromo-9-[(4-chlorophenyl)sulfanyl]-6-fluoro-2,3-dihydro-1H-pyrrolo[1,2-a]indol-1-yl]acetic acid (Example 7A).

Step 2: [9-[(4-Chlorophenyl)sulfanyl]-6-fluoro-8-(1-methoxyethyl)-2,3-dihydro-1h-pyrrolo[1,2-a]indol-1-yl]acetic acid Starting from the product of Step 1 and following the methods described in Steps 1–3 of Example 15, two diastereomers were obtained, which were resolved by preparative HPLC on a chiralpak A/D preparative column eluted with a mixture of 5% iPrOH in hexanes+0.2% AcOH. Both isomer A and isomer B were obtained as a white solid with diastereomeric excess >95%.

Isomer A (less polar isomer): $^1$H NMR (acetone-d$_6$) δ 7.27 (2H, d), 7.13 (1H, dd), 7.08 (2H, d), 6.97 (1H, dd), 5.29 (1H, q), 4.39–4.33 (1H, m), 4.24–4.18 (1H, m), 3.89–3.82 (1H, m), 3.14 (1H, dd), 3.05–2.95 (1H, m), 2.89 (3H, s), 2.67 (1H, dd), 2.52–2.46 (1H, m), 1.29 (3H, d), MS (−APCI) m/z 432.3 (M−H)$^-$. [α]$_D$=+151°, c=0.1 of sodium salt in acetone.

Isomer B (more polar isomer): $^1$H NMR (acetone-d$_6$) δ 7.27 (2H, d), 7.13 (1H, dd), 7.08 (2H, d), 6.97 (1H, dd), 5.49–5.44 (1H, m), 4.38–4.33 (1H, m), 4.24–4.18 (1H, m), 3.87–3.81 (1H, m), 3.23 (1H, dd), 3.05–2.96 (1H, m), 2.95 (3H, s), 2.70 (1H, dd), 2.52–2.45 (1H, m), 1.22 (3H, d), MS (−APCI) m/z 432.3 (M−H)$^-$. [α]$_D$=−5°, c=0.1 of sodium salt in acetone.

EXAMPLE 16

(+/−)-[8-acetyl-6-fluoro-9-(phenylsulfanyl-2,3-dihydro-1H-pyrrolo[1,2-a]indol-1-yl]acetic acid

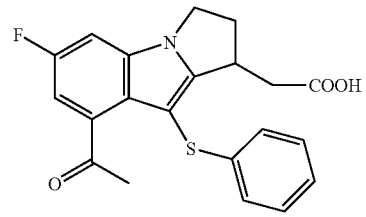

Step 1: (+/−)-Methyl (8-acetyl-6-fluoro-2,3-dihydro-1H-pyrrolo[1,2-a]indol-1-yl)acetate A mixture of tris(dibenzyllideneacetone)dipalladium (281 mg, 0.3 mmol) and triphenyl arsine (367 mg, 1.2 mmol) in DMF (4 mL) was sonicated for 10 minutes and then degassed. A solution of (+/−)-methyl (8-bromo-6-fluoro-2,3-dihydro-1H-pyrrolo[1,2-a]indol-1-yl)acetate (Example 7, Step 8, 200 mg, 0.6 mmol) in 3 mL of DMF and 1-ethoxyvinyltri-n-butyltin (650 mg, 1.8 mmol) were added and the mixture was degassed. The reaction mixture was stirred at 90° C. for 12 hours and 1N HCl (4 mL) was added. The mixture was stirred at 90° C. for 12 hours and extracted with EtOAc. The combined organic layers were washed with 1N HCl, brine and water, dried over Na$_2$SO$_4$ and concentrated. The residue was purified by silica gel chromatography eluted with 20% EtOAc in hexanes to provide the title compound (70% pure) as a pale yellow oil used as such.

Step 2: (+/−)-Methyl [8-acetyl-6-fluoro-9-(phenylsulfanyl)-2,3-dihydro-1H-pyrrolo[1,2-a]indol-1-yl]acetate Starting from diphenyl disulphide (93 mg, 0.43 mmol) and the ester of Step 1 (50 mg, 0.17 mmol) the title compound was synthesized as described Step 9, Example 7 as pale yellow foam.

$^1$H NMR (acetone-d$_6$) δ 7.34 (1H, dd), 7.19 (2H, t), 7.08 (1H, t), 6.98 (2H, d), 6.93 (1H, dd), 4.42–4.37 (1H, m), 4.28–4.23 (1H, m), 3.87–3.80 (1H, m), 3.61 (3H, s), 3.17 (1H, dd), 3.05–2.98 (1H, m), 2.69 (1H, dd), 2.49–2.44 (1H, m), 2.32 (3H, s).

Step 3: (+/−)-[8-Acetyl-6-fluoro-9-(phenylsulfanyl)-2,3-dihydro-1H-pyrrolo[1,2-a]indol-1-yl]acetic acid The ester of Step 2 (25 mg) was hydrolyzed using the procedure described in Example 10, Step 2 to provide the title compound as a pale yellow foam.

$^1$H NMR (acetone-d$_6$) δ 7.34 (1H, dd), 7.19 (2H, t), 7.07 (1H, t), 7.0 (2H, d), 6.93 (1H, dd), 4.43–4.37 (1H, m), 4.28–4.22 (1H, m), 3.83–3.77 (1H, m), 3.22 (1H, dd), 3.06–2.99 (1H, m), 2.65 (1H, dd), 2.53–2.46 (1H, m), 2.32 (3H, s), MS (–APCI) m/z 382.3 (M–H)⁻.

EXAMPLE 17

(+/−)-[8-acetyl-9-[(3,4-dichlorophenyl)sulfanyl]-6-fluoro-2,3-dihydro-1H-pyrrolo[1,2-a]indol-1-yl]acetic acid

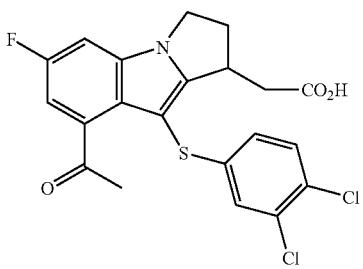

Step 1: (+/−)-Methyl [8-acetyl-9-[(3,4-dichlorophenyl)sulfanyl]-6-fluoro-2,3-dihydro-1H-pyrrolo[1,2-a]indol-1-yl]acetate Starting from bis(3,4-dichlorophenyl) disulphide (153 mg, 0.43 mmol) and (+/−)-methyl (8-acetyl-6-fluoro-2,3-dihydro-1H-pyrrolo[1,2-a]indol-1-yl)acetate (Example 16, Step 1, 50 mg, 0.17 mmol) the title compound was synthesized as described in Step 9 of Example 7 as a pale yellow foam.

¹H NMR (acetone-d₆) δ 7.37–7.34 (2H, m), 7.10 (1H, d), 7.02 (1H, dd), 6.93 (1H, dd), 4.41–4.35 (1H, m), 4.26–4.21 (1H, m), 3.86–3.80 (1H, m), 3.58 (3H, m), 3.09 (1H, dd), 3.02–2.94 (1H, m), 2.71 (1H, dd), 2.50–2.43 (1H, m), 2.39 (3H, s).

Step 2: (+/−)-[8-Acetyl-9-[(3,4-dichlorophenyl)sulfanyl]-6-fluoro-2,3-dihydro-1H-pyrrolo[1,2-a]indol-1-yl]acetic acid The ester of Step 1 (28 mg) was hydrolyzed using the procedure described in Example 10, Step 2 to provide the title compound as a pale yellow foam.

¹H NMR (acetone-d₆) δ 7.37 (2H, m), 7.15 (1H, d), 7.04 (1H, dd), 6.97 (1H, dd), 4.44–4.38 (1H, m), 4.29–4.23 (1H, m), 3.86–3.81 (1H, m), 3.16 (1H, dd), 3.05–2.99 (1H, m), 2.70 (1H, dd), 2.55–2.49 (1H, m), 2.43 (3H, s), MS (–APCI) ra/z 450.1 (M–H)⁻.

EXAMPLE 18

(+/−)-[9-[(4-chlorophenyl)sulfanyl]-6-fluoro-8-(2,2,2-trifluoro-1-methoxyethyl)-2,3-dihydro-1H-pyrrolo[1,2-a]indol-1-yl]acetic acid

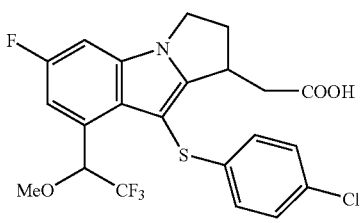

Step 1: (+/−)-Methyl [9-[(4-chlorophenyl)sulfanyl]-6-fluoro-8-(2,2,2-trifluoro-1-methoxyethyl)-2,3-dihydro-1H-pyrrolo[1,2-a]indol-1-yl]acetate To a solution of (+/−)-[9-[(4-chlorophenyl)sulfanyl]-6-fluoro-8-(2,2,2-trifluoro-1-hydroxyethyl)-2,3-dihydro-1H-pyrrolo[1,2-a]indol-1-yl]acetic acid (Example 12, 27 mg, 0.07 mmol) in DMF (4 mL) at 0° C. was added NaH (24 mg, 0.6 mmol, 60% in oil). The reaction mixture was stirred at 0° C. for 15 minutes and methyl iodide (52 mg, 0.36 mmol) was added. The reaction mixture was stirred for 15 minutes and quenched with saturated aqueous NH₄Cl and extracted with EtOAc. The combined organic layers were dried over Na₂SO₄, concentrated and used as such.

Step 2: (+/−)-[9-[(4-Chlorophenyl)sulfanyl]-6-fluoro-8-(2,2,2-trifluoro-1-methoxyethyl)-2,3-dihydro-1H-pyrrolo[1,2-a]indol-1-yl]acetic acid The ester of Step 1 (30 mg) was hydrolyzed using the procedure described in Example 10, Step 2 to provide the title compound as a white solid.

(Mixture of diastereomers) ¹H NMR (acetone-d₆) δ 7.39–7.34 (2H, m), 7.31–7.27 (4H, m), 7.12–7.0 (6H, m), 6.12–6.07 (1H, m), 5.96–5.91 (1H, m), 4.45–4.38 (2H, m), 4.30–4.24 (m, 2H), 3.93–3.85 (2H, m), 3.27 (1H, dd), 3.13 (1H, dd), 3.09–3.01 (2H, m), 3.00 (3H, s), 2.93 (3H, s), 2.80–2.69 (2H, m), 2.56–2.49 (2H, m), MS (–APCI) m/z 486.3(M–H)⁻.

EXAMPLE 19

[9-[(4-chlorophenyl)sulfanyl]-6-fluoro-8-(1-hydroxypropyl)-2,3-dihydro-1H-pyrrolo[1,2-a]indol-1-yl]acetic acid

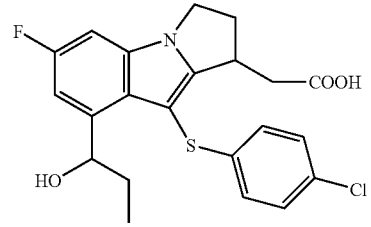

To a solution of (+)-[8-bromo-9-[(4-chlorophenyl)sulfanyl]-6-fluoro-2,3-dihydro-1H-pyrrolo[1,2-a]indol-1-yl]acetic acid (Example 7A, 700 mg, 1.5 mmol) in THF (15 mL) at −78° C. was added 3M MeMgBr in THF (1.9 mmol) followed by the addition of 1.6M nBuLi in hexane (3.1 mmol). The reaction mixture was stirred at −78° C. for 2 minutes and an excess of propionaldehyde was added. The reaction mixture was stirred at −78° C. for 15 minutes, warmed to r.t and quenched with saturated aqueous NH₄Cl The phases were separated and the aqueous layer was extracted with EtOAc. The combined organic layers were dried over Na₂SO₄ and concentrated. The residue was purified by silica gel chromatography eluted with EtOAc/hexanes/AcOH (20:30:1) to provide the title compound as a white solid.

(Mixture of two diastereomeres) ¹H NMR (acetone-d₆) δ 7.25–7.15 (6H, m), 7.08–7.03 (6H, m), 5.67–5.63 (1H, m), 5.56–5.52 (1H, m), 4.37–4.31 (2H, m), 4.23–4.16 (2H, m), 4.85–4.79 (2H, m), 3.22 (1H, dd), 3.12 (1H, m), 3.05–2.95 (2H, m), 2.70–2.60 (2H, m), 2.51–2.45 (2H, m), 1.78–1.65 (2H, m), 1.53–1.47 (2H, m), 0.93–0.85 (6H, m), MS (–APCI) m/z 432.3 (M–H)⁻.

EXAMPLE 20

[9-[(4-chlorophenyl)sulfanyl]-6-fluoro-8-(1-methoxypropyl)-2,3-dihydro-1H-pyrrolo[1,2-a]indol-1-yl]acetic acid

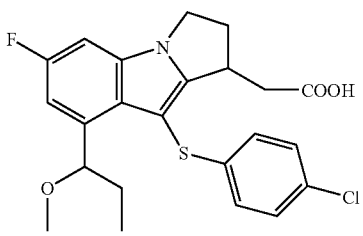

Step 1: Methyl[9-[(4-chlorophenyl)sulfanyl]-6-fluoro-8-(1-methoxypropyl)-2,3-dihydro-1H-pyrrolo[1,2-a]indol-1-yl]acetate To a solution of ([9-[(4-chlorophenyl)sulfanyl]-6-fluoro-8-(1-hydroxypropyl)-2,3-dihydro-1H-pyrrolo[1,2-a]indol-1-yl]acetic acid (Example 19, mixture of two diastereomers, 525 mg, 1.2 mmol) in DMF (20 mL) at 0° C. was added NaH (480 mg, 12 mmol). The reaction mixture was stirred at 0° C. for 15 minutes and methyl iodide (1.02 g, 7.2 mmol) was added. The reaction mixture was stirred for 15 minutes, quenched with saturated aqueous NH$_4$Cl and extracted with EtOAc. The combined organic layers were dried over Na$_2$SO$_4$ and concentrated. The residue was purified by silica gel chromatography eluted with EtOAc/hexanes (30:70) to provide the title compound as a yellow oil.

(Mixture of two diastereomeres) $^1$H NMR (acetone-d$_6$) δ 7.28–7.23 (4H, m), 7.11–7.01 (6H, m), 6.91 (2H, dd), 5.21–5.18 (1H, m), 5.03–5.0 (1H, m), 4.354.29 (2H, m), 4.21–4.16 (21H, m), 3.86–3.80 (2H, m), 3.61 (3H, s), 3.56 (3H, s), 3.16 (1H, dd), 3.07 (1H, dd), 3.01–2.93 (2H, m), 2.92 (3H, s), 2.85 (3H, s), 2.72–2.66 (2H, m), 2.47–2.41 (2H, m), 1.67–1.62 (1H, m), 1.55–1.46 (3H, m), 0.85 (3H, t), 0.77 (3H, t).

Step 2: [9-[(4-Chlorophenyl)sulfanyl]-6-fluoro-8-(1-methoxypropyl)-2,3-dihydro-1H-pyrrolo[1,2-a]indol-1-yl]acetic acid The ester of Step 1 (540 mg) was hydrolyzed using the procedure described in Example 10, Step 2 to provide the title compound (mixture of 2 diastereomers) as a yellow syrup. The two diastereomers were separated by preparative HPLC on a chiralpak A/D preparative column eluted with a mixture of 5% iPrOH in hexanes+0.2% AcOH, to give isomer A (less polar isomer) and isomer B (more polar isomer) as a white foam.

Isomer A: $^1$H NMR (acetone-d$_6$) δ 7.28 (2H, d), 7.13 (1H, dd), 7.08 (2H, d), 6.94 (1H, dd), 5.07–5.04 (1H, m), 4.38–4.33 (1H, m), 4.24–4.18 (1H, m), 3.88–3.82 (1H, m), 3.15 (1H, dd), 3.06–2.98 (1H, m), 2.88 (3H, s), 2.68 (1H, dd), 2.53–2.45 (1H, m), 1.70–1.65 (1H, m), 1.58–1.51 (1H, m), 0.88 (3H, t). [α]$_D$=+1480, c=0.1 of sodium salt in MeOH.

Isomer B: $^1$H NMR (acetone-d$_6$) δ 7.24 (2H, d), 7.10 (1H, dd), 7.05 (2H, d), 6.91 (1H, dd), 5.21–5.18 (1H, m), 4.35–4.30 (1H, m), 4.21–4.16 (1H, m), 3.84–3.80 (1H, m), 3.20 (1H, dd), 3.02–2.95 (1H, m), 2.92 (3H, s), 2.67 (1H, dd), 2.49–2.43 (1H, m), 1.55–1.47 (2H, m), 0.78 (3H, t). [α]$_D$=−5, c=0.1 of sodium salt in MeOH.

EXAMPLE 21

[9-[(4-chlorophenyl)sulfanyl]-6-fluoro-8-[1-(methylsulfanyl)ethyl]-2,3-dihydro-1H-pyrrolo[1,2-a]indol-1-yl]acetic acid

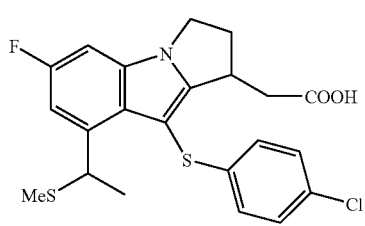

Methanethiol was bubbled into a solution of [9-[(4-chlorophenyl)-sulfanyl]-6-fluoro-8-(1-hydroxyethyl)-2,3-dihydro-1H-pyrrolo [1,2-a]indol-1-yl]acetic acid (Example 15A, Step 1, 48 mg, 0.1 mmol) in 5 mL of dichloro'methane at 0° C. and zinc iodide (5 mg, 0.015 mmol) was added. The reaction mixture was stirred at 0° C. for 15 minutes and quenched with saturated aqueous NH$_4$Cl and extracted with EtOAc. The combined organic layers were dried over Na$_2$SO$_4$ and concentrated. The residue was purified by preparative HPLC with a C18 Zorbax column using a mixture of 5% iPrOH in hexanes+0.2% AcOH as eluant to provide the title compound as a white solid foam.

Mixture of diastereomer: $^1$H NMR (acetone-d$_6$) δ 7.28–7.25 (4H, m), 7.18–7.07 (8H, m), 5.34–5.28 (1H, m), 5.24–5.22 (1H, m), 4.38–4.31 (2H, m), 4.24–4.17 (2H, m), 3.88–3.81 (2H, m), 3.21–3.15 (2H, m), 3.06–2.97 (2H, m), 2.73–2.62 (2H, m), 2.52–2.43 (2H, m), 1.75 (3H, s), 1.67 (3H, s), 1.40 (3H, d), 1.34 (3H, d), MS (−APCI) m/z 448.1 (M−H)$^−$.

EXAMPLE 22

(+/−)-[9-[(4-chlorophenyl)sulfanyl]-6-methoxy-8-(methyl-sulfonyl)-2,3-dihydro-1H-pyrrolo[1,2-a]indol-1-yl]acetic acid

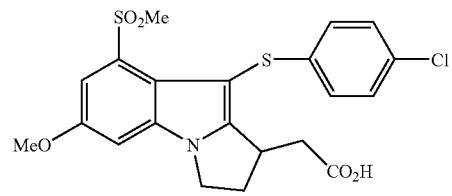

Step 1: 2-Bromo-4-methoxybenzaldehyde

To a solution of 2-bromo-4-fluorobenzaldehyde (50 g, 246 mmol), in MeOH (500 mL) in a 15° C. water bath was added a 25% solution of NaOMe/MeOH (88 mL). The mixture was stirred at r.t. for 1 hour followed by 2 hours at reflux. The solid was filtered and the filtrate was concentrated to dryness to give a second crop of solid. Both crops were taken up in CH$_2$Cl$_2$/H$_2$O. After washing with H$_2$O, the organic phase was dried (MgSO$_4$), filtered, and evaporated to give an off-white solid (52.2 g).

Step 2: Methyl(2Z)-2-azido-3-(2-bromo-4-methoxyphenyl)-2-propenoate

A solution of the aldehyde from Step 1 (25 g, 116 mmol) in MeOH (200 mL) and THF (20 mL) was prepared and methyl azidoacetate (53 g) Synth. Commun. 675 (1991) was added. The resulting solution was added, over 30 minutes to a –10° C. (internal probe) solution of 25% (w/w) NaOMe in MeOH (100 mL). The mixture was then stirred at 0° C. for 3 hours, followed by overnight in an ice bath in the cold room. The suspension was then poured onto a mixture of ice water and NH$_4$Cl, and the product was extracted with EtOAc. The organic phase was washed with saturated NH$_4$Cl and brine, dried (Na$_2$SO$_4$), filtered and evaporated. The crude material was dissolved in CH$_2$Cl$_2$ and filtered through a plug of silica gel. After evaporation, the solvent was stirred with 1:5 Et$_2$O/hexane to give, after filtration, 25.3 g of a yellow solid.

Step 3: Methyl 4-bromo-6-methoxy-1H-indole-2-carboxylate

To refluxing xylenes (10 mL) was added slowly a solution of the azido compound of Step 2 (1.0 g, 3.2 mmol) in xylenes (10 mL). When the addition was completed, heating was continued for a further 5 minutes, at which point the mixture was cooled to RT and finally to 0° C. for 30 minutes. The product was collected by filtration, washing with hexane. An off-white solid (0.8 g) was obtained.

Step 4: 8-Bromo-6-methoxy-2,3-dihydro-1H-pyrrolo[1,2-a]indol-1-one

To a solution of the ester from Step 3 (0.5 g, 1.76 mmol) in toluene (7 mL) and THF (1 mL) at RT was added 1M potassium t-butoxide (1.76 mL, 1.76 mmol). After 15 minutes, methyl acrylate (0.32 mL, 3.5 mmol) was added, and the mixture was brought to reflux for 1.5 hours. The reaction was quenched by the addition of saturated NH$_4$Cl solution, and the product was extracted with EtOAc/THF. The organic layer was washed with H$_2$O and brine, dried (MgSO$_4$), filtered, and evaporated. The intermediate was suspended in EtOH (10 mL), and concentrated HCl (2 mL) was added. After heating to reflux for 2 hours, the mixture was cooled and diluted with H$_2$O (30 mL). The product was extracted with CH$_2$Cl$_2$ and the organic phase was washed with H$_2$O before drying (MgSO$_4$). Following filtration and removal of solvent under vacuum, the product was stirred with 1:2 EtOAc:hexane to give a tan-coloured solid (0.4 g).

Step 5: Methyl(8-bromo-6-methoxy-2,3-dihydro-1H-pyrrolo[1,2-a]indol-1-yl)acetate A mixture of the ketone from Step 4 (0.4 g, 1.43 mmol), methyl bromoacetate (0.7 mL, 7.1 mmol), and Zn/Cu couple (0.46 g, 7.1 mmol) in THF (6 mL) was suspended in an ultrasound bath for 45 minutes. Saturated NH$_4$Cl solution and EtOAc were then added, and the suspension was filtered through a bed of Celite. The organic phase was washed with H$_2$O and brine, dried (MgSO$_4$), filtered and evaporated. The crude material was purified by flash chromatography (1:1 EtOAc/hexane) and the resulting intermediate was dissolved in CH$_3$CN (10 mL). This solution was then added to a stirring mixture of TMSCl (0.8 mL, 6.4 mmol) and NaI (0.95 g, 6.4 mmol) in CH$_3$CN (4 mL) in a RT H$_2$O bath. Saturated NaHCO$_3$ solution and sodium sulfite were added, and the product was extracted with EtOAc. The organic layer was washed with H$_2$O and brine, dried (MgSO$_4$), filtered, and evaporated to give a pale yellow solid (0.40 g).

Step 6: Methyl{8-bromo-9-[(4-chlorophenyl)sulfanyl]-6-methoxy-2.3-dihydro-1H-pyrrolo[1,2-a]indol-1-yl}acetate To a solution of bis(4-chlorophenyl)disulfide (0.59 g, 2.07 mmol) in dichloroethane (10 mL) at r.t. was added SO$_2$Cl$_2$ (0.12 mL, 1.55 mmol). After stirring at r.t. for 25 minutes 80% of this yellow solution was then added to a solution of the indole from Step 5 (0.35 g, 1.03 mmol) in DMF (10 mL). Saturated NaHCO$_3$ solution was then added, and the product was extracted with 1:1 Et$_2$O/EtOAc. The organic phase was washed with H$_2$O and brine, dried (MgSO$_4$), filtered, and evaporated. The crude product was purified by flash chromatography, eluting with 1:5 EtOAc:hexane (yield=0.37 g).

Step 7: Methyl[9-[(4-chlorophenyl)sulfanyl]-6-methoxy-8-(methylsulfonyl)-2,3-dihydro-1H-pyrrolo[1,2-a]indol-1-yl]acetate A degassed suspension of the product from Step 6 (0.15 g, 0.32 mmol) NaSO$_2$Me (0.30 g, 1.6 mmol), and CuI (0.16 g, 1.6 mmol) in NMP (4 mL) was stirred overnight at 130° C. EtOAc was then added, and the mixture was filtered through a pad of silica gel. The filtrate was washed with H$_2$O and brine, dried (MgSO$_4$), filtered, and evaporated. The residue was purified by flash chromatography, eluting with 1:2 and 1:1 EtOAc:hexane to give a tan coloured solid (23 mg).

Step 8: [9-[(4-chlorophenyl)sulfanyl]-6-methoxy-8-(methylsulfonyl)-2,3-dihydro-1H-pyrrolo[1,2-a]indol-1-yl]acetic acid To a solution of the ester from Step 7 (23 mg, 0.048 mmol) in THF (3 mL) and MeOH (1 mL) at RT was added 1M LiOH (0.24 mL, 0.24 mmol). After stirring at r.t. for 4.5 hours, HOAc (10 drops) was added and the solvent was evaporated. The residue was taken up in EtOAc/H$_2$O and the organic phase was washed with brine, dried (MgSO$_4$), and filtered. Upon removal of the solvent, the resulting solid was stirred with 1:5 EtOAc:hexane to give a beige solid (20 mg).

$^1$H NMR (acetone d$_6$) δ 2.43–2.52 (m 1H), 2.59–2.68 (m, 1H), 2.96–3.05 (m, 1H), 3.13–3.21 (m, 1H), 3.29 (s, 3H), 3.67–3.75 (m, 1H), 3.95 (s, 3H), 4.25–4.32 (m, 1H), 4.40–4.47 (m, 1H), 7.00–7.05 (m, 2H), 7.18–7.23 (m, 2H), 7.40–7.43 (m, 11), 7.50–7.53 (m, 1H), 10.80 (bs, 1H).

EXAMPLE 23

(+/–)-[6-(benzyloxy)-9-[(4-chlorophenyl)sulfanyl]-8-(methyl-sulfonyl)-2,3-dihydro-1H-pyrrolo[1,2-a]indol-1-yl]acetic acid

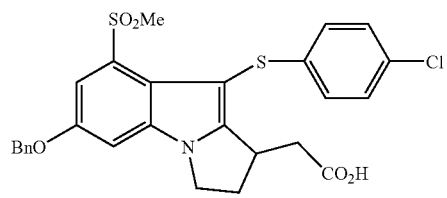

Step 1: Methyl[6-methoxy-8-(methylsulfonyl)-2,3-dihydro-1H-pyrrolo[1,2-a]-indol-1-yl]acetate In the same manner as Example 22 Step 7, the title compound was prepared from the bromide of Example 22 Step 5.

Step 2: Methyl[6-hydroxy-8-(methylsulfonyl)-2,3-dihydro-1H-pyrrolo[1,2-a]-indol-1-yl]acetate To a solution of the methyl ether from Step 1 (0.35 g, 1.03 mmol) in CH$_2$Cl$_2$ (5 mL) at 0° C. was added 1M BBr$_3$/CH$_2$Cl$_2$ (5.2 mL, 5.2 mmol) over a period of 55 minutes. The dark gummy suspension was then brought to RT for 2.5 hours. MeOH ($\approx$5 mL) was then added at −78° C. followed by saturated NaHCO$_3$ solution. The cold bath was removed and the mixture was stirred for 30 minutes. The product was then extracted with CH$_2$Cl$_2$ and the organic phase was washed with H$_2$O. After drying (MgSO$_4$), filtering, and evaporating, the residue was purified by flash chromatography (1:2, 1:1 EtOAc:hexane) to give a light brown solid (0.19 g).

Step 3: Methyl[6-(benzyloxy)-8-(methylsulfonyl)-2,3-dihydro-1H-pyrrolo[1,2-a]indol-1-yl]acetate To a solution of the alcohol from Step 2 (0.19 g, 0.59 mmol) and benzyl bromide (0.10 mL, 0.88 mmol) in DMF (4 mL) at 0° C. was added Cs$_2$CO$_3$ (0.29 g, 0.88 mmol). The mixture was stirred at RT for 1 hour, and then saturated NH$_4$Cl solution and H$_2$O were added. The product was extracted with 1:1 EtOAc:Et$_2$O and the organic layer was washed with H$_2$O and brine. After drying (MgSO$_4$), filtering, and removal of solvent, the crude product was purified by flash chromatography (1:2 EtOAc:hexane) to give a tan coloured foam (0.23 g).

Step 4: Methyl[6-(benzyloxy)-9-[(4-chlorophenyl)sulfanyl]-8-(methylsulfonyl)-2,3-dihydro-1H-pyrrolo[1,2-a}indol-1-yl]acetate In the same manner as in Example 22 Step 6, the title compound was prepared from the benzyl ether of Step 3.

Step 5: [6-(benzyloxy)-9-[(4-chlorophenyl)sulfanyl]-8-(methylsulfonyl)-2,3-dihydro-1H-pyrrolo[1,2-a]indol-1-yl]acetic acid In the same manner as in Example 22 Step 8, the title compound was prepared from the ester of Step 4.

$^1$H NMR (acetone d$_6$) δ 2.41–2.49 (m, 1H), 2.58–2.66 (m, 1H), 2.92–3.00 (m, 1H), 3.10–3.17 (m, 1H), 3.27 (s, 3H), 3.65–3.71 (m, 1H), 4.21–4.28 (m, 1H), 4.36–4.43 (m, 1H), 5.25 (s, 2H), 6.97–7.02 (m, 2H), 7.14–7.20 (m, 2H), 7.31–7.36 (m, 1H), 7.37–7.45 (m, 2H), 7.47–7.50 (m, 1H), 7.50–7.55 (m, 2H), 7.55–7.60 (m, 1H).

EXAMPLE 24

(+/−)-[9-[4-Chlorophenyl)thio]-8-(methylsulfonyl)-6-methylthio)-2,3-dihydro-1H-pyrrolo[1,2-a]indol-1-yl]acetic acid.

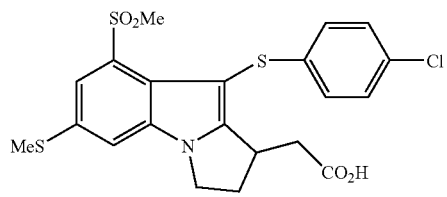

Step 1: 2-bromo-4-(methylthio)benzaldehyde

To 2-bromo-4-fluorobenzaldehyde (150 mg, 0.74 mmol) in methanol (2 mL) was added sodium thiomethoxide (80 mg, 1.1 mmol). The reaction mixture was heated to 50° C. for 1 hour. After cooling, the mixture was quenched with saturated aqueous NH$_4$Cl and extracted with EtOAc. The combined organic layers were dried over Na$_2$SO$_4$, concentrated, and used as such.

Step 2: (+/−)-[9-[(4-chlorophenyl)thio]-8-(methylsulfonyl)-6-methylthio)-2,3-dihydro-1H-pyrrolo[1-2-a]indol-1-yl] acetic acid The procedures of Example 22, Steps 2–8 were followed using the compound of Step 1 in place of 2-bromo-4-methoxybenzaldehyde to give the title compound.

$^1$H NMR (acetone d$_6$) δ 2.48 (m, 1H), 2.58 (s, 3H), 2.68(m, 1H), 3.00(m, 1H), 3.18(m, 1H), 3.29(m, 3H), 3.70 (m, 1H), 4.33 (m, 11), 4.48(m, 1H), 7.02 (d, 2H), 7.18(d, 2H), 7.50 (m, 2H).

EXAMPLE 25

(+/−)-[9-[(4-Chlorophenyl)thio]-8-isopropyl-6-(methylsulfonyl)-2,3-dihydro-1H-pyrrolo[1,2-a]indol-1-yl]acetic acid

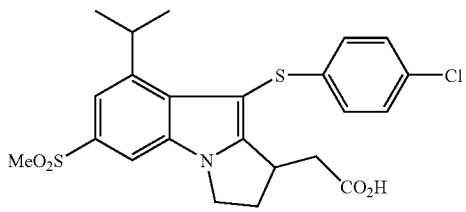

Step 1: Methyl[8-bromo-6-(methylsulfonyl)-2,3-dihydro-1H-pyrrolo[1,2-a]indol-1-yl]acetate To methyl[8-bromo-6-(methylthio)-2,3-dihydro-1H-pyrrolo(1,2-a]indol-1-yl]acetate (prepared according to the procedure of Example 22, Step 5, 500 mg, 1.48 mmol) in MeOH (25 mL) was added Na$_2$WO$_4$ (260 mg, 0.79 mmol) followed by H$_2$O$_2$ 30% (1.6 mL) slowly. After 5 minutes the reaction was quenched by adding H$_2$O and extracted with EtOAc. The organic layer was dried over Na$_2$SO$_4$, filtered and evaporated. The residue was stirred with hexane and EtOAc to give, after filtration, the title compound (300 mg).

Step 2: Methyl[8-isopropenyl-6-(methylsulfonyl)-2,3-dihydro-1H-pyrrolo[1,2-a]indol-1-yl]acetate Alpha-bromopropene (514 μL, 5.2 mmol) was added portionwise, in order to maintain 55° C. exotherm, to Mg (126 mg, 5.2 mmol) (in THF 4 mL) and a trace of iodine. The mixture was heated and stirred for 30 minutes. Dried ZnBr$_2$ (1.16 g, 5.2 mmol) in THF (4 mL) was added and the mixture was heated at 55° C. for 1 hour. The reaction mixture was cooled to room temperature, and Pd (dppf) CH$_2$Cl$_2$ (19 mg) was added followed by CuI (7 mg) after a further 5 minutes. The product of Step 1 (200 mg, 0.52 mmol) in 3 ml THF was then added. The reaction mixture was heated to 75° C. for 15 minutes. The reaction was quenched with saturated aqueous NH$_4$Cl and extracted with EtOAc. The combined organic layers were dried over Na$_2$SO$_4$ and concentrated. The residue was purified by silica gel chromatography to give the title compound (130 mg).

Step 3: Methyl[8-isopropyl-6-(methylsulfonyl)-2,3-dihydro-1H-pyrrolo[1,2-a]indol-1-yl]acetate To the product of Step 2 (130 mg, 0.39 mmol) in EtOH (3 mL) was added Pd/C 10% (40 mg). The mixture was hydrogenated with a Parr hydrogenator at 50 psi for 45 minutes, filtered on a pad of celite, and the filtrate evaporated to dryness and used as such in the next step.

Step 4: Methyl[9-[(4-chlorophenyl)thio]-8-isopropyl-6-(methylsulfonyl)-2,3-dihydro-1H-pyrrolo[1,2-a]indol-1-yl]acetate To 4,4'-dichlorodiphenyl disulfide (120 mg, 0.42 mmol) in 1,2-dichloroethane (4 ml) was added $SO_2Cl_2$ (25 μl, 0.31 mmol). The reaction mixture was stirred 25 minutes at r.t. Then, this yellow solution was added to the product of Step 3 (140 mg, 0.42 mmol) in DMF (4 ml) at r.t. The reaction mixture was stirred for 1 hour and was quenched with saturated $NaHCO_3$ and extracted with EtOAc. The combined organic layers were dried over $Na_2SO_4$ and concentrated. The residue was purified by silica gel chromatography to give the title compound (140 mg).

Step 5: [9-[(4-chlorophenyl)thio]-8-isopropyl-6-(methylsulfonyl)-2,3-dihydro-1H-pyrrolo[1,2-a]indol-1-yl]acetic acid To a solution of the ester of Step 4 (140 mg) in THF/MeOH (3/1) mixture at r.t. was added 1 M LiOH (aqueous solution). The reaction mixture was stirred at r.t. for 2 hours and AcOH was added and the solvent was evaporated. The residue was taken up in $EtOAc/H_2O$ and the organic phase was washed with brine, dried ($MgSO_4$), filtered and evaporated. The residue was purified by silica gel chromatography eluting with 1% AcOH in EtOAc to give 100 mg of the title compound.

$^1$H NMR (acetone $d_6$) δ 1.22(m, 6H), 2.55(m, 1H), 2.78(m, 1H), 3.05 (m, 1H), 3.22(m, 1H), 3.92 (m, 1H), 4.32 (m, 1H), 4.40 (m, 1H), 4.52(s, 1H), 7.08(d, 2H), 7.25 (s, 2H), 7.60 (s, 1H), 7.87(s, 1H).

EXAMPLE 26

(+/−)-[9-[(4-chlorophenyl)thio]-6-isopropoxy-8-(methylsulfonyl)-2,3-dihydro-1H-pyrrolo[1,2-a]indol-1-yl]acetic acid

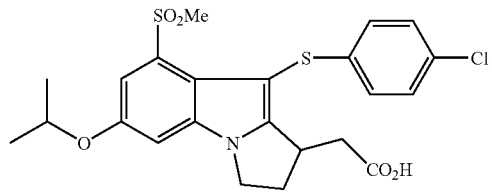

Step 1: Methyl[6-isopropoxy-8-(methylsulfonyl)-2,3-dihydro-1H-pyrrolo[1,2-a]indol-1-yl]acetate To methyl [6-hydroxy-8-(methylsulfonyl)-2,3-dihydro-1H-pyrrolo[1,2-a]indol-1-yl]acetate (Example 23, Step 2, 130 mg, 0.4 mmol) in DMF (1.5 mL) at r.t. was added 2-iodopropane (300 μL, 3 mmol) and $Cs_2CO_3$ (300 mg, 0.92 mmol). The reaction mixture was stirred for 15 minutes, and was then quenched with saturated aqueous $NH_4Cl$ and extracted with EtOAc. The combined organic layers were dried over $NaSO_4$ and concentrated. The residue was purified by silica gel chromatography to give the title compound (100 mg).

Step 2: Methyl[9-[(4-chlorophenyl)thio]-6-isopropoxy-8-(methylsulfonyl)-2,3-dihydro-1H-pyrrolo[1,2-a]indol-1-yl]acetate The procedure of Example 25, Step 4 was followed using the compound of Step 1 (80 mg, 0.23 mmol) in DMF (2 mL) to give the title compound (70 mg).

Step 3: (+/−)-[9-[(4-chlorophenyl)thio]-6-isopropoxy-8-(methylsulfonyl)-2,3-dihydro-1H-pyrrolo[1,2-a]indol-1-yl]acetic acid To a solution of the ester of Step 2 (70 mg) in THF/MeOH (3:1) mixture at r.t. was added 1 M LiOH aqueous solution (1 mL). The reaction mixture was stirred at r.t. for 1 hour. Then AcOH was added. The aqueous layer was extracted with EtOAC and the combined organic layers were dried over $Na_2SO_4$ and concentrated. The residue was purified by silica gel chromatography, eluting with 1% AcOH in EtOAc to give 60 mg of the title compound.

$^1$H NMR (acetone $d_6$) δ 1.34 (m, 6H), 2.45 (m, 1H), 2.60 (m, 1H), 2.98(m, 1H), 3.12(s, 1H), 3.28(m, 3H), 3.70 (s, 1H), 4.25(m, 1H), 4.40(m, 1H), 4.72(m, 1H), 7.00 (d, 2H), 7.20(d, 2H), 7.38(s, 1H), 7.50(s, 1H), 10.70 (bs, 1H).

EXAMPLE 27

(+/−)-{6-(benzyloxy-9-[(4-chlorophenyl)thio]-8-isopropyl-2,3-dihydro-1H-pyrrolo[1,2-a]indol-1-yl]acetic acid

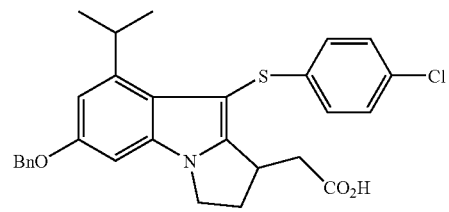

Step 1: Methyl(8-isopropenyl-6-methoxy-2,3-dihydro-1H-pyrrolo[1,2-a]indol-1-yl)acetate To Mg (143 mg, 5.8 mmol) in THF (4 mL) with trace of $I_2$ was added α-bromopropene (583 μL) in order to maintain a 60° C. exotherm. After 30 minutes, a solution of $ZnBr_2$ (1.31 g, 5.8 mmol) in THF (4 mL) was added. The reaction mixture was heated at 55° C. for 1 hour, cooled to r.t. and (Pd (dppf) $CH_2Cl_2$ (50 mg) was added followed by CuI (18.5 mg). After 5 minutes a solution of methyl (8-bromo-6-methoxy-2,3-dihydro-1H-pyrrolo[1,2-a]indol-1-yl)acetate (Example 22, Step 5, 200 mg, 0.59 mmol) in THF (7 mL) was added and the mixture was refluxed for 1 hour, cooled, quenched with saturated aqueous $NH_4Cl$ and extracted with EtOAc. The combined organic layers were dried over $Na_2SO_4$ and concentrated. The residue was purified by silica gel chromatography to give the title compound (50 mg).

Step 2: Methyl(8-isopropyl-6-methoxy-2,3-dihydro-1H-pyrrolo[1,2-a]indol-1-yl)acetate To the compound of Step 1 (200 mg, 0.67 mmol) in EtOH (20 mL) was added Pd/C 10% (100 mg). The mixture was hydrogenated with a Parr hydrogenator at 50 psi for 45 minutes the filtered on a pad of celite. The filtrate was evaporated to dryness and used as such in the next step (170 mg).

Step 3: Methyl(6-hydroxy-8-isopropyl-2,3-dihydro-1H-pyrrolo[1,2-a]indol-1-yl)acetate.

To a solution of the product of Step 2 (170 mg, 0.56 mmol) in $CH_2Cl_2$ (5 mL) at 0° C. was added slowly $BBr_3$ 1.0 M in dichloromethane (2.8 mL, 2.8 mmol) dropwise. The reaction mixture was warmed to r.t. for 30 minutes then cooled to −78° C., quenched with MeOH (5 mL), extracted with $CH_2Cl_2$, and washed with a saturated aqueous solution of NaHCO$_3$. The combined organic layers were dried over Na$_2$SO$_4$ and concentrated. The residue was purified by silica gel chromatography to give the title compound (130 mg).

Step 4: Methyl[6-(benzyloxy)-8-isopropyl-2,3-dihydro-1H-pyrrolo[1,2-a]indol-1-yl]acetate To the compound of Step 3 (130 mg, 0.45 mmol) in DMF (2 mL) at 0° C., was added benzyl bromide (100 mL) and Cs$_2$CO$_3$ (300 mg, 0.92 mmol). The reaction mixture was warmed to r.t for 1 hour. The reaction was quenched with saturated aqueous NH$_4$Cl and extracted with EtOAc. The combined organic layers were dried over Na$_2$SO$_4$ and concentrated. The residue was purified by silica gel chromatography to give the title compound (130 mg).

Step 5: Methyl{6-(benzyloxy)-9-[(4-chlorophenyl)thio]-8-isopropyl-2,3-dihydro-1H-pyrrolo[1,2-a]indol-1-yl}acetate The procedure of Example 25, Step 4 was followed using the compound of Step 4 (130 mg, 0.34 mmol) in DMF (4 mL) to give the title compound (100 mg).

Step 6: (+/−)-{6-(benzyloxy)-9-[(4-chlorophenyl)thio]-8-isopropyl-2,3-dihydro-1H-pyrrolo[1,2-a]indol-yl]acetic acid To a solution of the ester of Step 5 100 mg in THF/MeOH (3/1) mixture at r.t. was added in LiOH aqueous solution 1.0 mL. The reaction mixture was stirred at r.t. for 1 hour then AcOH was added and the solvent was evaporated. The residue was taken up in EtOAc/H$_2$O and the organic phase was washed with brine, dried (MgSO$_4$), filtered and evaporated. The residue was purified by silica gel chromatography, eluting with 1% AcOH in EtOAc to give 70 mg of the title compound.

$^1$H NMR (acetone d6) δ 1.10(m 3H), 1.15(m, 3H), 2.45 (m, 1H), 2.60(m, 1H), 2.95 (m, 1H), 3.18 (m, 1H), 3.80 (m, 1H), 4.15(m, 2H), 4.29(m, 1H), 5.18(s, 2H), 6.80(s, 1H), 6.94 (s, 1H), 7.06(d, 2H), 7.25(d, 2H), 7.38(m, 1H), 7.42(m, 2H), 7.55(d, 2H).

EXAMPLE 28

(+/−)-{9-[(4-chlorophenyl)thio]-8-isopropyl-6-methoxy-2,3-dihydro-1H-pyrrolo[1,2-a]indol-1-yl}acetic acid

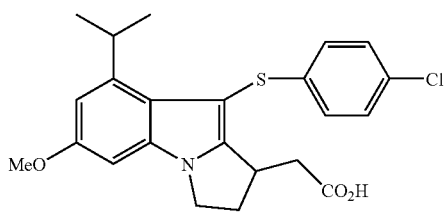

The procedures of Example 27, Steps 1, 2, 5 and 6 were followed using the product of Example 22, Step 5 to provide the title compound.

$^1$H NMR (acetone d6) δ 1.18(m 3H), 1.22(m, 3H), 2.32 (m, 1H), 2.60(m, 1H), 2.85(m, 1H), 3.15(m, 1H), 3.72 (m, 3H), 3.98(s, 1H), 4.33(m, 1H), 4.45(m, 1H), 4.65(m, 1H) 7.00(m, 1H), 7.08(m, 3H), 7.25(m, 2H),

EXAMPLE 29

(+/−)-[6-(4-chlorophenyl)-9-[(4-chlorophenyl)thio]-8-(methylsulfonyl)-2,3-dihydro-1H-pyrrolo[1,2-a]indol-1-yl]acetic acid

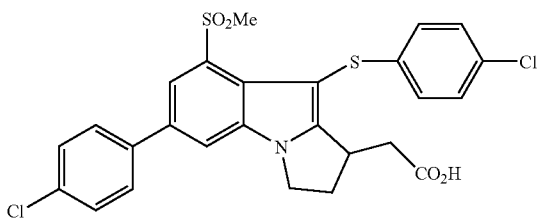

Step 1: Methyl(8-(methylsulfonyl)-6-{[(trifluoromethylsulfonyl]oxy}-2,3-dihydro-1H-pyrrolo[1,2-a]indol-yl)acetate To methyl [6-hydroxy-8-(methylsulfonyl)-2,3-dihydro-1H-pyrrolo[1,2-a]indol-1-yl]acetate (Example 23, Step 2, 74 mg, 0.28 mmol) in CH$_2$Cl$_2$ (3 mL) at 0° C. was added pyridine (28 μL, 0.36 mmol) followed by Tf$_2$O (77 μl, 0.46 mmol). The reaction mixture was then stirred for 1 hour at r.t. The reaction was quenched with a saturated solution of NaHCO$_3$ and extracted with CH$_2$Cl$_2$. The combined organic layers were dried over Na$_2$SO$_4$ and concentrated. The residue was purified by silica gel chromatography to give the title compound (63 mg).

Step 2: Methyl(9-[(4-chlorophenyl)thio]-8-(methylsulfonyl)-6-{[(trifluoro-methyl)sulfonyl]oxy}-2,3-dihydro-1H-pyrrolo[1,2-a]indol-1-yl)acetate The procedure of Example 25, Step 4 was followed using the compound of Step 1 (63 mg, 0.14 mmol) in DMF (1 mL) to give the title compound (53 mg).

Step 3: Methyl[6-(4-chlorophenyl)-9-[(4-chlorophenyl)thio]-8-(methylsulfonyl)-2,3-dihydro-1H-pyrrolo[1,2-a]indol-1-yl]acetate To the compound of Step 2 (53 mg, 0.089 mmol) in toluene/EtOH 3:1 mixture (4 mL) was added 4-chlorophenylboronic acid (28 mg, 0.18 mmol), K$_2$CO$_3$ (18 mg, 0.13 mmol), and tetrakis (triphenylphosphine) palladium (0) (5.1 mg, 0.04 mmol). The reaction mixture was stirred at 80° C. overnight. The reaction was quenched with saturated aqueous NH$_4$Cl and extracted with EtOAc. The combined organic layers were dried over Na$_2$SO$_4$ and concentrated. The residue was purified by silica gel chromatography to provide the title compound (40 mg)

Step 4: (+/−)-[6-(4-chlorophenyl)-9-[(4-chlorophenyl)thio]-8-(methylsulfonyl)-2,3-dihydro-1H-pyrrolo[1,2-a]indol-1-yl]acetic acid Starting from the product of Step 3 (40 mg, 0.07 mmol) the title compound (35 mg) was synthesized following the procedures described in Step 5 of Example 25.

$^1$H NMR (acetone d$_6$) δ 2.52(m 1H), 2.70(m, 1H), 3.05 (m, 1M), 3.20(m, 1H), 3.25 (s, 3H), 3.75 (m, 1H), 4.40(m, 1 h), 4.55(m 1H), 7.04(m, 2H), 7.20 (m, 2H), 7.55 (m, 2H), 7.80(m, 2H), 8.15 (m, 2H).

EXAMPLE 30

(+/−)-{8-bromo-9-[(4-chlorophenyl)thio]-6-iodo-2,3-dihydro-1H-pyrrolo[1,2-a]indol-1-yl}acetic acid

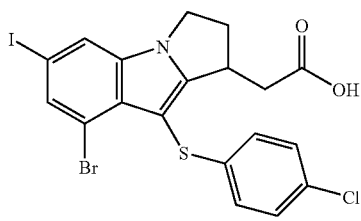

Step 1: 2-bromo-4-iodo-1-methylbenzene

To a vigorously stirred mixture of 3-bromo-4-methylaniline (40 g, 215 mmol), sulfuric acid (360 mL) and $H_2O$ (900 mL) at 0° C. was added dropwise a $NaNO_2$ solution (16.6 g, 240 mmol in 80 mL of $H_2O$). The mixture was stirred at 0° C. for 1 hour and a solution of potassium iodide (64 g, 387 mmol in 160 mL of $H_2O$) was added. The reaction was stirred for 8 hours at r.t. The aqueous layer was extracted with $Et_2O$ and the combined organic layers were washed with a 10% aqueous solution of $Na_2S_2O_3$, dried over $Na_2SO_4$ and concentrated. The residue was filtered through a silica gel pad eluted with 10% EtOAc/hexane and concentrated to give 60 g of the title compound as a reddish syrup used as such.

Step 2: (+/−)-{8-bromo-9-[(4-chlorophenyl)thio]-6-iodo-2,3-dihydro-1H-pyrrolo[1,2-a]indol-1-yl}acetic acid Starting from 2-bromo-4-iodo-1-methylbenzene, the title compound was synthesized by following the procedures described in Steps 1–10 of Example 7.

MS (−APCI) m/z 560.1 (M−H)⁻.

EXAMPLE 31

(+/−)-{8-bromo-9-[(4-chlorophenyl)thio]-6-cyano-2,3-dihydro-1H-pyrrolo[1,2-a]indol-yl}acetic acid

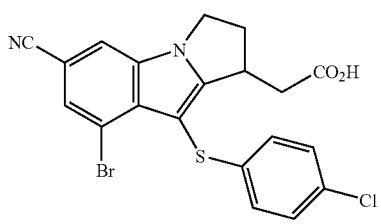

Step 1: (+/−)-methyl {8-bromo-9-[(4-chlorophenyl)thio]-6-cyano-2,3-dihydro-1H-pyrrolo[1,2-a]indol-1-yl}acetate To a solution of (+/−)-methyl {8-bromo-9-[(4-chlorophenyl)thio]-6-iodo-2,3-dihydro-1H-pyrrolo[1,2-a]indol-1-yl}acetate (see Example 30, 2.5 g, 4.3 mmol) in DMF (40 ml) were added zinc cyanide (1.27 g, 10.8 mmol), tris-(dibenzylideneacetone)dipalladium(0) (197 mg, 0.21 mmol), $H_2O$ (43 mmol) and 1,1'-bis(diphenylphosphino)ferrocene (120 mg, 0.21 mmol), and $N_2$ was bubbled for 2 minutes into the mixture. The reaction mixture was stirred for 10 hours at r.t. and poured into 1N HCl and extracted with EtOAc. The combined organic layers were washed with brine and dried over $Na_2SO_4$ and concentrated. The residue was purified by silica gel chromatography eluted with 20% EtOAc/hexane to give 1.6 g of a pale yellow solid.

MS (+APCI) m/z 476.9 (M+H)⁺.

Step 2: (+/−)-{8-bromo-9-[(4-chlorophenyl)thio]-6-cyano-2,3-dihydro-1H-pyrrolo[1,2-a]indol-1-yl}acetic acid The compound of Step 1 was hydrolyzed following the procedures described in Step 10 of Example 7 to give the title compound.

MS (−APCI) m/z 460.4 (M−H)⁻.

EXAMPLE 32

(+/−)-[8-bromo-9-[(4-chlorophenyl thio]-6-(2-methyl-2H-tetrazol-5-yl)-2,3-dihydro-1H-pyrrolo[1,2-a]indol-1-yl]acetic acid

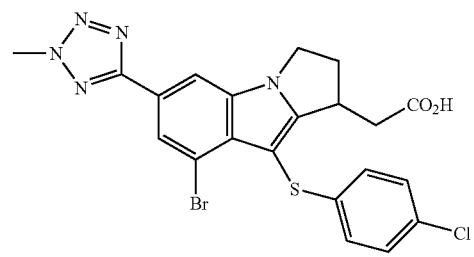

Step 1: (+/−)-methyl [8-bromo-9-[(4-chlorophenyl)thio]-6-(2H-tetrazol-5-yl)-2,3-dihydro-1H-pyrrolo[1,2-a]indol-1-yl]acetate To a solution of (+/−)-methyl {8-bromo-9-[(4-chlorophenyl)thio]-6-cyano-2,3-dihydro-1H-pyrrolo[1,2-a]indol-1-yl}acetate (example 31, Step 1, 200 mg, 0.42 mmol) in toluene (3 mL) was added azidotributyltin (279 mg, 0.84 mmol). The reaction mixture was stirred at 90° C. for 16 hours, AcOH (1 mL) was added and the reaction was stirred for 2 hours and concentrated. The residue was swished in acetone/hexane 1:2 to give 160 mg of the title compound as a white solid used as such for next reaction.

Step 2: (+/−)-[8-bromo-9-[(4-chlorophenyl)thio]-6-(2-methyl-2H-tetrazol-5-yl)-2,3-dihydro-1H-pyrrolo[1,2-a]indol-1-yl]acetic acid A solution of the product of Step 1 (160 mg) in THF (5 mL) was treated with an excess of $CH_2N_2$ at 0° C. The reaction mixture was stirred for 5 minutes and the solvent removed. The residue was purified by silica gel chromatography eluted with 80% EtOAc/hexane to give 130 mg of methyl ester of the title compound as a white solid, which was hydrolyzed following the procedures described in Steps 10 of Example 7 to give the title compound.

MS (−APCI) m/z 517.8 (M−H)_.

EXAMPLE 33

(+/−)-[8-bromo-9-[(4-chlorophenyl)thio]-6-(1-methyl-1H-tetrazol-5-yl)-2,3-dihydro-1H-pyrrolo[1,2-a]indol-1-yl]acetic acid

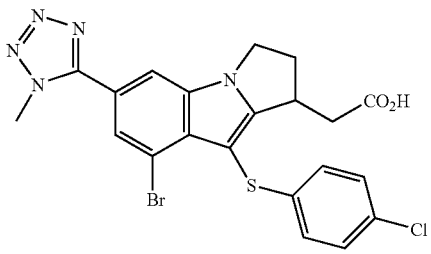

From Step 2 of Example 32 were isolated 30 mg of (+/−)-methyl [8-bromo-9-[(4-chlorophenyl)thio]-6-(1-methyl-1H-tetrazol-5-yl)-2,3-dihydro-1H-pyrrolo[1,2-a]indol-1-yl]acetate as a white solid and hydrolyzed following the procedures described in Steps 10 of Example 7.

MS (−APCI) m/z 518.0 (M−H)⁻.

EXAMPLE 34

(+/−)-[8-bromo-9-[(4-chlorophenyl)thio]-6-(1-methyl-1H-pyrrol-2-yl)-2,3-dihydro-1H-pyrrolo[1,2-a]indol-1-yl]acetic acid

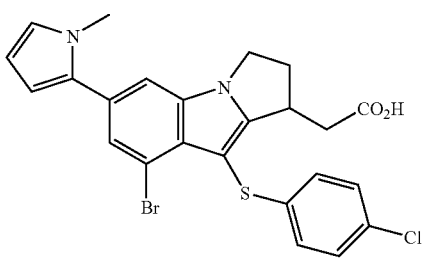

To a solution of (+/−)-methyl {8-bromo-9-[(4-chlorophenyl)thio]-6-iodo-2,3-dihydro-1H-pyrrolo[1,2-a]indol-1-yl}acetate (see Example 30, 145 mg, 0.25 mmol) in DMF (3 mL) were added tris(dibenzylideneacetone)dipalladium(0) (23 mg, 0.025 mmol), triphenyl arsine (31 mg, 0.1 mmol) and 1-methyl-2-(tributylstannyl)-1H-pyrrole (111 mg, 0.3 mmol). The mixture was degassed and stirred at r.t. for 2 hours. The reaction mixture was poured into 1N HCl and extracted with EtOAc. The combined organic layers were washed with brine, dried over Na₂SO₄ and concentrated. The residue was purified by silica gel chromatography eluted with 15% EtOAc/hexane to give methyle ester of the title compound which was hydrolyzed following the procedures described in Step 10 of Example 7.

MS (−APCI) m/z 513.5 (M−H)⁻.

EXAMPLE 35

(+/−)-{8-acetyl-9-[(4-chlorophenyl)thio]-6-cyano-2,3-dihydro-1H-pyrrolo[1,2-a]indol-1-yl}acetic acid

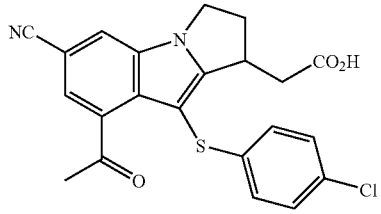

Starting from (+/−)-methyl {8-bromo-9-[(4-chlorophenyl)thio]-6-cyano-2,3-dihydro-1H-pyrrolo[1,2-a]indol-1-yl}acetate (Example 31, Step 1), the title compound was synthesized following the procedures described in Steps 1 and 2 of Example 10.

MS (−APCI) m/z 423.5 (M−H)⁻.

EXAMPLE 36

(+/−)-[8-acetyl-9-[(4-chlorophenyl)thio]-6-(2-methyl-2H-tetrazol-5-yl-2,3-dihydro-1H-pyrrolo[1,2-a]indol-1-yl]acetic acid

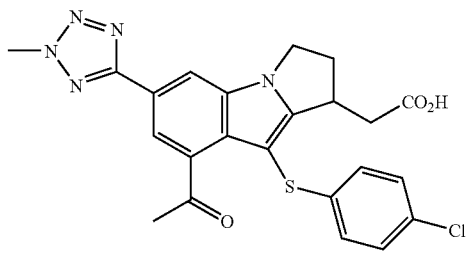

Step 1: (+/−)-[8-acetyl-9-[(4-chlorophenyl)thio]-6-(2-methyl-2H-tetrazol-5-yl) -2,3-dihydro-1H-pyrrolo[1,2-a]indol-1-yl]acetic acid Starting from (+/−)-methyl [8-bromo-9-[(4-chlorophenyl)thio]-6-(2-methyl-2H-tetrazol-5-yl)-2,3-dihydro-1H-pyrrolo[1,2-a]indol-1-yl]acetate (see Example 32), the title compound was synthesized following the procedures described in Steps 1 and 2 of Example 10.

MS (−APCI) m/z 479.9 (M−H)⁻.

EXAMPLE 37

(+/−)-[9-[(4-chlorophenyl)thio]-6-fluoro-8-(methylsulfonyl)-2,3-dihydro-1H-pyrrolo[1,2-a]indol-1-yl] acetic acid

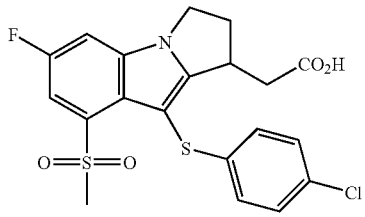

Step 1: (+/−)-methyl [6-fluoro-8-(methylthio)-2,3-dihydro-1H-pyrrolo[1,2-a]indol-1-yl]acetate To a solution of (+/−)-(8-bromo-6-fluoro-2,3-dihydro-1H-pyrrolo[1,2-a]indol-1-yl)acetic acid (Example 7A, Step 1, 400 mg, 1.3 mmol) in THF (10 mL) at −78° C. was added 3M MeMgBr (1.5 mmol) followed by the addition of n-BuLi (2.6 mmol, 1.6M solution). The reaction mixture was stirred at −78° C. for 5 minutes and an excess of methyl disulfide (300 mg) was added. The reaction mixture was warmed to r.t. and stirred for 15 minutes and 1N HCl was added. The phases were separated and the aqueous layer was extracted with EtOAc. The combined organic layers were dried over Na$_2$SO$_4$ and concentrated. The residue was dissolved in THF and the solution was cooled to 0° C. and treated with an excess of CH$_2$N$_2$. The reaction mixture was stirred for 5 minutes and the solvent removed to give 380 mg of the title compound as a pale yellow syrup used as such.

Step 2: (+/−)-methyl [6-fluoro-8-(methylsulfonyl)-2,3-dihydro-1H-pyrrolo[1,2-a]indol-1-yl]acetate To a solution of the compound of Step 1 (400 mg, 1.4 mmol) in MeOH (20 mL) at r.t. was added sodium tungstate dihydrate (225 mg, 0.7 mmol) and 30% H$_2$O$_2$ (1.4 mL, 13.6 mmol). The mixture was stirred for 3 hours at r.t. and excess of dimethyl sulfide was added. The solvent was removed and the residue was purified by silica gel chromatography eluted with 20% EtOAc/toluene to give 300 mg of the title compound as a pale yellow oil.

Step 3: (+/−)-[9-[(4-chlorophenyl)thio]-6-fluoro-8-(methylsulfonyl)-2,3-dihydro-1H-pyrrolo[1,2-a]indol-1-yl]acetic acid Starting from the compound of Step 2, the title compound was synthesized following the procedures described in Steps 9 and 10 of Example 7.

MS (−APCI) m/z 451.9 (M−H)$^-$.

EXAMPLE 37A

[(1R)-9-[(4-chlorophenyl)thio]-6-fluoro-8-(methylsulfonyl)-2,3-dihydro-1H-pyrrolo[1,2-a]indol-1-yl]acetic acid Step 1: [(1R)-9-[(4-chlorophenyl)thio]-6-fluoro-8-(methylsulfonyl)-2,3-dihydro-1H-pyrrolo[1,2-a]indol-1-yl]acetic acid The title compound was isolated from racemic (+/−)-[9-[(4-chlorophenyl)thio]-6-fluoro-8-(methylsulfonyl)-2,3-dihydro-1H-pyrrolo[1,2-a]indol-1-yl]-acetic acid by preparative HPLC on a chiralpak A/D preparative column eluted with 35% iPrOH/hexane containing 0.2% AcOH. The title compound was identified as the enantiomer with the shorter retention time (less polar).

MS (−APCI) m/z 451.9 (M−H)$^-$.

EXAMPLE 38

(+/−)-[9-[(4-chlorophenyl)thio]-8-(ethylsulfonyl)-6-fluoro-2,3-dihydro-1H pyrrolo[1,2-a]indol-1-yl]acetic acid

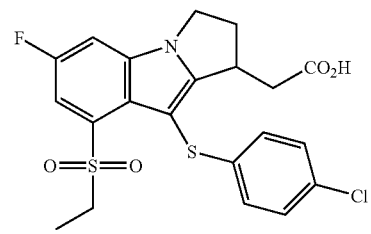

Step 1: (+/−)-methyl [8-(ethylthio)-6-fluoro-2,3-dihydro-1H-pyrrolo[1,2-a]indol-1-yl]acetate The procedure described in Example 37, Step 1 was followed using ethyl disulfide (300 mg) instead of methyl disulfide to give 450 mg of the title compound as a pale yellow syrup used as such.

Step 2: (+/−)-[9-[(4-chlorophenyl)thio]-8-(ethylsulfonyl)-6-fluoro-2,3-dihydro-1H-pyrrolo[1,2-a]indol-1-yl]acetic acid Starting from the compound of Step 1, the title compound was synthesized following the procedures described in Step 2 of Example 37 and Steps 9 and 10 of Example 7.

MS (−APCI) m/z 465.9 (M−H)$^-$.

EXAMPLE 39

[(1R)-9-[(4-chlorophenyl)thio]-6-fluoro-8-(1-methyl-1H-pyrrol-2-yl-2,3-dihydro-1H-pyrrolo[1,2-a]indol-1-yl]acetic acid

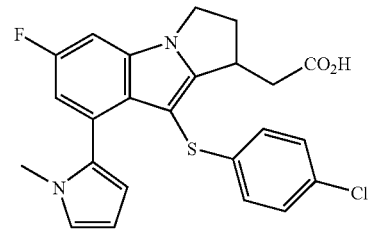

Step 1: (4S)-4-benzyl-3-{[9-[(4-chlorophenyl)thio]-6-fluoro-8-(1-methyl-1H-pyrrol-2-yl)-2,3-dihydro-1H-pyrrolo[1,2-a]indol-1-yl]acetyl}-1,3-oxazolidin-2-one

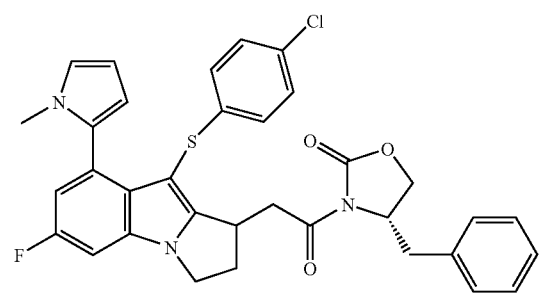

To a solution of (4S)-4-benzyl-3-({8-bromo-9-[(4-chlorophenyl)thio]-6-fluoro-2,3-dihydro-1H-pyrrolo[1,2-a]indol-1-yl}acetyl)-1,3-oxazolidin-2-one (Example 7A, Step 3, 230 mg, 0.38 mmol) in DMF (4 mL) were added tris(dibenzylideneacetone)dipalladium(0) (37 mg, 0.04 mmol), triphenyl arsine (49 mg, 0.16 mmol) and 1-methyl-2-(tributylstannyl)-1H-pyrrole (211 mg, 0.57 mmol). The mixture was degassed and stirred at 90° C. for 4 hours. The reaction was poured in 1N HCl and extracted with EtOAc. The combined organic layers were washed with brine, dried over $Na_2SO_4$ and concentrated. The residue was purified by silica gel chromatography eluted with 20% EtOAc/toluene to give 240 mg of the title compound as an orange oil.

Step 2: [(1R)-9-[(4-chlorophenyl)thio]-6-fluoro-8-(1-methyl-1H-pyrrol-2-yl)-2,3-dihydro-1H-pyrrolo[1,2-a]indol-1-yl]acetic acid Starting from the compound of Step 1, the title compound was synthesized following the procedures described in Step 4 of Example 7A.

MS (-APCI) m/z 453.2 (M-H)⁻.

EXAMPLE 40

{9-[(4-chlorophenyl)thio]-6-fluoro-8-propyl-2,3-dihydro-1H-pyrrolo[1,2-a]indol-1-yl}acetic acid

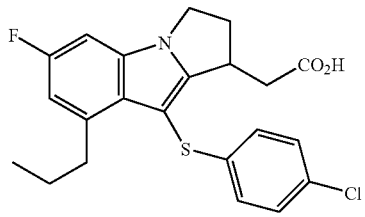

To a solution of [9-[(4-chlorophenyl)thio]-6-fluoro-8-(1-hydroxypropyl)-2,3-dihydro-1H-pyrrolo[1,2-a]indol-1-yl]acetic acid (Example 19, 36 mg, 0.08 mmol) in $CH_2Cl_2$ were added trifluoroacetic acid (0.5 mL) and triethylsilane (0.2 mL). The mixture was stirred for 1 hour at r.t. and solvent was removed. The residue was purified by silica gel chromatography eluted with 40% EtOAc/hexane containing 1% of AcOH to give 10 mg the title compound as a white foam.

MS (-APCI) m/z 416.1 (M-H)⁻.

EXAMPLE 41

(+/-)-{9-[(4-chlorophenyl)thio]-8-ethyl-6-fluoro-2,3-dihydro-1H-pyrrolo[1,2-a]indol-1-yl}acetic acid

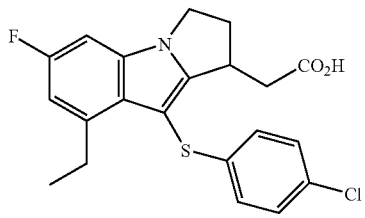

Step 1: (+/-)-methyl [9-[(4-chlorophenyl)thio]-6-fluoro-6-8-(1-hydroxyethyl)-2,3-dihydro-1H-pyrrolo[1,2-a]indol-1-yl]acetate To a solution of [9-[(4-chlorophenyl)thio]-6-fluoro-8-(1-hydroxyethyl)-2,3-dihydro-1H-pyrrolo[1,2-a]indol-1-yl]acetic acid (85 mg) in THF at 0° C. was added an excess of $CH_2N_2$. The reaction was stirred for 5 minutes and the solvent was removed to give 85 mg of the title compound as a pale yellow oil used as such.

Step 2: (+/-)-{9-[(4-chlorophenyl)thio]-8-ethyl-6-fluoro-2,3-dihydro-1H-pyrrolo[1,2-a]indol-1-yl}acetic acid To a solution of (+/-)-methyl [9-[(4-chlorophenyl)thio]-6-fluoro-8-(1-hydroxyethyl)-2,3-dihydro-1H-pytrolo[1,2-a]indol-1-yl]acetate (see Example 14, 85 mg) in $CH_2Cl_2$ were added trifluoroacetic acid (0.5 mL) and triethylsilane (0.2 mL). The mixture was stirred for 1 hour at r.t. and solvent was removed. The residue was purified by silica gel chromatography eluted with 30% EtOAc/hexane to give 70 mg of the title compound as a white foam which has hydrolyzed following the procedures described in Step 10 of Example 7.

MS (-APCI) m/z 402.1 (M-H)⁻.

EXAMPLE 42

(+/-)-{9-[(4-chlorophenyl)thio]-6-fluoro-8-isoprepenyl-2,3-dihydro-1H-pyrrolo[1,2-a]indol-1-yl}acetic acid

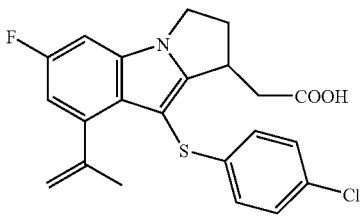

To a solution of (+/-)-methyl {8-bromo-9-[(4-chlorophenyl)thio]-6-fluoro-2,3-dihydro-1H-pyrrolo[1,2-a]indol-1-yl}acetate (200 mg, 0.43 mmol) in DMF (4 mL) were added tris(dibenzylideneacetone)dipalladium(0) (37 mg, 0.04 mmol), triphenyl arsine (49 mg, 0.16 mmol) and tributyl (isopropenyl)stannane (285 mg, 0.86 mmol). The mixture was degassed and stirred at 90° C. for 4 hours. The reaction was poured in 1N HCl and extracted with EtOAc. The combined organic layers were washed with brine, dried over $Na_2SO_4$ and concentrated. The residue was purified by silica gel chromatography eluted with 30% EtOAc/hexane to give (+/-)-methyl{9-[(4-chlorophenyl)thio]-6-fluoro-8-isopropenyl-2,3-dihydro-1H-pyrrolo[1,2-a]indol-1-yl}acetate which was hydrolyzed following the procedures described in Step 10 of Example 7.

MS (-APCI) m/z 414.3 (M-H)⁻.

EXAMPLE 43

(+/−)-[9-[(4-chlorophenyl)thio]-6-fluoro-8-(1-methyl-1H-pyrazol-5-yl)-2,3-dihydro-1H-pyrrolo[1,2-a]indol-1-yl]acetic acid

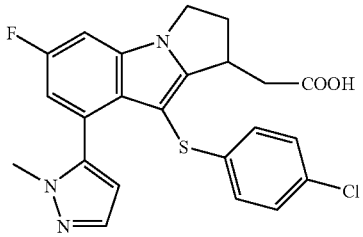

Starting from (+/−)-methyl{8-bromo-9-[(4-chlorophenyl)thio]-6-fluoro-2,3-dihydro-1H-pyrrolo[1,2-a]indol-1-yl}acetate (Example 7, Step 9, 200 mg, 0.43 mmol) and 1-methyl-5-(tributylstannyl)-1H-pyrazole (239 mg, 0.64 mmol), the title compound was synthesized following the procedures described in Example 42 and Step 10 of Example 7.

MS (−APCI) m/z 454.2 (M−H)⁻.

EXAMPLE 44

(+/−)-{9-[(4-chlorophenyl)thio]-6-fluoro-8-isopropyl-2,3-dihydro-1H-pyrrolo[1,2-a]indol-1-yl}acetic acid

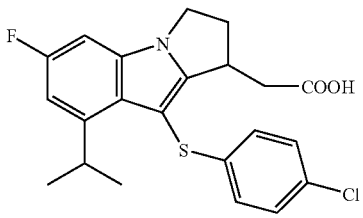

Step 1: (+/−)-methyl(6-fluoro-8-isopropenyl-2,3-dihydro-1H-pyrrolo[1,2-a]indol-1-yl)acetate To bromo(isopropenyl)magnesium (21.5 mmol, 4.2M THF solution) was added zinc bromide (4.84 g. 21.5 mmol) dissolved in THF (15 mL). The mixture was stirred at 60° C. for 2 hours, cooled to r.t. and dichloro[1,1'-bis(diphenylphosphino)ferrocene]palladium (II) dichloromethane adduct (112 mg, 0.15 mmol) and copper iodide (41 mg, 0.21 mmol) were added. The mixture was stirred for 2 minutes at r.t. and a solution of (+/−)-methyl (8-bromo-6-fluoro-2,3-dihydro-1H-pyrrolo[1,2-a]indol-1-yl)acetate (Example 7, Step 8, 1 g, 3.1 mmol in 5 mL of THF) was added. The reaction mixture was stirred at 55° C. for 2 hours, cooled to r.t., poured into 1N HCl and extracted with EtOAc. The combined organic layers were washed with brine, dried over Na₂SO₄ and concentrated. The residue was purified by silica gel chromatography eluted with 20% EtOAc/hexane to give 600 mg of the title compound as a pale yellow oil.

Step 2: (+/−)-methyl(6-fluoro-8-isopropyl-2,3-dihydro-1H-pyrrolo[1,2-a]indol-1-yl)acetate A mixture of the compound of Step 1 (600 mg) and 100 mg of Pd/C (10% w/w) in EtOH (7 mL) was shaken under 50 psi of H₂ for 1 hour. The mixture was then filtered through a silica gel pad eluted with EtOAc and the filtrate was concentrated to give 600 mg of the title compound as a pale yellow oil.

Step 3: (+/−)-{9-[(4-chloropheny)thio]-6-fluoro-8-isopropyl-2,3-dihydro-1H-pyrrolo[1,2-a]indol-1-yl}acetic acid Starting from the compound of Step 2, the title compound was synthesized following the procedures described in Steps 9 and 10 of Example 7.

MS (−APCI) m/z 416.2 (M−H)⁻.

EXAMPLE 44A

{(1R)-9-[chlorophenyl)thio]-6-fluoro-8-isopropyl-2,3-dihydro-1H-pyrrolo[1,2-a]indol-1-yl}acetic acid Step 1: methyl[(1R)-6-fluoro-8-isopropyl-2,3-dihydro-1H-pyrrolo[1,2-a]indol-1-yl]acetate Starting from [(1R)-8-bromo-6-fluoro-2,3-dihydro-1H-pyrrolo[1,2-a]indol-1-yl]acetic acid (from Step 1 of Example 62A) which was converted to methyl[(1R)-8-bromo-6-fluoro-2,3-dihydro-1H-pyrrolo[1,2-a]indol-1-yl]acetate by addition of CH₂N₂, the title compound was synthesized following the procedures described in Steps 1 and 2 of Example 44.

Step 2: {(1R)-9-[(4-chlorophenyl)thio]-6-fluoro-8-isopropyl-2,3-dihydro-1H-pyrrolo[1,2-a]indol-1-yl}acetic acid Starting from the compound of Step 1, the title compound was synthesized following the procedures described in Steps 9 and 10 of Example 7.

MS (−APCI) m/z 416.2 (M−H)⁻.

EXAMPLE 45

(+/−)-{9-[(4-chlorophenyl)thio]-8-cyclopent-1-en-1-yl-6-fluoro-2,3-dihydro-1H-pyrrolo[1,2-a]indol-1-yl}acetic acid

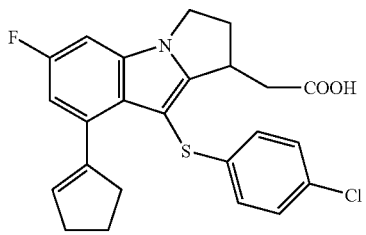

Starting from tributyl(cyclopent-1-en-1-yl)stannane the title compound was synthesized following the procedures described in Example 42 and Step 10 of Example 7.

MS (−APCI) m/z 440.2 (M−H)⁻.

EXAMPLE 46

(+/−)-(Z/E)-{9-[(4-chlorophenyl)thio]-8-[1-ethyl-prop-1-enyl]-6-fluoro-2,3-dihydro-1H-pyrrolo[1,2-a]indol-1-yl}acetic acid

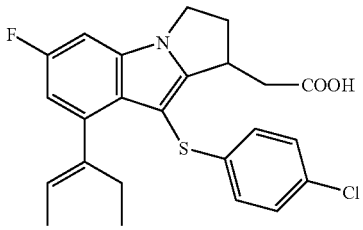

Starting from (+/−)-methyl{8-bromo-9-[(4-chlorophenyl)thio]-6-fluoro-2,3-dihydro-1H-pyrrolo[1,2-a]indol-1-yl}acetate (300 mg, 0.64 mmol) and (Z/E)-tributyl[1-ethyl-prop-1-enyl]stannane (300 mg, 0.84 mmol), the title compound was synthesized following the procedures described in Example 42 and Step 10 of Example 7.

MS (−APCI) m/z 442.3 (M−H)⁻.

EXAMPLE 47

(+/−)-[9-[(4-chlorophenylthio]-8-(1-ethylpropyl)-6-fluoro-2,3-dihydro-1H-pyrrolo[1,2-a]indol-1-yl]acetic acid

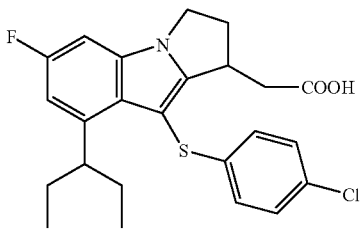

Step 1: (+/−)-methyl[8-(1-ethyl-1-hydroxypropyl)-6-fluoro-2,3-dihydro-1H-pyrrolo[1,2-a]indol-1-yl]acetate To a solution of (+/−)-(8-bromo-6-fluoro-2,3-dihydro-1H-pyrrolo[1,2-a]indol-1-yl)acetic acid (Example 7A, Step 1, 500 mg, 1.6 mmol) in THF (10 mL) at −78° C. was added 3M MeMgBr (1.9 mmol) followed by the addition of n-BuLi (4.8 mmol, 1.6M solution). The reaction mixture was stirred at −78° C. for 5 minutes and an excess of 3-pentanone (700 mg) was added. The reaction mixture was warmed to r.t. and stirred for 15 minutes. 1N HCl was added, the phases were separated and the aqueous layer was extracted with EtOAc. The combined organic layers were dried over Na₂SO₄ and concentrated. The residue was dissolved in THF and the solution was cooled to 0° C. and treated with an excess of CH₂N₂. The reaction mixture was stirred for 5 minutes and the solvent removed to give 480 mg of an yellow oil containing ~30% of the title compound and 70% of methyl (6-fluoro-2,3-dihydro-1H-pyrrolo[1,2-a]indol-1-yl)acetate used as such.

Step 2: (+/−)-methyl[8-(1-ethylpropyl)-6-fluoro-2,3-dihydro-1H-pyrrolo[1,2-a]indol-1-yl]acetate To a solution of the mixture of Step 1 (480 mg) in CH₂Cl₂ were added trifluoroacetic acid (1.5 mL) and triethylsilane (0.6 mL). The mixture was stirred for 1 hour at r.t. and the solvent was removed. The residue was purified by silica gel chromatography eluted with 10% EtOAc/hexane to give 140 mg of the title compound as a colorless oil.

Step 3: (+/−)-[9-[(4-chlorophenyl)thio]-8-(1-ethylpropyl)-6-fluoro-2,3-dihydro-1H-pyrrolo[1,2-a]indol-1-yl]acetic acid Starting from the compound of Step 2, the title compound was synthesized following the procedures described in Steps 9 and 10 of Example 7.

MS (−APCI) m/z 444.3 (M−H)⁻.

EXAMPLE 48

(+/−)-[9-[(4-chlorophenyl)thio]-8-cyclopentyl-6-fluoro-2,3-dihydro-1H-pyrrolo[1,2-a]indol-1-yl}acetic acid

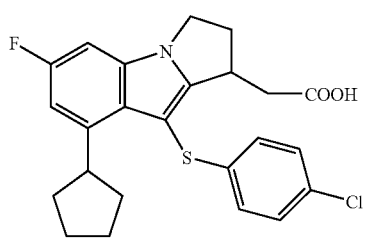

Step 1: (+/−)-methyl(8-cyclopent-1-en-1-yl-6-fluoro-2,3-dihydro-1H-pyrrolo[1,2-a]indol-1-yl)acetate Starting from (+/−)-methyl(8-bromo-6-fluoro-2,3-dihydro-1H-pyrrolo[1,2-a]indol-1-yl)acetate (Example 7, Step 8, 300 mg, 0.92 mmol) and tributyl(cyclopent-1-en-1-yl)stannane, the title compound (150 mg) was synthesized as described in Example 42 as a pale yellow oil.

Step 2: (+/−)-methyl(8-cyclopentyl-6-fluoro-2,3-dihydro-1H-pyrrolo[1,2-a]indol-1-yl)acetate A mixture of the compound of Step 1 (150 mg) and 70 mg of Pd/C (10% w/w) in EtOH (7 mL) was shaken under 50 psi of H₂ for 12 hours. The mixture was then filtered through a silica gel pad eluted with EtOAc and the filtrate was concentrated. The residue was purified by silica gel chromatography eluted with 10% EtOAc/hexane to give 90 mg of the title compound as an yellow oil.

Step 3: (+/−)-{9-[(4-chlorophenyl)thio]-8-cyclopentyl-6-fluoro-2,3-dihydro-1H-pyrrolo[1,2-a]indol-1-yl}acetic acid Starting from the compound of Step 2, the title compound was synthesized following the procedures described in Steps 9 and 10 of Example 7.

MS (−APCI) m/z 442.2 (M−H)⁻.

EXAMPLE 49

(+/−)-{9-[(4-chlorophenyl)thio]-6-fluoro-8-phenyl-2,3-dihydro-1H-pyrrolo[1,2-a]indol-1-yl}acetic acid

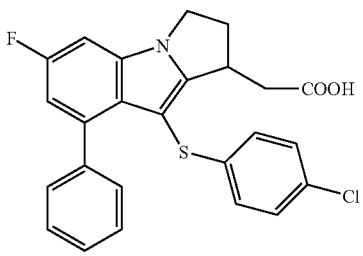

Starting from (+/−)-methyl{8-bromo-9-[(4-chlorophenyl)thio]-6-fluoro-2,3-dihydro-1H-pyrrolo[1,2-a]indol-1-yl}acetate (200 mg, 0.43 mmol) and tributyl(phenyl)stannane the title compound was synthesized following the procedures described in Example 42 and Step 10 of Example 7.

MS (−APCI) m/z 450.0 (M−H)⁻.

EXAMPLE 50

(+/−)-{9-[(4-chlorophenyl)thio]-6-fluoro-8-thien-2-yl-2,3-dihydro-1H-pyrrolo[1,2-a]indol-1-yl}acetic acid

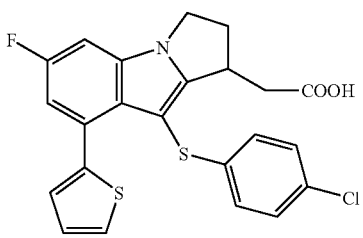

Starting from (+/−)-methyl{8-bromo-9-[(4-chlorophenyl)thio]-6-fluoro-2,3-dihydro-1H-pyrrolo[1,2-a]indol-1-yl}acetate and tributyl(thien-2-yl)-stannane, the title compound was synthesized following the procedures described in Example 42 and Step 10 of Example 7.

MS (−APCI) m/z 456.1 (M−H)⁻.

EXAMPLE 51

(+/−)-[9-[(4-chlorophenyl)thio]-6-fluoro-8-(3-methylthien-2-YL)-2,3-dihydro-1H-pyrrolo[1,2-a]indol-1-yl]acetic acid

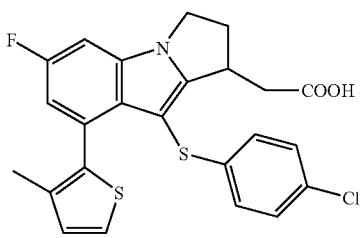

Starting from (+/−)-methyl{8-bromo-9-[(4-chlorophenyl)thio]-6-fluoro-2,3-dihydro-1H-pyrrolo[1,2-a]indol-1-yl}acetate and tributyl(3-methylthien-2-yl)stannane, the title compound was synthesized following the procedures described in Example 42 and Step 10 of Example 7.

MS (−APCI) m/z 470.0 (M−H)⁻.

EXAMPLE 52

(+/−)-{9-[(4-chlorophenyl)thio]-6-fluoro-8-vinyl-2,3-dihydro-1H-pyrrolo[1,2-a]indol-1-yl}acetic acid

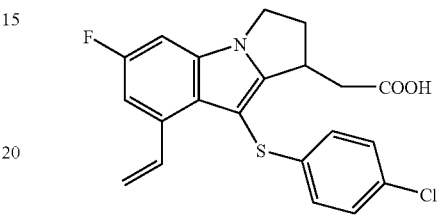

Starting from (+/−)-methyl{8-bromo-9-[(4-chlorophenyl)thio]-6-fluoro-2,3-dihydro-1H-pyrrolo[1,2-a]indol-1-yl}acetate and tributyl(vinyl)stannane, the title compound was synthesized following the procedures described in Example 42 and Step 10 of Example 7.

¹H NMR (acetone-d₆) δ 7.86–7.80 (1H, m), 7.22 (2H, dd), 7.15–7.10 (2H, m), 7.04 (2H, dd), 5.70 (1H, d), 5.12 (1H, d), 4.34–4.29 (1H, m), 4.21–4.15 (1H, m), 3.83–3.78 (1H, m), 3.14 (1H, dd), 3.01–2.93 (1H, m), 2.63 (1H, dd), 2.49–2.41 (1H, m).

EXAMPLE 53

(+/−)-{8-bromo-9-[(4-chlorophenyl)thio]-6-vinyl-2,3-dihydro-1H-pyrrolo[1,2-a]indol-1-yl}acetic acid

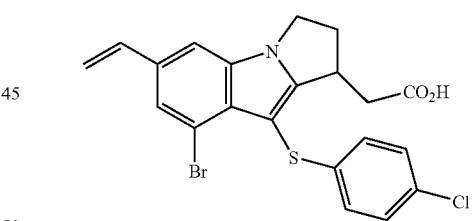

To a solution of methyl{8-bromo-9-[(4-chlorophenyl)thio]-6-iodo-2,3-dihydro-1H-pyrrolo[1,2-a]indol-1-yl}acetate (see Example 30, 200 mg, 0.35 mmol) in DMF (3 mL) were added tris(dibenzylideneacetone)dipalladium(0) (32 mg, 0.035 mmol), triphenyl arsine (43 mg, 0.14 mmol) and tributyl(vinyl)stannane (166 mg, 0.53 mmol). The mixture was degassed and stirred at r.t. for 12 hours. The reaction was poured in 1N HCl and extracted with EtOAc. The combined organic layers were washed with brine, dried over Na₂SO₄ and concentrated. The residue was purified by silica gel chromatography eluted with 20% EtOAc/hexane to give (+/−)-methyl{8-bromo-9-[(4-chlorophenyl)thio]-6-vinyl-2,3-dihydro-1H-pyrrolo[1,2-a]indol-1-yl}-acetate which was hydrolyzed following the procedures described in Steps 10 of Example 7.

MS (−APCI) m/z 460.3 (M−H)⁻.

EXAMPLE 54

(+/−)-{9-[(4-chlorophenyl)thio]-6-fluoro-8-[2,2,2-trifluoro-1-hydroxy-1-(trifluoromethyl)ethyl]-2,3-dihydro-1H-pyrrolo [1,2-a]indol-1-yl}acetic acid

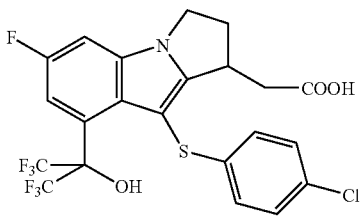

Step 1: (+/−)-methyl{6-fluoro-8-[2,2,2-trifluoro-1-hydroxy-1-(trifluoromethyl)ethyl]-2,3-dihydro-1H-pyrrolo[1,2-a]indol-1-yl}acetate To a solution of (+/−)-(8-bromo-6-fluoro-2,3-dihydro-1H-pyrrolo[1,2-a]indol-1-yl)acetic acid (300 mg, 1 mmol) in THF (7 mL) at −78° C. was added 3M MeMgBr (1.2 mmol) followed by the addition of n-BuLi (3 mmol, 1.6M solution). The reaction was stirred at −78° C. for 5 minutes and an excess of 1,1,1,3,3,3-hexafluoroacetone (700 mg) was added. The reaction was warmed to −40° C. and stirred for 15 minutes. 1N HCl was added, the phases were separated and the aqueous layer was extracted with EtOAc. The combined organic layers were dried over $Na_2SO_4$ and concentrated. The residue was dissolved in THF and the solution was cooled to 0° C. and treated with an excess of $CH_2N_2$. The reaction was stirred for 5 min and the solvent removed. The residue was purified by silica gel chromatography eluted with 20% EtOAc/hexane to 180 mg of the title compound as colorless oil.

Step 2: (+/−)-9-[(4-chlorophenyl)thio]-6-fluoro-8-[2,2,2-trifluoro-1-hydroxy-1-(trifluoromethyl)ethyl]-2,3-dihydro-1H-pyrrolo[1,2-a]indol-1-yl}-acetic acid Starting from the compound of Step 1, the title compound was synthesized following the procedures described in Steps 9 and 10 of Example 7.

MS (−APCI) m/z 540.3 (M−H)⁻.

EXAMPLE 55

(+)-{9-[(4-chlorophenyl)thio]-6-fluoro-8-thien-3-yl-2,3-dihydro-1H-pyrrolo[1,2-a]indol-1-yl}acetic acid

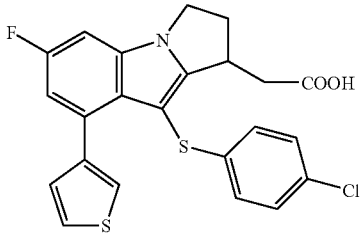

Starting from (+)-methyl{8-bromo-9-[(4-chlorophenyl)thio]-6-fluoro-2,3-dihydro-1H-pyrrolo[1,2-a]indol-1-yl}acetate and tributyl(thien-3-yl)stannane, the title compound was synthesized following the procedures described in Example 42 and Step 10 of Example 7.

MS (−APCI) m/z 455.9 (M−H)⁻.

EXAMPLE 56

(+/−)-[9-[(4-chlorophenyl)thio]-6-cyclopropyl-8-(1-methyl-1H-pyrrol-2-yl)-2,3-dihydro-1H-pyrrolo[1,2-a]indol-1-yl]acetic acid

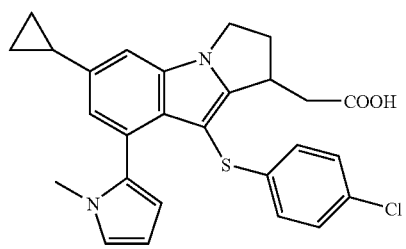

Step 1: (+/−)-methyl{8-bromo-9-[(4-chlorophenyl)thio]-6-cyclopropyl-2,3-dihydro-1H-pyrrolo[1,2-a]indol-1-yl}acetate To a solution of (+/−)-methyl{8-bromo-9-[(4-chlorophenyl)thio]-6-vinyl-2,3-dihydro-1H-pyrrolo[1,2-a]indol-1-yl}acetate (see Example 53, 100 mg) in THF (3 mL) were added $CH_2N_2$ (excess) and palladium (II) acetate (5 mg). The reaction mixture was stirred for 30 minutes and the addition of reagents was repeated twice. The mixture was stirred for 2 hours at r.t. and filtered through a silica gel pad eluted with EtOAc and the filtrated was concentrated. The residue was purified by silica gel chromatography eluted with 20% EtOAc/hexane to give 90 mg of the title compound as a white foam.

Step 2: (+/−)-[9-[(4-chlorophenyl)thio]-6-cyclopropyl-8-(1-methyl-1H-pyrrol-2-yl)-2,3-dihydro-1H-pyrrolo[1,2-a]indol-1-yl]acetic acid Starting from the compound of Step 1, the title compound was synthesized following the procedures described in Example 42 and Step 10 of Example 7.

MS (−APCI) m/z 475.1 (M−H)⁻.

EXAMPLE 57

(+/−)-[9-[(4-chlorophenyl)thio]-8-(1-methyl-1H-pyrrol-2-yl)-6-(2-methyl-2H-tetrazol-5-yl)-2,3-dihydro-1H-pyrrolo[1,2-a]indol-1-yl]acetic acid

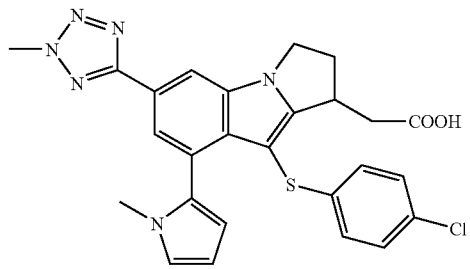

Starting from (+/−)-methyl[8-bromo-9-[(4-chlorophenyl)thio]-6-(2-methyl-2H-tetrazol-5-yl)-2,3-dihydro-1H-pyrrolo[1,2-a]indol-1-yl]acetate (see Example 32) and 1-methyl-2-(tributylstannyl)-1H-pyrrole, the title compound was synthesized following the procedures described in Example 42 and Step 10 of Example 7.

MS (–APCI) m/z 517.0 (M–H)⁻.

EXAMPLE 58

(+/–)-[9-[(4-chlorophenyl)thio]-6-(2-methyl-2H-tetrazol-5-yl)-8-phenyl-2,3-dihydro-1H-pyrrolo[1,2-a]indol-1-yl]acetic acid

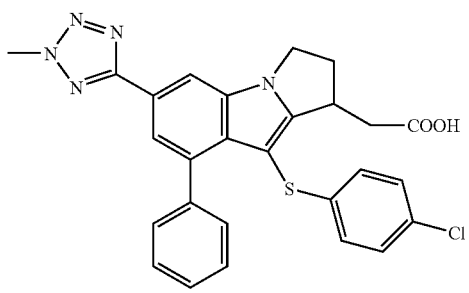

Starting from (+/–)-methyl[8-bromo-9-[(4-chlorophenyl)thio]-6-(2-methyl-2H-tetrazol-5-yl)-2,3-dihydro-1H-pyrrolo[1,2-a]indol-1-yl]acetate and tributyl(phenyl)stannane, the title compound was synthesized by following the procedures described in Example 42 and Step 10 of Example 7.

MS (–APCI) m/z 514.0 (M–H)⁻.

EXAMPLE 59

(+/–)-{9-[(4-chlorophenyl)thio]-8-cyclopropyl-6-fluoro-2,3-dihydro-1H-pyrrolo[1,2-a]indol-1-yl}acetic acid

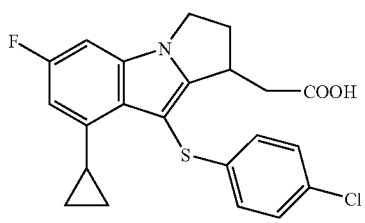

Step 1: (+/–)-methyl(6-fluoro-8-vinyl-2,3-dihydro-1H-pyrrolo[1,2-a]indol-1-yl)acetate To a solution of (+/–)-methyl(8-bromo-6-fluoro-2,3-dihydro-1H-pyrrolo[1,2-a]indol-1-yl)acetate (Example 7, Step 8, 330 mg, 1 mmol) in DMF (4 mL) were added Tris(dibenzylideneacetone)dipalladium(0) (92 mg, 0.1 mmol), triphenyl arsine (122 mg, 0.4 mmol) and tributyl(vinyl)stannane (475 mg, 1.5 mmol). The mixture was degassed and stirred at 60° C. for 12 hours. The reaction was poured in 1N HCl and extracted with EtOAc. The combined organic layers were washed with brine, dried over Na₂SO₄ and concentrated. The residue was purified by silica gel chromatography eluted with 20% EtOAc/hexane to give 200 mg of the title compound as an yellow oil.

Step 2: (+/–)-methyl(8-cyclopropyl-6-fluoro-2,3-dihydro-1H-pyrrolo[1,2-a]indol-1-yl)acetate Starting from the compound of Step 1 (100 mg), the title compound (70 mg, colorless oil) was synthesized following the procedures described in Example 56, Step 1.

Step 3: (+/–)-{-9-[(4-chlorophenyl)thio]-8-cyclopropyl-6-fluoro-2,3-dihydro-1H-pyrrolo[1,2-a]indol-1-yl}acetic acid Starting from the compound of Step 2, the title compound was synthesized following the procedures described in Steps 9 and 10 of Example 7.

MS (–APCI) m/z 414.0 (M–H)⁻.

EXAMPLE 60

(+/–)-methyl[8-bromo-9-(4-chlorobenzyl)-6-fluoro-2,3-dihydro-1H-pyrrolo[1,2-a]indol-1-yl]acetic acid

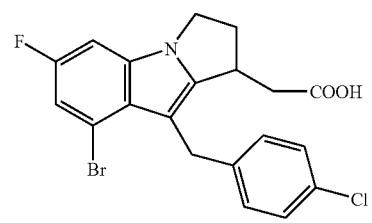

Step 1: (+/–)-methyl[8-bromo-9-(4-chlorobenzyl)-6-fluoro-2,3-dihydro-1H-pyrrolo[1,2-a]indol-1-yl]acetate To a mixture of trifluoroacetic acid (79 mg, 0.7 mmol) and triethylsilane (161 mg, 1.38 mmol) in CH₂Cl₂ (1 mL) at 0° C. was added a mixture of (+/–)-methyl(8-bromo-6-fluoro-2,3-dihydro-1H-pyrrolo[1,2-a]indol-1-yl)acetate (Example 7, Step 8, 150 mg, 0.46 mmol) and 4-chlorobenzaldehyde (71 mg, 0.51 mmol) in CH₂Cl₂ (3 mL). The mixture was stirred at r.t. for 1 hour and concentrated. The residue was purified by silica gel chromatography eluted with 20% EtOAc/hexane to give 155 mg of the title compound.

Step 2: (+/–)-[8-bromo-9-(4-chlorobenzyl)-6-fluoro-2,3-dihydro-1H-pyrrolo[1,2-a]indol-1-yl]acetic acid Starting from the compound of Step 1, the title compound was synthesized following the procedures described in Step 10 of Example 7.

MS (–APCI) m/z 436.0 (M–H)⁻.

EXAMPLE 61

(+/–)-[9-(4-chlorobenzoyl)-6-fluoro-8-(methylsulfonyl)-2,3-dihydro-1H-pyrrolo[1,2-a]indol-1-yl]acetic acid

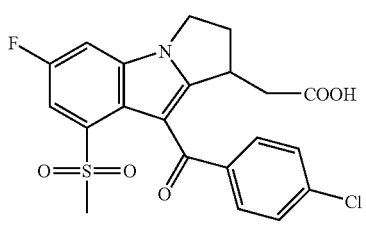

Step 1: (+/−)-methyl[8-bromo-9-(4-chlorobenzoyl)-6-fluoro-2,3-dihydro-1H-pyrrolo[1,2-a]indol-1-yl]acetate To a suspension of trichloroaluminum (1.9 g, 14.4 mmol) in 1,2 dichloroethane (20 mL) at r.t. was added 4-chlorobenzoyl chloride (2.5 g, 14.4 mmol). The mixture was stirred for 5 minutes at r.t. and (+/−)-methyl(8-bromo-6-fluoro-2,3-dihydro-1H-pyrrolo[1,2-a]indol-1-yl)acetate (Example 7, Step 8, 1.5 g, 4.8 mmol) in 1,2 dichloroethane (10 mL) was added. The mixture was stirred at 75° C. for 4 hours, cooled to r.t. and quenched with a solution of aqueous saturated NaHCO$_3$ and poured into a mixture of EtOAc and 1N HCl. The phases were separated and the aqueous layer was extracted with EtOAc. The combined organic layers were washed with aqueous saturated NaHCO$_3$ and brine, dried over Na$_2$SO$_4$ and concentrated. The residue was purified by silica gel chromatography eluted with 30% EtOAc/hexane to give 1.5 g of the title compound as a fade yellow solid.

Step 2: (+/−)-[9-(4-chlorobenzoyl)-6-fluoro-8-(methylsulfonyl)-2,3-dihydro-1H-pyrrolo[1,2-a]indol-1-yl]acetic acid To the compound of Step 1 (100 mg, 0.22 mmol) in 1-methyl-2-pyrrolidinone (4 mL) were added methanesulphinic acid sodium salt (113 mg, 1.1 mmol) and copper iodide (209 mg, 1.1 mmol). The mixture was degassed and stirred at 130° C. for 3 hours, cooled to r.t., diluted with EtOAc and filtered through a silica gel pad eluted with EtOAc. The filtrate was washed with brine, dried over Na$_2$SO$_4$ and concentrated to give (+/−)-methyl[9-(4-chlorobenzoyl)-6-fluoro-8-(methylsulfonyl)-2,3-dihydro-1H-pyrrolo[1,2-a]indol-1-yl]acetate which was hydrolyzed following the procedures described in Step 10 of the Example 7.

MS (−APCI) m/z 448.0 (M−H)$^-$.

EXAMPLE 62

[(1R)-9-(4-chlorobenzyl)-6-fluoro-8-(methylsulfonyl)-2,3-dihydro-1H-pyrrolo[1,2-a]indol-1-yl]acetic acid

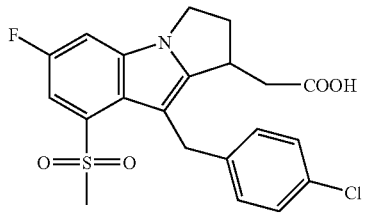

Starting from (+/−)-methyl[6-fluoro-8-(methylsulfonyl)-2,3-dihydro-1H-pyrrolo[1,2-a]indol-1-yl]acetate (Example 37, Step 2), the title compound was synthesized following the procedures described in Step 1 of Example 60 and Step 10 of Example 7.

MS (−APCI) m/z 434.0 (M−H)$^-$.

EXAMPLE 62A

[(1R)-9-(4-chlorobenzyl)-6-fluoro-8-(methylsulfonyl)-2,3-dihydro-1H-pyrrolo[1,2-a]indol-1-yl]acetic acid

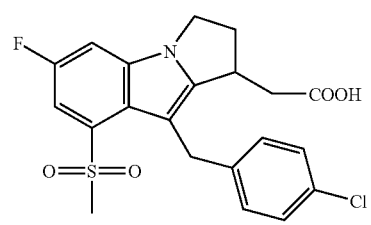

Step 1: [(1R)-8-bromo-6-fluoro-2,3-dihydro-1H-pyrrolo[1,2-a]indol-1-yl]acetic acid (+/−)-(8-Bromo-6-fluoro-2,3-dihydro-1H-pyrrolo[1,2-a]indol-1-yl)acetic acid (Example 7A, Step 1) was resolved by preparative HPLC on a chiralpak A/D preparative column eluted with 5% iPrOH/hexane containing 0.2% AcOH. The less polar isomer (shorter retention time) was identified as [(1R)-8-bromo-6-fluoro-2,3-dihydro-1H-pyrrolo[1,2-a]indol-1-yl]acetic acid.

Step 2: methyl[(1R)-6-fluoro-8-(methylsulfonyl)-2,3-dihydro-1H-pyrrolo[1,2-a]indol-1-yl]acetate Starting from the compound of Step 1, the title compound was synthesized following the procedures described in Steps 1 and 2 of Example 37.

Step 3: [(1R)-9-(4-chlorobenzyl)-6-fluoro-8-(methylsulfonyl)-2,3-dihydro-1H-pyrrolo[1,2-a]indol-1-yl]acetic acid Starting from the compound of Step 2, the title compound was synthesized following the procedures described in Step 1 of Example 60 and Step 10 of Example 7.

MS (−APCI) m/z 434.1 (×−H)$^-$.

EXAMPLE 63

(+/−)-{9-[(4-chloropheny)thio]-6-fluoro-8-[2,2,2-trifluoro-1-methoxy-1-(trifluoromethyl)ethyl]-2,3-dihydro-1H-pyrrolo[1,2-a]indol-1-yl}acetic acid

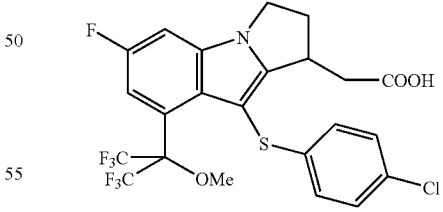

Step 1: (+/−)-methyl {6-fluoro-8-[2,2,2-trifluoro-1-methoxy-1-(trifluoromethyl)ethyl]-2,3-dihydro-1H-pyrrolo[1,2-a]indol-1-yl}acetate To (+/−)-methyl{6-fluoro-8-[2,2,2-trifluoro-1-hydroxy-1-(trifluoromethyl)ethyl]-2,3-dihydro-1H-pyrrolo[1,2-a]indol-1-yl}acetate (Example 54, Step 1, 115 mg, 0.28 mmol) in acetonitrile (3 mL) were added cesium carbonate (300 mg, 0.9 mmol) and methyl iodide (114 mg, 0.8 mmol). The mixture was stirred at 50° C. for 2 hours, filtered through a silica gel pad eluted with 50% EtOAc/hexane and the filtrate was concentrated to give 100 mg of the title compound used as such.

Step 2: (+/−)-{9-[(4-chlorophenyl)thio]-6-fluoro-8-[2,2,2-trifluoro-1-methoxy-1-(trifluoromethyl)ethy]-2,3-dihydro-1H-pyrrolo[1,2-a]indol-1-yl}-acetic acid Starting from the compound of Step 1, the title compound was synthesized following the procedures described in Steps 9 and 10 of Example 7.

MS (−APCI) m/z 554.2 (M−H)⁻.

EXAMPLE 64

(+/−)-[9-(4-chlorobenzoyl)-6-fluoro-8-isopropyl-2,3-dihydro-1H-pyrrolo[1,2-a]indol-1-yl]acetic acid

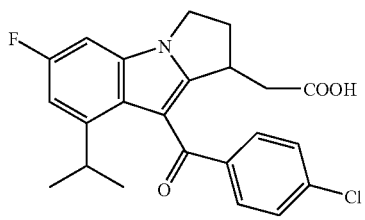

Starting from (+/−)-methyl(6-fluoro-8-isopropyl-2,3-dihydro-1H-pyrrolo[1,2-a]indol-1-yl)acetate (Example 44, Step 1), the title compound was synthesized following the procedures described in Step 1 of Example 61 and Step 10 of Example 7.

MS (−APCI) m/z 412.1 (M−H)⁻.

EXAMPLE 65

(+/−)-[9-(4-chlorobenzoyl)-6-fluoro-8-(1-methyl-1H-pyrrol-2-yl)-2,3-dihydro-1H-pyrrolo[1,2-a]indol-1-yl]acetic acid

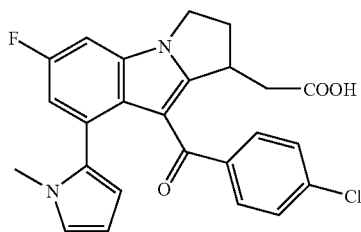

Starting from (+/−)-methyl[8-bromo-9-(4-chlorobenzoyl)-6-fluoro-2,3-dihydro-1H-pyrrolo[1,2-a]indol-1-yl]acetate (see Example 69) and 1-methyl-2-(tributylstannyl)-1H-pyrrole, the title compound was synthesized following the procedures described in Example 42 and Step 10 of Example 7.

MS (−APCI) m/z 449.1 (M−H)⁻.

EXAMPLE 66

(+/−)-[9-(4-chlorobenzyl)-6-fluoro-8-isopropyl-2,3-dihydro-1H-pyrrolo[1,2-a]indol-1-yl]acetic acid

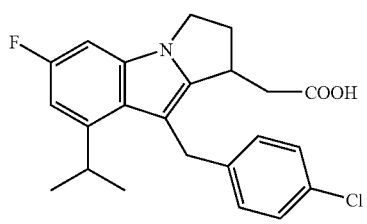

Starting from (+/−)-methyl(6-fluoro-8-isopropyl-2,3-dihydro-1H-pyrrolo[1,2-a]indol-1-yl)acetate (Example 44, Step 2), the title compound was synthesized following the procedures described in Step 1 of Example 60 and Step 10 of Example 7.

MS (−APCI) m/z 398.0 (M−H)⁻.

EXAMPLE 67

[(1R)-9-(2,4-dichlorobenzyl)-6-fluoro-8-(methylsulfonyl)-2,3-dihydro-1H-pyrrolo[1,2-a]indol-1-yl]acetic acid

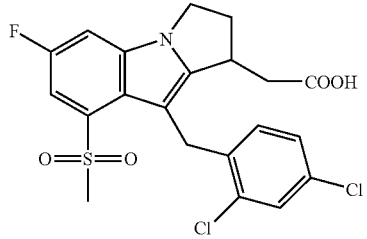

Starting from methyl[(1R)-6-fluoro-8-(methylsulfonyl)-2,3-dihydro-1H-pyrrolo[1,2-a]indol-1-yl]acetate (Example 62A, Step 2, 120 mg, 0.37 mmol) and 2,4-dichlorobenzaldehyde (71 mg, 0.51 mmol), the title compound was synthesized following the procedures as described in Step 1 of Example 60 and Step 10 of Example 7.

MS (−APCI) m/z 469.9 (M−H)⁻.

EXAMPLE 68

[(1R)-9-(2,6-dichlorobenzyl)-6-fluoro-8-(methylsulfonynl)-2,3-dihydro-1H-pyrrolo[1,2-a]indol-1-yl]acetic acid

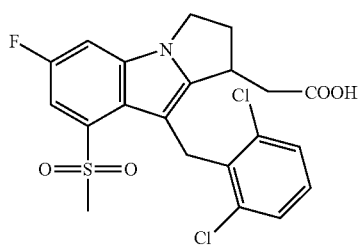

Starting from methyl[(1R)-6-fluoro-8-(methylsulfonyl)-2,3-dihydro-1H-pyrrolo[1,2-a]indol-1-yl]acetate (Example 62A, Step 2, 64 mg, 0.2 mmol) and 2,6-dichlorobenzaldehyde (39 mg, 0.22 mmol), the title compound was synthesized following the procedures as described in Step 1 of Example 60 and Step 10 of Example 7.

MS (APCI) m/z 470.0 (M−H)⁻.

EXAMPLE 69

(+/−)-[8-bromo-9-(4-chlorobenzoyl)-6-fluoro-2,3-dihydro-1H-pyrrolo[1,2-a]indol-1-yl]acetic acid

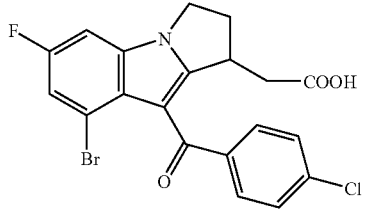

Starting from (+/−)-methyl[8-bromo-9-(4-chlorobenzoyl)-6-fluoro-2,3-dihydro-1H-pyrrolo[1,2-a]indol-1-yl]acetate (Example 61, Step 1), the title compound was synthesized following the procedures described in Step 10 of Example 7.

MS (−APCI) m/z 449.9 (M−H)⁻.

EXAMPLE 70

(+/−)-[9-(4-chlorobenzoyl)-8-cyclopropyl-6-fluoro-2,3-dihydro-1H-pyrrolo[1,2-a]indol-1-yl]acetic acid

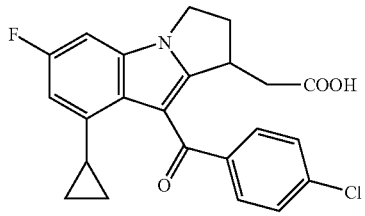

Starting from (+/−)-methyl[8-bromo-9-(4-chlorobenzoyl)-6-fluoro-2,3-dihydro-1H-pyrrolo[1,2-a]indol-1-yl]acetate (Example 61, Step 1), the title compound was synthesized following the procedures described in Steps 1 and 2 of Example 59 and Step 10 of Example 7.

¹H NMR (acetone-d₆) δ 7.81 (2H, dd), 7.50 (2H, dd), 7.03 (1H, dd), 6.56 (1H, dd), 4.27–4.18 (2H, m), 3.69–3.64 (1H, m), 2.95–2.90 (1H, m), 2.64 (1H, dd), 2.49 (1H, dd), 2.47–2.41 (1H, m), 1.95–1.87 (1H, m), 0.66–0.60 (2H, m), 0.50–0.46 (1H, m), 0.38–0.33 (1H, m).

EXAMPLE 71

(+/−)-[9-(4-chlorobenzoyl)-6-fluoro-8-(1-methoxypropyl)-2,3-dihydro-1H-pyrrolo[1,2-a]indol-1-yl]acetic acid

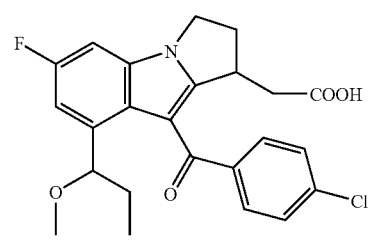

Starting from (+/−)-[8-bromo-9-(4-chlorobenzoyl)-6-fluoro-2,3-dihydro-1H-pyrrolo[1,2-a]indol-1-yl]acetic acid (Example 69), the title compound was synthesized following the procedures described in Step 1 of Example 19, Step 1 of Example 20 and Step 10 of Example 7.

MS (−APCI) m/z 442.1 (M−H)⁻.

EXAMPLE 72

(+/−)-[9-(4-chlorobenzoyl)-6-fluoro-8-phenyl-2,3-dihydro-1H-pyrrolo[1,2-a]indol-1-yl]acetic acid

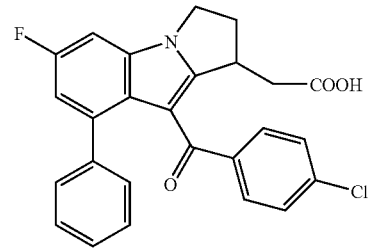

Starting from (+/−)-methyl[8-bromo-9-(4-chlorobenzoyl)-6-fluoro-2,3-dihydro-1H-pyrrolo[1,2-a]indol-1-yl]acetate (Example 61, Step 1, 100 mg, 0.22 mmol) and tributylephenyl)stannane (121 mg, 0.33 mmol), the title compound was synthesized following the procedures as described in Example 42 and Step 10 of Example 7.

MS (−APCI) m/z 446.0 (M−H)⁻.

EXAMPLE 73

(+/−)-[9-(4-chlorobenzoyl)-6-fluoro-8-thien-2-yl-2,3-dihydro-1H-pyrrolo[1,2-a]indol-1-yl]acetic acid

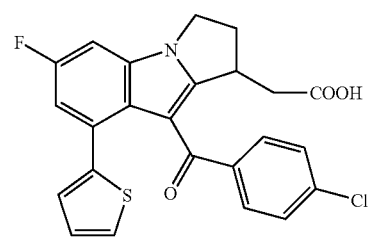

Starting from (+/−)-methyl[8-bromo-9-(4-chlorobenzoyl)-6-fluoro-2,3-dihydro-1H-pyrrolo[1,2-a]indol-1-yl]acetate and tributyl(thien-2-yl)stannane, the title compound was synthesized following the procedures described in Example 42 and Step 10 of Example 7.

MS (−APCI) m/z 452.2 (M−H)⁻.

EXAMPLE 74

(+/−)-[6-fluoro-8-(methylsulfonyl)-9-(2,4,6-trichlorobenzyl)-2,3-dihydro-1H-pyrrolo[1,2-a]indol-1-yl]acetic acid

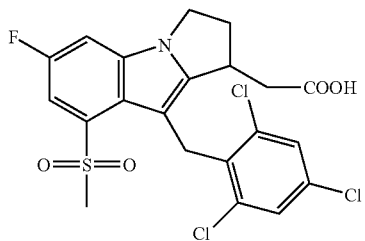

Step 1: (+/−)-methyl[8-bromo-6-fluoro-9-(2,4,6-trichlorobenzyl)-2,3-dihydro-1H-pyrrolo[1,2-a]indol-1-yl]acetate Starting from (+/−)-methyl(8-bromo-6-fluoro-2,3-dihydro-1H-pyrrolo-[1,2-a]indol-1-yl)acetate (Example 7, Step 8, 326 mg, 1 mmol) and 2,4,6-trichlorobenzaldehyde (250 mg, 1.2 mmol), the title compound (350 mg) was synthesized following the procedures described in Step 1 of Example 60.

Step 2: (+/−)-[6-fluoro-8-(methylsulfonyl)-9-(2,4,6-trichlorobenzyl)-2,3-dihydro-1H-pyrrolo[1,2-a]indol-1-yl]acetic acid Starting from the compound of Step 1, the title compound was synthesized following the procedures described in Step 2 of Example 61 and Step 10 of Example 7.

MS (−APCI) m/z 504.2 (M−H)⁻.

EXAMPLE 75

(+/−)-{6-fluoro-8-(methyldulfonyl)-9-[(2,4,5-trichlorophenyl)thio]-2,3-dihydro-1H-pyrrolo[1,2-a]indol-1-yl}acetic acid

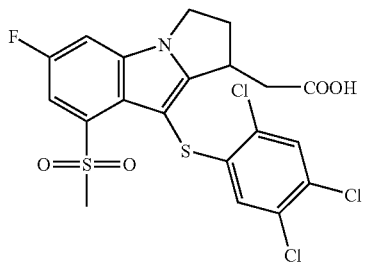

Step 1: (+/−)-methyl {8-bromo-6-fluoro-9-[(2,4,5-trichlorophenyl)thio]-2,3-dihydro-1H-pyrrolo[1,2-a]indol-1-yl}acetate Starting from bis(2,4,5-trichlorophenyl) disulfide (638 mg, 1.5 mmol) and (+/−)-methyl(8-bromo-6-fluoro-2,3-dihydro-1H-pyrrolo[1,2-a]indol-1-yl)acetate (Example 7, Step 8, 326 mg, 1 mmol), the title compound (70 mg) was synthesized as described in Step 9 of Example 7.

Step 2: (+/−)-{6-fluoro-8-(methylsulfonyl)-9-[(2,4,5-trichlorophenyl)thio]-2,3-dihydro-1H-pyrrolo[1,2-a]indol-1-yl}acetic acid Starting from the compound of Step 1, the title compound was synthesized following the procedures described in Step 2 of Example 61 and Step 10 of Example 7.

¹H NMR (acetone-d₆) δ 7.73 (1H, dd), 7.64 (1H, dd), 7.60 (1H, s), 6.85 (1H, s), 4.54–4.48 (1H, m), 4.41–4.35 (1H, m), 3.95–3.88 (1H, m); 3.43 (3H, s), 3.15–3.04 (2H, m), 2.79 (1H, dd), 2.59–2.53 (1H, m).

EXAMPLE 76

(+/−)-[9-(1,1'-biphenyl-4-ylcarbonyl)-6-fluoro-8-(methylfulfonyl)-2,3-dihydro-1H-pyrrolo[1,2-a]indol-1-yl]acetic acid

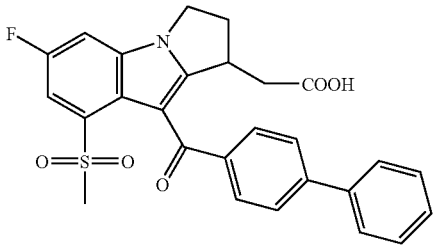

Starting from 4-biphenylcarbonyl chloride (72 mg, 0.33 mmol) and (+/−)-methyl[6-fluoro-8-(methylsulfonyl)-2,3-dihydro-1H-pyrrolo[1,2-a]indol-1-yl]acetate (35 mg, 0.11 mmol) the title compound was synthesized following the procedures described in Step 1 of Example 61 and Step 10 of Example 7.

MS (−APCI) m/z 490.2 (M−H)⁻.

EXAMPLE 77

(+/−)-[6-fluoro-8-(methylsulfonyl)-9-(2-naphthoyl)-2,3-dihydro-1H-pyrrolo[1,2-a]indol-1-yl]acetic acid

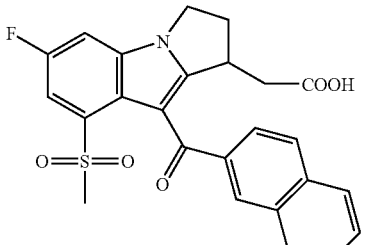

Step 1: (+/−)-methyl[8-bromo-6-fluoro-9-(2-naphthoyl)-2,3-dihydro-1H-pyrrolo[1,2-a]indol-1-yl]acetate Starting from 2-naphthoyl chloride (343 mg, 1.8 mmol) and (+/−)-methyl(8-bromo-6-fluoro-2,3-dihydro-1H-pyrrolo[1,2-a]indol-1-yl)acetate (Example 7, Step 8, 200 mg, 0.6 mmol) the title compound (250 mg, fade yellow solid) was synthesized following the procedures described in Step 1, Example 61.

Step 2: (+/−)-[6-fluoro-8-(methylsulfonyl)-9-(2-naphthoyl)-2,3-dihydro-1H-pyrrolo[1,2-a]indol-1-yl]acetic acid Starting from the compound of Step 1 (190 mg, 0.4 mmol), the title compound was synthesized following the procedures described in Step 2 of Example 61 and Step 10 of the Example 7.

MS (−APCI) m/z 464.1 (M−H)⁻.

EXAMPLE 78

(+/−)-[8-bromo-6-fluoro-9-(2-naphthoyl)-2,3-dihydro-1H-pyrrolo[1,2-a]indol-1-yl]acetic acid

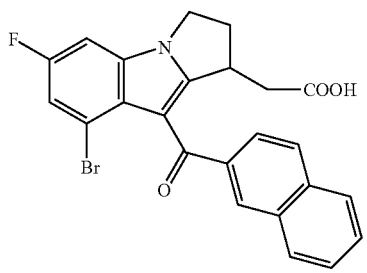

Starting from To (+/−)-methyl[8-bromo-6-fluoro-9-(2-naphthoyl)-2,3-dihydro-1H-pyrrolo[1,2-a]indol-1-yl]acetate (Example 77, Step 1), the title compound was synthesized following the procedures described in Step 10 of Example 7.

MS (−APCI) m/z 464.0 (M−H)⁻.

EXAMPLE 79

(+/−)-[9-[(4-chlorophenyl)thio]-6-fluoro-8-(methylsulfonyl)-3-oxo-2,3-dihydro-1H-pyrrolo[1,2-a]indol-1-yl]acetic acid

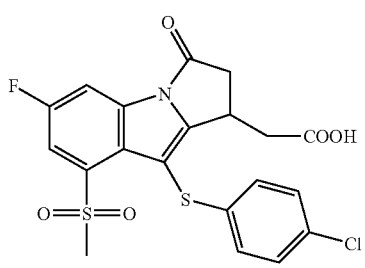

Step 1: (4-bromo-6-fluoro-1H-indol-2-yl)methanol

To a solution of methyl 4-bromo-6-fluoro-1H-indole-2-carboxylate (3 g, 11 mmol) in THF (50 mL) at −30° C. was added diisobutylaluminum hydride (33 mmol, 1.5M toluene solution). The mixture was stirred for 1 hour at −30° C. and 1N HCl was added. The phases were separated and the aqueous layer was extracted with Et₂O. The combined organic layers were dried over Na₂SO₄ and concentrated to give 2.6 g of the title compound used as such.

Step 2: 4-bromo-6-fluoro-1H-indole-2-carbaldehyde

To a solution of (4-bromo-6-fluoro-1H-indol-2-yl)methanol (2.6 g, 11 mmol) in CH₂Cl₂ (100 mL) at r.t. was added Dess-Martin periodinane (6.4 g, 15 mmol). The mixture was stirred for 30 minutes at r.t. and saturated aqueous NaHCO₃ was added. The mixture was filtered through a celite pad and the filtrate was extracted with CH₂Cl₂. The combined organic layers were dried over Na₂SO₄ and concentrated. The residue was purified by silica gel chromatography eluted with 30% EtOAc to give 2 g of the title compound.

Step 3: ethyl-3-(4-bromo-6-fluoro-1H-indol-2-yl)prop-2-enoate

To a solution of 4-bromo-6-fluoro-1H-indole-2-carbaldehyde (1.8 g, 7.4 mmol) in THF (100 mL) at r.t. was added (ethoxycarbonylmethylene)triphenylphosphorane (5 g, 14 mmol). The mixture was stirred for 2 hours at r.t. and the mixture was filtered through a silica gel pad eluted with 40% EtOAc and the filtrate was concentrated. The residue was purified by silica gel chromatography eluted with 20% EtOAc to give 1.6 g of the title compound.

Step 4: (+/−)-ethyl 8-bromo-1-(2-ethoxy-2-oxoethyl)-6-fluoro-3-oxo-2,3-dihydro-1H-pyrrolo[1,2-a]indole-2-carboxylate To a solution of diethyl malonate (1.67 g, 10.4 mmol) in EtOH (30 mL) at r.t. was added sodium methoxide (2.26 mL, 25% solution in MeOH). The mixture was stirred for 5 minutes and a solution of the compound of Step 3 (1.3 g, 4.2 mmol) in EtOH (10 mL) was added. The mixture was stirred at 75° C. for 12 hours, saturated aqueous NH₄Cl was added and the aqueous layer was extracted with EtOAc. The combined organic layers were dried over Na₂SO₄ and concentrated. The residue was purified by silica gel chromatography eluted with 20% EtOAc to give 1.6 g of the title compound.

MS (+APCI) m/z 426.2 (M+H)⁺.

Step 5: (+/−)-ethyl(8-bromo-6-fluoro-3-oxo-2,3-dihydro-1H-pyrrolo[1,2-a]indol-1-yl)acetate To a solution of the compound of Step 4 (1 g, 2.4 mmol) in DMSO (20 mL) at r.t. were added sodium chloride (420 mg, 7.2 mmol) and H₂O (260 mg, 14.4 mmol). The mixture was stirred at 120° C. for 3 hours, cooled, and partitioned between H₂O and CH₂Cl₂. The aqueous layer was extracted with CH₂Cl₂ and the combined organic layers were washed with brine, dried over Na₂SO₄ and concentrated to give 900 mg of the title compound.

MS (+APCI) m/z 354.1 (M+H)⁺.

Step 6: (+/−)-4-ethyl{8-bromo-9-[(4-chlorophenyl)thio]-6-fluoro-3-oxo-2,3-dihydro-1H-pyrrolo[1,2-a]indol-1-yl}acetate Starting from bis(2,4,5-chlorophenyl) disulfide (2.1, 7.2 mmol) and the compound of Step 5 the title compound (500 mg, as a 60% pure yellow oil) was synthesized following the procedures described in Step 9 of Example 7, and the product was used as such.

Step 7: (+/−)-ethyl[9-[(4-chlorophenyl)thio]-6-fluoro-8-(methylsulfonyl)-3-oxo-2,3-dihydro-1H-pyrrolo[1,2-a]indol-1-yl]acetate Starting from the product of Step 6 (500 mg, 1.06 mmol) the title compound was synthesized following the procedures described in Step 2, Example 61, and the residue was purified by silica gel chromatography eluted with 40% EtOAc/hexane to give 100 mg of the title compound.

Step 8: (+/−)-[9-[(4-chlorophenyl)thio]-6-fluoro-8-(methylsulfonyl)-3-oxo-2,3-dihydro-1H-pyrrolo[1,2-a]indol-1-yl]acetic acid To the compound of Step 7 (40 mg) in 2-butanone (4 mL) was added 6N HCl (0.5 mL). The mixture was stirred at 80° C. for 3 hours, cooled to r.t., diluted with H₂O and the aqueous layer was extracted with EtOAc. The combined organic layers were dried over Na₂SO₄ and concentrated. The residue was purified by silica gel chromatography eluted with 40% EtOAc/hexane containing 1% AcOH to give 23 mg of the title compound as a white solid.

MS (−APCI) m/z 466.1 (M−H)⁻.

EXAMPLE 80

(+/−)-[6-fluoro-9-(2-furoyl)-8-(methylsulfonyl)-2,3-dihydro-1H-pyrrolo[1,2-a]indol-1-yl]acetic acid

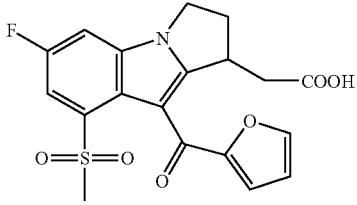

Starting from (+/−)-methyl(8-bromo-6-fluoro-2,3-dihydro-1H-pyrrolo[1,2-a]indol-1-yl)acetate (Example 7, Step 8) and 2-furoyl chloride, the title compound was synthesized following the procedures described in Steps 1 and 2 of Example 61 and Step 10 of Example 7.

MS (−APCI) m/z 404.1 (M−H)−.

EXAMPLE 81

(+/−)-[9-(2,4-dichlorobenzoyl)-6-fluoro-8-(methylsulfonyl)-2,3-dihydro-1H-pyrrolo[1,2-a]indol-1-yl]acetic acid

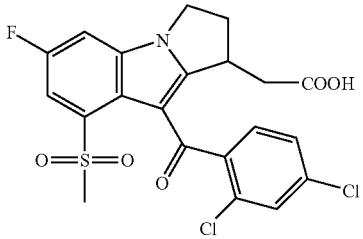

Starting from (+/−)-methyl(8-bromo-6-fluoro-2,3-dihydro-1H-pyrrolo[1,2-a]indol-1-yl)acetate (Example 7, Step 8) and 2,4-dichlorobenzoyl chloride, the title compound was synthesized following the procedures described in Steps 1 and 2 of Example 61 and Step 10 of Example 7.

MS (−APCI) m/z 482.0 (M−H)−.

EXAMPLE 82

(+/−)-[9-[4-chloro-2-(methylsulfonyl)benzoyl]-6-fluoro-8-(methylsulfonyl)2,3-dihydro-1H-pyrrolo[1,2-a]indol-1-yl]acetic acid

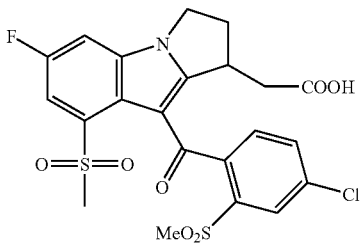

Starting from (+/−)-methyl(8-bromo-6-fluoro-2,3-dihydro-1H-pyrrolo[1,2-a]indol-1-yl)acetate (Example 7, Step 8) and 4-chloro-2-iodobenzoyl chloride, the title compound was synthesized following the procedures described in Steps 1 and 2 of Example 61 and Step 10 of Example 7.

MS (−APCI) m/z 526.1 (M−H)−.

EXAMPLE 83

(+/−)-[8-bromo-9-(4-chloro-2-iodobenzoyl)-6-fluoro-2,3-dihydro-1H-pyrrolo[1,2-a]indol-1-yl]acetic acid

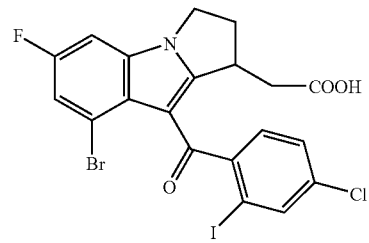

Starting from (+/−)-methyl(8-bromo-6-fluoro-2,3-dihydro-1H-pyrrolo[1,2-a]indol-1-yl)acetate (example 7, Step 8) and 4-chloro-2-iodobenzoyl chloride, the title compound was synthesized following the procedures described in Step 1 of Example 61 and Step 10 of Example 7.

MS (−APCI) m/z 576.0 (M−H)−.

EXAMPLE 84

(+/−)-{9-[2-(AMINOCARBONYL)-4-CHLOROBENZOYL]-8-BROMO-6-FLUORO-2,3-DIHYDRO-1H-PYRROLO[1,2-a]INDOL-1-YL}ACETIC ACID

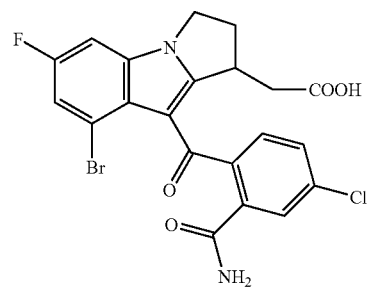

Step 1: (+/−)-methyl[8-bromo-9-(4-chloro-2-cyanobenzoyl)-6-fluoro-2,3-dihydro-1H-pyrrolo[1,2-a]indol-1-yl]acetate Starting from (+/−)-methyl[8-bromo-9-(4-chloro-2-iodobenzoyl)-6-fluoro-2,3-dihydro-1H-pyrrolo[1,2-a]indol-1-yl]acetate (see Example 83, 150 mg, 0.25 mmol), the title compound (100 mg brownish solid) was synthesized as described in Step 1 of Example 31.

Step 2: (+/−)-{9-[2-(aminocarbonyl)-4-chlorobenzoyl]-8-bromo-6-fluoro-2,3-dihydro-1H-pyrrolo[1,2-a]indol-1-yl}acetic acid To a solution of the compound of Step 1 (30 mg) in a 3/1 mixture of THF/MeOH (3 mL) was added 1N LiOH (1 mL, aqueous solution). The reaction mixture was stirred at r.t. for 16 h and AcOH (0.5 mL) and brine (5 mL) were added. The aqueous layer was extracted with EtOAc. The combined organic layers were dried over Na₂SO₄ and concentrated. The residue was swished in EtOAc to give 18 mg of the title compound as a white solid.

MS (−APCI) m/z 491.0 (M−H)⁻.

EXAMPLE 85

(+/−)-[9-(4-chloro-2-cyanobenzoyl)-6-fluoro-8-(methylsulfonyl)-2,3-dihydro-1H-pyrrolo[1,2-a]indol-1-yl]acetic acid

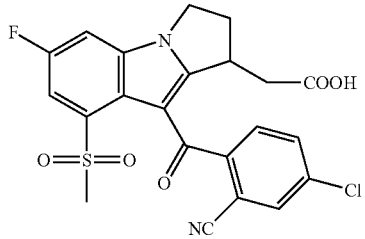

Starting from (+/−)-methyl[8-bromo-9-(4-chloro-2-cyanobenzoyl)-6-fluoro-2,3-dihydro-1H-pyrrolo[1,2-a]indol-1-yl]acetate (Example 84, Step 1), the title compound was synthesized following the procedures described in Step 2 of Example 61 and Step 10 of Example 7.

MS (−APCI) m/z 473.3 (M−H)⁻.

EXAMPLE 86

[(1R)-9-(4-CHLORO-2-IODOBENZOYL)-6-FLUORO-8-ISOPROPYL-2,3-DIHYDRO-1H-PYRROLO[1,2-a]INDOL-1-yl]ACETIC ACID

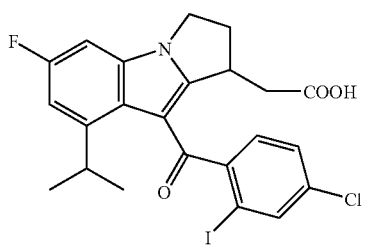

Starting from 4-chloro-2-iodobenzoyl chloride (542 mg, 1.8 mmol) and methyl[(1R)-6-fluoro-8-isopropyl-2,3-dihydro-1H-pyrrolo[1,2-a]indol-1-yl]acetate (Example 44A, Step 1, 173 mg, 0.6 mmol), the title compound was synthesized following the procedures described in Step 1 of Example 61 and Step 10 of Example 7.

MS (−APCI) m/z 538.1 (M−H)⁻.

EXAMPLE 87

(+/−)-[9-(1,3-BENZOTHIAZOL-2-YLCARBONYL)-8-BROMO-6-FLUORO-2,3-DIHYDRO-1H-PYRROLO[1,2-a]INDOL-1-yl]ACETIC ACID

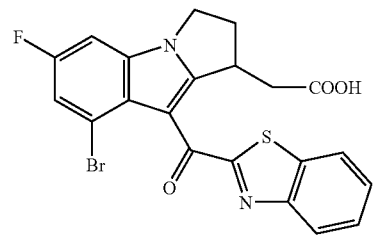

Starting from (+/−)-methyl(8-bromo-6-fluoro-2,3-dihydro-1H-pyrrolo[1,2-a]indol-1-yl)acetate (Example 7, Step 8) and 1,3-benzothiazole-2-carbonyl chloride, the title compound was synthesized following the procedures described in Step 1 of Example 61 and Step 10 of Example 7.

MS (−APCI) m/z 472.9 (M−H)⁻.

EXAMPLE 88

{(1R)-9-[4-CHLORO-2-(METHYLSULFONYL)BENZOYL]-6-FLUORO-8-ISOPROPYL-2,3-DIHYDRO-1H-PYRROLO[1,2-a]INDOL-1-yl}ACETIC ACID

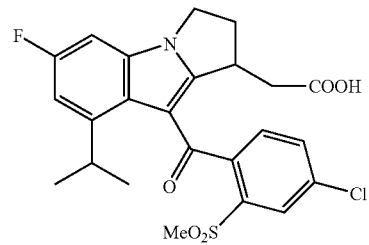

Starting from methyl[(1R)-9-(4-chloro-2-iodobenzoyl)-6-fluoro-8-isopropyl-2,3-dihydro-1H-pyrrolo[1,2-a]indol-1-yl]acetate (see Example 86), the title compound was synthesized following the procedures described in Step 2 of Example 61 and Step 10 of Example 7.

MS (−APCI) m/z 490.3 (M−H)⁻.

EXAMPLE 89

((1R)-6-FLUORO-8-(METHYLSULFONYL)-9-{[4-(TRIFLUOROMETHYL)-PHENYL]THIO}-2,3-DIHYDRO-1H-PYRROLO[1,2-a]INDOL-1-YL)ACETIC ACID

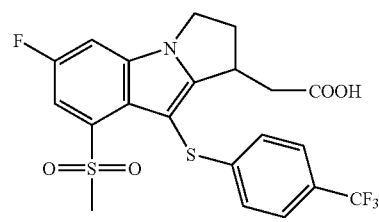

Step 1: bis[4-(trifluoromethyl)phenyl]disulfide

To a solution of 4-(trifluoromethyl)benzenethiol (1 g) in Et$_2$O was added bromine until orange color remained. The addition was stopped and the organic layer was washed with 1:1 aqueous saturated NaHCO$_{3/10}$% aqueous Na$_2$S2O3, dried over Na$_2$SO$_4$ and concentrated to give the title compound used as such.

Step 2: methyl((1R)-8-bromo-6-fluoro-9-{[4-(trifluoromethyl)phenyl]thio}-2,3-dihydro-1H-pyrrolo[1,2-a]indol-1-yl)acetate Starting from bis[4-(trifluoromethyl)phenyl] disulfide (454 mg, 1.28 mmol) and methyl[(1R)-8-bromo-6-fluoro-2,3-dihydro-1H-pyrrolo[1,2-a]indol-1-yl]acetate (Example 62A, 200 mg, 0.64 mmol), the title compound (280 mg, 70% pure) was synthesized as described in Step 9 of Example 7.

Step 3: ((1R)-6-fluoro-8-(methylsulfonyl)-9-{[4-(trifluoromethyl)phenyl]thio}-2,3-dihydro-1H-pyrrolo[1,2-a]indol-1-yl)acetic acid Starting from the compound of Step 2, the title compound was synthesized following the procedures described in Step 2 of Example 61 and Step 10 of Example 7.

MS (−APCI) m/z 486.3 (M−H)$^-$.

EXAMPLE 90

((1R)-6-FLUORO-8-(METHYLSULFONYL)-9-{[4-(METHYLSULFONYL)-PHENYL]THIO}-2,3-DIHYDRO-1H-PYRROLO[1,2-a]INDOL-1-YL)ACETIC ACID

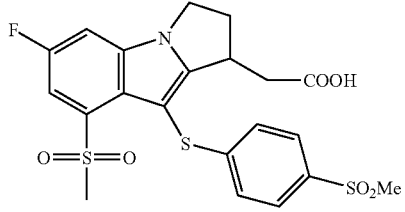

Step 1:1-bromo-4-[(4-bromophenyl)dithio]benzene

Starting from 4-bromobenzenethiol, the title compound was synthesized following the procedures described in Step 1 of Example 89.

Step 2: Methyl{(1R)-8-bromo-9-[(4-bromophenyl)thio]-6-fluoro-2,3-dihydro-1H-pyrrolo[1,2-a]indol-1-yl}acetate Starting from 1-bromo-4-[(4-bromophenyl)dithio]benzene and methyl[(1R)-8-bromo-6-fluoro-2,3-dihydro-1H-pyirolo[1,2-a]indol-1-yl]acetate (Example 62A), the title compound was synthesized following the procedures described in Step 9 of Example 7.

Step 3: {(1R)-6-fluoro-8-(methylsulfonyl)-9-{[4-(methylsulfonyl)phenyl]thio}-2,3-dihydro-1H-pyrrolo[1,2-a]indol-1-yl)acetic acid Starting from the compound of Step 2, the title compound was synthesized following the procedures described in Step 2 of Example 61 and Step 10 of Example 7.

MS (−APCI) m/z 496.3 (M−H)$^-$.

EXAMPLE 91

(+/−)-[8-BROMO-6-FLUORO-9-(QUINOLIN-2-YLCARBONYL)-2,3-DIHYDRO-1H-PYRROLO[1,2-a]INDOL-1-YL]ACETIC ACID

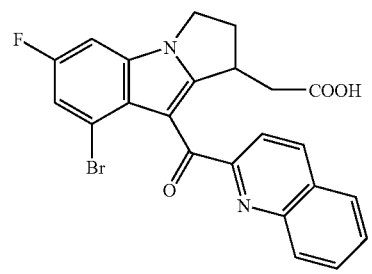

Starting from (+/−)-methyl(8-bromo-6-fluoro-2,3-dihydro-1H-pyrrolo[1,2-a]indol-1-yl)acetate (Example 7, Step 8) and quinoline-2-carbonyl chloride, the title compound was synthesized following the procedures described in Step 1 of Example 61 and Step 10 of Example 7.

MS (−APCI) m/z 465.2 (M−H)$^-$.

EXAMPLE 92

(+/−)-[6-FLUORO-8-(METHYLSULFONYL)-9-(QUINOLIN-2-YLCARBONYL)-2,3-DIHYDRO-1H-PYRROLO[1,2-a]INDOL-1-YL]ACETIC ACID

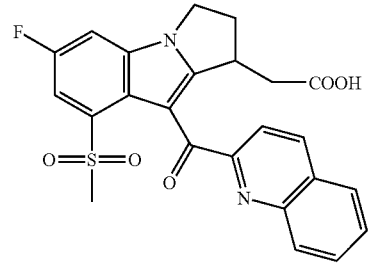

Starting from methyl[8-bromo-6-fluoro-9-(quinolin-2-yl-carbonyl)-2,3-dihydro-1H-pyrrolo[1,2-a]indol-1-yl]acetate (see Example 91), the title compound was synthesized following the procedures described in Step 2 of Example 61 and Step 10 of Example 7.

MS (−APCI) m/z 465.2 (M−H)$^-$.

EXAMPLE 93

(+/−)-[9-(1,3-BENZOTHIAZOL-2-YLTHIO)-8-BROMO-6-FLUORO-2,3-DIHYDRO-1H-PYRROLO[1,2-a]INDOL-1-YL]ACETIC ACID

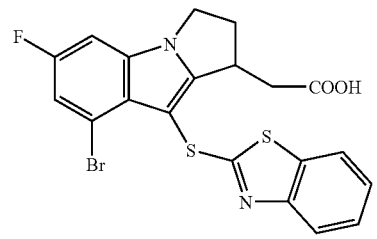

Step 1: 2-(1,3-benzothiazol-2-yldithio)-1,3-benzothiazole

Starting from 1,3-benzothiazole-2-thiol, the title compound was synthesized following the procedures described in Step 1 of Example 89.

Step 2: (+/−)-[9-(1,3-benzothiazol-2-ylthio)-8-bromo-6-fluoro-2,3-dihydro-1H-pyrrolo[1,2-a]indol-1-yl]acetic acid Starting from 2-(1,3-benzothiazol-2-yldithio)-1,3-benzothiazole and (+/−)-methyl(8-bromo-6-fluoro-2,3-dihydro-1H-pyrrolo[1,2-a]indol-1-yl)acetate (Example 7, Step 8), the title compound was synthesized following the procedures described in Step 9 of Example 7 and Step 10 of Example 7.

MS (−APCI) m/z 476.9 (M−H)⁻.

EXAMPLE 94

(+/−)-[9-(1,3-BENZOTHIAZOL-2-YLTHIO)-6-FLUORO-8-(METHYLSULFONYL)-2,3-DIHYDRO-1H-PYRROLO[1,2-a]INDOL-1-YL]ACETIC ACID

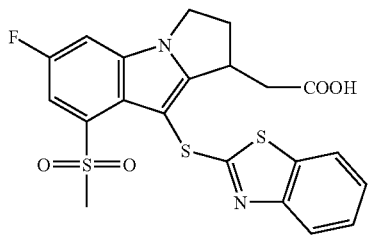

Starting from methyl[9-(1,3-benzothiazol-2-ylthio)-8-bromo-6-fluoro-2,3-dihydro-1H-pyrrolo[1,2-a]indol-1-yl]acetate (see Example 93) the title compound was synthesized following the procedures described in Step 2 of Example 61 and Step 10 of Example 7.

MS (−APCI) m/z 475.0 (M−H)⁻.

EXAMPLE 95

(+/−)-[9-[(4-CHLOROPHENYL)THIO]-8-(METHYLSULFONYL)-6-(2-METHYL-2H-TETRAZOL-5-YL)-2,3-DIHYDRO-1H-PYRROLO[1,2-a]INDOL-1-YL]ACETIC ACID

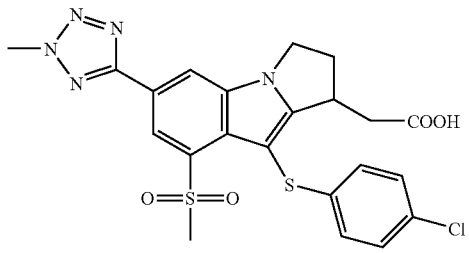

Starting from (+/−)-methyl[8-bromo-9-[(4-chlorophenyl)thio]-6-(2-methyl-2H-tetrazol-5-yl)-2,3-dihydro-1H-pyrrolo[1,2-a]indol-1-yl]acetate (see Example 32, 70 mg, 0.13 mmol), the title compound was synthesized following the procedures described in Step 2 of Example 61 and Step 10 of the Example 7.

MS (−APCI) m/z 516.1 (M−H)⁻.

EXAMPLE 96

(+/−)-[9-[1-(4-CHLOROPHENYL)ETHYL]-6-FLUORO-8-(METHYLSULFONYL)-2,3-DIHYDRO-1H-PYRROLO[1,2-a]INDOL-1-YL]ACETIC ACID

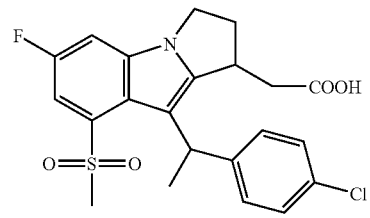

Step 1: (+/−)-tert-butyl [8-bromo-9-(4-chlorobenzoyl)-6-fluoro-2,3-dihydro-1H-pyrrolo[1,2-a]indol-1-yl]acetate To (+/−)-[8-bromo-9-(4-chlorobenzoyl)-6-fluoro-2,3-dihydro-1H-pyrrolo[1,2-a]indol-1-yl]acetic acid (Example 69, 500 mg) in toluene (10 mL) at 100° C. was slowly added 1,1-ditert-butoxy-N,N-dimethylmethanamine (0.7 mL). The mixture was stirred at 110° C. for 1 h, cooled to r.t., washed with aqueous saturated NaHCO₃ and brine, dried over Na₂SO₄ and concentrated. The residue was purified by silica gel chromatography eluted with 30% EtOAc/hexane to give 410 mg of the title compound.

Step 2: (+/−)-tert-butyl {8-bromo-9-[1-(4-chlorophenyl)vinyl]-6-fluoro-2,3-dihydro-1H-pyrrolo[1,2-a]indol-1-yl}acetate

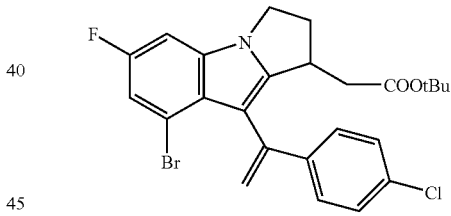

To a suspension of methyltriphenylphosphonium bromide (536 mg, 1.5 mmol) in THF (7 mL) at r.t. was added potassium tert-butoxide (1.5 mL, 1M THF solution). The mixture was stirred for 30 minutes at r.t. and a solution of the compound of Step 1 (190 mg, 0.38 mmol) in THF (7 mL) was added. The reaction mixture was stirred at 60° C. for 2 h, cooled and poured into aqueous saturated NH₄Cl. The phases were separated and the aqueous layer was extracted with EtOAc. The combined organic layers were dried over Na₂SO₄ and concentrated. The residue was purified by silica gel chromatography eluted with 20% EtOAc/hexane to give 150 mg of the title compound.

Step 3: (+/−)-tert-butyl [9-[1-(4-chlorophenyl)vinyl]-6-fluoro-8-(methylsulfonyl)-2,3-dihydro-1H-pyrrolo[1,2-a]indol-1-yl]acetate Starting from the compound of Step 2 (108 mg, 0.21 mmol), the title compound (80 mg) was synthesized as described in Example 61, Step 2 but without carrying out the hydrolysis.

Step 4: (+/−)-tert-butyl [9-[1-(4-chlorophenyl)ethyl]-6-fluoro-8-(methylsulfonyl)-2,3-dihydro-1H-pyrrolo[1,2-a]indol-1-yl]acetate A mixture of the compound of Step 3 (78 mg) and 20 mg of Pd/C (10% w/w) in EtOH (3 mL) was stirred under $H_2$ (balloon) for 1 h. The mixture was then filtered through a silica gel pad eluted with EtOAc and the filtrate was concentrated to give 75 mg of the title compound used as such.

Step 4: (+/−)-[9-[1-(4-chlorophenyl)ethyl]-6-fluoro-8-(methylsulfonyl)-2,3-dihydro-1H-pyrrolo[1,2-a]indol-1-yl]acetic acid A mixture of the compound of Step 1 (75 mg) and trifluoroacetic acid (0.9 mL) in $CH_2Cl_2$ (3 mL) was stirred for 5 h at r.t. and concentrated. The residue was purified by silica gel chromatography eluted with 40% EtOAc/hexane containing 1% AcOH to give 35 mg of the title compound.

MS (−APCI) m/z 448.2 (M−H)⁻.

EXAMPLE 97

(+/−)-[9-[(4-CHLOROPHENYL)ACETYL]-6-FLUORO-8-(METHYLSULFONYL)-2,3-DIHYDRO-1H-PYRROLO[1,2-a]INDOL-1-YL]ACETIC ACID

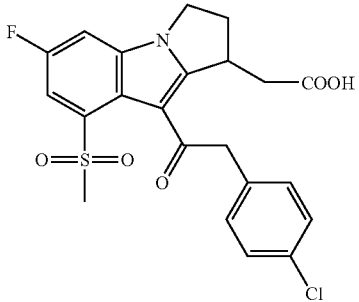

Starting from (+/−)-methyl(8-bromo-6-fluoro-2,3-dihydro-1H-pyrrolo[1,2-a]indol-1-yl)acetate (Example 7, Step 8) and (4-chlorophenyl)acetyl chloride, the title compound was synthesized following the procedures described in Steps 1 and 2 of Example 61 and Step 10 of Example 7.

MS (−APCI) m/z 462.1 (M−H)⁻.

EXAMPLE 98

(+/−)-[6-FLUORO-8-ISOPROPYL-9-(1-NAPHTHYLTHIO)-2,3-DIHYDRO-1H-PYRROLO[1,2-a]INDOL-YL]ACETIC ACID

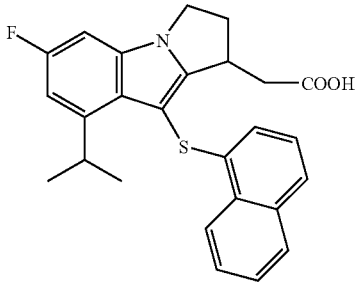

Step 1: 1-(1-naphthyldithio)naphthalene

Starting from naphthalene-1-thiol, the title compound was synthesized following the procedures described in Step 1 of Example 89.

Step 2: (+/−)-[6-fluoro-8-isopropyl-9-(1-naphthylthio)-2,3-dihydro-1H-pyrrolo[1,2-a]indol-1-yl]acetic acid Starting from 1-(1-naphthyldithio)naphthalene and (+/−)-methyl(6-fluoro-8-isopropyl-2,3-dihydro-1H-pyrrolo[1,2-a]indol-1-yl)acetate (Example 44, Step 1), the title compound was synthesized following the procedures described in Step 9 of Example 7 and Step 10 of Example 7.

MS (−APCI) m/z 432.0 (M−H)⁻.

EXAMPLE 99

(+/−)-[6-FLUORO-8-ISOPROPYL-9-(2-NAPHTHYLTHIO)-2,3-DIHYDRO-1H-PYRROLO[1,2-a]INDOL-1-YL]ACETIC ACID

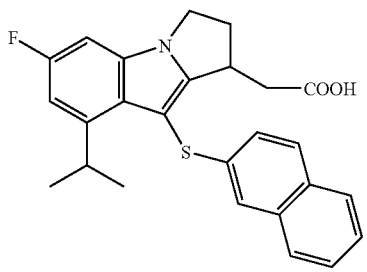

Step 1: 2-(2-naphthyldithio)naphthalene

Starting from naphthalene-2-thiol, the title compound was synthesized following the procedures described in Step 1 of Example 89.

Step 2: (+/−)-[6-fluoro-8-isopropyl-9-(2-naphthylthio)-2,3-dihydro-1H-pyrrolo[1,2-a]indol-1-yl]acetic acid Starting from 2-(2-naphthyldithio)naphthalene and (+/−)-methyl(6-fluoro-8-isopropyl-2,3-dihydro-1H-pyrrolo[1,2-a]indol-1-yl)acetate (Example 44, Step 1), the title compound was synthesized following the procedures described in Step 9 of Example 7 and Step 10 of Example 7.

MS (−APCI) m/z 432.0 (M−H)⁻.

EXAMPLE 100

(+/−)-[8-BROMO-6-FLUORO-9-(PYRIMIDIN-2-YLTHIO)-2,3-DIHYDRO-1H-PYRROLO[1,2-a]INDOL-1-YL]ACETIC ACID

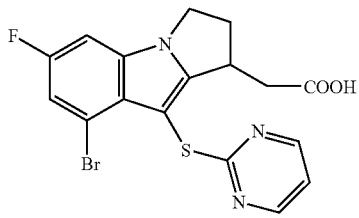

Step 1: 2-(pyrimidin-2-yldithio)pyrimidine

Starting from pyrimidine-2-thiol, the title compound was synthesized following the procedures described in Step 1 of Example 89.

Step 2: (+/−)-[8-bromo-6-fluoro-9-(pyrimidin-2-ylthio)-2,3-dihydro-1H-pyrrolo[1,2-a]indol-1-yl]acetic acid Starting from 2-(pyrimidin-2-yldithio)pyrimidine and (+/−)-methyl(8-bromo-6-fluoro-2,3-dihydro-1H-pyrrolo[1,2-a]indol-1-yl)acetate (Example 7, Step 8), the title compound was synthesized following the procedures described in Step 9 of Example 7 and Step 10 of Example 7.

MS (−APCI) m/z 420.0 (M−H)⁻.

EXAMPLE 101

(+/−)-[6-FLUORO-8-(METHYLSULFONYL)-9-(PYRIMIDIN-2-YLTHIO)-2,3-DIHYDRO-1H-PYRROLO[1,2-a]INDOL-1-YL]ACETIC ACID

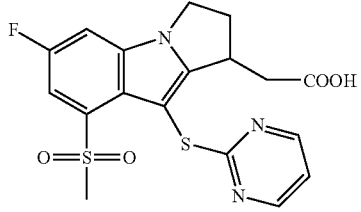

Starting from methyl[8-bromo-6-fluoro-9-(pyrimidin-2-ylthio)-2,3-dihydro-1H-pyrrolo[1,2-a]indol-1-yl]acetate (see Example 100), the title compound was synthesized following the procedures described in Step 2 of Example 61 and Step 10 of Example 7.

MS (−APCI) m/z 420.0 (M−H)⁻.

EXAMPLE 102

(+/−)-[9-[2-(4-CHLOROPHENYL)ETHYL]-6-FLUORO-87(METHYLSULFONYL)-2,3-DIHYDRO-1H-PYRROLO[1,2-a]INDOL-1-YL]ACETIC ACID

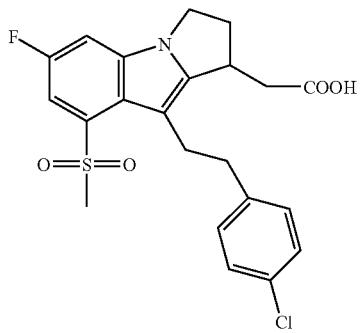

Step 1: (+/−)-methyl{8-bromo-9-[2-(4-chlorophenyl)ethyl]-6-fluoro-2,3-dihydro-1H-pyrrolo[1,2-a]indol-1-yl}acetate To a mixture of trifluoroacetic acid (79 mg, 0.7 mmol) and triethylsilane (161 mg, 1.38 mmol) in CH₂Cl₂ (1 mL) at 0° C. was added a mixture of (+/−)-methyl(8-bromo-6-fluoro-2,3-dihydro-1H-pyrrolo[1,2-a]indol-1-yl)acetate (Example 7, Step 8, 150 mg, 0.46 mmol) and (4-chlorophenyl)acetaldehyde (85 mg, 0.55 mmol) in CH₂Cl₂ (3 mL). The mixture was stirred at r.t. for 1 h and concentrated. The residue was purified by silica gel chromatography eluted with 30% EtOAc/hexane to give 190 mg of the title compound.

Step 2: (+/−)-[9-[2-(4-chlorophenyl)ethyl]-6-fluoro-8-(methylsulfonyl)-2,3-dihydro-1H-pyrrolo[1,2-a]indol-1-yl]acetic acid Starting from the compound of Step 1, the title compound was synthesized following the procedures described in Step 2 of Example 61 and Step 10 of Example 7.

MS (−APCI) m/z 448.1 (M−H)⁻.

EXAMPLE 103

(+/−)-[9-[(4-CHLOROPHENYL)THIO]-8-(1-METHOXYPROPYL)-6-(2-METHYL-2H-TETRA-ZOL-5-YL)-2,3-DIHYDRO-1H-PYRROLO[1,2-a]INDOL-1-YL]ACETIC ACID

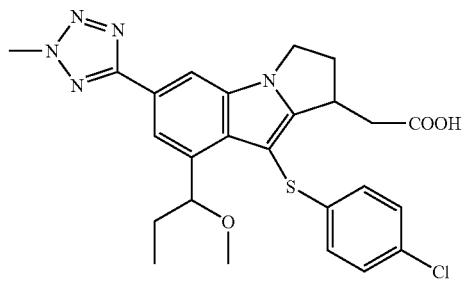

Starting from (+/−)-[8-bromo-9-[(4-chlorophenyl)thio]-6-(2-methyl-2H-tetrazol-5-yl)-2,3-dihydro-1H-pyrrolo[1,2-a]indol-1-yl]acetic acid (Example 32), the title compound was synthesized following the procedures described in Example 19, Step 1 of Example 20 and Step 10 of Example 7.

MS (−APCI) m/z 510.1 (M−H)⁻.

EXAMPLE 104

[(1R)-6-FLUORO-8-ISOPROPYL-9-(2-NAPH-THOYL)-2,3-DIHYDRO-1H-PYRROLO[1,2-a]INDOL-YL]ACETIC ACID

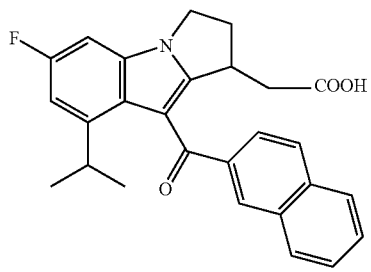

Starting from methyl[(1R)-6-fluoro-8-isopropyl-2,3-dihydro-1H-pyrrolo[1,2-a]indol-1-yl]acetate (Example 44A, Step 1) and 2-naphthoyl chloride, the title compound was synthesized following the procedures described in Step 1' of Example 61 and Step 10 of Example 7.

MS (−APCI) m/z 428.2 (M−H)⁻.

EXAMPLE 105

(+/−)-[6-FLUORO-8-(METHYLSULFONYL)-9-(2-NAPHTHYLTHIO)-2,3-DIHYDRO-1H-PYRROLO[1,2-a]INDOL-1-YL]ACETIC ACID

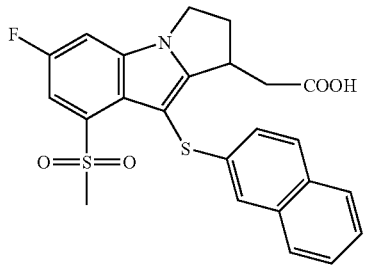

Starting from 2-(2-naphthyldithio)naphthalene and (+/−)-methyl(8-bromo-6-fluoro-2,3-dihydro-1H-pyrrolo[1,2-a]indol-1-yl)acetate (Example 7, Step 8), the title compound was synthesized following the procedures described in Step 9 of Example 7, Step 2 of Example 61 and Step 10 of Example 7.

MS (−APCI) m/z 468.1 (M−H)⁻.

EXAMPLE 106

(+/−)-{9-[(4-CHLORO-2-FLUOROPHENYL)THIO]-6-FLUORO-8-ISOPROPYL 2,3-DIHYDRO-1H-PYRROLO[1,2-a]INDOL-1-YL}ACETIC ACID

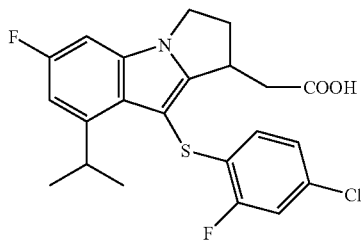

Step 1: bis(4-chloro-2-fluorophenyl)disulfide

Starting from 4-chloro-2-fluorobenzenethiol, the title compound was synthesized following the procedures described in Step 1 of Example 89.

Step 2: (+/−)-{9-[(4-chloro-2-fluorophenyl)thio]-6-fluoro-8-isopropyl-2,3-dihydro-1H-pyrrolo[1,2-a]indol-1-yl}acetic acid Starting from bis(4-chloro-2-fluorophenyl) disulfide and (+/−)-methyl (6-fluoro-8-isopropyl-2,3-dihydro-1H-pyrrolo[1,2-a]indol-1-yl)acetate (Example 44, Step 1), the title compound was synthesized following the procedures described in Steps 9 and 10 of Example 7.

MS (−APCI) m/z 434.1 (M−H)⁻.

EXAMPLE 107

(+/−)-[9-[(4-CHLORO-2-FLUOROPHENYL)THIO]-6-FLUORO-8-(METHYLSULFONYL)-2,3-DIHYDRO-1H-PYRROLO[1,2-a]INDOL-1-yl]ACETIC ACID

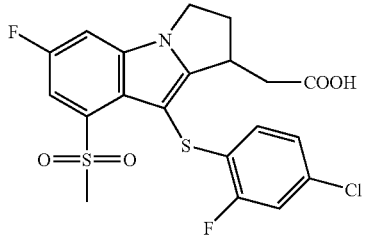

Starting from bis(4-chloro-2-fluorophenyl) disulfide and (+/−)-methyl (8-bromo-6-fluoro-2,3-dihydro-1H-pyrrolo[1,2-a]indol-1-yl)acetate (example 7, Step 8), the title compound was synthesized following the procedures described in Step 9 of Example 7, Step 2 of Example 61 and Step 10 of Example 7.

MS (−APCI) m/z 470.0 (M−H)⁻.

EXAMPLE 108

(+/−)-[9-[(4-CHLOROPHENYL)THIO]-6-FLUORO-8-(2-METHYLPHENYL)-2,3-DIHYDRO-1H-PYRROLO[1,2-a]INDOL-1-YL]ACETIC ACID

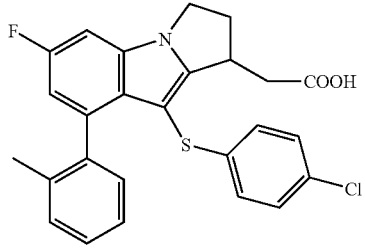

To (+/−)-methyl[8-bromo-9-[(4-chlorophenyl)sulfanyl]-6-fluoro-2,3-dihydro-1H-pyrrolo[1,2-a]indol-1-yl]acetate (Example 7, Step 9, 100 mg, 0.21 mmol) in 1-propanol (2 mL) were added 2-methylphenylboronic acid (57 mg, 0.42 mmol), 3:1 mixture of triphenylphosphine/palladium (>) acetate (11 mg) and 2M aqueous potassium carbonate (0.3 mL). The mixture was degassed and stirred at 80° C. for 6 h and the reaction mixture was cooled to r.t. Then THF (3 mL) and 1N LiOH were added and the mixture was stirred for 2 h at r.t. AcOH (0.5 mL) and brine were added and the aqueous layer was extracted with EtOAc. The combined organic layers were dried over Na₂SO₄ and concentrated. The residue was purified by silica gel chromatography eluted with 40% EtOAc/hexane containing 1% AcOH to give 90 mg of the title compound.

MS (−APCI) m/z 464.0 (M−H)⁻.

EXAMPLE 109

(+/−)-{9-[(4-CHLOROPHENYL)THIO]-6-FLUORO-8-QUINOLIN-8-YL-2,3-DIHYDRO-1H-PYRROLO[1,2-a]INDOL-1-YL}ACETIC ACID

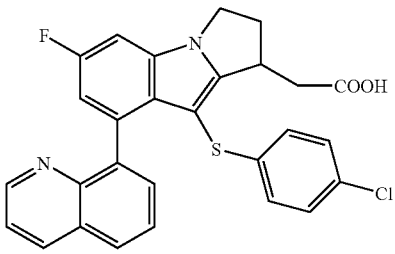

Starting from (+/−)-methyl[8-bromo-9-[(4-chlorophenyl)sulfanyl]-6-fluoro-2,3-dihydro-1H-pyrrolo[1,2-a]indol-1-yl]acetate (Example 7, Step 9) and quinolin-8-ylboronic acid, the title compound was synthesized following the procedures described in Example 108.

MS (−APCI) m/z 501.3 (M−H)⁻.

EXAMPLE 110

(+/−)-{8-(1-BENZOTHIEN-3-YL)-9-[(4-CHLOROPHENYL)THIO]-6-FLUORO-2,3-DIHYDRO-1H-PYRROLO[1,2-a]INDOL-1-YL}ACETIC ACID

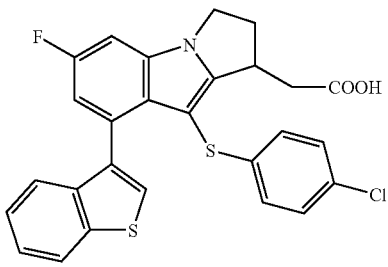

Starting from (+/−)-methyl[8-bromo-9-[(4-chlorophenyl)sulfanyl]-6-fluoro-2,3-dihydro-1H-pyrrolo[1,2-a]indol-1-yl]acetate (Example 7, Step 9) and 1-benzothien-3-ylboronic acid, the title compound was synthesized following the procedures described in Example 108.

MS (−APCI) m/z 506.1 (M−H)⁻.

EXAMPLE 111

(+/−)-[9-[(4-CHLOROPHENYL)THIO]-8-(3,5-DIMETHYLISOXAZOL-4-YL)-6-FLUORO-2,3-DIHYDRO-1H-PYRROLO[1,2-a]INDOL-1-YL]ACETIC ACID

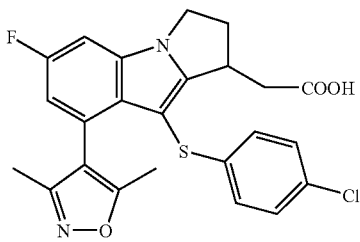

Starting from (+/−)-methyl[8-bromo-9-[(4-chlorophenyl)sulfanyl]-6-fluoro-2,3-dihydro-1H-pyrrolo[1.12-a]indol-1-yl]acetate (Example 7, Step 9) and 3,5-dimethylisoxazol-4-ylboronic acid, the title compound was synthesized following the procedures described Example 108.

MS (−APCI) m/z 469.0 (M−H)⁻.

EXAMPLE 112

(+/−)-[9-[(4-CHLOROPHENYL)THIO]-6-FLUORO-8-(4-METHYLTHIEN-3-YL)-2,3-DIHYDRO-1H-PYRROLO[1,2-a]INDOL-1-YL]ACETIC ACID

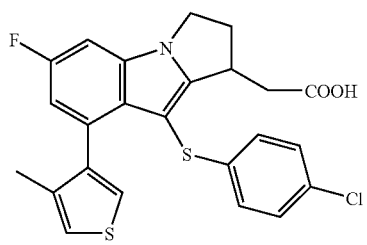

Step 1: 4,4,5,5-tetramethyl-2-(4-methylthien-3-yl)-1,3,2-dioxaborolane

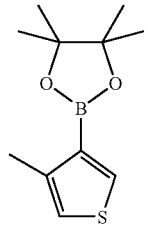

To a solution of 3-bromo-4-methylthiophene (600 mg, 3.4 mmol) in DMF (12 mL) were added 4,4,4',4',5,5,5',5'-octamethyl-2,2'-bi-1,3,2-dioxaborolane (908 mg, 3.6 mmol), potassium acetate (1 g, 10.2 mmol) and dichloro[1,1'-bis(diphenylphosphino)ferrocene]palladium (II) dichloromethane adduct (73 mg, 0.1 mmol). The reaction mixture was degassed and stirred at 8° C. for 4 h, cooled and poured in brine. The aqueous layer was extracted with EtOAc. The combined organic layers were washed with brine, dried over Na₂SO₄ and concentrated. The residue was purified by short silica gel chromatography eluted with 10% EtOAc/hexane to give 500 mg of the title compound used as such.

Step 2: (+/−)-[9-[(4-chlorophenyl)thio]-6-fluoro-8-(4-methylthien-3-yl)-2,3-dihydro-1H-pyrrolo[1,2-a]indol-1-yl]acetic acid Starting from (+/−)-methyl[8-bromo-9-[(4-chlorophenyl)sulfanyl]-6-fluoro-2,3-dihydro-1H-pyrrolo[1,2-a]indol-1-yl]acetate (Example 7, Step 9) and 4,4,5,5-tetramethyl-2-(4-methylthien-3-yl)-1,3,2-dioxaborolane, the title compound was synthesized following the procedures described Example 108.

MS (−APCI) m/z 470.0 (M−H)⁻.

EXAMPLE 113

(+/−)-{9-[(4-CHLOROPHENYL)THIO]-6-FLUORO-8-[3-(1H-PYRAZOL-1-YL)PHENYL]-2,3-DIHYDRO-1H-PYRROLO[1,2-a]INDOL-1-YL}ACETIC ACID

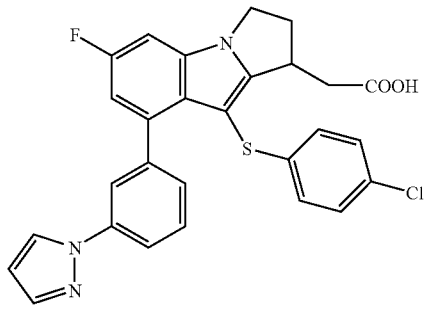

Starting from (+/−)-methyl[8-bromo-9-[(4-chlorophenyl)sulfanyl]-6-fluoro-2,3-dihydro-1H-pyrrolo[1,2-a]indol-1-yl]acetate (Example 7, Step 9) and 3-(1H-pyrazol-1-yl)phenylboronic acid, the title compound was synthesized following the procedures described Example 108.

MS (−APCI) m/z 516.3 (M−H)⁻.

EXAMPLE 114

(+/−)-[9-[(4-CHLOROPHENYL)TIHO]-6-FLUORO-8-(2-FORMYLTHIEN-3-YL)-2,3-DIHYDRO-1H-PYRROLO[1,2-a]INDOL-YL]ACETIC ACID

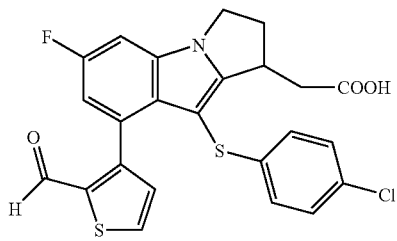

Starting from (+/−)-methyl[8-bromo-9-[(4-chlorophenyl)sulfanyl]-6-fluoro-2,3-dihydro-1H-pyrrolo[1,2-a]indol-1-yl]acetate (Example 7, Step 9) and 2-formylthien-3-ylboronic acid, the title compound was synthesized following the procedures described in Example 108.

MS (−APCI) m/z 484.2 (M−H)⁻.

EXAMPLE 115

(+/−)-[9-[(4-CHLOROPHENYL)THIO]-6-FLUORO-8-(2-METHOXYPHENYL)-2,3-DIHYDRO-1H-PYRROLO[1,2-a]INDOL-1-YL]ACETIC ACID

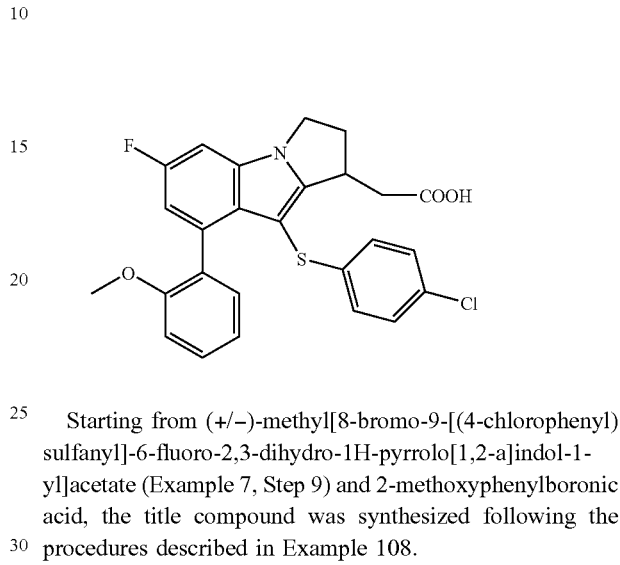

Starting from (+/−)-methyl[8-bromo-9-[(4-chlorophenyl)sulfanyl]-6-fluoro-2,3-dihydro-1H-pyrrolo[1,2-a]indol-1-yl]acetate (Example 7, Step 9) and 2-methoxyphenylboronic acid, the title compound was synthesized following the procedures described in Example 108.

MS (−APCI) m/z 480.1 (M−H)⁻.

EXAMPLE 116

(+/−)-[9-[(4-chlorophenyl)thio]-8-(3,4-dichlorophenyl)-6-fluoro-2,3-dihydro-1H-pyrrolo[1,2-a]indol-1-yl]acetic acid

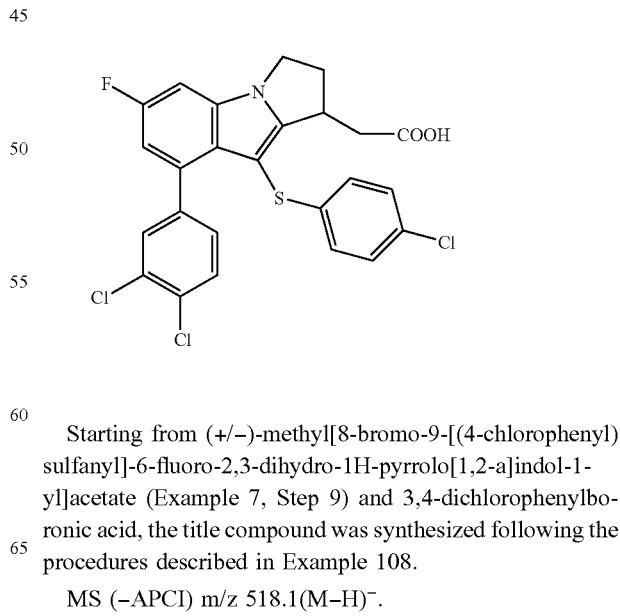

Starting from (+/−)-methyl[8-bromo-9-[(4-chlorophenyl)sulfanyl]-6-fluoro-2,3-dihydro-1H-pyrrolo[1,2-a]indol-1-yl]acetate (Example 7, Step 9) and 3,4-dichlorophenylboronic acid, the title compound was synthesized following the procedures described in Example 108.

MS (−APCI) m/z 518.1(M−H)⁻.

EXAMPLE 117

(+/−)-{9-[(4-chlorophenyl)thio]-6-fluoro-8-quinolin-6-yl-2,3-dihydro-1H-pyrrolo[1,2-a]indol-1-yl}acetic acid

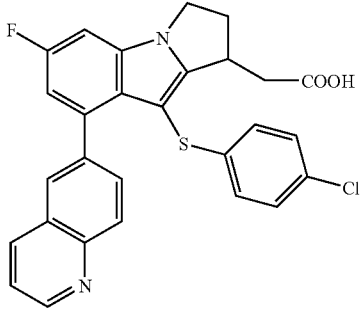

Starting from (+/−)-methyl[8-bromo-9-[(4-chlorophenyl)sulfanyl]-6-fluoro-2,3-dihydro-1H-pyrrolo[1,2-a]indol-1-yl]acetate (Example 7, Step 9) and quinolin-6-ylboronic acid, the title compound was synthesized following the procedures described in Example 108.

MS (−APCI) m/z 501.1(M−H)⁻.

EXAMPLE 118

(+/−)-[9-[(4-CHLOROPHENYL)THIO]-6-FLUORO-8-(2-NAPHTHYL)-2,3-DIHYDRO-1H-PYRROLO[1,2-a]INDOL-1-YL]ACETIC ACID

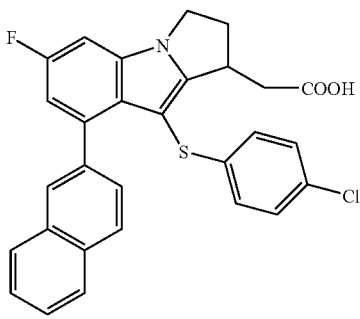

Staring from (+/−)-methyl[8-bromo-9-[(4-chlorophenyl)sulfanyl]-6-fluoro-2,3-dihydro-1H-pyrrolo[1,2-a]indol-1-yl]acetate (Example 7, Step 9) and 2-naphthylboronic acid, the title compound was synthesized following the procedures described in Example 108.

MS (−APCI) m/z 500.2 (M−H)⁻.

EXAMPLE 119

(+/−)-{9-[(4-CHLOROPHENYL)THIO]-8-CYANO-6-FLUORO-2,3-DIHYDRO-1H-PYRROLO[1,2-a]INDOL-1-YL}ACETIC ACID

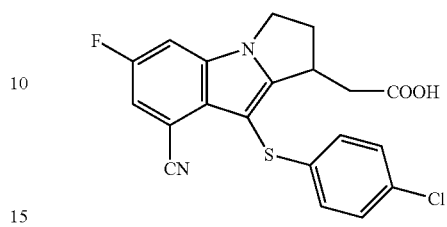

The title compound was synthesized from (+/−)-methyl{8-bromo-9-[(4-chlorophenyl)thio]-6-fluoro-2,3-dihydro-1H-pyrrolo[1,2-a]indol-1-yl}acetate (Example 7, Step 9, 500 mg, 1.07 mmol) using the procedure as described in Step 1 of Example 31 but carrying out the reaction at 90° C. for 12 hours, and Step 10 of Example 7.

MS (−APCI) m/z 399.0 (M−H)⁻.

EXAMPLE 120

(+/−)-[6-FLUORO-8-ISOPROPYL-9-(1-NAPHTHOYL)-2,3-DIHYDRO-1H-PYRROLO[1,2-a]INDOL-1-YL]ACETIC ACID

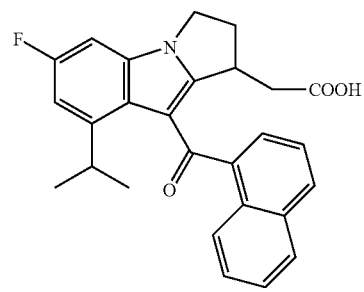

Starting from methyl(6-fluoro-8-isopropyl-2,3-dihydro-1H-pyrrolo[1,2-a]indol-1-yl)acetate (Example 44, Step 2) and 1-naphthoyl chloride, the title compound was synthesized following the procedures described in Step 1 of Example 61 and Step 10 of Example 7.

MS (−APCI) m/z 428.1 (M−H)⁻.

EXAMPLE 121

(+/−)-[9-(3,4-DICHLOROBENZOYL)-6-FLUORO-8-ISOPROPYL-2,3-DIHYDRO-1H-PYRROLO[1,2-a]INDOL-1-YL]ACETIC ACID

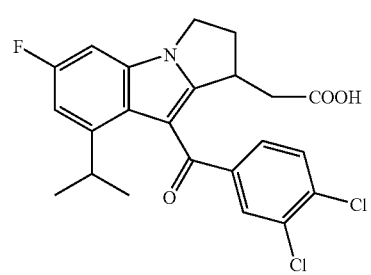

Starting from methyl(6-fluoro-8-isopropyl-2,3-dihydro-1H-pyrrolo[1,2-a]indol-1-yl)acetate (Example 44, Step 2) and 3,4-dichlorobenzoyl chloride, the title compound was synthesized following the procedures described in Step 1 of Example 61 and Step 10 of Example 7.

MS (−APCI) m/z 446.1 (M−H)⁻.

EXAMPLE 122

(+/−)-{10-[(4-CHLOROPHENYL)THIO]-3-FLUORO-1-ISOPROPYL-6,7,8,9-TETRAHYDRO-PYRIDO[1,2-a]INDOL-9-YL}ACETIC ACID

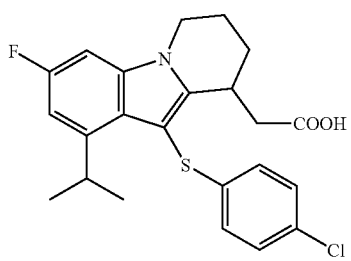

Step 1: methyl 4-bromo-1-(4-ethoxy-4-oxobutyl)-6-fluoro-1H-indole-2-carboxylate

To a solution of methyl 4-bromo-6-fluoro-1H-indole-2-carboxylate (10 g, 36.8 mmol) in DMF (100 mL) at 0° C. was added NaH (1.8 g, 44.2 mmol, 60% in oil). The mixture was stirred at r.t. for 30 minutes and tetra-n-butylammonium iodide (500 mg) was added, followed by the addition of ethyl 4-bromobutyrate (10.1 g, 51.5 mmol). The reaction mixture was stirred at r.t. for 3 h, poured into saturated aqueous NH₄Cl and the aqueous layer was extracted with EtOAc. The combined organic layers were washed with brine, dried over Na₂SO₄ and concentrated. The residue was purified by silica gel chromatography eluted with 20% EtOAc to give 13.2 g of the title compound.

Step 2: (+/−)-ethyl 1-bromo-3-fluoro-9-oxo-6,7,8,9-tetrahydropyrido[1,2-a]indole-8-carboxylate To a solution of the compound of Step 1 (13.2 g, 34.1 mmol) in THF (100 mL) at 0° C. was added potassium t-butoxide (34.1 mmol, 1M THF solution). The mixture was stirred at 0° C. for 2 h, poured into 1N HCl and the aqueous layer was extracted with EtOAc. The combined organic layers were washed with brine, dried over Na₂SO₄, concentrated and swished in EtOAc to give 11.6 g of the title compound.

Step 3: (+/−)-methyl(1-bromo-3-fluoro-6,7,8,9-tetrahydropyrido[1,2-a]indol-9-yl)acetate Starting from the compound of Step 2, the title compound was synthesized following the procedures described in Steps 6–8 of Example 7.

Step 4: (+/−)-methyl(3-fluoro-1-isopropyl-6,7,8,9-tetrahydropyrido[1,2-a]indol-9-yl)acetate Starting from the compound of Step 3, the title compound was synthesized following the procedures described in Steps 1 and 2 of Example 44.

Step 5: (+/−)-{10-[(4-chlorophenyl)thio]-3-fluoro-1-isopropyl-6,7,8,9-tetrahydropyrido[1,2-a]indol-9-yl}acetic acid Starting from the compound of Step 4, the title compound was synthesized following the procedures described in Steps 9 and 10 of Example 7.

MS (−APCI) m/z 430.0 (M−H)⁻.

EXAMPLE 123

(+/−)-[3-FLUORO-1-ISOPROPYL-10-(2-NAPHTHOYL)-6,7,8,9-TETRAHYDROPYRIDO[1,2-a]INDOL-9-YL]ACETIC ACID

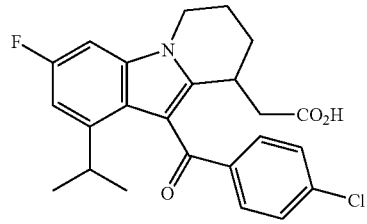

Starting from (+/−)-methyl(3-fluoro-1-isopropyl-6,7,8,9-tetrahydropyrido[1,2-a]indol-9-yl)acetate (Example 122, Step 4) and 2-naphthoyl chloride, the title compound was synthesized following the procedures described in Step 1 of Example 61 and Step 10 of Example 7.

MS (−APCI) m/z 442.2 (M−H)⁻.

EXAMPLE 124

(+/−)-[10-(4-CHLOROBENZOYL)-3-FLUORO-1-ISOPROPYL-6,7,8,9-TETRAHYDROPYRIDO[1,2-a]INDOL-9-YL]ACETIC ACID

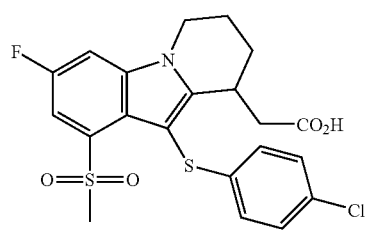

Starting from (+/−)-methyl(3-fluoro-1-isopropyl-6,7,8,9-tetrahydropyrido[1,2-a]indol-9-yl)acetate (Example 122, Step 4) and 4-chlorobenzoyl chloride, the title compound was synthesized following the procedures described in Step 1 of Example 61 and Step 10 of Example 7.

MS (−APCI) m/z 426.0 (M−H)⁻.

EXAMPLE 125

(+/−)-[10-[(4-CHLOROPHENYL)THIO]-3-FLUORO-1-(METHYLSULFONYL)-6,7,8,9-TETRAHYDROPYRIDO[1,2-a]INDOL-9-YL]ACETIC ACID

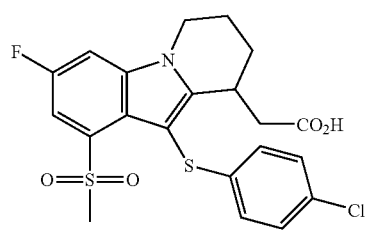

Starting from bis(4-chlorophenyl) disulfide and (+/−)-methyl(1-bromo-3-fluoro-6,7,8,9-tetrahydropyrido[1,2-a]indol-9-yl)acetate (Example 122, Step 3), the title compound was synthesized following the procedures described in Step 9 of Example 7, Step 2 of Example 61 and Step 10 of Example 7.

MS (−APCI) m/z 466.0 (M−H)⁻.

EXAMPLE 126

(+/−)-[9-(1,1'-BIPHENYL-4-YL)-6-FLUORO-8-(METHYLSULFONYL)-2,3-DIHYDRO-1H-PYRROLO[1,2-a]INDOL-1-YL]ACETIC ACID

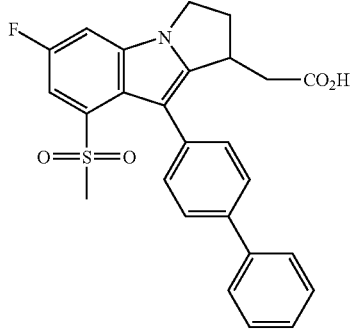

Step 1: (+/−)-methyl[9-bromo-6-fluoro-8-(methylsulfonyl)-2,3-dihydro-1H-pyrrolo[1,2-a]indol-1-yl]acetate To a solution of (+/−)-methyl[6-fluoro-8-(methylsulfonyl)-2,3-dihydro-1H-pyrrolo[1,2-a]indol-1-yl]acetate (Example 37, Step 2, 256 mg, 0.79 mmol) in THF (5 mL) at 0° C. was added NBS (169 mg, 0.95 mmol). The mixture was stirred for 10 minutes at 0° C. and poured into aqueous 10% sodium thiosulfate. The aqueous layer was extracted with EtOAc. The combined organic layers were washed with saturated aqueous NaHCO₃ and brine, dried over Na₂SO₄ and concentrated to give 320 mg of the title compound used as such.

Step 2: (+/−)-[9-(1,1'-biphenyl-4-yl)-6-fluoro-8-(methylsulfonyl)-2,3-dihydro-1H-pyrrolo[1,2-a]indol-1-yl]acetic acid To a solution of the compound of Step 1 (60 mg, 0.15 mmol) in DMF (3 mL) at r.t. were added 1,1'-biphenyl-4-ylboronic acid (60 mg, 0.3 mmol), cesium fluoride (68 mg, 0.45 mmol) and dichloro[1,1'-bis(diphenylphosphino)ferrocene]-palladium (II) dichloromethane adduct (11 mg, 0.015 mmol). The mixture was degassed and stirred at 80° C. for 12 h, cooled to r.t. and 1N HCl was added. The aqueous layer was extracted with EtOAc. The combined organic layers were washed with brine, dried over. Na₂SO₄ and concentrated. The residue was purified by silica gel chromatography eluted with 40% EtOAc/hexane to give 40 mg of the methyl ester of the title compound, which was hydrolyzed following the procedures described in Step 10 of Example 7.

MS (−APCI) m/z 462.2 (M−H)⁻.

EXAMPLE 127

(+/−)-[6-FLUORO-8-(METHYLSULFONYL)-9-(2-NAPHTHYL)-2,3-DIHYDRO-1H-PYRROLO[1,2-a]INDOL-1-YL]ACETIC ACID

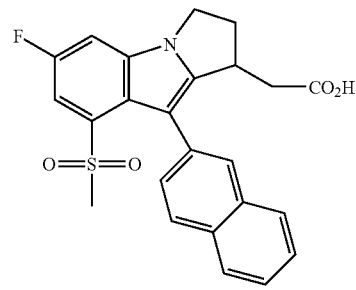

Starting from 2-naphthylboronic acid and (+/−)-methyl [9-bromo-6-fluoro-8-(methylsulfonyl)-2,3-dihydro-1H-pyrrolo[1,2-a]indol-1-yl]acetate (Example 126, Step 1), the title compound was synthesized following the procedures described in Step 2 of Example 126 and Step 10 of Example 7.

MS (−APCI) m/z 436.1 (M−H)⁻.

EXAMPLE 128

(+/−)-[9-(1,1'-BIPHENYL-3-YL)-6-FLUORO-8-(METHYLSULFONYL)-2,3-DIHYDRO-1H-PYRROLO[1,2-a]INDOL-1-YL]ACETIC ACID

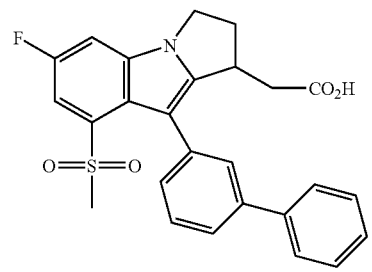

Starting from 1,1'-biphenyl-3-ylboronic acid and (+/−)-methyl[9-bromo-6-fluoro-8-(methylsulfonyl)-2,3-dihydro-1H-pyrrolo[1,2-a]indol-1-yl]acetate (Example 126, Step 1), the title compound was synthesized following the procedures described in Step 2 of Example 126 and Step 10 of Example 7.

MS (−APCI) m/z 462.2 (M−H)⁻.

EXAMPLE 129

(+/−)-{9-[(4-chlorophenyl)thio]-6-cyano-8-isopropyl-2,3-dihydro-1H-pyrrolo[1,2-a]indol-1-yl}acetic acid

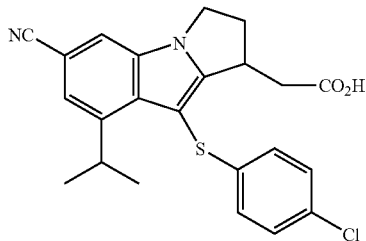

Step 1: (+/−)-methyl(8-isopropyl-6-methoxy-2,3-dihydro-1H-pyrrolo[1,2-a]indol-1-yl)acetate Starting from (+/−)-methyl(8-bromo-6-methoxy-2,3-dihydro-1H-pyrrolo[1,2-a]indol-1-yl)acetate (Example 22, Step 5, 1 g, 2.96 mmol in 5 mL of THF) and using the procedure described in Example 44, Steps 1 and 2, the title compound (800 mg) was obtained.

Step 2: (+/−)-methyl(6-hydroxy-8-isopropyl-2,3-dihydro-1H-pyrrolo[1,2-a]indol-1-yl)acetate To a solution of the compound of Step 1 (800 mg, 2.65 mmol) in CH$_2$Cl$_2$ (10 mL) at 0° C. was added boron tribromide (13.3 mmol, 1M solution in CH$_2$Cl$_2$). The mixture was stirred at 0° C. for 5 minutes, cooled to −78° C. and MeOH (2 mL) was added. The mixture was poured into saturated aqueous NaHCO$_3$ and the aqueous layer was extracted with EtOAc. The combined organic layers were washed with brine, dried over Na$_2$SO$_4$ and concentrated. The residue was purified by silica gel chromatography eluted with 40% EtOAc/hexane to give 525 mg of the title compound.

Step 3: (+/−)-methyl(8-isopropyl-6-{[(trifluoromethyl)sulfonyl]oxy}-2,3-dihydro-1H-pyrrolo[1,2-a]indol-1-yl)acetate To a solution of the compound of Step 2 (510 mg, 1.78 mmol) in CH$_2$Cl$_2$ (10 mL) at 0° C. were added pyridine (211 mg, 2.6 mmol) and triflic anhydride (604 mg, 2.14 mmol). The mixture was stirred at r.t. for 2 h and poured into saturated aqueous NaHCO$_3$. The aqueouslayer was extracted with EtOAc. The combined organic layers were washed with brine, dried over Na$_2$SO$_4$ and concentrated to give the title compound used as such.

Step 4: (+/−)-methyl(9-[(4-chlorophenyl)thio]-8-isopropyl-6-{[(trifluoromethyl)-sulfonyl]oxy}-2,3-dihydro-1H-pyrrolo[1,2-a]indol-1-yl)acetate The title compound was synthesized from the compound of Step 3 using the procedure described in Example 7, Step 9.

Step 5: (+/−)-(9-[(4-chlorophenyl)thio]-6-cyano-8-isopropyl-2,3-dihydro-1H-pyrrolo[1,2-a]indol-1-yl}acetic acid The title compound was synthesized from the compound of Step 4 using the procedures described in Step 1 of Example 31 but carrying out the reaction at 80° C. for 2 hrs., and Step 10 of Example 7.

MS (−APCI) m/z 423.1 (M−H)$^-$.

EXAMPLE 130

(+/−)-[9-[(4-CHLOROPHENYL)THIO]-8-ISOPROPYL-6-(2-METHYL-2H-TETRAZOL-5-YL)-2,3-DIHYDRO-1H-PYRROLO[1,2-a]INDOL-1-YL] ACETIC ACID

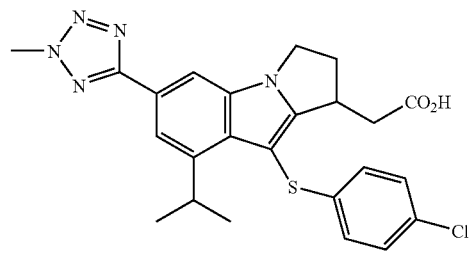

Step 1: (+/−)-methyl[9-[(4-chlorophenyl)thio]-8-isopropyl-6-(2H-tetrazol-5-yl)-2,3-dihydro-1H-pyrrolo[1,2-a]indol-1-yl]acetate To a solution of (+/−)-{9-[(4-chlorophenyl)thio]-6-cyano-8-isopropyl-2,3-dihydro-1H-pyrrolo[1,2-a]indol-1-yl}acetic acid (Example 129, 400 mg, 0.91 mmol) in toluene (5 mL) was added azidotributyltin (604 mg, 1.82 mmol). The reaction was stirred at 110° C. for 24 h, AcOH (2 mL) was added and the reaction was stirred for 2 h and concentrated and used as such.

Step 2: (+/−)-methyl[9-[(4-chlorophenyl)thio]-8-isopropyl-6-(2-methyl-2H-tetrazol-5-yl)-2,3-dihydro-1H-pyrrolo[1,2-a]indol-1-yl]acetate A solution of the compound of Step 1 in THF (10 mL) was treated with an excess of CH$_2$N$_2$ at 0° C. The reaction mixture was stirred for 5 minutes and the solvent removed. The residue was purified by silica gel chromatography eluted with 50% EtOAc/hexane to give 65 mg of (+/−)-methyl[9-[(4-chlorophenyl)thio]-8-isopropyl-6-(2-methyl-2H-tetrazol-5-yl)-2,3-dihydro-1H-pyrrolo[1,2-a]indol-1-yl]acetate and 150 mg of (+/−)-methyl[9-[(4-chlorophenyl)thio]-8-isopropyl-6-(1-methyl-1H-tetrazol-5-yl)-2,3-dihydro-1H-pyrrolo[1,2-a]indol-1-yl]acetate.

Step 3: (+/−)-[9-[(4-chlorophenyl)thio]-8-isopropyl-6-(2-methyl-2H-tetrazol-5-yl)-2,3-dihydro-1H-pyrrolo[1,2-a]indol-1-yl]acetic acid Starting from the compound of Step 2 the title compound was synthesized following the procedures described in Step 10 of Example 7.

MS (−APCI) m/z 480.1 (M−H)$^-$.

EXAMPLE 131

(+/−)-[9-[(4-CHLOROPHENYL)THIO]-8-ISOPROPYL-6-(1-METHYL-1H-TETRAZOL-5-YL)-2,3-DIHYDRO-1H-PYRROLO[1,2-a]INDOL-1-YL] ACETIC ACID

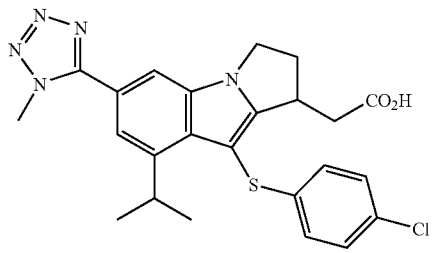

Starting from (+/−)-methyl[9-[(4-chlorophenyl)thio]-8-isopropyl-6-(1-methyl-1H-tetrazol-5-yl)-2,3-dihydro-1H-pyrrolo[1,2-a]indol-1-yl]acetate (Example 130, Step 2), the title compound was synthesized following the procedures described in Step 10 of Example 7.

MS (−APCI) m/z 480.1 (M−H)⁻.

EXAMPLE 132

(+/−)-[9-[(4-CHLOROPHENYL)THIO]-6,8-BIS(METHYLSULFONYL)-2,3-DIHYDRO-1H-PYRROLO[1,2-a]INDOL-1-YL]ACETIC ACID

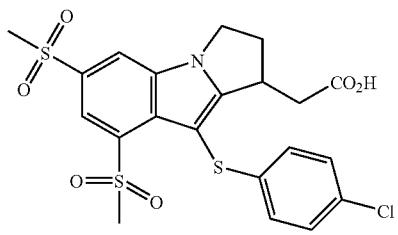

Starting from (+/−)-methyl{8-bromo-9-[(4-chlorophenyl)thio]-6-iodo-2,3-dihydro-1H-pyrrolo[1,2-a]indol-1-yl}acetate (see Example 30, Step 2), the title compound was synthesized following the procedures described in Step 2 of Example 61 and Step 10 of Example 7.

MS (−APCI) m/z 512.0 (M−H)⁻.

EXAMPLE 133

(+/−)-[9-[(4-CHLOROPHENYL)THIO]-8-(1-METHYL-1H-PYRROL-2-YL)-2,3-DIHYDRO-1H-PYRROLO[1,2-a]INDOL-1-YL]ACETIC ACID

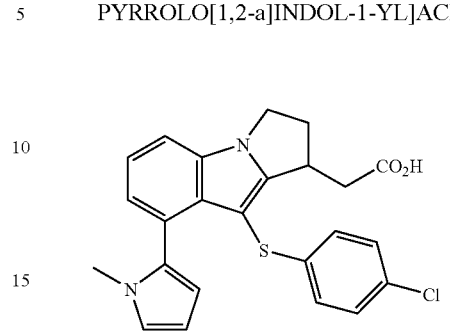

Step 1: (+/−)-Methyl{8-bromo-9-[(4-chlorophenyl)thio]-2,3-dihydro-1H-pyrrolo[1,2-a]indol-1-yl}acetate.

A mixture of (+/−)-methyl{8-bromo-9-[(4-chlorophenyl)thio]-6-iodo-2,3-dihydro-1H-pyrrolo[1,2-a]indol-1-yl}acetate (see Example 30, Step 2, 125 mg) and 10 mg of Pd/C (10% w/w) in EtOAc (3 mL) and MeOH (7 mL) was shaken under 30 psi of H₂ for 48 h. The mixture was then filtered through a short pad of celite and the filtrate was concentrated in vacuo. The residue was purified by flash chromatography on silica gel eluting with 25% EtOAc/hexane to give 66 mg of the title compound.

Step 2: (+/−)-Methyl[9-[(4-chlorophenyl)thio]-8-(1-methyl-1H-pyrrol-2-yl)-2,3-dihydro-1H-pyrrolo[1,2-a]indol-1-yl]acetate.

Starting with the compound of Step 1, the title compound was synthesized following the procedures described in Step 1 of Example 39.

Step 3: (+/−)-[9-[(4-Chlorophenyl)thio]-8-(1-methyl-1H-pyrrol-2-yl)-2,3-dihydro-1H-pyrrolo[1,2-a]indol-1-yl]acetic acid From the compound of Step 2, the title compound was synthesized following the procedures described in Step 10 of Example 7.

MS (−APCI) m/z 435.2 (M−H)⁻.

EXAMPLE 134

(+/−)-{9-[(4-CHLOROPHENYL)THIO]-6-FLUORO-8-PYRIDIN-3-YL-2,3-DIHYDRO-1H-PYRROLO[1,2-a]INDOL-1-YL}ACETIC ACID

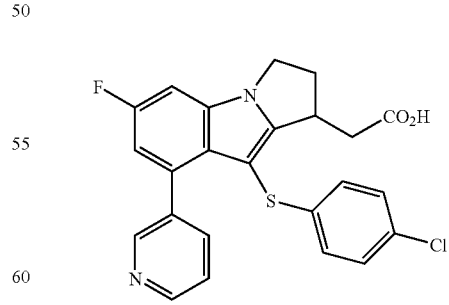

(+/−)-Methyl(8-bromo-6-fluoro-2,3-dihydro-1H-pyrrolo[1,2-a]indol-1-yl)acetate was allowed to react with 3-(1,3,2-dioxaborinan-2-yl)pyridine under the conditions described in Example 108 to give the title compound.

MS (−APCI) m/z 451.0 (M−H)⁻, m/z 453.0 (+H)⁺.

EXAMPLE 135

(+/−)-[9-[(4-CHLOROPHENYL)THIO]-5,6-DIF-LUORO-8-(1-METHYL-1H-PYRROL-2-YL)-2,3-DIHYDRO-1H-PYRROLO[1,2-a]INDOL-1-YL]ACETIC ACID

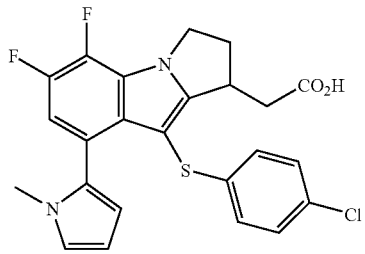

Step 1: 2-Bromo-4,5-difluorobenzoic acid

To a 0° C. slurry of CuBr$_2$ (7.4 g, 33.2 mmol) in CH$_3$CN (150 mL) was added tert-BuONO (5.2 mL, 43.3 mmol). 2-Amino-4,5-difluorobenzoic acid was then added portion wise over 5 min and the resulting mixture was allowed to stir for 2 h. at 0° C. followed by 16 h. at room temperature. The reaction mixture was concentrated in vacuo to ~50% of its volume, quenched with excess 1N HCl, and extracted with i-Pr$_2$O (3×30 mL). The combined organic layers were extracted with 1 N NaOH (3×30 mL). This aqueous phase was acidified with excess 1N HCl and re-extracted with i-Pr$_2$O (3×30 mL). The combined organic layers were washed with brine, dried over MgSO$_4$ and concentrated in vacuo to give the crude bromo acid (6.5 g) that was used without further purification.

Step 2: 2-Bromo-4,5-difluorobenzaldehyde

To a 0° C. THF (20 mL) solution of crude 2-bromo-4,5-difluorobenzoic acid (6.5 g) was slowly added BH$_3$ THF (35.6 mmol). The solution was stirred overnight at +4° C. Excess aqueous K$_2$CO$_3$ was added and the mixture was extracted with Et$_2$O (2×40 mL). The combined organic layers were washed with H$_2$O, brine, and dried over MgSO$_4$. Evaporation of the volatiles gave the crude benzyl alcohol (6.7 g) as an oil. This residue was treated overnight with MnO$_2$ (13.2 g, 152 mmol) in refluxing EtOAc (40 mL). More MnO$_2$ was added (12.0 g, 138 mmol) and the mixture was refluxed for another 24 h. Filtration through a short pad of celite/silica gel and concentration afforded a oily residue. Purification by flash chromatography on silica gel eluting with 15% Et$_2$O/hexane gave 2.65 g of the desired benzaldehyde as a beige solid.

Step 3: (+/−)-Methyl{8-bromo-9-[(4-chlorophenyl)thio]-5,6-difluoro-2,3-dihydro-1H-pyrrolo[1,2-a]indol-1-yl}acetate Starting with the compound of Step 2, the title compound was synthesized following the procedures described in Steps 3 to 9 of Example 7.

Step 4: (+/−)-[9-[(4-Chlorophenyl)thio]-5,6-difluoro-8-(1-methyl-1H-pyrrol-2-yl)-2,3-dihydro-1H-pyrrolo[1,2-a]indol-1-yl]acetic acid Starting from the compound of Step 3, the title compound was synthesized following the procedures described in Step 1 of Example 39 and Step of Example 7.

MS (−APCI) m/z 471.2 (M−H)$^−$.

EXAMPLE 136

(+/−)-[9-[(4-CHLOROPHENYL)THIO]-5,6-DIFLUORO-8-(METHYLSULFONYL)-2,3-DIHYDRO-1H-PYRROLO[1,2-a]INDOL-1-YL]ACETIC ACID

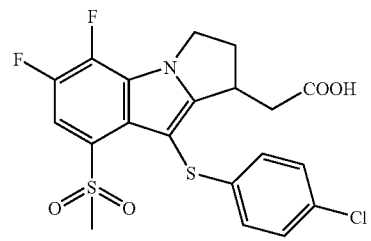

Step 1: (+/−)-Methyl[9-[(4-chlorophenyl)thio]-5,6-difluoro-8-(methylsulfonyl)-2,3-dihydro-1H-pyrrolo[1,2-a]indol-1-yl]acetate To (+/−)-methyl{8-bromo-9-[(4-chlorophenyl)thio]-5,6-difluoro-2,3-dihydro-1H-pyrrolo[1,2-a]indol-1-yl}acetate (Example 135, Step 3, 300 mg, 0.62 mmol) in 1-methyl-2-pyrrolidinone (6 mL) were added methanesulphinic acid sodium salt (315 mg, 3.1 mmol) and copper iodide (587 mg, 3.1 mmol). The mixture was purged with nitrogen and stirred at 140° C. for 4.5 h, cooled to room temperature, diluted with excess EtOAc and filtered through a silica gel pad eluted with EtOAc. The filtrate was washed with brine, dried over MgSO$_4$, and concentrated to a oily residue. Purification by silica gel flash chromatography eluting with 25% to 60% EtOAc/hexane afforded the desired monomethylsulphonyl derivative (90 mg).

Also isolated from this reaction were the following by-products: (+/−)-methyl{8,9-bis[(4-chlorophenyl)thio]-5,6-difluoro-2,3-dihydro-1H-pyrrolo[1,2-a]indol-1-yl}acetate, 60 mg, and (+/−)-methyl[9-[(4-chlorophenyl)thio]-6-fluoro-5,8-bis(methylsulfonyl)-2,3-dihydro-1H-pyrrolo[1,2-a]indol-1-yl]acetate, 80 mg.

Step 2: [9-[(4-Chlorophenyl)thio]-5,6-difluoro-8-(methylsulfonyl)-2,3-dihydro-1H-pyrrolo[1,2-a]indol-1-yl]acetic acid The compound of Step 1 was hydrolyzed following the procedures described in Step 10 of Example 7.

MS (−APCI) m/z 469.9 (M−H)$^−$.

EXAMPLE 137

(+/−)-{8,9-BIS[(4-CHLOROPHENYL)THIO]-5,6-DIFLUORO-2,3-DIHYDRO-1H-PYRROLO[1,2-a]INDOL-1-YL}ACETIC ACID

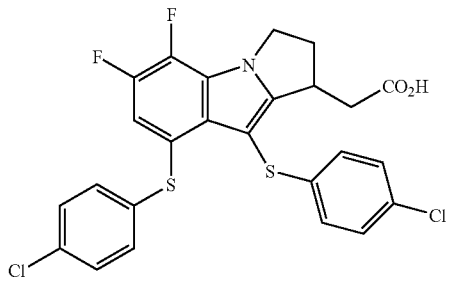

(+/−)-Methyl{8,9-bis[(4-chlorophenyl)thio]-5,6-difluoro-2,3-dihydro-1H-pyrrolo[1,2-a]indol-1-yl}acetate (isolated as a by-product from step 1 of Example 136, 60 mg) was hydrolyzed following the procedures described for Step 10 of Example 7 to give the title compound.

MS (−APCI) m/z 533.8 (M−H)⁻.

EXAMPLE 138

(+/−)-[9-[(4-CHLOROPHENYL)THIO]-6-FLUORO-5,8-BIS(METHYLSULFONYL)-2,3-DIHYDRO-1H-PYRROLO[1,2-a]INDOL-1-YL]ACETIC ACID

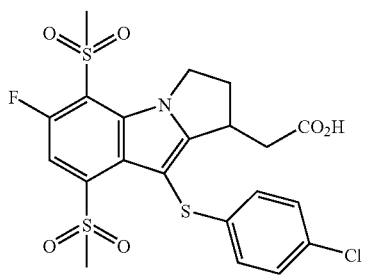

(+/−)-Methyl[9-[(4-chlorophenyl)thio]-6-fluoro-5,8-bis(methyl-sulfonyl)-2,3-dihydro-1H-pyrrolo[1,2-a]indol-1-yl]acetate (isolated as a by-product from step 1 of Example 136, 20 mg) was hydrolyzed by stirring overnight with 1N LiOH aq. (0.5 mL) in a mixture of THF (1 mL) and 1,4-dioxane (1 mL). The reaction was quenched with excess 1M NaH₂PO₄ aq. and extracted with EtOAc (3×15 mL). The combined organic extracts were washed with brine, dried over MgSO₄ and concentrated in vacuo. The solid residue was stirred 30 min in 1:1 mixture of acetone and Et₂O and filtered to give the title compound (9 mg) as a white solid.

MS (−APCI) m/z 530.0 (M−H)⁻.

EXAMPLE 139

(+/−)-[9-[(4-CHLOROPHENYL)THIO]-6-METHOXY-5,8-BIS(METHYLSULFONYL)-2,3-DIHYDRO-1H-PYRROLO[1,2-a]INDOL-1-YL]ACETIC ACID

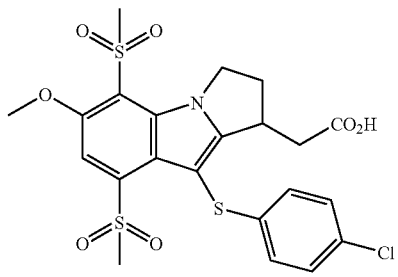

Step 1: (+/−)-Methyl[9-[(4-chlorophenyl)thio]-6-methoxy-5,8-bis(methylsulfonyl)-2,3-dihydro-1H-pyrrolo[1,2-a]indol-1-yl]acetate (+/−)-Methyl[9-[(4-chlorophenyl)thio]-6-fluoro-5,8-bis(methylsulfonyl)-2,3-dihydro-1H-pyrrolo[1,2-a]indol-1-yl]acetate (isolated as a by-product from step 1 of Example 136, 60 mg), was stirred at 60° C. for 1 h in 0.1 N MeONa in MeOH (2 mL) and 1,4-dioxane (2 mL). Excess 1 N NaH₂PO₄ was added and the mixture was extracted with EtOAc (3×). The combined organic layers were dried over MgSO₄. Purification by silica gel flash chromatography eluting with 40% to 70% EtOAc/hexane gave the desired compound (39 mg).

Step 2: (+/−)-[9-[(4-Chlorophenyl)thio]-6-methoxy-5,8-bis(methylsulfonyl)-2,3-dihydro-1H-pyrrolo[1,2-a]indol-1-yl]acetic acid The compound of Step 1 was dissolved in MeOH (2 mL) and 1,4-dioxane (2 mL) and treated with 1N LiOH for 2 h at room temperature. Addition of 1N NaH₂PO₄ (3 mL) and 1N HCl (0.4 mL) led to a suspension that was filtered through paper. The solid was air dried overnight yielding 14 mg of the title compound as a white solid.

MS (−APCI) m/z 541.8 (M−H)⁻.

EXAMPLE 140

(+/−)-[9-[(4-CHLOROPHENYL)THIO]-5-FLUORO-8-(METHYLSULFONYL)-2,3-DIHYDRO-1H-PYRROLO[1,2-a]INDOL-1-YL]ACETIC ACID

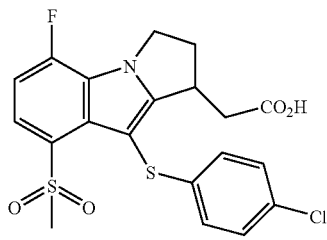

Step 1: (+/−)-Methyl{8-bromo-9-[(4-chlorophenyl)thio]-5-fluoro-2,3-dihydro-1H-pyrrolo[1,2-a]indol-1-yl}acetate Starting from 2-bromo-5-fluorotoluene, the title compound was synthesized following the procedures described in Steps 1 to 9 of Example 7.

Step 2: (+/−)-[9-[(4-Chlorophenyl)thio]-5-fluoro-8-(methylsulfonyl)-2,3-dihydro-1H-pyrrolo[1,2-a]indol-1-yl]acetic acid Starting from the compound of Step 1, the title compound was synthesized following the procedures described in Step 2 of Example 61 and Step 10 of Example 7.

MS (−APCI) m/z 452.0 (M−H)⁻.

EXAMPLE 141

(+/−)-{8-BROMO-9-[(4-CHLOROPHENYL)THIO]-6-FLUORO-2,3-DIHYDRO-1H-PYRROLO[1,2-a]INDOL-1-YL}(DIFLUORO)ACETIC ACID

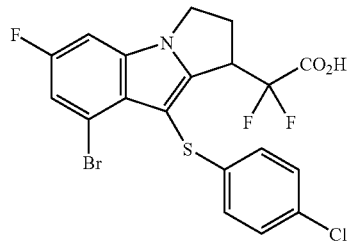

Step 1: (+/−)-Ethyl{8-bromo-9-[(4-chlorophenyl)thio]-6-fluoro-2,3-dihydro-1H-pyrrolo[1,2-a]indol-1-yl}(difluoro)acetate Starting from 8-bromo-6-fluoro-2,3-dihydro-1H-pyrrolo[1,2-a]indol-1-one (Example 7, Step 6) and ethyl bromo(difluoro)acetate, the title compound was synthesized following the procedures described in Steps 7 to 9 of Example 7.

Step 2: (+/−)-{8-Bromo-9-[(4-chlorophenyl)thio]-6-fluoro-2,3-dihydro-1H-pyrrolo[1,2-a]indol-1-yl} (difluoro)acetic acid The ethyl ester (65 mg) from Step 1 was dissolved in 2 mL of old (peroxide containing) 1,4-dioxane. 1 N LiOH was added (0.25 mL) and the mixture was stirred at room temperature for 2 h. Excess 1 N NaH₂PO₄ was added and the mixture was extracted with EtOAc (2×). The combined organic layers were washed with brine, dried over MgSO₄ and concentrated in vacuo. Purification by silica gel chromatography on preparative plates eluting with 25% EtOH/CH₂CL₂+3% AcOH gave the desired compound (32 mg).

MS (−APCI) m/z 488.0, 489.9 (M−H)⁻.

EXAMPLE 142

(+/−)-{8-BROMO-9-[(4-CHLOROPHENYL)SULFINYL]-6-FLUORO-2,3-DIHYDRO-1H-PYRROLO[1,2-a]INDOL-1-YL}(DIFLUORO)ACETIC ACID

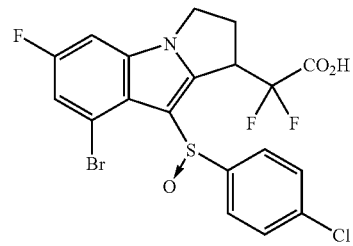

Two diastereoisomers of the title compound (13 mg and 10 mg) were isolated from Step 2 of Example 141.
MS (−APCI) m/z 504.0, 506.1 (M−H)⁻.

EXAMPLE 143

(+/−)-[9-[(4-CHLOROPHENYL)THIO]-6-FLUORO-8-(METHYLSULFONYL)-2,3-DIHYDRO-1H-PYRROLO[1,2-a]INDOL-1-YL](DIFLUORO)ACETIC ACID

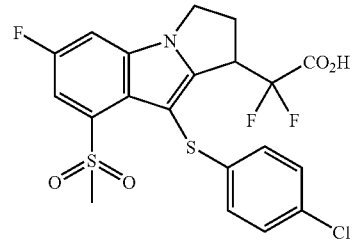

Starting from (+/−)-ethyl{8-bromo-9-[(4-chlorophenyl)thio]-6-fluoro-2,3-dihydro-1H-pyrrolo[1,2-a]indol-1-yl}(difluoro)acetate (Example 141, Step 1) the title compound was synthesized following the procedures described in Step 2 of Example 61.
MS (−APCI) m/z 488.0 (M−H)⁻.

EXAMPLE 144

(+/−)-[10-(4-CHLOROBENZOYL)-3-FLUORO-1-(METHYLSULFONYL)-6,7,8,9-TETRAHYDROPYRIDO[1,2-a]INDOL-9-YL]ACETIC ACID

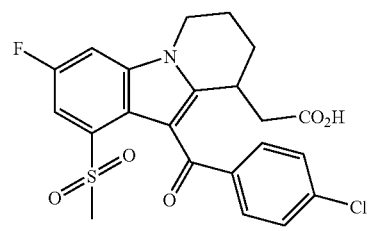

Step 1: (+/−)-Methyl[3-fluoro-1-(methylsulfonyl)-6,7,8,9-tetrahydropyrido[1,2-a]indol-9-yl]acetate Starting from methyl(1-bromo-3-fluoro-6,7,8,9-tetrahydropyrido[1,2-a]indol-9-yl)acetate (Example 122, Step 3) the title compound was synthesized following the procedures described in Step 1 of Example 136.

Step 2: (+/−)-[10-(4-Chlorobenzoyl)-3-fluoro-1-(methylsulfonyl)-6,7,8,9-tetrahydropyrido[1,2-a]indol-9-yl]acetic acid The compound of Step 1 was acylated following the procedures described in Step 1 of Example 61 and hydrolyzed as in Step 10 of Example 7.

MS (−APCI) m/z 462.1 (M−H)⁻.

EXAMPLE 145

(+/−)-[3-FLUORO-1-(METHYLSULFONYL)-10-(2-NAPHTHOYL)-6,7,8,9-TETRAHYDROPYRIDO[1,2-a]INDOL-9-YL]ACETIC ACID

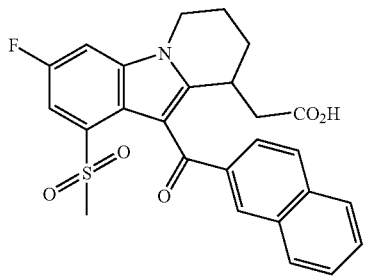

Starting from (+/−)-methyl[3-fluoro-1-(methylsulfonyl)-6,7,8,9-tetrahydropyrido[1,2-a]indol-9-yl]acetate (Example 144, Step 1) the title compound was acylated following the procedures described in Step 1 of Example 61 and hydrolyzed as in Step 10 of Example 7.

MS (−APCI) m/z 478.1 M−H)⁻.

The following compounds were prepared according to the general methodologies indicated, each of which has been exemplified in the previous examples:

What is claimed is:

1. A compound having the formula I:

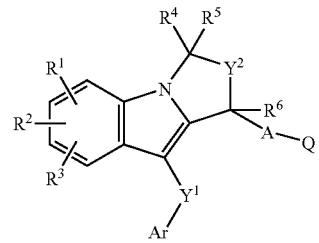

and pharmaceutically acceptable salts and hydrates thereof, wherein:

$R^1$, $R^2$ and $R^3$ are each independently selected from hydrogen and $R^g$;

$R^4$ is selected from H, CN, $C_{1-6}$alkyl optionally substituted with one to six halogen, $OR^a$ and $S(O)_n C_{1-6}$alkyl;

$R^5$ is selected from H and $C_{1-6}$alkyl optionally substituted with one to six halogen; or $R^4$ and $R^5$ together represent an oxo;

$R^6$ is selected from H and $C_{1-6}$alkyl optionally substituted with one to six groups independently selected from $OR^a$ and halogen, Ar is aryl optionally substituted with one to four groups independently selected from $R^g$;

A is $C_{1-3}$alkyl optionally substituted with one to four halogen atoms, $O(CH_2)_{1-2}$, or $S(CH_2)_{1-2}$;

Q is selected from:
(1) COOH,
(2) $CONR^a R^b$,
(3) $C(O)NHSO_2 R^c$,
(4) $SO_2 NHR^a$,
(5) $SO_3 H$, and
(6) $PO_3 H_2$ $Y^1$ is $-(CR^d R^e)_a-X-(CR^d R^e)_b-$, phenylene, $C_{3-6}$cycloalkylidene or $C_{3-6}$cycloalkylene, wherein a and b are integers 0–1 such that the sum of a and b equals 0, 1 or 2;

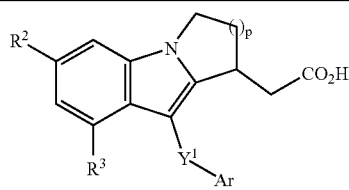

| Ex. | R² | R³ | Y¹ | Ar | p | Meth. | MS* |
|---|---|---|---|---|---|---|---|
| 146 | F | (CH₃)₂CH | C(O) | 3-Br-4-Cl—Ph | 2 | 3,10 | 504.1 |
| 147 | F | (CH₃)₂CH | CH₂ | 4-Cl—Ph | 2 | 3,9 | 412.1 |
| 148 | F | (CH₃)₂CH | S | 3-Br-4-Cl—Ph | 2 | 3 | 510 |
| 149 | F | (CH₃)(CH₂=)C | C(O) | 4-Cl—Ph | 2 | 3,10 | 424.2 |
| 150 | F | CH₃S(O)₂ | C(O) | 6-Cl—Pyr | 2 | 2 | 463.0 |
| 151 | F | CH₃S(O)₂ | C(O) | 3,4-diCl—Ph | 2 | 2 | 496.0 |
| 152 | F | CH₃S(O)₂ | C(O) | 4-nBu-Ph | 2 | 2 | 500.2 |
| 153 | F | CH₃S(O)₂ | C(O) | 4-Ph-Ph | 2 | 2 | 504.3 |
| 154 | PhCH₂O | CH₃S(O)₂ | S | 4-Cl—Ph | 2 | 6 | 554 |
| 155 | PhCH₂S | CH₃S(O)₂ | S | 4-Cl—Ph | 1 | 13 | 556 |
| 156 | F | CH₃S(O)₂ | C(O) | 4-Cl—Ph | 2 | 2 | 462.1 |

*MS(—APCI) m/z (M − H)⁻

X is a bond, O, S, NR$^a$, C(O), OC(O), C(O)O, C(O)NR$^a$, OC(O)NR$^a$, NR$^a$C(O), CR$^d$=CR$^e$ or C≡C;

Y$^2$ is CR$^d$R$^e$, CR$^d$R$^e$—CR$^d$R$^e$, or CR$^d$=CR$^e$,

R$^a$ and R$^b$ are independently selected from H, C$_{1-10}$alkyl, C$_{2-10}$alkenyl, C$_{2-10}$alkynyl, aryl and aryl-C$_{1-10}$ alkyl wherein alkyl, alkenyl, alkynyl and aryl are optionally substituted with one to six substituents independently selected from halogen, amino, carboxy, C$_{1-4}$alkyl, C$_{1-4}$alkoxy, aryl, aryl C$_{1-4}$alkyl, hydroxy, CF$_3$, OC(O)C$_{1-4}$alkyl, OC(O)NR$^i$R$^j$, and aryloxy;

R$^c$ is selected from C$_{1-6}$alkyl optionally substituted with one to six halogen and aryl optionally substituted with halogen, OC$_{1-6}$alkyl, C$_{1-6}$alkyl and wherein said alkyl is optionally substituted with one to six halogen;

R$^d$ and R$^e$ are independently H, halogen, aryl, C$_{1-6}$alkyl or haloC$_{1-6}$alkyl;

R$^f$ is selected from H, C$_{1-6}$alkyl, haloC$_{1-6}$alkyl, aryl, C(O)C$_{1-6}$alkyl, C(O)haloC$_{1-6}$alkyl, and C(O)-aryl;

R$^g$ is selected from
(1) halogen,
(2) CN,
(3) C$_{1-6}$alkyl optionally substituted with one to eight groups independently selected from aryl, halogen, NR$^a$R$^b$, C(O)R$^a$, C(OR$^a$)R$^a$R$^b$, SR$^a$ and OR$^a$, wherein aryl is optionally substituted with one to six groups independently selected from halogen, CF$_3$, and COOH,
(4) C$_{2-6}$alkenyl optionally substituted with one to six groups independently selected from halogen and OR$^a$,
(5) aryl, optionally substituted with one to eight groups independently selected from halogen, C(O)R$^a$, OR$^a$, C$_{1-3}$alkyl, aryl and CF$_3$;
(6) C(O)R$^a$,
(7) C(O)OR$^a$,
(8) CONR$^a$R$^b$,
(9) OCONR$^a$R$^b$,
(10) OC$_{1-6}$alkyl, wherein alkyl is optionally substituted with one to six substituents selected from halogen, aryl, OH and OC(O)R$^a$,
(11) O-aryl
(12) S(O)$_n$C$_{1-6}$alkyl, wherein alkyl is optionally substituted with one to six substituents selected from halogen, aryl, OH, and OC(O)R$^a$,
(13) S(O)$_n$aryl,
(14) —NR$^a$S(O)$_n$R$^b$,
(15) —NR$^a$R$^b$,
(16) —NR$^a$C(O)R$^b$,
(17) —NR$^a$C(O)OR$^b$,
(18) —NR$^a$C(O)NR$^a$R$^b$,
(19) S(O)$_n$NR$^a$R$^b$,
(20) NO$_2$, and
C$_{5-8}$cycloalkenyl;

R$^i$ and R$^j$ are independently selected from hydrogen, C$_{1-10}$alkyl, aryl and aryl-C$_{1-10}$alkyl n is 0, 1 or 2.

2. A compound of claim 1 wherein Y$^1$ is selected from a bond, O, S, NR$^a$, CHR$^d$, CHR$^d$CHR$^d$, C(O), C(O)CHR$^d$, phenylene, and C$_{3-6}$cycloalkylidene.

3. A compound of claim 1 wherein Y$^1$ is selected from S, CH$_2$, and C(O).

4. A compound of claim 1 wherein A is C$_{1-3}$alkyl optionally substituted with one to four halogen atoms and Q is COOH.

5. A compound of claim 1 wherein A-Q is CH$_2$COOH.

6. A compound of claim 1 wherein Y$^2$ is selected from CH$_2$ and CH$_2$CH$_2$.

7. A compound of claim 1 wherein Ar is phenyl or naphthyl optionally substituted wit one to three groups independently selected from halogen, aryl, S(O)$_n$C$_{1-6}$alkyl optionally substituted wit one to six halogen, C$_{1-6}$alkyl optionally substituted with one to five halogen atoms, CN, CONR$^a$R$^b$, and C(O)R$^a$, where R$^a$ and R$^b$ are as defined in claim 1.

8. A compound of claim 1 wherein Ar is phenyl optionally substituted with one to three groups independently selected from halogen, aryl, S(O)$_n$C$_{1-6}$alkyl optionally substituted with one to six halogen, C$_{1-6}$alkyl optionally substituted with one to five halogen atoms, (ZN, CONR$^a$R$^b$, and C(O)R$^a$, where R$^a$ and R$^b$ are as defined in claim 1.

9. A compound of claim 1 wherein Ar is 4-chlorophenyl optionally substituted with a second halogen atom.

10. A compound of claim 1 wherein R$^4$ and R$^5$ are each hydrogen.

11. A compound of claim 8 wherein Y$^1$ is selected from C(O), S and CH$_2$, Y$^2$ is CH$_2$ or CH$_2$CH$_2$, R$^4$ and R$^5$ are each hydrogen, and A-Q is CH$_2$COOH.

12. A compound of claim 9 wherein Y$^1$ is selected from C(O), S and CH$_2$, Y$^2$ is CH$_2$ or CH$_2$CH$_2$, R$^4$ and R$^5$ are each hydrogen, and A-Q is CH$_2$COOH.

13. A compound of claim 1 wherein R$^1$, R$^2$ and R$^3$ are independently selected from (1) hydrogen, (2) CN, (3) halogen, (4) S(O)$_n$C$_{1-3}$alkyl, (5) OC$_{1-6}$alkyl optionally substituted with one to six substituents selected from halogen, aryl OH and OC(O)R$^a$, (6) C$_{1-6}$alkyl (optionally substitued with one to eight groups selected from aryl, halogen, NR$^a$R$^b$, C(O)R$^a$, C(OR$^a$)R$^a$R$^b$, SR$^a$, and OR$^a$, wherein aryl is optionally substituted with one to six groups independently selected from halogen, CF$_3$, and COOH, (7) aryl optionally substituted with one to eight groups independently selected from halogen, C(O)R$^a$, OR$^a$, C$_{1-3}$alkyl, aryl, and CF$_3$; (8) C$_{2-6}$alkenyl optionally substituted with one to six groups independently selected front halogen and OR$^a$, (9) C(O)OC$_{1-3}$alkyl, (10) S(O)$_n$NR$^a$R$^b$, (11) C(O)R$^a$, (12) C(OH)R$^a$R$^b$, (13) C$_{5-8}$cycloalkenyl, and (14) C(OC$_{1-3}$alkyl)R$^a$R$^b$, n=0, 1 or 2; R$^a$ and R$^b$ are independently selected from hydrogen arid C$_{1-6}$alkyl optionally substituted with halogen.

14. A compound of claim 13 wherein one of R$^1$, R$^2$ and R$^3$ is hydrogen.

15. A compound of claim 1 having the formula Ia:

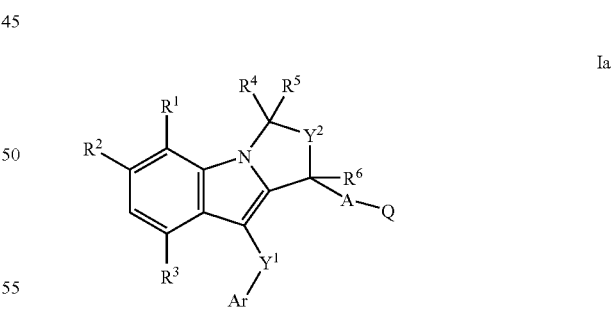

Ia

16. A compound of claim 15 wherein R$^1$, R$^2$ and R$^3$ are independently selected from (1) hydrogen, (2) CN, (3) halogen, (4) S(O)$_n$C$_{1-3}$alkyl, (5) OC$_{1-6}$alkyl optionally substituted with one to six substituents selected from halogen, aryl, OH and OC(O)R$^a$, (6) C$_{1-6}$alkyl optionally substituted with one to eight groups selected from aryl, halogen, NR$^a$R$^b$, C(O)R$^a$, C(OR$^a$)R$^a$R$^b$, SR$^a$, and OR$^a$, wherein aryl is optionally substituted with one to six groups independently selected from halogen, CF$_3$, and COOH, (7) aryl optionally substituted with one to eight groups independently selected from halogen, C(O)R$^a$, OR$^a$, C$_{1-3}$alkyl, aryl and CF$_3$; (8) C$_{2-6}$alkenyl optionally substituted with one to six groups independently selected from halogen and OR$^a$, (9) C(O)OC$_{1-3}$alkyl, (10) S(O)$_n$NR$^a$R$^b$, (11) C(O)R$^a$, (12) C(OH)R$^a$R$^b$, (13) C$_{5-8}$cycloalkenyl, and (14) C(OC$_{1-3}$alkyl)R$^a$R$^b$, n=0, 1 or 2; R$^a$ and R$^b$ are independently selected from hydrogen and C$_{1-6}$alkyl optionally substituted with halogen.

17. A compound of claim 16 wherein R$^1$ is hydrogen and A-Q is CH$_2$COOH.

18. A compound of claim 17 wherein R$^2$ is selected from (1) halogen, (2) S(O)$_n$C$_{1-3}$alkyl, (3) OC$_{1-6}$alkyl optionally substituted with aryl, (4) CN, (5) C$_{2-6}$alkenyl and (6) C$_{1-6}$alkyl.

19. A compound of claim 17 wherein R$^3$ is selected from (1) halogen, (2) S(O)$_n$C$_{1-3}$alkyl, (3) OC$_{1-6}$alkyl, (4) C(O)R$^a$, (5) C$_{1-6}$alkyl optionally substitued with 3 to 6 halogen atoms, and 0 or 1 group selected from OR$^a$, SR$^a$, (6) C$_{2-6}$alkenyl, (7) C$_{5-8}$cycloalkenyl, (8) phenyl optionally substituted with a group selected from C$_{1-3}$alkyl and OR$^a$, and (9) naphthyl.

20. A compound of claim 1 having the formula Ib:

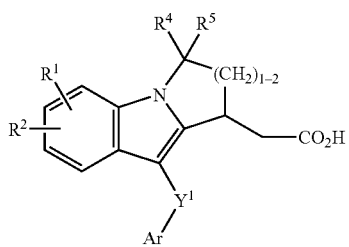

Ib wherein Y$^1$ is O, S, C(O) or CH$_2$, R$^4$ and R$^5$ are each hydrogen or R$^4$ and R$^5$ together represent oxo, and R$^2$ and R$^3$ represent one or two non-H substituent.

21. A compound of claim 20, wherein R$^4$ and R$^5$ are each hydrogen, R$^2$ is selected from (1) halogen, (2) S(O)$_n$C$_{1-3}$alkyl, (3) OC$_{1-6}$alkyl optionally substituted with aryl, (4) CN, (5) C$_{2-6}$alkenyl and (6) C$_{1-6}$alkyl, R$^3$ *is selected from* (1) halogen, (2) S(O)$_n$C$_{1-3}$alkyl, (3) OC$_{1-6}$alkyl, (4) C(O)R$^a$, (5) C$_{1-6}$alkyl optionally substitued with 3 to 6 halogen atoms, and 0 or 1 group selected from OR$^a$, SR$^a$, (6) C$_{2-6}$alkenyl, (7) C$_{5-8}$cycloalkenyl, (8) phenyl optionally substituted with a group selected from C$_{1-3}$alkyl and OR$^a$, and (9) naphthyl, and Ar is selected from (1) 1- and 2-napthyl, and (2) phenyl optionally substituted with one to three groups independently selected from halogen, aryl, S(O)$_n$C$_{1-6}$alkyl optionally substituted with one to six halogen, C$_{1-6}$alkyl optionally substituted with one to five halogen atoms, CN, CONR$^a$R$^b$, and C(O)R$^a$, where R$^a$ and R$^b$ are as defined in claim 1.

22. A compound of claim 1 having the formula Ic:

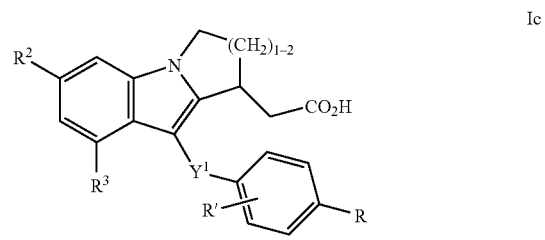

wherein Y$^1$ is C(O), CH$_2$ or S, B, and R' are independently hydrogen, halogen, cyano, C$_{1-3}$alkanoyl or CF$_3$, R$^2$ is selected from (1) halogen, (2) S(O)$_n$C$_{1-3}$alkyl, (3) OC$_{1-6}$alkyl optionally substituted with aryl, (4) CN, (5) C$_{2-6}$alkenyl and (6) C$_{1-6}$alkyl, and R$^3$ is selected from (1) halogen, (2) S(O)$_n$C$_{1-3}$alkyl, (3) OC$_{1-6}$alkyl, (4) C(O)R$^a$, (5) C$_{1-6}$alkyl optionally substitued with 3 to 6 halogen atoms, and 0 or 1 group selected from OR$^a$, SR$^a$, (6) C$_{2-6}$alkenyl, (7) C$_{5-8}$cycloalkenyl, (8) phenyl optionally substituted with a group selected from C$_{1-3}$alkyl and OR$^a$, and (9) naphthyl.

23. A compound of claim 22 wherein R$^2$ is F, R is Cl, R' is hydrogen, and R$^3$ is selected from (1) halogen, (2) S(O)$_n$C$_{1-3}$alkyl, (3) OC$_{1-6}$alkyl, (4) C(O)R$^a$, (5) C$_{1-6}$alkyl optionally substitued with 3 to 6 halogen atoms, and 0 or 1 group selected from OR$^a$, SR$^a$, (6) C$_{2-6}$alkenyl, (7) C$_{5-8}$cycloalkenyl, (8) phenyl optionally substituted with a group selected from C$_{1-3}$alkyl and OR$^a$, and (9) naphthyl.

24. A compound selected from
- (+/−)-[9-[(4-chlorophenyl)thio]-6-fluoro-8-(methylsulfonyl)-3-oxo-2,3-dihydro-1H-pyrrolo[1,2-a]indol-1-yl] acetic acid;
- (+/−)-{8-bromo-9-[(4-chlorophenyl)sulfinyl]-6-fluoro-2,3-dihydro-1H-pyrrolo[1,2-a]indol-1-yl}(difluoro)acetic acid;

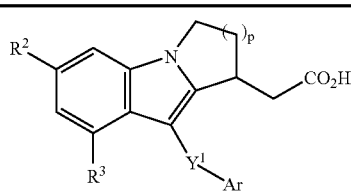

| R$^2$ | R$^3$ | Y$^1$ | Ar | p |
|---|---|---|---|---|
| H | H | CH$_2$ | 4-Cl—Ph | 2 |
| H | H | CH$_2$ | 4-Cl—Ph | 1 |
| H | H | S | 4-Cl—Ph | 2 |
| CH$_3$S(O)$_2$ | H | S | 4-Cl—Ph | 2 |
| H | CH$_3$S(O) | — | 4-Cl—Ph | 2 |
| H | CH$_3$S(O) | CH$_2$ | 4-Cl—Ph | 2 |
| F | Br | S | 4-Cl—Ph | 1 |
| F | Br | S | 4-Cl—Ph | 2 |
| CH$_3$S(O)$_2$ | CH$_3$O | S | 4-Cl—Ph | 2 |
| F | CH$_3$C(O) | S | 4-Cl—Ph | 1 |

-continued

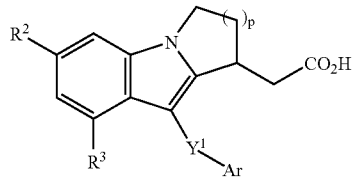

| R² | R³ | Y¹ | Ar | p |
|---|---|---|---|---|
| F | CF₃C(O) | S | 4-Cl—Ph | 1 |
| F | CF₃CH(OH) | S | 4-Cl—Ph | 1 |
| F | (CH₃)₂CHCH(OH) | S | 4-Cl—Ph | 1 |
| F | CH₃CH(OH) | S | 4-Cl—Ph | 1 |
| F | CH₃CH(OCH₃) | S | 4-Cl—Ph | 1 |
| F | CH₃C(O) | S | Ph | 1 |
| F | CH₃C(O) | S | 3,4-diCl—Ph | 1 |
| F | CF₃CH(OCH₃) | S | 4-Cl—Ph | 1 |
| F | CH₃CH₂CH(OH) | S | 4-Cl—Ph | 1 |
| F | CH₃CH₂CH(OCH₃) | S | 4-Cl—Ph | 1 |
| F | CH₃CH(SCH₃) | S | 4-Cl—Ph | 1 |
| CH₃O | CH₃S(O)₂ | S | 4-Cl—Ph | 1 |
| PhCH₂O | CH₃S(O)₂ | S | 4-Cl—Ph | 1 |
| CH₃S | CH₃S(O)₂ | S | 4-Cl—Ph | 1 |
| CH₃S(O)₂ | (CH₃)₂CH | S | 4-Cl—Ph | 1 |
| (CH₃)₂CHO | CH₃S(O)₂ | S | 4-Cl—Ph | 1 |
| PhCH₂O | (CH₃)₂CH | S | 4-Cl—Ph | 1 |
| CH₃O | (CH₃)₂CH | S | 4-Cl—Ph | 1 |
| 4-Cl—Ph | CH₃S(O)₂ | S | 4-Cl—Ph | 1 |
| I | Br | S | 4-Cl—Ph | 1 |
| CN | Br | S | 4-Cl—Ph | 1 |
| CN | CH₃C(O) | S | 4-Cl—Ph | 1 |
| F | CH₃S(O)₂ | S | 4-Cl—Ph | 1 |
| F | CH₃CH₂S(O)₂ | S | 4-Cl—Ph | 1 |
| F | CH₃CH₂CH₂ | S | 4-Cl—Ph | 1 |
| F | CH₃CH₂ | S | 4-Cl—Ph | 1 |
| F | CH₃C(=CH₂) | S | 4-Cl—Ph | 1 |
| F | (CH₃)₂CH | S | 4-Cl—Ph | 1 |
| F | 1-cyclopentenyl | S | 4-Cl—Ph | 1 |
| F | (CH₃CH=)(CH₃CH₂)C | S | 4-Cl—Ph | 1 |
| F | (CH₃CH₂)₂CH | S | 4-Cl—Ph | 1 |
| F | cyclopentyl | S | 4-Cl—Ph | 1 |
| F | Ph | S | 4-Cl—Ph | 1 |
| F | CH₂=CH | S | 4-Cl—Ph | 1 |
| CH₂=CH | Br | S | 4-Cl—Ph | 1 |
| F | (CF₃)₂C(OH) | S | 4-Cl—Ph | 1 |
| F | cyclopropyl | S | 4-Cl—Ph | 1 |
| F | Br | CH₂ | 4-Cl—Ph | 1 |
| F | CH₃S(O)₂ | CO | 4-Cl—Ph | 1 |
| F | CH₃S(O)₂ | CH₂ | 4-Cl—Ph | 1 |
| F | (CF₃)₂C(OCH₃) | S | 4-Cl—Ph | 1 |
| F | (CH₃)₂CH | C(O) | 4-Cl—Ph | 1 |
| F | 1-CH₃-2-pyrrolyl | C(O) | 4-Cl—Ph | 1 |
| F | (CH₃)₂CH | CH₂ | 4-Cl—Ph | 1 |
| F | CH₃S(O)₂ | CH₂ | 2,4-diCl—Ph | 1 |
| F | CH₃S(O)₂ | CH₂ | 2,6-diCl—Ph | 1 |
| F | Br | C(O) | 4-Cl—Ph | 1 |
| F | cyclopropyl | C(O) | 4-Cl—Ph | 1 |
| F | (CH₃O)(CH₃CH₂)CH | C(O) | 4-Cl—Ph | 1 |
| F | Ph | C(O) | 4-Cl—Ph | 1 |
| F | CH₃S(O)₂ | CH₂ | 2,4,6-triCl—Ph | 1 |
| F | CH₃S(O)₂ | S | 2,4,5-triCl—Ph | 1 |
| F | CH₃S(O)₂ | C(O) | 4-biphenyl | 1 |
| F | CH₃S(O)₂ | C(O) | 2-naphthyl | 1 |
| F | Br | C(O) | 2-naphthyl | 1 |
| F | CH₃S(O)₂ | C(O) | 2,4-diCl—Ph | 1 |
| F | CH₃S(O)₂ | C(O) | 4-Cl-2-CH₃S(O)₂—Ph | 1 |
| F | Br | C(O) | 4-Cl-2-I—Ph | 1 |
| F | Br | C(O) | 4-Cl-2-CONH₂—Ph | 1 |
| F | CH₃S(O)₂ | C(O) | 4-Cl-2-CN—Ph | 1 |
| F | (CH₃)₂CH | C(O) | 4-Cl-2-I—Ph | 1 |
| F | (CH₃)₂CH | C(O) | 4-Cl-2-CH₃S(O)₂—Ph | 1 |
| F | CH₃S(O)₂ | S | 4-CF₃—Ph | 1 |
| F | CH₃S(O)₂ | S | 4-CH₃S(O)₂—Ph | 1 |

-continued

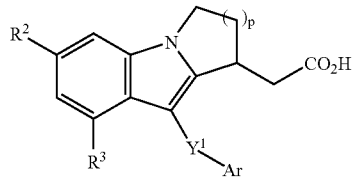

| R² | R³ | Y¹ | Ar | p |
|---|---|---|---|---|
| F | $CH_3S(O)_2$ | $CH(CH_3)$ | 4-Cl—Ph | 1 |
| F | $CH_3S(O)_2$ | $C(O)CH_2$** | 4-Cl—Ph | 1 |
| F | $(CH_3)_2CH$ | S | 1-naphthyl | 1 |
| F | $(CH_3)_2CH$ | S | 2-naphthyl | 1 |
| F | $CH_3S(O)_2$ | $CH_2CH_2$ | 4-Cl—Ph | 1 |
| F | $(CH_3)_2CH$ | C(O) | 2-naphthyl | 1 |
| F | $CH_3S(O)_2$ | S | 2-naphthyl | 1 |
| F | $(CH_3)_2CH$ | S | 4-Cl-2-F—Ph | 1 |
| F | $CH_3S(O)_2$ | S | 4-Cl-2-F—Ph | 1 |
| F | 2-$CH_3$—Ph | S | 4-Cl—Ph | 1 |
| F | 2-$OCH_3$—Ph | S | 4-Cl—Ph | 1 |
| F | 3,4-diCl—Ph | S | 4-Cl—Ph | 1 |
| F | 2-naphthyl | S | 4-Cl—Ph | 1 |
| F | CN | S | 4-Cl—Ph | 1 |
| F | $(CH_3)_2CH$ | C(O) | 1-naphthyl | 1 |
| F | $(CH_3)_2CH$ | C(O) | 3,4-diCl—Ph | 1 |
| F | $(CH_3)_2CH$ | S | 4-Cl—Ph | 2 |
| F | $(CH_3)_2CH$ | C(O) | 2-naphthyl | 2 |
| F | $(CH_3)_2CH$ | C(O) | 4-Cl—Ph | 2 |
| F | $CH_3S(O)_2$ | S | 4-Cl—Ph | 2 |
| F | $CH_3S(O)_2$ | 1,4-phenylene | Ph | 1 |
| F | $CH_3S(O)_2$ | — | 2-naphthyl | 1 |
| F | $CH_3S(O)_2$ | 1,3-phenylene | Ph | 1 |
| CN | $(CH_3)_2CH$ | S | 4-Cl—Ph | 1 |
| $CH_3S(O)_2$ | $(CH_3)_2CH$ | S | 4-Cl—Ph | 1 |
| F | $CH_3S(O)_2$ | C(O) | 4-Cl—Ph | 2 |
| F | $CH_3S(O)_2$ | C(O) | 2-naphthyl | 2 |
| F | $(CH_3)_2CH$ | C(O) | 3-Br-4-Cl—Ph | 2 |
| F | $(CH_3)_2CH$ | $CH_2$ | 4-Cl—Ph | 2 |
| F | $(CH_3)_2CH$ | S | 3-Br-4-Cl—Ph | 2 |
| F | $(CH_3)(CH_2=)C$ | C(O) | 4-Cl—Ph | 2 |
| F | $CH_3S(O)_2$ | C(O) | 3,4-diCl—Ph | 2 |
| F | $CH_3S(O)_2$ | C(O) | 4-nBu—Ph | 2 |
| F | $CH_3S(O)_2$ | C(O) | 4-Ph—Ph | 2 |
| $PhCH_2O$ | $CH_3S(O)_2$ | S | 4-Cl—Ph | 2 |
| $PhCH_2S$ | $CH_3S(O)_2$ | S | 4-Cl—Ph | 1 |
| F | $CH_3S(O)_2$ | C(O) | 4-Cl—Ph | 2 |

**$Y^1$—Ar = —C(O)—$CH_2$—(4-Cl—Ph),

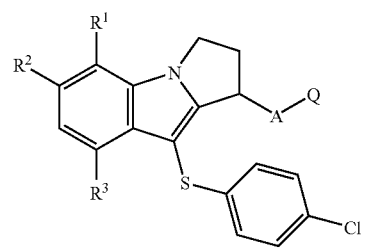

and

| R¹ | R² | R³ | A—Q |
|---|---|---|---|
| F | F | $CH_3S(O)_2$ | $CH_2CO_2H$ |
| F | F | S-(4-Cl-Ph) | $CH_2CO_2H$ |
| $CH_3S(O)_2$ | F | $CH_3S(O)_2$ | $CH_2CO_2H$ |
| $CH_3S(O)_2$ | $CH_3O$ | $CH_3S(O)_2$ | $CH_2CO_2H$ |
| F | H | $CH_3S(O)_2$ | $CH_2CO_2H$ |

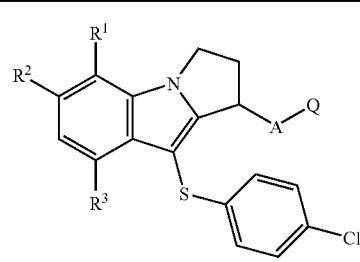

and

| R¹ | R² | R³ | A—Q |
|---|---|---|---|
| H | F | Br | $CF_2CO_2H$ |
| H | F | $CH_3S(O)_2$ | $CF_2CO_2H$. |

25. A pharmaceutical composition comprising a compound of claim 1 and a pharmaceutically acceptable carrier.

26. The composition of claim 25 further comprising a second active ingredient selected from an antihistamine, a leukotriene antagonist and a leukotriene biosynthesis inhibitor.

27. A method for the treatment of nasal congestion which comprises administering to a patient in need of such treatment a therapeutically effective amount of a compound of claim 1.

28. A method for the treatment of allergic asthma which comprises administering to a patient in need of such treatment a therapeutically effective amount of a compound of claim 1.

29. A method for the treatment of allergic rhinitis which comprises administering to a patient in need of such treatment a therapeutically effective amount of a compound of claim 1.

* * * * *